US011421212B2

(12) United States Patent
Miller et al.

(10) Patent No.: US 11,421,212 B2
(45) Date of Patent: Aug. 23, 2022

(54) ENGINEERED YEAST STRAINS WITH SIGNAL SEQUENCE-MODIFIED GLUCOAMYLASE POLYPEPTIDES AND ENHANCED ETHANOL PRODUCTION

(71) Applicant: CARGILL, INCORPORATED, Wayzata, MN (US)

(72) Inventors: Christopher K. Miller, Andover, MN (US); Gregory Michael Poynter, St. Paul, MN (US); Amit Vas, Minneapolis, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 16/323,458

(22) PCT Filed: Aug. 4, 2017

(86) PCT No.: PCT/US2017/045493

§ 371 (c)(1),
(2) Date: Feb. 5, 2019

(87) PCT Pub. No.: WO2018/027131

PCT Pub. Date: Feb. 8, 2018

(65) Prior Publication Data

US 2019/0345471 A1 Nov. 14, 2019

Related U.S. Application Data

(60) Provisional application No. 62/371,681, filed on Aug. 5, 2016.

(51) Int. Cl.

| | |
|---|---|
| ***C12N 9/34*** | (2006.01) |
| ***C12P 7/06*** | (2006.01) |
| ***C12P 13/04*** | (2006.01) |
| ***C12P 17/04*** | (2006.01) |
| ***C12P 19/14*** | (2006.01) |

(52) U.S. Cl.

CPC .............. *C12N 9/2428* (2013.01); *C12P 7/06* (2013.01); *C12P 13/04* (2013.01); *C12P 17/04* (2013.01); *C12P 19/14* (2013.01); *C12Y 302/01003* (2013.01)

(58) Field of Classification Search

None

See application file for complete search history.

(56) References Cited

U.S. PATENT DOCUMENTS

| | | | |
|---|---|---|---|
| 4,546,082 A | 10/1985 | Kurjan et al. | |
| 4,870,008 A | 9/1989 | Brake | |
| 4,959,317 A | 9/1990 | Sauer | |
| 5,024,941 A | 6/1991 | Maine et al. | |
| 5,231,017 A | 7/1993 | Lantero | |
| 5,422,267 A | 6/1995 | Yocum et al. | |
| 5,521,086 A | 5/1996 | Scott et al. | |
| 5,587,290 A | 12/1996 | Klionsky et al. | |
| 5,876,988 A | 3/1999 | Selten | |
| 6,214,577 B1 | 4/2001 | Yocum | |
| 7,785,872 B2 | 8/2010 | Chang et al. | |
| 8,067,339 B2 * | 11/2011 | Prinz | C12N 15/1034 506/9 |
| 8,394,622 B2 | 3/2013 | Haefele et al. | |
| 8,592,194 B2 | 11/2013 | Aehle | |
| 8,664,475 B2 | 3/2014 | Puzio et al. | |
| 8,697,412 B2 | 4/2014 | Landvik | |
| 8,733,149 B2 | 5/2014 | Yu et al. | |
| 8,733,321 B2 | 5/2014 | Cohn et al. | |
| 8,735,544 B1 | 5/2014 | Hammond et al. | |
| 8,809,023 B2 | 8/2014 | Degn | |
| 10,344,288 B2 * | 7/2019 | Miller | C12Y 302/01003 |
| 10,364,421 B2 * | 7/2019 | Miller | C07K 14/395 |
| 10,724,023 B2 * | 7/2020 | Miller | C12P 19/14 |
| 2004/0110295 A1 | 6/2004 | Punnonen | |
| 2007/0015266 A1 | 1/2007 | Dunn-Coleman | |
| 2007/0065905 A1 * | 3/2007 | Branduardi | C12N 15/815 435/69.1 |
| 2007/0117186 A1 | 5/2007 | Sahara | |
| 2007/0166788 A1 | 7/2007 | Jin et al. | |
| 2010/0317078 A1 | 12/2010 | Villa-Garcia et al. | |
| 2011/0033907 A1 | 2/2011 | Forrester et al. | |

(Continued)

FOREIGN PATENT DOCUMENTS

| | | |
|---|---|---|
| CN | 1069768 A | 3/1993 |
| CN | 1478097 A | 2/2004 |

(Continued)

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Accession Q2VC81. Jan. 10, 2006 (Year: 2006).*
Accession AAP40245. Nov. 29, 1991 (Year: 1991).*
Alignment of SEQ ID No. 77 to SEQ ID No. 34 of U.S. Pat. No. 8,067,339. Nov. 29, 2011 (Year: 2011).*

(Continued)

*Primary Examiner* — Christian L Fronda

(57) ABSTRACT

The invention is directed to non-natural yeast able to secrete significant amounts of glucoamylase into a fermentation media. The glucoamylase can promote degradation of starch material generating glucose for fermentation to a desired bioproduct, such as ethanol. The glucoamylase can be provided in the form of a glucoamylase fusion protein having secretion signal that is: derived from at least AA 1-19 of SEQ ID NO: 73, (ii) an amino acid sequence of at least AA 1-19 of SEQ ID NO: 74, (iii) SEQ ID NO: 77 (An aa), (iv) SEQ ID NO: 75 (Sc IV), (v) SEQ ID NO: 76 (Gg LZ), or (vi) SEQ ID NO: 78(Hs SA).

12 Claims, 9 Drawing Sheets

Specification includes a Sequence Listing.

(56) References Cited

U.S. PATENT DOCUMENTS

| | | | |
|---|---|---|---|
| 2011/0104331 | A1 | 5/2011 | Hatanaka |
| 2011/0209248 | A1 | 8/2011 | Frommer |
| 2011/0229968 | A1 | 9/2011 | Sohn et al. |
| 2011/0318799 | A1 | 12/2011 | Feldman |
| 2012/0064591 | A1 | 3/2012 | Gasch et al. |
| 2013/0137181 | A1 | 5/2013 | Choi et al. |
| 2013/0149760 | A1 | 6/2013 | Forrester et al. |
| 2013/0323822 | A1 | 12/2013 | Brevnova et al. |
| 2014/0162335 | A1 | 6/2014 | Bortiri |
| 2014/0248689 | A1 | 9/2014 | Hatanaka |

FOREIGN PATENT DOCUMENTS

| | | | |
|---|---|---|---|
| CN | 101194015 | A | 6/2008 |
| CN | 101646767 | A | 2/2010 |
| CN | 101952425 | A | 1/2011 |
| CN | 102869771 | A | 1/2013 |
| CN | 103814134 | A | 5/2014 |
| CN | 104395454 | A | 3/2015 |
| CN | 104560847 | A | 4/2015 |
| EP | 123544 | A2 | 10/1984 |
| EP | 228254 | A2 | 7/1987 |
| EP | 2734490 | A1 | 5/2014 |
| EP | 2735301 | A1 | 5/2014 |
| JP | 62228284 | A | 10/1987 |
| WO | 9613600 | W | 5/1996 |
| WO | 9914335 | W | 3/1999 |
| WO | 0071738 | A1 | 11/2000 |
| WO | 0242471 | W | 5/2002 |
| WO | 03105889 | A1 | 12/2003 |
| WO | 2004/042036 | A2 | 5/2004 |
| WO | 2007032792 | A2 | 3/2007 |
| WO | 2009037279 | A1 | 3/2009 |
| WO | 2011153516 | A2 | 12/2011 |
| WO | 2013011208 | A1 | 1/2013 |
| WO | 2013092840 | A1 | 6/2013 |
| WO | 2014029808 | A1 | 2/2014 |
| WO | 2014078920 | A1 | 5/2014 |
| WO | 2014081803 | A1 | 5/2014 |
| WO | 2015023989 | A1 | 2/2015 |
| WO | 2015195934 | A2 | 12/2015 |
| WO | 2016127083 | A1 | 8/2016 |
| WO | 2016160584 | A1 | 10/2016 |
| WO | 2017106739 | A1 | 6/2017 |

OTHER PUBLICATIONS

Favaro et al. Biotechnol Bioeng. Sep. 2015;112(9):1751-60. Epub Jul. 14, 2015. (Year: 2015).*

Arora et al. Renewable and Sustainable Energy Reviews. vol. 51, Nov. 2015, pp. 699-717. Available online Jul. 16, 2015. (Year: 2015).*

Accession E9P9V2. Apr. 5, 2011 (Year: 2011).

Accession Q8TFE5. Jun. 1, 2002 (Year: 2002).

Accession U3N160. Dec. 11, 2013 (Year: 2013).

Brake, Anthony J., et al., "a-Factor-directed synthesis and secretion of mature foreign proteins in *Saccharomyces cerevisiae*", Prov. Natl. Acad. Sci., vol. 81, pp. 4642-4646, Aug. 1984 Biochemistry.

Chica, Roberto A., et al., "Semi-rational approaches to engineering enzyme activity: combining the benefits of directed evolution and rational design", Curr Opin Biotechnol. 16(4), Aug. 2005, 378-84.

Das R C , et al., "Chapter 10: Host cell control of heterologous protein production in *Saccharomycescerevisiae*", Marcel Dekker, Inc., New York / Basel, XP008179956, 1990, 311-342.

Eva Hostinová , et al., "Molecular cloning and 3D structure prediction of the first raw-starch-degrading glucoamylase without a separate starch-binding domain", XP055266201, Archives of Biochemistry and Biophysics, Mar. 1, 2003 Academic Press, US-ISSN 0003-9861, vol. 411, Issue 2, Mar. 15, 2003, 189-195.

Eva Hostinová , et al., "Yeast glucoamylases: molecular-genetic and structural characterization", Biologia, SAP—Slovak Academic Press, Bratislava, SK, vol. 65 No. 4, Aug. 1, 2010, 559-568.

Flessel, Monica C., et al., "The MFa1 Gene of *Saccharomyces cerevisiae*: Genetic Mapping and Mutational Analysis of Promoter Elements", Genetics 121: 223-236 (Feb. 1989).

I. Ballesteros, , et al., "Optimization of the simultaneous saccharification and fermentation process using thermotolerant yeasts", Applied Biochemistry and Biotechnology, Spring 1993, vol. 39-40, Issue 1,, 1993, 201-211.

Lau, W.T. Walter, et al., "A Genetic Study of Signaling Processes for Repression of PH05 Transcription in *Saccharomyces cerevisiae*", Genetics Society of America 150: 1349-1359 (Dec. 1998).

Li, Jincai , et al., "Impediments to Secretion of Green Fluorescent Protein and Its Fusion from *Saccharomyces cerevisiae*", Biotechnol. Prog. 2002, 18, 831-838.

Liu, Zengran , et al., "Integrative Expression of Glucoamylase Gene in a Brewer's Yeast *Saccharomyces pastorianus* Strain", Food Technol. Biotechnol. 46 (1) 32-37 (2008.

Luo Jinxian , et al., "Expression and secretion of alpha-amylase and glucoamylase in *Saccharomyces cerevisiae*", Chinese Journal of Biotechnology, Allerton Press, vol. 10, No. 4, 1994, 241-248.

Nakamura , et al., "Alcohol fermentation of starch by a genetic recombinant yeast having glucoamylase activity", Biotechnology and Bioengineering, Wiley etc—ISSN 0006-3592, DOI: http://dx.doi.org/10.1002/(SICI)1097-0290(19970105)53:1<21::AID-BIT4>3.0.CO;2-0, vol. 53, Jan. 1, 1997, 21-25.

Punt P J , et al., "Intracellular and extracellular production of proteins in Aspergillus under the control of expression signals of the highly expressed Aspergillus nidulans gpdA gene", Journal of Biotechnology, Elsevier Science Publishers, Amsterdam, NL—ISSN 0168-1656, vol. 17, Nr:1, Jan. 1, 1991, 19-33.

Shi-Hwei Liu , et al., "Improved secretory production of glucoamylase in Pichia pastoris by combination of genetic manipulations", Biochemical and Biophysical Research Communications, Elsevier, 2005, 817-824.

Sidhu, Rajinder Singh, et al., "Selection of secretory protein-enoding genes by fusion with PH05 in *Saccharomyces cerevisiae*", Gene, 107 (1991) 111-118.

Singh, Raushan Kumar, et al., "Protein Engineering Approaches in the Post-Genomic Era", Curr Protein Pept Sci. 18, 2017, 1-11.

Tang Guomin , et al., "Integration of glucoamylase gene from Aspergillus niger into *Saccharomyces cerevisiae* genome and its stable expression", Chinese Journal of Biotechnology, Allerton Press, vol. 11 (4), 1995, 237-241.

Tetsuya Itoh , et al., "Nucleotide sequence of the glucoamylase gene GLU1 in the yeast *Saccharomycopsis fibuligera*", Journal of Bacteriology, Sep. 1987 vol. 169 No. 9, Sep. 1, 1987, 4171-4176.

"GenBank Accession No. CAC83969 1", Apr. 15, 2005.

Bourbonnais et al., J. Bio. Chem. 263(30): 15342, 1988.

Coutinho et al., "Structural similarities in glucoamylases by hydrophobic cluster analysis," Protein Eng., 1994 7 (6):749-760.

Coutinho et al., "Structure-function relationships in the catalytic and starch binding domains of glucoamylase," Protein Eng., 1994 7(3):393-400.

Evans et al. (Gene, 91:131; 1990).

Fukuda et al., "A mutated ARO4 gene for feedback-resistant DAHP synthase which causes both o-fluoro-DL-phenylalanine resistance and beta-phenethyl-alcohol overproduction in Saccharomyces cerevisiae," Curr Genet. 1991, 20(6):453-6.

GenBank ABB77799.1 Rhizopus oryzae amyB, Mar. 9, 2007.

Gonzalez-Siso, M.I., et al. (2015) Microb Biotechnol. 8:319-330.

Llmen, M., et al. (2007) Appl Environ Microbiol. 73:117-123.

Inoue, et al., Biosci Biotechnol Biochem. 2000; 64:229-236.

Kajiwara (Appl Microbiol Biotechnol. 2000; 53:568-74).

Kim et al., Appl Environ Microbiol. 1996; 62:1563-1569.

Meyhack et al. (EMBO J. 6:675-680, 1982).

Li YC et al. Application of omics technology in construction of Saccharomyces cerevisiae strains for ethanol production [J] China Biotechnol, 2014 34 (2): 118-128, machine translation.

Pascale Daran-Lapujade et al., Role of Transcriptional Regulation in Controlling Fluxes in Central Carbon Metabolism of Saccharomyces cerevisiae, The Journal of Biological Chemistry, vol. 279, No. 10, Issue of Mar. 15, pp. 9125-9138, 2004.

Rosario Lagunas, Sugar transport in Saccharomyces cerevisiae, FEMS Microbiology Reviews 104(1993) 229-242.

(56) References Cited

OTHER PUBLICATIONS

Sierks, M. R., and Svensson, B., 1993, Biochemistry 32:1113-1117.
Sierks, M.R., et al., 1994, Protein Eng. 7(12):1479-1484.
Takagi et al., Appl Environ Microbiol. 2005; 71:8656-8662.
Tamakawa, H et al. (2011) Biosci Biotechnol Biochem. 75:1994-2000.
UniProt O60087 Sachizosaccharomyces pombe meu17, Aug. 1, 1998.
UniProt O74254 Candida albicvans (strain SC5314/ATCC MYA-2876) GAMI, Mar. 15, 2017.
UniProt P04065 Saccharomyces cerevisiae STA1, Nov. 1, 1990.
UniProt P08017 Saccharomycopsis fibuligera GLU1, Aug. 1, 1988.
UniProt P22832 Aspergillus shirousami glaA, Aug. 1, 1991.
UniProt P22861 Ashwanniomyces occidentalis GAM1, Aug. 1, 1991.
UniProt P23176 Aspergillus kawachii gal, Nov. 1, 1991.
UniProt P26989 Saccharomycopsis fibuligera GLA1, Jul. 15, 1998.
UniProt P29760 Saccharomyces cerevisiae STA2, Apr. 1, 1993.
UniProt P36914 Aspergillus oryzae (strain ATCC 42149/RIB40), May 2, 2006.
UniProt Q8TFE5 Saccharomycopsis fibuligera Glm (CAC83969), Jun. 1, 2002.
Von Heijne, G., (1986) Nucleic Acids Res. 14, 4683-4690.
Waugh, D.S., Protein Expr Purif. 80(2): 283-293,2011.
Xie, D., et al. (2015) Appl Microbiol Biotechnol. 99: 1599-1610.
Yamashita, I et al., (1985) J. Bacteriol. 161, 567-573.
Zhang, J. et al. (2014) Bioresour Technol. 152:192-201.
Zhou et al., Microbial Cell Factories 13:44, 2014.
UniProt P69327 Aspergillus awamori, Nov. 1, 1986.
Ichiro Shibuya, Katsuya Gomi, Yuzuru Iimura, Kojiro Takahashi, Gakuzo Tamura & Shodo Hara (1990) Molecular Cloning of the Glucoamylase Gene of Aspergillus shirousami and Its Expression in Aspergillusoryzae, Agricultural and Biological Chemistry, 54:8, 1905-1914, DOI: 10.1080/00021369.1990.10870276.
UniProt P07683, Rhizopus oryzae glucoamylase, Nov. 1, 1995.
Kober et al., "Optimized signal peptides for the development of high expressing CHO cell lines," Biotechnology and Bioengineering, 110:1164-1173, 2013.
Jigami et al. "Expression of synthetic human-lysozyme gene in Saccharomyces cerevisiae: use of a synthetic chicken-lysozyme signal sequence for secretion and processing," Gene, 43:273-279, 1986.
Carlson, M. et al. Mol. Cell. Biol. 3:439-447, 1983.
Kurjan J., et al. "Structure of a yeast pheromone gene (MF$\alpha$): a putative $\alpha$-factor precursor contains four tandem copies of mature $\alpha$-factor," Cell 30:933-943, 1982.
UniProt P29761, Clostridium sp. cga, Apr. 1, 1993.
UniProt G8JZS4, Bacteroides thetaiotaomicron susB, Jan. 25, 2012.
Li W-C, et al., "Trichoderma reesei complete genome sequence, repeat-induced point mutations, and partitioning of CAZyme gene clusters," Biotechnology for Biofuels, 10, 170(2017).
UniProt Q0CK04, Aspergillus terreus ATEG_05980, Oct. 17, 2006.
UniProt A0A0H5C316, Cyberlindnera jadinii pep7, Oct. 14, 2015.
UniProt I2K2N7, Brettanomyces bruxellensis AWRI1499_0572, Jul. 11, 2012.
UniProt P42042, Blastobotrys adeninivorans GAA, Nov. 1, 1995.
UniProt P69328, Aspergillus niger GLAA, Nov. 1, 1986.
UniProt Q03045, Amorphotheca resinae GAMP, Feb. 1, 1994.
Lin, S.-C., et al. (BMC Biochemistry 8:9, 2007).
Ashikari T., et al. Agric. Biol. Chem. 49:2521-2523, 1985.
UniProt Q0CPK9, Aspergillus terreus glucoamylase, Oct. 17, 2006.
GenBank L15383, Aspergillus terreus glucoamylase, Jul. 14, 1995.
Ventura L. et al., "Molecular cloning and transcriptional analysis of the Aspergillus terreus gla1 gene encoding a glucoamylase," Appl Environ. Microbiol. 61:399-402, 1995.
Ghose A et al. "Characterization of glucoamylase from Aspergillus terreus 4" FEMS Microbiol Lett, 54:345-349, 1990.
NCBI glucoamylase [Saccharomycopsis fibuligera]; Apr. 15, 2005.

* cited by examiner

SEQUENCE LISTING

```
<160> NUMBER OF SEQ ID NOS: 86

<210> SEQ ID NO 1
<211> LENGTH: 3182
<212> TYPE: DNA
<213> ORGANISM: Artificial Sequence
<220> FEATURE:
```

-continued

<223> OTHER INFORMATION: Synthetic sequence containing elements from
      Saccharomyces cerevisiae

<400> SEQUENCE: 1
cctactgcgc caattgatga caatacagac gatgataaca aaccgaagtt atctgatgta 60
gaaaaggatt aaagatgcta agagatagtg atgatatttc ataaataatg taattctata 120
tatgttaatt accttttttg cgaggcatat ttatggtgaa ggataagttt tgaccatcaa 180
agaaggttaa tgtggctgtg gtttcagggt ccataaagct tttcaattca tcttttttt 240 ttttgttctt ttttttgatt ccggtttctt tgaaattttt ttgattcggt aatctccgag 300
cagaaggaag aacgaaggaa ggagcacaga cttagattgg tatatatacg catatgtggt 360
gttgaagaaa catgaaattg cccagtattc ttaacccaac tgcacagaac aaaaacctgc 420
aggaaacgaa gataaagcgg ccgcataact tcgtataatg tatgctatac gaagttatct 480
gccagtatac agctagcctt gaaagtgatg gaaaacattg tcatcggcac ataaataaaa 540
aaattatgaa tcacgtgatc aacagcaaat tatgtactcg tatatatgca agcgcattcc 600
ttatattgac actctttcat tgggcatgag gctgtgtaaa cataagctgt aacggtctca 660
cggaacactg tgtagttgca ttactgtcag gcagttatgt tgcttaatat aaaggcaaag 720
gcatggcaga atcactttaa aacgtggccc cacccgctgc accctgtgca ttttgtacgt 780
tactgcgaaa tgactcaacg atgaaatgaa aaaattttgc ttgaaatttt gaaaaaaaga 840
tgtgcgggac gcattgttag ctcattgaat acatcgtgat cgaatccaat caatgtttaa 900
tttcatatta atacagaaac tttttctcat actttcttct tcttttcatt ggtatattat 960
ctatatatcg tgttaattcc tctttcgtca tttttagcat cgttataaga gtaattaaga 1020
ataactagaa gagtctctct ttatattcgt ttattttata tatttaaccg ctaaatttag 1080
taaacaaaag aatctatcag aaatgagtga atctccaatg ttcgctgcca acggcatgcc 1140
aaaggtaaat caaggtgctg aagaagatgt cagaatttta ggttacgacc cattagcttc 1200
tccagctctc cttcaagtgc aaatcccagc cacaccaact tctttggaaa ctgccaagag 1260
aggtagaaga gaagctatag atattattac cggtaaagac gacagagttc ttgtcattgt 1320
cggtccttgt tccatccatg atctagaagc cgctcaagaa tacgctttga gattaaagaa 1380
attgtcagat gaattaaaag gtgatttatc catcattatg agagcatact tggagaagcc 1440
aagaacaacc gtcggctgga aaggtctaat taatgaccct gatgttaaca acactttcaa 1500
catcaacaag ggtttgcaat ccgctagaca attgtttgtc aacttgacaa atatcggttt 1560
gccaattggt tctgaaatgc ttgataccat ttctcctaaa tacttggctg atttggtctc 1620
cttcggtgcc attggtgcca gaaccaccga atctcaactg cacagagaat tggcctccgg 1680
tttgtctttc ccagttggtt tcaagaacgg taccgatggt accttaaatg ttgctgtgga 1740
tgcttgtcaa gccgctgctc attctcacca tttcatgggt gttactaagc atggtgttgc 1800
tgctatcacc actactaagg gtaacgaaca ctgcttcgtt attctaagag gtggtaaaaa 1860
gggtaccaac tacgacgcta agtccgttgc agaagctaag gctcaattgc ctgccggttc 1920
caacggtcta atgattgact actctcacgg taactccaat aaggatttca gaaaccaacc 1980
aaaggtcaat gacgttgttt gtgagcaaat cgctaacggt gaaaacgcca ttaccggtgt 2040
catgattgaa tcaaacatca acgaaggtaa ccaaggcatc ccagccgaag gtaaagccgg 2100
cttgaaatat ggtgtttcca tcactgatgc ttgtataggt tgggaaacta ctgaagacgt 2160
cttgaggaaa ttggctgctg ctgtcagaca aagaagagaa gttaacaaga aatagatgtt 2220

```
tttttaatga tatatgtaac gtacattctt tcctctacca ctgccaattc ggtattattt   2280

aattgtgttt agcgctattt actaattaac tagaaactca atttttaaag gcaaagctcg   2340

ctgacctttc actgatttcg tggatgttat actatcagtt actcttctgc aaaaaaaaat   2400

tgagtcatat cgtagctttg ggattatttt tctctctctc cacggctaat taggtgatca   2460

tgaaaaaatg aaaaattcat gagaaaagag tcagacatcg aaacatacat aagttgatat   2520

tcctttgata tcgacgacta ctcaatcagg ttttaaaaga aaagaggcag ctattgaagt   2580

agcagtatcc agtttaggtt ttttaattat ttacaagtaa agaaaaagag aatgccggtc   2640

gttcacgata acttcgtata atgtatgcta tacgaagtta tgcggccgcg agaagatgcg   2700

gccagcaaaa ctaaaaaact gtattataag taaatgcatg tatactaaac tcacaaatta   2760

gagcttcaat ttaattatat cagttattac ccgggaatct cggtcgtaat gatttctata   2820

atgacgaaaa aaaaaaaatt ggaaagaaaa agcttcatgg cctttataaa aaggaactat   2880

ccaatacctc gccagaacca agtaacagta ttttacgggg cacaaatcaa gaacaataag   2940

acaggactgt aaagatggac gcattgaact ccaaagaaca acaagagttc caaaaagtag   3000

tggaacaaaa gcaaatgaag gatttcatgc gtttgtactc taatctggta gaaagatgtt   3060

tcacagactg tgtcaatgac ttcacaacat caaagctaac caataaggaa caaacatgca   3120

tcatgaagtg ctcagaaaag ttcttgaagc atagcgaacg tgtagggcag cgtttccaag   3180

ag                                                                  3182
```

<210> SEQ ID NO 2
<211> LENGTH: 3275
<212> TYPE: DNA
<213> ORGANISM: Artificial Sequence
<220> FEATURE:
<223> OTHER INFORMATION: Sequence put together from multiple organisms: Saccharomyces cerevisiae and Aspergillus nidulans

<400> SEQUENCE: 2

```
cctactgcgc caattgatga caatacagac gatgataaca aaccgaagtt atctgatgta     60

gaaaaggatt aaagatgcta agagatagtg atgatatttc ataaataatg taattctata    120

tatgttaatt accttttttg cgaggcatat ttatggtgaa gaataagttt tgaccatcaa    180

agaaggttaa tgtggctgtg gtttcagggt ccataaagct tttcaattca tcattttttt    240

tttattcttt tttttgattc cggtttcctt gaaatttttt tgattcggta atctccgaac    300

agaaggaaga acgaaggaag gagcacagac ttagattggt atatatacgc atatgtagtg    360

ttgaagaaac atgaaattgc ccagtattct taacccaact gcacagaaca aaaatctgca    420

ggaaacgaag ataaagcggc cgcataactt cgtatagcat acattatacg aagttatcgc    480

ctgttaagat ataactgaaa aaagagggga atttttagat actgaaatga tattttagaa    540

taaccagact atatataagg ataaattaca aaaaattaac taatagataa gatttaaata    600

taaaagatat gcaactagaa aagtcttatc aatctcctta tggagtgacg acgttaccca    660

acaatttacc gacttcttcg gcgatagcca aagttctctc ttcggacaat cttctaccaa    720

taacttgaac agcaacagga gcaccgtgat aagcctctgg gtcgtattct tcttgaacca    780

aagcatccaa ttcggaaaca gctttaaaag attcgttctt cttatcaata ttcttatcag    840

cgaaagtgac tgggacgaca acagaggtga aatccaataa gttaataacg gaggcgtaac    900

cgtagtatct gaattgatcg tgtctgacag cggcggtagg agtaattgga gcgataatag    960

cgtccaattc cttaccagct tttcttcag cttcacgcca cttttccaag tattccattt   1020
```

-continued

```
gatagttcca cttttgtaaa tgagtgtccc acaattcgtt catgttaaca gccttaatat   1080
ttgggttcaa caagtcctta atgttaggga tggctggctc accagaggca gaaatgtctc   1140
tcatgacgtc ggcagaacca tcagcagcat agatgtggga aatcaagtca tgaccgaaat   1200
catgcttgta tggagtccat ggagtaacgg tgtgaccagc cttggccaaa gcggcaacgg   1260
tagtttcgac accacgtaaa attggtgggt gtggcaagac gttaccgtcg aaattgtaat   1320
aaccaatgtt caaaccacca ttcttaatct tagaggcaat gatgtcagat tcagattgtc   1380
tccatggcat tgggatgacc ttagagtcgt acttccaagg ttcttgaccc aagacagatt   1440
tggtgaacaa tctcaagtct tcgacggagt gagtgatagg accaacgacg gagtgaacgg   1500
tttcttgacc ttccatagag ttagccattt tagcatatgg caatctaccg tgagatggtc   1560
tcaaaccgta taaaaagttg aaagcagctg ggactctaat ggaaccacca atgtcagtac   1620
cgacaccaat aacaccacct ctaataccaa caatagcacc ttcaccacca gaagaaccac   1680
cacaggacca atttttgttt cttggattga cagttctacc aatgatgttg ttgacggttt   1740
cacagaccat caaggtttgt gggacagagg tcttaacgta gaaaacagca ccagcttttc   1800
tcaacatggt ggttaagacg gaatcacctt catcgtattt gtttaaccag gaaatgtaac   1860
ccatggaggt ttcgtaaccc ttaacacgca attggtcctt taaagagatt ggtaaaccgt   1920
gtaatggacc aactggtctc ttatgcttag cgtagtattc atctaattct ctagcttgag   1980
ctaaagcagc atctgggaag aattcgtgag cacagttggt taattgttga gcaatagcag   2040
ctctcttaca aaaagccaaa gtgacttcaa cagaagtcaa ctcaccagcg gccaacttgg   2100
agaccaaatc agcagcagag gcttcggtaa tcttcaattc agcctcagac aaaataccgg   2160
acttctttgg gaaatcaata acggaatctt cggcaggcaa agtttgaacc ttccattcgt   2220
caggaatggt tttagccaaa cgggcacgtt tgtcggcggc caattcttcc caggattgtg   2280
gcattttgta attaaaactt agattagatt gctatgcttt ctttctaatg agcaagaagt   2340
aaaaaaagtt gtaatagaac aagaaaaacg aaactgaaac ttgagaaatt gaagaccatt   2400
tattaactta aatatcaatg ggaggtcatc gaaagagaaa aaaatcaaaa aaaaaatttt   2460
tcaagaaaaa gaaacgtgat aaaaattttt attgcctttt tcgacgaaga aaaagaaacg   2520
aggcggtctc ttttttcttt tccaaacctt tagtacgggt aattaacgcc accctagagg   2580
aagaaagagg ggaaatttag tatgctgtgc ttgggtgttt tgaagtggta cggcgatgcg   2640
cggagtccga gaaaatctgg aagagtaaaa aaggagtaga aacattttga agctatggtg   2700
tgtgggggat cacttgtggg ggattgggtg tgatgtaagg ataacttcgt atagcataca   2760
ttatacgaag ttatgcggcc gcgagaagat gcggccagca aaactaaaaa actgtattat   2820
aagtaaatgc atgtatacta aactcacaaa ttagagcttc aatttaatta tatcagttat   2880
tacccgggaa tctcggtcgt aatgattttt ataatgacga aaaaaaaaaa attggaaaga   2940
aaaagcttca tggcctttat aaaaaggaac catccaatac ctcgccagaa ccaagtaaca   3000
gtattttacg gggcacaaat caagaacaat aagacaggac tgtaaagatg gacgcattga   3060
actccaaaga acaacaagag ttccaaaaag tagtggaaca aaagcaaatg aaggatttca   3120
tgcgtttgta ctctaatctg gtagaaagat gttttacaga ctgtgtcaat gacttcacaa   3180
catcaaagct aaccaataag gaacaaacat gcatcatgaa gtgctcagaa aagttcttga   3240
agcatagcga acgtgtaggg cagcgtttcc aagag                              3275
```

<210> SEQ ID NO 3
<211> LENGTH: 1132

<212> TYPE: DNA
<213> ORGANISM: Artificial Sequence
<220> FEATURE:
<223> OTHER INFORMATION: Sequence put together from multiple organisms: Saccharomyces cerevisiae and Aspergillus nidulans

<400> SEQUENCE: 3

```
ctcttttta cagatcatca aggaagtaat tatctacttt ttacaagaat tcatgtctaa     60
tttacttact gttcaccaaa acttgcctgc attaccagtt gacgcaacct ccgatgaagt    120
cagaaagaac cttatggata tgtttagaga tagacaagct ttctccgaac atacttggaa    180
aatgttatta tccgtttgta gatcctgggc cgcttggtgt aaacttaaca atagaaaatg    240
gtttcctgct gaaccagaag acgtcagaga ttacttactt tacttacaag ctagaggttt    300
ggctgttaaa actatccaac aacacttagg tcaattgaat atgttacaca gaagatccgg    360
tttaccaaga ccatccgatt ccaacgcagt ttcccttgtt atgagaagaa ttagaaaaga    420
aaatgttgac gctggtgaaa gagctaaaca agcattagca tttgaaagaa ccgatttcga    480
tcaagttaga tccttaatgg aaaattccga tagatgtcaa gatattagaa acttagcttt    540
cttaggtatt gcttacaaca cattattaag aatcgctgaa attgctagaa ttagagttaa    600
agatatttca agaaccgatg gcggtagaat gttaatccac attggcagaa caaaaacctt    660
agtctccaca gcaggcgtcg aaaaagcatt atcattaggt gttactaaat tagttgaacg    720
ttggatttcc gtttccggtg ttgcagatga cccaaacaac tacttattct gtcgtgttag    780
aaaaaatggt gttgccgctc cttccgctac ctcacaatta tccacaagag cattagaagg    840
catttttgaa gctacccaca gacttattta tggtgcaaaa gacgattccg gtcaaagata    900
tttagcttgg tctggtcatt ccgctagagt tggtgccgca agagacatgg caagagctgg    960
tgtttctatt cctgaaatta tgcaagccgg tggttggact aatgttaaca ttgttatgaa   1020
ctatatcaga aacttagatt ccgaaacagg tgctatggtt agattacttg aagacggtga   1080
ttaagctagc taagatccgc tctaaccgaa aaggaaggag ttagacaacc tg           1132
```

<210> SEQ ID NO 4
<211> LENGTH: 6376
<212> TYPE: DNA
<213> ORGANISM: Artificial Sequence
<220> FEATURE:
<223> OTHER INFORMATION: Sequence put together from multiple organisms: Saccharomyces cerevisiae and Aspergillus nidulans

<400> SEQUENCE: 4

```
ctagctaaga tccgctctaa ccgaaaagga aggagttaga caacctgaag tctaggtccc     60
tatttatttt tttatagtta tgttagtatt aagaacgtta tttatatttc aaatttttct    120
ttttttctg tacagacgcg tgtacgcatg taacattata ctgaaaacct tgcttgagaa    180
ggttttggga cgctcgaaga tccagctgca ttaatgaatc ggccaacgcg cggggagagg    240
cggtttgcgt attgggcgct cttccgcttc ctcgctcact gactcgctgc gctcggtcgt    300
tcggctgcgg cgagcggtat cagctcactc aaaggcggta atacggttat ccacagaatc    360
aggggataac gcaggaaaga acatgtgagc aaaaggccag caaaaggcca ggaaccgtaa    420
aaaggccgcg ttgctggcgt ttttccatag gctccgcccc cctgacgagc atcacaaaaa    480
tcgacgctca agtcagaggt ggcgaaaccc gacaggacta taaagatacc aggcgtttcc    540
ccctggaagc tccctcgtgc gctctcctgt tccgaccctg ccgcttaccg gatacctgtc    600
cgcctttctc ccttcgggaa gcgtggcgct ttctcatagc tcacgctgta ggtatctcag    660
```

```
ttcggtgtag gtcgttcgct ccaagctggg ctgtgtgcac gaaccccccg ttcagcccga    720

ccgctgcgcc ttatccggta actatcgtct tgagtccaac ccggtaagac acgacttatc    780

gccactggca gcagccactg gtaacaggat tagcagagcg aggtatgtag gcggtgctac    840

agagttcttg aagtggtggc ctaactacgg ctacactaga aggacagtat ttggtatctg    900

cgctctgctg aagccagtta ccttcggaaa aagagttggt agctcttgat ccggcaaaca    960

aaccaccgct ggtagcggtg gtttttttgt ttgcaagcag cagattacgc gcagaaaaaa   1020

aggatctcaa gaagatcctt tgatcttttc tacggggtct gacgctcagt ggaacgaaaa   1080

ctcacgttaa gggattttgg tcatgagatt atcaaaaagg atcttcacct agatcctttt   1140

aaattaaaaa tgaagtttta aatcaatcta aagtatatat gagtaaactt ggtctgacag   1200

ttaccaatgc ttaatcagtg aggcacctat ctcagcgatc tgtctatttc gttcatccat   1260

agttgcctga ctccccgtcg tgtagataac tacgatacgg gagggcttac catctggccc   1320

cagtgctgca atgataccgc gagacccacg ctcaccggct ccagatttat cagcaataaa   1380

ccagccagcc ggaagggccg agcgcagaag tggtcctgca actttatccg cctccatcca   1440

gtctattaat tgttgccggg aagctagagt aagtagttcg ccagttaata gtttgcgcaa   1500

cgttgttgcc attgctacag gcatcgtggt gtcacgctcg tcgtttggta tggcttcatt   1560

cagctccggt tcccaacgat caaggcgagt tacatgatcc cccatgttgt gcaaaaaagc   1620

ggttagctcc ttcggtcctc cgatcgttgt cagaagtaag ttggccgcag tgttatcact   1680

catggttatg gcagcactgc ataattctct tactgtcatg ccatccgtaa gatgcttttc   1740

tgtgactggt gagtactcaa ccaagtcatt ctgagaatag tgtatgcggc gaccgagttg   1800

ctcttgcccg gcgtcaatac gggataatac cgcgccacat agcagaactt taaaagtgct   1860

catcattgga aaacgttctt cggggcgaaa actctcaagg atcttaccgc tgttgagatc   1920

cagttcgatg taacccactc gtgcacccaa ctgatcttca gcatctttta ctttcaccag   1980

cgtttctggg tgagcaaaaa caggaaggca aaatgccgca aaaaagggaa taagggcgac   2040

acggaaatgt tgaatactca tactcttcct ttttcaatat tattgaagca tttatcaggg   2100

ttattgtctc atgagcggat acatatttga atgtatttag aaaaataaac aaataggggt   2160

tccgcgcaca tttccccgaa aagtgccacc tgaacgaagc atctgtgctt cattttgtag   2220

aacaaaaatg caacgcgaga gcgctaattt ttcaaacaaa gaatctgagc tgcattttta   2280

cagaacagaa atgcaacgcg aaagcgctat tttaccaacg aagaatctgt gcttcatttt   2340

tgtaaaacaa aaatgcaacg cgagagcgct aatttttcaa acaaagaatc tgagctgcat   2400

ttttacagaa cagaaatgca acgcgagagc gctattttac caacaaagaa tctatacttc   2460

ttttttgttc tacaaaaatg catcccgaga gcgctatttt tctaacaaag catcttagat   2520

tacttttttt ctcctttgtg cgctctataa tgcagtctct tgataacttt ttgcactgta   2580

ggtccgttaa ggttagaaga aggctacttt ggtgtctatt ttctcttcca taaaaaaagc   2640

ctgactccac ttcccgcgtt tactgattac tagcgaagct gcgggtgcat tttttcaaga   2700

taaaggcatc cccgattata ttctataccg atgtggattg cgcatacttt gtgaacagaa   2760

agtgatagcg ttgatgattc ttcattggtc agaaaattat gaacggtttc ttctattttg   2820

tctctatata ctacgtatag gaaatgttta cattttcgta ttgttttcga ttcactctat   2880

gaatagttct tactacaatt tttttgtcta aagagtaata ctagagataa acataaaaaa   2940

tgtagaggtc gagtttagat gcaagttcaa ggagcgaaag gtggatgggt aggttatata   3000

gggatatagc acagagatat atagcaaaga gatacttttg agcaatgttt gtggaagcgg   3060
```

```
tattcgcaat attttagtag ctcgttacag tccggtgcgt ttttggtttt ttgaaagtgc   3120
gtcttcagag cgcttttggt tttcaaaagc gctctgaagt tcctatactt tctagagaat   3180
aggaacttcg gaataggaac ttcaaagcgt ttccgaaaac gagcgcttcc gaaaatgcaa   3240
cgcgagctgc gcacatacag ctcactgttc acgtcgcacc tatatctgcg tgttgcctgt   3300
atatatatat acatgagaag aacggcatag tgcgtgttta tgcttaaatg cgtacttata   3360
tgcgtctatt tatgtaggat gaaaggtagt ctagtacctc ctgtgatatt atcccattcc   3420
atgcggggta tcgtatgctt ccttcagcac taccctttag ctgttctata tgctgccact   3480
cctcaattgg attagtctca tccttcaatg ctatcatttc ctttgatatt ggatcatact   3540
aagaaaccat tattatcatg acattaacct ataaaaatag gcgtatcacg aggccctttc   3600
gtctcgcgcg tttcggtgat gacggtgaaa acctctgaca catgcagctc ccggagacgg   3660
tcacagcttg tctgtaagcg gatgccggga gcagacaagc ccgtcagggc gcgtcagcgg   3720
gtgttggcgg gtgtcggggc tggcttaact atgcggcatc agagcagatt gtactgagag   3780
tgcaccatac cacagctttt caattcaatt catcattttt tttttattct tttttttgat   3840
ttcggtttct ttgaaatttt tttgattcgg taatctccga acagaaggaa gaacgaagga   3900
aggagcacag acttagattg gtatatatac gcatatgtag tgttgaagaa acatgaaatt   3960
gcccagtatt cttaacccaa ctgcacagaa caaaaacctg caggaaacga agataaatca   4020
tgtcgaaagc tacatataag gaacgtgctg ctactcatcc tagtcctgtt gctgccaagc   4080
tatttaatat catgcacgaa aagcaaacaa acttgtgtgc ttcattggat gttcgtacca   4140
ccaaggaatt actggagtta gttgaagcat taggtcccaa aatttgttta ctaaaaacac   4200
atgtggatat cttgactgat tttccatgg agggcacagt taagccgcta aaggcattat   4260
ccgccaagta caatttttta ctcttcgaag acagaaaatt tgctgacatt ggtaatacag   4320
tcaaattgca gtactctgcg ggtgtataca gaatagcaga atgggcagac attacgaatg   4380
cacacggtgt ggtgggccca ggtattgtta gcggtttgaa gcaggcggca gaagaagtaa   4440
caaaggaacc tagaggcctt ttgatgttag cagaattgtc atgcaagggc tccctatcta   4500
ctggagaata tactaagggt actgttgaca ttgcgaagag cgacaaagat tttgttatcg   4560
gctttattgc tcaaagagac atgggtggaa gagatgaagg ttacgattgg ttgattatga   4620
cacccggtgt gggtttagat gacaagggag acgcattggg tcaacagtat agaaccgtgg   4680
atgatgtggt ctctacagga tctgacatta ttattgttgg aagaggacta tttgcaaagg   4740
gaagggatgc taaggtagag ggtgaacgtt acagaaaagc aggctgggaa gcatatttga   4800
gaagatgcgg ccagcaaaac taaaaaactg tattataagt aaatgcatgt atactaaact   4860
cacaaattag agcttcaatt taattatatc agttattacc ctatgcggtg tgaaataccg   4920
cacagatgcg taaggagaaa ataccgcatc aggaaattgt aaacgttaat attttgttaa   4980
aattcgcgtt aaatttttgt taaatcagct cattttttaa ccaataggcc gaaatcggca   5040
aaatccctta taaatcaaaa gaatagaccg agatagggtt gagtgttgtt ccagtttgga   5100
acaagagtcc actattaaag aacgtggact ccaacgtcaa agggcgaaaa accgtctatc   5160
agggcgatgg cccactacgt gaaccatcac cctaatcaag ttttttgggg tcgaggtgcc   5220
gtaaagcact aaatcggaac cctaaaggga gcccccgatt tagagcttga cggggaaagc   5280
cggcgaacgt ggcgagaaag gaagggaaga aagcgaaagg agcgggcgct agggcgctgg   5340
caagtgtagc ggtcacgctg cgcgtaacca ccacacccgc cgcgcttaat gcgccgctac   5400
```

agggcgcgtc cattcgccat tcaggctgcg caactgttgg gaagggcgat cggtgcgggc 5460
ctcttcgcta ttacgccagc tgaattggag cgacctcatg ctatacctga gaaagcaacc 5520
tgacctacag gaaagagtta ctcaagaata agaattttcg ttttaaaacc taagagtcac 5580
tttaaaattt gtatacactt atttttttta taacttattt aataataaaa atcataaatc 5640
ataagaaatt cgcttattta gaagtgtcaa caacgtatct accaacgatt tgaccctttt 5700
ccatcttttc gtaaatttct ggcaaggtag acaagccgac aaccttgatt ggagacttga 5760
ccaaacctct ggcgaagaat tgttaattaa gccagaaaaa ggaagtgttt ccctccttct 5820
tgaattgatg ttaccctcat aaagcacgtg gcctcttatc gagaaagaaa ttaccgtcgc 5880
tcgtgatttg tttgcaaaaa gaacaaaact gaaaaaaccc agacacgctc gacttcctgt 5940
cttcctattg attgcagctt ccaatttcgt cacacaacaa ggtcctagcg acggctcaca 6000
ggttttgtaa caagcaatcg aaggttctgg aatggcggga aagggtttag taccacatgc 6060
tatgatgccc actgtgatct ccagagcaaa gttcgttcga tcgtactgtt actctctctc 6120
tttcaaacag aattgtccga atcgtgtgac aacaacagcc tgttctcaca cactcttttc 6180
ttctaaccaa gggggtggtt tagtttagta gaacctcgtg aaacttacat ttacatatat 6240
ataaacttgc ataaattggt caatgcaaga aatacatatt tggtcttttc taattcgtag 6300
tttttcaagt tcttagatgc tttctttttc tctttttttac agatcatcaa ggaagtaatt 6360
atctactttt tacaag 6376

<210> SEQ ID NO 5
<211> LENGTH: 5735
<212> TYPE: DNA
<213> ORGANISM: Artificial Sequence
<220> FEATURE:
<223> OTHER INFORMATION: Sequence put together from multiple organisms:
Saccharomyces cerevisiae and Aspergillus shirousami

<400> SEQUENCE: 5
taaacaggcc ccttttcctt tgtcgatatc atgtaattag ttatgtcacg cttacattca 60
cgccctcctc ccacatccgc tctaaccgaa aaggaaggag ttagacaacc tgaagtctag 120
gtccctattt attttttttat agttatgtta gtattaagaa cgttatttat atttcaaatt 180
tttctttttt ttctgtacaa acgcgtgtac gcatgtaacg ggcagacgcg gccgccaccg 240
cggtggagct ccaattcgcc ctatagtgag tcgtattaca attcactggc cgtcgtttta 300
caacgtcgtg actgggaaaa ccctggcgtt acccaactta atcgccttgc agcacatccc 360
cccttcgcca gctggcgtaa tagcgaagag gcccgcaccg atcgcccttc ccaacagttg 420
cgcagcctga atggcgaatg gcgcgacgcg ccctgtagcg gcgcattaag cgcggcgggt 480
gtggtggtta cgcgcagcgt gaccgctaca cttgccagcg ccctagcgcc cgctcctttc 540
gctttcttcc cttcctttct cgccacgttc gccggctttc cccgtcaagc tctaaatcgg 600
gggctccctt tagggttccg atttagtgct ttacggcacc tcgaccccaa aaaacttgat 660
tagggtgatg gttcacgtag tgggccatcg ccctgataga cggtttttcg ccctttgacg 720
ttggagtcca cgttctttaa tagtggactc ttgttccaaa ctggaacaac actcaaccct 780
atctcggtct attcttttga tttataaggg attttgccga tttcggccta ttggttaaaa 840
aatgagctga tttaacaaaa atttaacgcg aattttaaca aaatattaac gtttacaatt 900
tcctgatgcg gtattttctc cttacgcatc tgtgcggtat ttcacaccgc agggtaataa 960
ctgatataat taaattgaag ctctaatttg tgagtttagt atacatgcat ttacttataa 1020

```
tacagttttt tagttttgct ggccgcatct tctcaaatat gcttcccagc ctgcttttct   1080
gtaacgttca ccctctacct tagcatccct tccctttgca aatagtcctc ttccaacaat   1140
aataatgtca gatcctgtag agaccacatc atccacggtt ctatactgtt gacccaatgc   1200
gtctcccttg tcatctaaac ccacaccggg tgtcataatc aaccaatcgt aaccttcatc   1260
tcttccaccc atgtctcttt gagcaataaa gccgataaca aaatctttgt cgctcttcgc   1320
aatgtcaaca gtacccttag tatattctcc agtagatagg gagcccttgc atgacaattc   1380
tgctaacatc aaaaggcctc taggttcctt tgttacttct tctgccgcct gcttcaaacc   1440
gctaacaata cctgggccca ccacaccgtg tgcattcgta atgtctgccc attctgctat   1500
tctgtataca cccgcagagt actgcaattt gactgtatta ccaatgtcag caaattttct   1560
gtcttcgaag agtaaaaaat tgtacttggc ggataatgcc tttagcggct taactgtgcc   1620
ctccatggaa aaatcagtca agatatccac atgtgttttt agtaaacaaa ttttgggacc   1680
taatgcttca actaactcca gtaattcctt ggtggtacga acatccaatg aagcacacaa   1740
gtttgtttgc ttttcgtgca tgatattaaa tagcttggca gcaacaggac taggatgagt   1800
agcagcacgt tccttatatg tagctttcga catgatttat cttcgtttcc tgcaggtttt   1860
tgttctgtgc agttgggtta agaatactgg gcaatttcat gtttcttcaa cactacatat   1920
gcgtatatat accaatctaa gtctgtgctc cttccttcgt tcttccttct gttcggagat   1980
taccgaatca aaaaaatttc aaagaaaccg aaatcaaaaa aaagaataaa aaaaaaatga   2040
tgaattgaat tgaaaagcgt ggtgcactct cagtacaatc tgctctgatg ccgcatagtt   2100
aagccagccc cgacacccgc caacacccgc tgacgcgccc tgacgggctt gtctgctccc   2160
ggcatccgct tacagacaag ctgtgaccgt ctccgggagc tgcatgtgtc agaggttttc   2220
accgtcatca ccgaaacgcg cgagacgaaa gggcctcgtg atacgcctat ttttataggt   2280
taatgtcatg ataataatgg tttcttagga cggatcgctt gcctgtaact tacacgcgcc   2340
tcgtatcttt taatgatgga ataatttggg aatttactct gtgtttattt atttttatgt   2400
tttgtatttg gattttagaa agtaaataaa gaaggtagaa gagttacgga atgaagaaaa   2460
aaaaataaac aaaggtttaa aaaatttcaa caaaaagcgt actttacata tatatttatt   2520
agacaagaaa agcagattaa atagatatac attcgattaa cgataagtaa aatgtaaaat   2580
cacaggattt tcgtgtgtgg tcttctacac agacaagatg aaacaattcg gcattaatac   2640
ctgagagcag gaagagcaag ataaaaggta gtatttgttg gcgatccccc tagagtcttt   2700
tacatcttcg gaaaacaaaa actatttttt ctttaatttc ttttttact ttctatttt   2760
aatttatata tttatattaa aaaatttaaa ttataattat ttttatagca cgtgatgaaa   2820
aggacccagg tggcactttt cggggaaatg tgcgcggaac ccctatttgt ttatttttct   2880
aaatacattc aaatatgtat ccgctcatga gacaataacc ctgataaatg cttcaataat   2940
attgaaaaag gaagagtatg agtattcaac atttccgtgt cgcccttatt ccctttttg   3000
cggcattttg ccttcctgtt tttgctcacc cagaaacgct ggtgaaagta aaagatgctg   3060
aagatcagtt gggtgcacga gtgggttaca tcgaactgga tctcaacagc ggtaagatcc   3120
ttgagagttt tcgccccgaa gaacgttttc caatgatgag cacttttaaa gttctgctat   3180
gtggcgcggt attatcccgt attgacgccg ggcaagagca actcggtcgc cgcatacact   3240
attctcagaa tgacttggtt gagtactcac cagtcacaga aaagcatctt acggatggca   3300
tgacagtaag agaattatgc agtgctgcca taaccatgag tgataacact gcggccaact   3360
tacttctgac aacgatcgga ggaccgaagg agctaaccgc ttttttcac aacatggggg   3420
```

```
atcatgtaac tcgccttgat cgttgggaac cggagctgaa tgaagccata ccaaacgacg   3480
agcgtgacac cacgatgcct gtagcaatgg caacaacgtt gcgcaaacta ttaactggcg   3540
aactacttac tctagcttcc cggcaacaat taatagactg gatggaggcg gataaagttg   3600
caggaccact tctgcgctcg gcccttccgg ctggctggtt tattgctgat aaatctggag   3660
ccggtgagcg tgggtctcgc ggtatcattg cagcactggg gccagatggt aagccctccc   3720
gtatcgtagt tatctacacg acgggcagtc aggcaactat ggatgaacga aatagacaga   3780
tcgctgagat aggtgcctca ctgattaagc attggtaact gtcagaccaa gtttactcat   3840
atatacttta gattgattta aaacttcatt tttaatttaa aaggatctag gtgaagatcc   3900
tttttgataa tctcatgacc aaaatccctt aacgtgagtt ttcgttccac tgagcgtcag   3960
accccgtaga aaagatcaaa ggatcttctt gagatccttt ttttctgcgc gtaatctgct   4020
gcttgcaaac aaaaaaacca ccgctaccag cggtggtttg tttgccggat caagagctac   4080
caactctttt tccgaaggta actggcttca gcagagcgca gataccaaat actgtccttc   4140
tagtgtagcc gtagttaggc caccacttca agaactctgt agcaccgcct acatacctcg   4200
ctctgctaat cctgttacca gtggctgctg ccagtggcga taagtcgtgt cttaccgggt   4260
tggactcaag acgatagtta ccggataagg cgcagcggtc gggctgaacg gggggttcgt   4320
gcacacagcc cagcttggag cgaacgacct acaccgaact gagataccta cagcgtgagc   4380
attgagaaag cgccacgctt cccgaaggga gaaaggcgga caggtatccg gtaagcggca   4440
gggtcggaac aggagagcgc acgagggagc ttccaggggg gaacgcctgg tatctttata   4500
gtcctgtcgg gtttcgccac ctctgacttg agcgtcgatt tttgtgatgc tcgtcagggg   4560
ggcgagcct atggaaaaac gccagcaacg cggccttttt acggttcctg gccttttgct   4620
ggccttttgc tcacatgttc tttcctgcgt tatcccctga ttctgtggat aaccgtatta   4680
ccgcctttga gtgagctgat accgctcgcc gcagccgaac gaccgagcgc agcgagtcag   4740
tgagcgagga agcggaagag cgcccaatac gcaaaccgcc tctccccgcg cgttggccga   4800
ttcattaatg cagctggcac gacaggtttc ccgactggaa agcgggcagt gagcgcaacg   4860
caattaatgt gagttacctc actcattagg caccccaggc tttacacttt atgcttccgg   4920
ctcctatgtt gtgtggaatt gtgagcggat aacaatttca cacaggaaac agctatgacc   4980
atgattacgc caagctcgga attaaccctc actaaaggga acaaaagctg ggtaccgggc   5040
ccccctcga gatctcccga gtttatcatt atcaatactg ccatttcaaa gaatacgtaa   5100
ataattaata gtagtgattt tcctaacttt atttagtcaa aaaattggcc ttttaattct   5160
gctgtaaccc gtacatgccc aaaatagggg gcgggttaca cagaatatat aacatcatag   5220
gtgtctgggt gaacagttta ttcctggcat ccactaaata taatggagcc cgcttttttt   5280
aagctggcat ccagaaaaaa aaagaatccc agcaccaaaa tattgttttc ttcaccaacc   5340
atcagttcat aggtccattc tcttagcgca actacacaga acaggggcac aaacaggcaa   5400
aaaacgggca caacctcaat ggagtgatgc aacctgcttg gagtaaatga tgacacaagg   5460
caattgacct acgcatgtat ctatctcatt ttcttacacc ttctattacc ttctgctctc   5520
tctgatttgg aaaaagctga aaaaaaaggt tgaaaccagt tccctgaaat tattccccta   5580
tttgactaat aagtatataa agacggtagg tattgattgt aattctgtaa atctatttct   5640
taaacttctt aaattctact tttatagtta gtcttttttt tagttttaaa acactaagaa   5700
cttagtttcg aataaacaca cataaacaaa caaat                              5735
```

<210> SEQ ID NO 6
<211> LENGTH: 2017
<212> TYPE: DNA
<213> ORGANISM: Artificial Sequence
<220> FEATURE:
<223> OTHER INFORMATION: Sequence put together from multiple organisms: Saccharomyces cerevisiae and Aspergillus shirousami

<400> SEQUENCE: 6

```
cactaagaac ttagtttcga ataaacacac ataaacaaac aaatctagaa tgagctttag     60

gtcattgctt gctctgtctg gcttagtttg tagtggtttg gcaagcgtta tctctaagag    120

agcaacgttg gatagttggt tatcaaatga agcaactgtc gctagaaccg caattctaaa    180

caatattgga gctgatggtg catgggttag cggtgcagac tctggtattg tggtagcctc    240

tccatccaca gataatccag attatttcta tacttggact agagattccg gaatagtttt    300

gaaaacgctg gtggatttgt ttcgtaatgg ggacaccgac ttgttatcaa ccattgagca    360

ttatatctcc agtcaagcaa ttattcaagg tgtctcaaat ccatccggcg acttgagcag    420

tggggggctg ggagaaccta agttcaatgt ggacgaaacg gcttacgctg gaagttgggg    480

cagaccacag agagacggac cagctctaag agcaacagcc atgattggat tcggtcagtg    540

gctactagac aatggataca ctagcgccgc gacagaaatt gtttggccac tagtcaggaa    600

cgacctaagt tacgttgctc aatattggaa ccaaaccggg tatgatctgt gggaagaggt    660

taatggatct agtttcttca ccatcgcagt tcagcataga gctttggttg aaggtagcgc    720

cttcgcaacg gcagttggga gttcatgctc ttggtgtgat tcacaggcac cacaaatctt    780

atgttatctt cagagctttt ggaccggttc ctatattcta gccaatttcg acagttccag    840

atccggtaag gatactaaca ctttacttgg ctcaatacat accttcgacc ctgaagctgg    900

gtgtgatgat tctacattcc aaccctgttc tccgagagca ctggccaatc ataaagaagt    960

ggttgattca tttagaagta tttatacact aaatgacgga ttaagtgaca gtgaagccgt   1020

agccgtcgga agatatccag aagattccta ttacaatggt aatccatggt tcttatgtac   1080

acttgctgct gctgaacaat tatatgacgc attgtatcaa tgggataagc aaggctcttt   1140

agaaattacc gacgtaagtt tagacttctt taaagcattg tatagcggtg cagccacggg   1200

tacatactca tcttcttcta gtacgtactc ttctattgtt tctgcggtga aaacttttgc   1260

tgacggcttt gtttctatcg tcgagaccca tgccgccagt aacggttctt tatccgaaca   1320

atttgacaag tccgatggcg atgagttaag cgcaagagat ctaacctggt cttatgccgc   1380

attacttaca gccaacaaca gacgtaattc cgttgtacca ccatcttggg gtgaaacaag   1440

tgcttcttca gttccgggca cctgcgcggc cacaagtgca tcaggaactt attcatcagt   1500

gactgtaaca tcttggccta gtattgtcgc aaccggtggt acaactacca ctgcaactac   1560

gacgggttct ggaggagtca cttccacaag caagactacg actactgcaa gtaaaaccag   1620

tactactacc tcctccacta gctgtacgac acccaccgcc gtagccgtca ctttcgattt   1680

gactgctaca accacctacg gcgagaatat ctacttggtg ggatcaatct cacaactagg   1740

tgactgggag acttccgacg ggatcgcttt gtcagcagat aaatacacat catctaaccc   1800

accatggtat gtgacggtca ctttacctgc cggggagtct ttcgaataca agtttataag   1860

ggtagaatcc gatgacagtg tggaatggga atctgatcct aatagagagt acacagtgcc   1920

acaagcttgt ggggaatcta cagccacagt taccgataca tggaggtagt taattaaaca   1980

ggcccctttt cctttgtcga tatcatgtaa ttagtta                            2017
```

<210> SEQ ID NO 7
<211> LENGTH: 2014
<212> TYPE: DNA
<213> ORGANISM: Artificial Sequence
<220> FEATURE:
<223> OTHER INFORMATION: Sequence put together from multiple organisms: Saccharomyces cerevisiae and Aspergillus shirousami

<400> SEQUENCE: 7

```
cactaagaac ttagtttcga ataaacacac ataaacaaac aaatctagaa tgttcaagtc     60

tgttgtttac tctattttgg ctgcctcttt ggctaacgct agtgttatct ctaagagagc    120

aacgttggat agttggttat caaatgaagc aactgtcgct agaaccgcaa ttctaaacaa    180

tattggagct gatggtgcat gggttagcgg tgcagactct ggtattgtgg tagcctctcc    240

atccacagat aatccagatt atttctatac ttggactaga gattccggaa tagttttgaa    300

aacgctggtg gatttgtttc gtaatgggga caccgacttg ttatcaacca ttgagcatta    360

tatctccagt caagcaatta ttcaaggtgt ctcaaatcca tccggcgact tgagcagtgg    420

ggggctggga gaacctaagt tcaatgtgga cgaaacggct tacgctggaa gttggggcag    480

accacagaga gacggaccag ctctaagagc aacagccatg attggattcg gtcagtggct    540

actagacaat ggatacacta gcgccgcgac agaaattgtt tggccactag tcaggaacga    600

cctaagttac gttgctcaat attggaacca aaccgggtat gatctgtggg aagaggttaa    660

tggatctagt ttcttcacca tcgcagttca gcatagagct ttggttgaag gtagcgcctt    720

cgcaacggca gttgggagtt catgctcttg gtgtgattca caggcaccac aaatcttatg    780

ttatcttcag agcttttgga ccggttccta tattctagcc aatttcgaca gttccagatc    840

cggtaaggat actaacactt tacttggctc aatacatacc ttcgaccctg aagctgggtg    900

tgatgattct acattccaac cctgttctcc gagagcactg gccaatcata aagaagtggt    960

tgattcattt agaagtattt atacactaaa tgacggatta agtgacagtg aagccgtagc   1020

cgtcggaaga tatccagaag attcctatta caatggtaat ccatggttct tatgtacact   1080

tgctgctgct gaacaattat atgacgcatt gtatcaatgg gataagcaag gctctttaga   1140

aattaccgac gtaagtttag acttctttaa agcattgtat agcggtgcag ccacgggtac   1200

atactcatct tcttctagta cgtactcttc tattgtttct gcggtgaaaa cttttgctga   1260

cggctttgtt tctatcgtcg agacccatgc cgccagtaac ggttctttat ccgaacaatt   1320

tgacaagtcc gatggcgatg agttaagcgc aagagatcta acctggtctt atgccgcatt   1380

acttacagcc aacaacagac gtaattccgt tgtaccacca tcttggggtg aaacaagtgc   1440

ttcttcagtt ccgggcacct gcgcggccac aagtgcatca ggaacttatt catcagtgac   1500

tgtaacatct tggcctagta ttgtcgcaac cggtggtaca actaccactg caactacgac   1560

gggttctgga ggagtcactt ccacaagcaa gactacgact actgcaagta aaaccagtac   1620

tactacctcc tccactagct gtacgacacc caccgccgta gccgtcactt tcgatttgac   1680

tgctacaacc acctacggcg agaatatcta cttggtggga tcaatctcac aactaggtga   1740

ctgggagact tccgacggga tcgctttgtc agcagataaa tacacatcat ctaacccacc   1800

atggtatgtg acggtcactt tacctgccgg ggagtctttc gaatacaagt ttataagggt   1860

agaatccgat gacagtgtgg aatgggaatc tgatcctaat agagagtaca cagtgccaca   1920

agcttgtggg gaatctacag ccacagttac cgatacatgg aggtagttaa ttaaacaggc   1980

ccctttttcct ttgtcgatat catgtaatta gtta                              2014
```

<210> SEQ ID NO 8
<211> LENGTH: 2020
<212> TYPE: DNA
<213> ORGANISM: Artificial Sequence
<220> FEATURE:
<223> OTHER INFORMATION: Sequence put together from multiple organisms: Saccharomyces cerevisiae and Aspergillus shirousami

<400> SEQUENCE: 8

```
cactaagaac ttagtttcga ataaacacac ataaacaaac aaatctagaa tgaagttcat     60

ttccactttc ttgaccttca ttttggctgc tgtctctgtc accgctagtg ttatctctaa    120

gagagcaacg ttggatagtt ggttatcaaa tgaagcaact gtcgctagaa ccgcaattct    180

aaacaatatt ggagctgatg gtgcatgggt tagcggtgca gactctggta ttgtggtagc    240

ctctccatcc acagataatc cagattattt ctatacttgg actagagatt ccggaatagt    300

tttgaaaacg ctggtggatt tgtttcgtaa tggggacacc gacttgttat caaccattga    360

gcattatatc tccagtcaag caattattca aggtgtctca aatccatccg gcgacttgag    420

cagtgggggg ctgggagaac ctaagttcaa tgtggacgaa acggcttacg ctggaagttg    480

ggcagacca cagagagacg gaccagctct aagagcaaca gccatgattg gattcggtca     540

gtggctacta gacaatggat acactagcgc cgcgacagaa attgtttggc cactagtcag    600

gaacgaccta agttacgttg ctcaatattg gaaccaaacc gggtatgatc tgtgggaaga    660

ggttaatgga tctagtttct tcaccatcgc agttcagcat agagctttgg ttgaaggtag    720

cgccttcgca acggcagttg ggagttcatg ctcttggtgt gattcacagg caccacaaat    780

cttatgttat cttcagagct tttggaccgg ttcctatatt ctagccaatt tcgacagttc    840

cagatccggt aaggatacta acactttact tggctcaata cataccttcg accctgaagc    900

tgggtgtgat gattctacat tccaaccctg ttctccgaga gcactggcca atcataaaga    960

agtggttgat tcatttagaa gtatttatac actaaatgac ggattaagtg acagtgaagc   1020

cgtagccgtc ggaagatatc cagaagattc ctattacaat ggtaatccat ggttcttatg   1080

tacacttgct gctgctgaac aattatatga cgcattgtat caatgggata agcaaggctc   1140

tttagaaatt accgacgtaa gtttagactt ctttaaagca ttgtatagcg gtgcagccac   1200

gggtacatac tcatcttctt ctagtacgta ctcttctatt gtttctgcgg tgaaaacttt   1260

tgctgacggc tttgtttcta tcgtcgagac ccatgccgcc agtaacggtt ctttatccga   1320

acaatttgac aagtccgatg gcgatgagtt aagcgcaaga gatctaacct ggtcttatgc   1380

cgcattactt acagccaaca acagacgtaa ttccgttgta ccaccatctt ggggtgaaac   1440

aagtgcttct tcagttccgg gcacctgcgc ggccacaagt gcatcaggaa cttattcatc   1500

agtgactgta acatcttggc ctagtattgt cgcaaccggt ggtacaacta ccactgcaac   1560

tacgacgggt tctggaggag tcacttccac aagcaagact acgactactg caagtaaaac   1620

cagtactact acctcctcca ctagctgtac gacacccacc gccgtagccg tcactttcga   1680

tttgactgct acaaccacct acggcgagaa tatctacttg gtgggatcaa tctcacaact   1740

aggtgactgg gagacttccg acgggatcgc tttgtcagca gataaataca catcatctaa   1800

cccaccatgg tatgtgacgg tcactttacc tgccggggag tctttcgaat acaagtttat   1860

aagggtagaa tccgatgaca gtgtggaatg ggaatctgat cctaatagag agtacacagt   1920

gccacaagct tgtggggaat ctacagccac agttaccgat acatggaggt agttaattaa   1980

acaggcccct tttcctttgt cgatatcatg taattagtta                        2020
```

<210> SEQ ID NO 9
<211> LENGTH: 2008
<212> TYPE: DNA
<213> ORGANISM: Artificial Sequence
<220> FEATURE:
<223> OTHER INFORMATION: Sequence put together from multiple organisms: Saccharomyces cerevisiae and Aspergillus terreus

<400> SEQUENCE: 9
cactaagaac ttagtttcga ataaacacac ataaacaaac aaatctagaa tgacaagaat 60
cttaacacta gctttgcacg gtttggctct agttcaaagt gtggttggcg ccccccaatt 120
agcacccaga gctacgacta gcttagacgc atggttagcg tccgaaacaa cagttgcttt 180
agatggaata ctagacaatg ttggatcaag cggagcctat gccaagtctg caaaaagcgg 240
tattgtgata gcgtcccctt ctactagtga cccagattat tattatacct ggaccagaga 300
tgctgcgttg accgtaaaag ccttgatcga tttgtttaga aacggagaaa catccttaca 360
aacagtaatt atggaataca tatctagcca agcatattta caaacagttt ctaatccatc 420
cggatcgtta agtaccggtg gtttggctga accaaaatac tacgtagatg aaactgcgta 480
cactggaagc tggggaaggc cacaaagaga tggccctgcc ctaagagcca ctgctatgat 540
cgattttgga aattggctga tcgataatgg ttactctact tacgccagtt ccattgtctg 600
gcctattgtt agaaacgatc tttcttatgt tgcgcagtac tggaatcaaa ccggttacga 660
tctttgggag gaggtaaatg ggagttcatt tttcactata gctgttcagc atagagcttt 720
ggtggaaggt agtacattcg catctaaagt tggtgcttca tgctcctggt gcgattcaca 780
agctcctcaa gtgctttgct tcctacaaag gttttggact ggttcttaca taatggcaaa 840
ctttggaggg ggtagatccg gtaaagatgc taatacagtt ctggggagta ttcatacctt 900
cgaccctaat gcgggttgtg acgacacgac tttccagcca tgctcaccac gtgcgttggc 960
aaaccataaa gtctatactg actcttttag atctatctac agtataaatt ctggcattag 1020
ctctggtaag gctgtggcag ttggaagata ccccgaagat tcttactata acggtaaccc 1080
gtggtttctt accacattgg ctgctgcaga acaactttat gatgccatct atcaatggca 1140
aaaaatcgga tctatcacca ttacagacgt atctttggct tttttcaaag acctttattc 1200
ttcagccgct gtgggtactt acgcctccag ttcctcagca ttcactagta tagtttctgc 1260
ggtaaaaacc tatgctgatg gttatatgtc tatagtccag acacatgcta tgacaaacgg 1320
atcattaagt gagcagtttg gtaaatctga cggtttttct ttgtctgcaa gagatttaac 1380
ctggtcttat gctgctctgt tgactgcaaa tcttaggagg aactccgtcg ttccaccctc 1440
ttggggtgaa actactgcaa catcagtccc cagtgtgtgt tcagccacta gtgctacagg 1500
gacatatagt actgctacta acactgcttg gccgtctaca ttgactagcg gtacaggagc 1560
cacaaccacg acatcaaaag ctacgtcttc atcaactacc actacatctt ctgcgtctag 1620
tacgacagtt gagtgtgtag ttccaacagc tgtggcggtc acttttgatg aggtcgcaac 1680
cactacatac ggtgaaaatg tttacgtcgt cggttcaata tcacagttgg gttcttggga 1740
cacgtctaaa gcagtggcat tatctgcatc caaatatacc tcctccaata acctgtggta 1800
tgtgactgtg acattgccag caggaacaac atttcaatac aaatttatca gagtgagttc 1860
ttctggtagt gtcacctggg agtcagatcc gaaccgttct tacacagtac catcagcctg 1920
tggcaccagc acggctgtag ttaatacaac ttggagatag ttaattaaac aggccccttt 1980
tcctttgtcg atatcatgta attagtta 2008

<210> SEQ ID NO 10
<211> LENGTH: 1999
<212> TYPE: DNA
<213> ORGANISM: Artificial Sequence
<220> FEATURE:
<223> OTHER INFORMATION: Sequence put together from multiple organisms: Saccharomyces cerevisiae and Aspergillus terreus

<400> SEQUENCE: 10

```
cactaagaac ttagtttcga ataaacacac ataaacaaac aaatctagaa tgttcaagtc     60
tgttgtttac tctattttgg ctgcctcttt ggctaacgct gccccccaat tagcacccag    120
agctacgact agcttagacg catggttagc gtccgaaaca acagttgctt tagatggaat    180
actagacaat gttggatcaa gcggagccta tgccaagtct gcaaaaagcg gtattgtgat    240
agcgtcccct tctactagtg acccagatta ttattatacc tggaccagag atgctgcgtt    300
gaccgtaaaa gccttgatcg atttgtttag aaacggagaa acatccttac aaacagtaat    360
tatggaatac atatctagcc aagcatattt acaaacagtt tctaatccat ccggatcgtt    420
aagtaccggt ggtttggctg aaccaaaata ctacgtagat gaaactgcgt acactggaag    480
ctggggaagg ccacaaagag atggccctgc cctaagagcc actgctatga tcgattttgg    540
aaattggctg atcgataatg gttactctac ttacgccagt tccattgtct ggcctattgt    600
tagaaacgat ctttcttatg ttgcgcagta ctggaatcaa accggttacg atctttggga    660
ggaggtaaat gggagttcat ttttcactat agctgttcag catagagctt tggtggaagg    720
tagtacattc gcatctaaag ttggtgcttc atgctcctgg tgcgattcac aagctcctca    780
agtgctttgc ttcctacaaa ggttttggac tggttcttac ataatggcaa actttggagg    840
gggtagatcc ggtaaagatg ctaatacagt tctggggagt attcatacct tcgaccctaa    900
tgcgggttgt gacgacacga ctttccagcc atgctcacca cgtgcgttgg caaaccataa    960
agtctatact gactctttta gatctatcta cagtataaat tctggcatta gctctggtaa   1020
ggctgtggca gttggaagat accccgaaga ttcttactat aacggtaacc cgtggtttct   1080
taccacattg gctgctgcag aacaacttta tgatgccatc tatcaatggc aaaaaatcgg   1140
atctatcacc attacagacg tatctttggc tttttcaaa gacctttatt cttcagccgc   1200
tgtgggtact tacgcctcca gttcctcagc attcactagt atagtttctg cggtaaaaac   1260
ctatgctgat ggttatatgt ctatagtcca gacacatgct atgacaaacg gatcattaag   1320
tgagcagttt ggtaaatctg acggtttttc tttgtctgca agagatttaa cctggtctta   1380
tgctgctctg ttgactgcaa atcttaggag gaactccgtc gttccaccct cttggggtga   1440
aactactgca acatcagtcc ccagtgtgtg ttcagccact agtgctacag ggacatatag   1500
tactgctact aacactgctt ggccgtctac attgactagc ggtacaggag ccacaaccac   1560
gacatcaaaa gctacgtctt catcaactac cactacatct tctgcgtcta gtacgacagt   1620
tgagtgtgta gttccaacag ctgtggcggt cacttttgat gaggtcgcaa ccactacata   1680
cggtgaaaat gtttacgtcg tcggttcaat atcacagttg ggttcttggg acacgtctaa   1740
agcagtggca ttatctgcat ccaaatatac ctcctccaat aacctgtggt atgtgactgt   1800
gacattgcca gcaggaacaa catttcaata caaatttatc agagtgagtt cttctggtag   1860
tgtcacctgg gagtcagatc cgaaccgttc ttacacagta ccatcagcct gtggcaccag   1920
cacggctgta gttaatacaa cttggagata gttaattaaa caggcccctt ttcctttgtc   1980
gatatcatgt aattagtta                                                1999
```

```
<210> SEQ ID NO 11
<211> LENGTH: 2005
<212> TYPE: DNA
<213> ORGANISM: Artificial Sequence
<220> FEATURE:
<223> OTHER INFORMATION: Sequence put together from multiple organisms:
      Saccharomyces cerevisiae and Aspergillus terreus

<400> SEQUENCE: 11

cactaagaac ttagtttcga ataaacacac ataaacaaac aaatctagaa tgaagttcat     60

ttccactttc ttgaccttca ttttggctgc tgtctctgtc accgctgccc cccaattagc    120

acccagagct acgactagct tagacgcatg gttagcgtcc gaaacaacag ttgctttaga    180

tggaatacta gacaatgttg gatcaagcgg agcctatgcc aagtctgcaa aaagcggtat    240

tgtgatagcg tccccttcta ctagtgaccc agattattat tatacctgga ccagagatgc    300

tgcgttgacc gtaaaagcct tgatcgattt gtttagaaac ggagaaacat ccttacaaac    360

agtaattatg gaatacatat ctagccaagc atatttacaa acagtttcta atccatccgg    420

atcgttaagt accggtggtt tggctgaacc aaaatactac gtagatgaaa ctgcgtacac    480

tggaagctgg ggaaggccac aaagagatgg ccctgcccta agagccactg ctatgatcga    540

ttttggaaat tggctgatcg ataatggtta ctctacttac gccagttcca ttgtctggcc    600

tattgttaga aacgatcttt cttatgttgc gcagtactgg aatcaaaccg gttacgatct    660

ttgggaggag gtaaatggga gttcattttt cactatagct gttcagcata gagctttggt    720

ggaaggtagt acattcgcat ctaaagttgg tgcttcatgc tcctggtgcg attcacaagc    780

tcctcaagtg ctttgcttcc tacaaaggtt ttggactggt tcttacataa tggcaaactt    840

tggagggggt agatccggta aagatgctaa tacagttctg gggagtattc ataccttcga    900

ccctaatgcg ggttgtgacg acacgacttt ccagccatgc tcaccacgtg cgttggcaaa    960

ccataaagtc tatactgact cttttagatc tatctacagt ataaattctg gcattagctc   1020

tggtaaggct gtggcagttg gaagataccc cgaagattct tactataacg gtaacccgtg   1080

gtttcttacc acattggctg ctgcagaaca actttatgat gccatctatc aatggcaaaa   1140

aatcggatct atcaccatta cagacgtatc tttggctttt ttcaaagacc tttattcttc   1200

agccgctgtg ggtacttacg cctccagttc ctcagcattc actagtatag tttctgcggt   1260

aaaaacctat gctgatggtt atatgtctat agtccagaca catgctatga caaacggatc   1320

attaagtgag cagtttggta aatctgacgg tttttctttg tctgcaagag atttaacctg   1380

gtcttatgct gctctgttga ctgcaaatct taggaggaac tccgtcgttc caccctcttg   1440

ggtgaaaact actgcaacat cagtccccag tgtgtgttca gccactagtg ctacagggac   1500

atatagtact gctactaaca ctgcttggcc gtctacattg actagcggta caggagccac   1560

aaccacgaca tcaaaagcta cgtcttcatc aactaccact acatcttctg cgtctagtac   1620

gacagttgag tgtgtagttc caacagctgt ggcggtcact tttgatgagg tcgcaaccac   1680

tacatacggt gaaaatgttt acgtcgtcgg ttcaatatca cagttgggtt cttgggacac   1740

gtctaaagca gtggcattat ctgcatccaa atatacctcc tccaataacc tgtggtatgt   1800

gactgtgaca ttgccagcag gaacaacatt tcaatacaaa tttatcagag tgagttcttc   1860

tggtagtgtc acctgggagt cagatccgaa ccgttcttac acagtaccat cagcctgtgg   1920

caccagcacg gctgtagtta atacaacttg gagatagtta attaaacagg ccccttttcc   1980

tttgtcgata tcatgtaatt agtta                                         2005
```

```
<210> SEQ ID NO 12
<211> LENGTH: 5745
<212> TYPE: DNA
<213> ORGANISM: Artificial Sequence
<220> FEATURE:
<223> OTHER INFORMATION: Sequence put together from multiple organisms:
      Saccharomyces cerevisiae and Aspergillus nidulans

<400> SEQUENCE: 12

tcgagatctc ccgagtttat cattatcaat actgccattt caaagaatac gtaaataatt     60

aatagtagtg attttcctaa ctttatttag tcaaaaaatt ggccttttaa ttctgctgta    120

acccgtacat gcccaaaata gggggcgggt tacacagaat atataacatc ataggtgtct    180

gggtgaacag tttattcctg gcatccacta aatataatgg agcccgcttt ttttaagctg    240

gcatccagaa aaaaaaagaa tcccagcacc aaaatattgt tttcttcacc aaccatcagt    300

tcataggtcc attctcttag cgcaactaca cagaacaggg gcacaaacag gcaaaaaacg    360

ggcacaacct caatggagtg atgcaacctg cttggagtaa atgatgacac aaggcaattg    420

acctacgcat gtatctatct cattttctta caccttctat taccttctgc tctctctgat    480

ttggaaaaag ctgaaaaaaa aggttgaaac cagttccctg aaattattcc cctatttgac    540

taataagtat ataaagacgg taggtattga ttgtaattct gtaaatctat ttcttaaact    600

tcttaaattc tacttttata gttagtcttt tttttagttt taaaacacta agaacttagt    660

ttcgaataaa cacacataaa caaacaaatc tagattaatt aaacaggccc cttttccttt    720

gtcgatatca tgtaattagt tatgtcacgc ttacattcac gccctcctcc cacatccgct    780

ctaaccgaaa aggaaggagt tagacaacct gaagtctagg tccctattta ttttttttata    840

gttatgttag tattaagaac gttatttata tttcaaattt ttcttttttt tctgtacaaa    900

cgcgtgtacg catgtaacgg gcagacgcgg ccgccaccgc ggtggagctc caattcgccc    960

tatagtgagt cgtattacaa ttcactggcc gtcgttttac aacgtcgtga ctgggaaaac   1020

cctggcgtta cccaacttaa tcgccttgca gcacatcccc ccttcgccag ctggcgtaat   1080

agcgaagagg cccgcaccga tcgcccttcc caacagttgc gcagcctgaa tggcgaatgg   1140

cgcgacgcgc cctgtagcgg cgcattaagc gcggcgggtg tggtggttac gcgcagcgtg   1200

accgctacac ttgccagcgc cctagcgccc gctcctttcg ctttcttccc ttcctttctc   1260

gccacgttcg ccggctttcc ccgtcaagct ctaaatcggg ggctcccttt agggttccga   1320

tttagtgctt tacggcacct cgaccccaaa aaacttgatt agggtgatgg ttcacgtagt   1380

gggccatcgc cctgatagac ggtttttcgc cctttgacgt tggagtccac gttctttaat   1440

agtggactct tgttccaaac tggaacaaca ctcaacccta tctcggtcta ttcttttgat   1500

ttataaggga ttttgccgat ttcggcctat tggttaaaaa atgagctgat ttaacaaaaa   1560

tttaacgcga attttaacaa aatattaacg tttacaattt cctgatgcgg tattttctcc   1620

ttacgcatct gtgcggtatt tcacaccgca gggtaataac tgatataatt aaattgaagc   1680

tctaatttgt gagtttagta tacatgcatt tacttataat acagtttttt agttttgctg   1740

gccgcatctt ctcaaatatg cttcccagcc tgcttttctg taacgttcac cctctacctt   1800

agcatccctt ccctttgcaa atagtcctct tccaacaata ataatgtcag atcctgtaga   1860

gaccacatca tccacggttc tatactgttg acccaatgcg tctcccttgt catctaaacc   1920

cacaccgggt gtcataatca accaatcgta accttcatct cttccaccca tgtctctttg   1980

agcaataaag ccgataacaa aatctttgtc gctcttcgca atgtcaacag tacccttagt   2040
```

```
atattctcca gtagataggg agcccttgca tgacaattct gctaacatca aaaggcctct   2100

aggttccttt gttacttctt ctgccgcctg cttcaaaccg ctaacaatac ctgggcccac   2160

cacaccgtgt gcattcgtaa tgtctgccca ttctgctatt ctgtatacac ccgcagagta   2220

ctgcaatttg actgtattac caatgtcagc aaattttctg tcttcgaaga gtaaaaaatt   2280

gtacttggcg gataatgcct ttagcggctt aactgtgccc tccatggaaa aatcagtcaa   2340

gatatccaca tgtgttttta gtaaacaaat tttgggacct aatgcttcaa ctaactccag   2400

taattccttg gtggtacgaa catccaatga agcacacaag tttgtttgct tttcgtgcat   2460

gatattaaat agcttggcag caacaggact aggatgagta gcagcacgtt ccttatatgt   2520

agctttcgac atgatttatc ttcgtttcct gcaggttttt gttctgtgca gttgggttaa   2580

gaatactggg caatttcatg tttcttcaac actacatatg cgtatatata ccaatctaag   2640

tctgtgctcc ttccttcgtt cttccttctg ttcggagatt accgaatcaa aaaaatttca   2700

aagaaaccga aatcaaaaaa aagaataaaa aaaaaatgat gaattgaatt gaaaagcgtg   2760

gtgcactctc agtacaatct gctctgatgc cgcatagtta agccagcccc gacacccgcc   2820

aacacccgct gacgcgccct gacgggcttg tctgctcccg gcatccgctt acagacaagc   2880

tgtgaccgtc tccgggagct gcatgtgtca gaggttttca ccgtcatcac cgaaacgcgc   2940

gagacgaaag ggcctcgtga tacgcctatt tttataggtt aatgtcatga taataatggt   3000

ttcttaggac ggatcgcttg cctgtaactt acacgcgcct cgtatctttt aatgatggaa   3060

taatttggga atttactctg tgtttattta tttttatgtt ttgtatttgg attttagaaa   3120

gtaaataaag aaggtagaag agttacggaa tgaagaaaaa aaaataaaca aaggtttaaa   3180

aaatttcaac aaaaagcgta ctttacatat atatttatta gacaagaaaa gcagattaaa   3240

tagatataca ttcgattaac gataagtaaa atgtaaaatc acaggatttt cgtgtgtggt   3300

cttctacaca gacaagatga aacaattcgg cattaatacc tgagagcagg aagagcaaga   3360

taaaaggtag tatttgttgg cgatccccct agagtctttt acatcttcgg aaaacaaaaa   3420

ctattttttc tttaatttct ttttttactt tctattttta atttatatat ttatattaaa   3480

aaatttaaat tataattatt tttatagcac gtgatgaaaa ggacccaggt ggcacttttc   3540

ggggaaatgt gcgcggaacc cctatttgtt tatttttcta aatacattca aatatgtatc   3600

cgctcatgag acaataaccc tgataaatgc ttcaataata ttgaaaaagg aagagtatga   3660

gtattcaaca tttccgtgtc gcccttattc cctttttttgc ggcattttgc cttcctgttt   3720

ttgctcaccc agaaacgctg gtgaaagtaa aagatgctga agatcagttg ggtgcacgag   3780

tgggttacat cgaactggat ctcaacagcg gtaagatcct tgagagtttt cgccccgaag   3840

aacgttttcc aatgatgagc acttttaaag ttctgctatg tggcgcggta ttatcccgta   3900

ttgacgccgg gcaagagcaa ctcggtcgcc gcatacacta ttctcagaat gacttggttg   3960

agtactcacc agtcacagaa aagcatctta cggatggcat gacagtaaga gaattatgca   4020

gtgctgccat aaccatgagt gataacactg cggccaactt acttctgaca acgatcggag   4080

gaccgaagga gctaaccgct tttttcaca acatggggga tcatgtaact cgccttgatc   4140

gttgggaacc ggagctgaat gaagccatac caaacgacga gcgtgacacc acgatgcctg   4200

tagcaatggc aacaacgttg cgcaaactat taactggcga actacttact ctagcttccc   4260

ggcaacaatt aatagactgg atggaggcgg ataaagttgc aggaccactt ctgcgctcgg   4320

cccttccggc tggctggttt attgctgata aatctggagc cggtgagcgt gggtctcgcg   4380

gtatcattgc agcactgggg ccagatggta agccctcccg tatcgtagtt atctacacga   4440
```

```
cgggcagtca ggcaactatg gatgaacgaa atagacagat cgctgagata ggtgcctcac   4500

tgattaagca ttggtaactg tcagaccaag tttactcata tatactttag attgatttaa   4560

aacttcattt ttaatttaaa aggatctagg tgaagatcct ttttgataat ctcatgacca   4620

aaatccctta acgtgagttt tcgttccact gagcgtcaga ccccgtagaa aagatcaaag   4680

gatcttcttg agatcctttt tttctgcgcg taatctgctg cttgcaaaca aaaaaaccac   4740

cgctaccagc ggtggtttgt ttgccggatc aagagctacc aactcttttt ccgaaggtaa   4800

ctggcttcag cagagcgcag ataccaaata ctgtccttct agtgtagccg tagttaggcc   4860

accacttcaa gaactctgta gcaccgccta catacctcgc tctgctaatc ctgttaccag   4920

tggctgctgc cagtggcgat aagtcgtgtc ttaccgggtt ggactcaaga cgatagttac   4980

cggataaggc gcagcggtcg ggctgaacgg ggggttcgtg cacacagccc agcttggagc   5040

gaacgaccta caccgaactg agatacctac agcgtgagca ttgagaaagc gccacgcttc   5100

ccgaagggag aaaggcggac aggtatccgg taagcggcag ggtcggaaca ggagagcgca   5160

cgagggagct tccaggggg aacgcctggt atctttatag tcctgtcggg tttcgccacc   5220

tctgacttga gcgtcgattt ttgtgatgct cgtcaggggg gccgagccta tggaaaaacg   5280

ccagcaacgc ggccttttta cggttcctgg ccttttgctg gccttttgct cacatgttct   5340

ttcctgcgtt atcccctgat tctgtggata accgtattac cgcctttgag tgagctgata   5400

ccgctcgccg cagccgaacg accgagcgca gcgagtcagt gagcgaggaa gcggaagagc   5460

gcccaatacg caaaccgcct ctccccgcgc gttggccgat tcattaatgc agctggcacg   5520

acaggtttcc cgactggaaa gcgggcagtg agcgcaacgc aattaatgtg agttacctca   5580

ctcattaggc accccaggct ttacacttta tgcttccggc tcctatgttg tgtggaattg   5640

tgagcggata acaatttcac acaggaaaca gctatgacca tgattacgcc aagctcggaa   5700

ttaaccctca ctaaagggaa caaaagctgg gtaccgggcc ccccc                   5745
```

<210> SEQ ID NO 13
<211> LENGTH: 1932
<212> TYPE: DNA
<213> ORGANISM: Artificial Sequence
<220> FEATURE:
<223> OTHER INFORMATION: Sequence put together from multiple organisms: Saccharomyces cerevisiae and Rhizopus oryzae

<400> SEQUENCE: 13

```
cactaagaac ttagtttcga ataaacacac ataaacaaac aaatctagaa tgcagttatt     60

caatctacca ctgaaggtga gtttcttctt ggtcttgtct tatttctcat tattggtttc    120

tgccgcatct attccatcta gtgcatctgt acaattggac tcctacaatt acgatggttc    180

cacattttcc ggcaagattt atgtcaaaaa catcgcttac tctaaaaagg ttactgttgt    240

gtacgcagac ggttctgaca actggaacaa taacggcaac actattgctg catcattttc    300

aggcccaatc tctggatcaa attacgaata ctggacattc tcagcatcag tgaagggcat    360

aaaggagttc tacatcaaat acgaagtttc aggtaagaca tattacgaca ataacaactc    420

tgcaaactac caagtctcaa cttctaaacc tactacaact actgcagcta caaccacaac    480

tacagctcca tcaacttcta caacaacccg tccatctagt tcagagcctg ccaccttccc    540

tactggtaat tctaccatca gctcttggat caaaaagcag gaagatattt ccagattcgc    600

tatgcttaga aacatcaacc cacctggttc tgccacaggg tttatcgccg catcactctc    660

taccgctggt ccagattact actacgcgtg gacaagagat gccgctttga catctaacgt    720
```

```
tatcgtttac gaatacaaca ccacattgtc tgggaataag acaattctaa acgtacttaa    780

ggattacgtc acattcagtg ttaagacaca gtctacttca acagtttgta attgccttgg    840

tgaaccaaag ttcaatccag acggcagtgg ttacacaggt gcttggggta gacctcaaaa    900

tgatggtcct gcagaaagag cgactacatt tgttctgttt gccgacagct acttgactca    960

aactaaggat gcctcatacg tcactggtac attaaagcca gcaattttca aagatctcga   1020

ttacgttgtt aacgtctgga gtaacggatg tttcgattta tgggaggagg tgaacggagt   1080

tcatttctac acccttatgg ttatgagaaa agggctattg ttgggggctg atttcgcgaa   1140

gagaaacggt gactcaacta gagcctcaac ttactcttct actgcttcca caattgctaa   1200

caagatatca agtttctggg ttagctcaaa caactgggtg caagtatccc aatctgtcac   1260

aggaggtgta agtaaaaagg ggttagacgt tagcaccctg ttagctgcga atctaggatc   1320

agtcgatgat ggatttttca ctccaggttc tgaaaagata ttagctacag ctgtggcagt   1380

cgaagattcc tttgccagtc tatacccaat caacaaaaac cttccatcat acttggggaa   1440

cgctattgga agataccctg aagatacata caacggtaat ggtaactcac aaggcaatcc   1500

ttggtttctg gcggttaccg gctacgcaga gttgtactat agagcaatta aggaatggat   1560

ttctaatgga ggcgttacag tgtcctctat ctcattgcca tttttcaaaa agttcgatag   1620

ctctgcaaca tccggtaaaa agtacaccgt aggtacttct gacttcaaca atttagcaca   1680

aaacattgct cttgctgcag atcgtttcct atctactgta caactccatg caccaaacaa   1740

tggttcatta gcagaggaat ttgatagaac aacaggtttt tctaccggcg ctagagattt   1800

aacatggtcc cacgcctcat tgataacagc atcctatgcc aaagccggtg ctccagctgc   1860

ataattaatt aaacaggccc cttttccttt gtcgatatca tgtaattagt tatgtcacgc   1920

ttacattcac gc                                                       1932
```

```
<210> SEQ ID NO 14
<211> LENGTH: 1908
<212> TYPE: DNA
<213> ORGANISM: Artificial Sequence
<220> FEATURE:
<223> OTHER INFORMATION: Sequence put together from multiple organisms:
      Saccharomyces cerevisiae and Rhizopus oryzae

<400> SEQUENCE: 14
```

```
cactaagaac ttagtttcga ataaacacac ataaacaaac aaatctagaa tgttcaagtc     60

tgttgtttac tctattttgg ctgcctcttt ggctaacgct gcatctattc catctagtgc    120

atctgtacaa ttggactcct acaattacga tggttccaca ttttccggca agatttatgt    180

caaaaacatc gcttactcta aaaaggttac tgttgtgtac gcagacggtt ctgacaactg    240

gaacaataac ggcaacacta ttgctgcatc attttcaggc ccaatctctg gatcaaatta    300

cgaatactgg acattctcag catcagtgaa gggcataaag gagttctaca tcaaatacga    360

agtttcaggt aagacatatt acgacaataa caactctgca aactaccaag tctcaacttc    420

taaacctact acaactactg cagctacaac cacaactaca gctccatcaa cttctacaac    480

aacccgtcca tctagttcag agcctgccac cttccctact ggtaattcta ccatcagctc    540

ttggatcaaa aagcaggaag atatttccag attcgctatg cttagaaaca tcaacccacc    600

tggttctgcc acagggttta tcgccgcatc actctctacc gctggtccag attactacta    660

cgcgtggaca agagatgccg ctttgacatc taacgttatc gtttacgaat acaacaccac    720

attgtctggg aataagacaa ttctaaacgt acttaaggat tacgtcacat tcagtgttaa    780
```

```
gacacagtct acttcaacag tttgtaattg ccttggtgaa ccaaagttca atccagacgg    840

cagtggttac acaggtgctt ggggtagacc tcaaaatgat ggtcctgcag aaagagcgac    900

tacatttgtt ctgtttgccg acagctactt gactcaaact aaggatgcct catacgtcac    960

tggtacatta aagccagcaa ttttcaaaga tctcgattac gttgttaacg tctggagtaa   1020

cggatgtttc gatttatggg aggaggtgaa cggagttcat ttctacaccc ttatggttat   1080

gagaaaaggg ctattgttgg gggctgattt cgcgaagaga aacggtgact caactagagc   1140

ctcaacttac tcttctactg cttccacaat tgctaacaag atatcaagtt tctgggttag   1200

ctcaaacaac tgggtgcaag tatcccaatc tgtcacagga ggtgtaagta aaaaggggtt   1260

agacgttagc accctgttag ctgcgaatct aggatcagtc gatgatggat tttcactcc    1320

aggttctgaa aagatattag ctacagctgt ggcagtcgaa gattcctttg ccagtctata   1380

cccaatcaac aaaaaccttc catcatactt ggggaacgct attggaagat accctgaaga   1440

tacatacaac ggtaatggta actcacaagg caatccttgg tttctggcgg ttaccggcta   1500

cgcagagttg tactatagag caattaagga atggatttct aatggaggcg ttacagtgtc   1560

ctctatctca ttgccatttt tcaaaaagtt cgatagctct gcaacatccg gtaaaaagta   1620

caccgtaggt acttctgact tcaacaattt agcacaaaac attgctcttg ctgcagatcg   1680

tttcctatct actgtacaac tccatgcacc aaacaatggt tcattagcag aggaatttga   1740

tagaacaaca ggtttttcta ccggcgctag agatttaaca tggtcccacg cctcattgat   1800

aacagcatcc tatgccaaag ccggtgctcc agctgcataa ttaattaaac aggccccttt   1860

tcctttgtcg atatcatgta attagttatg tcacgcttac attcacgc                1908
```

```
<210> SEQ ID NO 15
<211> LENGTH: 1914
<212> TYPE: DNA
<213> ORGANISM: Artificial Sequence
<220> FEATURE:
<223> OTHER INFORMATION: Sequence put together from multiple organisms:
      Saccharomyces cerevisiae and Rhizopus oryzae

<400> SEQUENCE: 15
```

```
cactaagaac ttagtttcga ataaacacac ataaacaaac aaatctagaa tgaagttcat     60

ttccactttc ttgaccttca ttttggctgc tgtctctgtc accgctgcat ctattccatc    120

tagtgcatct gtacaattgg actcctacaa ttacgatggt tccacatttt ccggcaagat    180

ttatgtcaaa aacatcgctt actctaaaaa ggttactgtt gtgtacgcag acggttctga    240

caactggaac aataacggca acactattgc tgcatcattt tcaggcccaa tctctggatc    300

aaattacgaa tactggacat tctcagcatc agtgaagggc ataaaggagt tctacatcaa    360

atacgaagtt tcaggtaaga catattacga caataacaac tctgcaaact accaagtctc    420

aacttctaaa cctactacaa ctactgcagc tacaaccaca actacagctc catcaacttc    480

tacaacaacc cgtccatcta gttcagagcc tgccaccttc cctactggta attctaccat    540

cagctcttgg atcaaaaagc aggaagatat ttccagattc gctatgctta gaaacatcaa    600

cccacctggt tctgccacag ggtttatcgc cgcatcactc tctaccgctg gtccagatta    660

ctactacgcg tggacaagag atgccgcttt gacatctaac gttatcgttt acgaatacaa    720

caccacattg tctgggaata agacaattct aaacgtactt aaggattacg tcacattcag    780

tgttaagaca cagtctactt caacagtttg taattgcctt ggtgaaccaa agttcaatcc    840

agacggcagt ggttacacag gtgcttgggg tagacctcaa aatgatggtc ctgcagaaag    900
```

```
agcgactaca tttgttctgt ttgccgacag ctacttgact caaactaagg atgcctcata    960

cgtcactggt acattaaagc cagcaatttt caaagatctc gattacgttg ttaacgtctg   1020

gagtaacgga tgtttcgatt tatgggagga ggtgaacgga gttcatttct acacccttat   1080

ggttatgaga aaagggctat tgttgggggc tgatttcgcg aagagaaacg gtgactcaac   1140

tagagcctca acttactctt ctactgcttc cacaattgct aacaagatat caagtttctg   1200

ggttagctca aacaactggg tgcaagtatc ccaatctgtc acaggaggtg taagtaaaaa   1260

ggggttagac gttagcaccc tgttagctgc gaatctagga tcagtcgatg atggattttt   1320

cactccaggt tctgaaaaga tattagctac agctgtggca gtcgaagatt cctttgccag   1380

tctataccca atcaacaaaa accttccatc atacttgggg aacgctattg gaagataccc   1440

tgaagataca tacaacggta atggtaactc acaaggcaat ccttggtttc tggcggttac   1500

cggctacgca gagttgtact atagagcaat taaggaatgg atttctaatg gaggcgttac   1560

agtgtcctct atctcattgc catttttcaa aaagttcgat agctctgcaa catccggtaa   1620

aaagtacacc gtaggtactt ctgacttcaa caatttagca caaaacattg ctcttgctgc   1680

agatcgtttc ctatctactg tacaactcca tgcaccaaac aatggttcat tagcagagga   1740

atttgataga acaacaggtt tttctaccgg cgctagagat ttaacatggt cccacgcctc   1800

attgataaca gcatcctatg ccaaagccgg tgctccagct gcataattaa ttaaacaggc   1860

ccctttccct ttgtcgatat catgtaatta gttatgtcac gcttacattc acgc         1914
```

```
<210> SEQ ID NO 16
<211> LENGTH: 1920
<212> TYPE: DNA
<213> ORGANISM: Artificial Sequence
<220> FEATURE:
<223> OTHER INFORMATION: Sequence put together from multiple organisms:
      Saccharomyces cerevisiae and Rhizopus oryzae

<400> SEQUENCE: 16

cactaagaac ttagtttcga ataaacacac ataaacaaac aaatctagaa tgaagttcat     60

ttccactttc ttgaccttca ttttggctgc tgtctctgtc accgctgcaa agagatctat    120

tccatctagt gcatctgtac aattggactc ctacaattac gatggttcca cattttccgg    180

caagatttat gtcaaaaaca tcgcttactc taaaaaggtt actgttgtgt acgcagacgg    240

ttctgacaac tggaacaata acggcaacac tattgctgca tcattttcag gcccaatctc    300

tggatcaaat tacgaatact ggacattctc agcatcagtg aagggcataa aggagttcta    360

catcaaatac gaagtttcag gtaagacata ttacgacaat aacaactctg caaactacca    420

agtctcaact tctaaaccta ctacaactac tgcagctaca accacaacta cagctccatc    480

aacttctaca acaacccgtc catctagttc agagcctgcc accttcccta ctggtaattc    540

taccatcagc tcttggatca aaaagcagga agatatttcc agattcgcta tgcttagaaa    600

catcaaccca cctggttctg ccacagggtt tatcgccgca tcactctcta ccgctggtcc    660

agattactac tacgcgtgga caagagatgc cgctttgaca tctaacgtta tcgtttacga    720

atacaacacc acattgtctg ggaataagac aattctaaac gtacttaagg attacgtcac    780

attcagtgtt aagacacagt ctacttcaac agtttgtaat tgccttggtg aaccaaagtt    840

caatccagac ggcagtggtt acacaggtgc ttggggtaga cctcaaaatg atggtcctgc    900

agaaagagcg actacatttg ttctgtttgc cgacagctac ttgactcaaa ctaaggatgc    960

ctcatacgtc actggtacat taaagccagc aattttcaaa gatctcgatt acgttgttaa   1020
```

cgtctggagt aacggatgtt tcgatttatg ggaggaggtg aacggagttc atttctacac 1080
ccttatggtt atgagaaaag ggctattgtt gggggctgat ttcgcgaaga gaaacggtga 1140
ctcaactaga gcctcaactt actcttctac tgcttccaca attgctaaca agatatcaag 1200
tttctgggtt agctcaaaca actgggtgca agtatcccaa tctgtcacag gaggtgtaag 1260
taaaaagggg ttagacgtta gcaccctgtt agctgcgaat ctaggatcag tcgatgatgg 1320
atttttcact ccaggttctg aaaagatatt agctacagct gtggcagtcg aagattcctt 1380
tgccagtcta tacccaatca acaaaaacct tccatcatac ttggggaacg ctattggaag 1440
ataccctgaa gatacataca acggtaatgg taactcacaa ggcaatcctt ggtttctggc 1500
ggttaccggc tacgcagagt tgtactatag agcaattaag gaatggattt ctaatggagg 1560
cgttacagtg tcctctatct cattgccatt tttcaaaaag ttcgatagct ctgcaacatc 1620
cggtaaaaag tacaccgtag gtacttctga cttcaacaat ttagcacaaa acattgctct 1680
tgctgcagat cgtttcctat ctactgtaca actccatgca ccaaacaatg gttcattagc 1740
agaggaattt gatagaacaa caggtttttc taccggcgct agagatttaa catggtccca 1800
cgcctcattg ataacagcat cctatgccaa agccggtgct ccagctgcat aattaattaa 1860
acaggcccct tttcctttgt cgatatcatg taattagtta tgtcacgctt acattcacgc 1920

<210> SEQ ID NO 17
<211> LENGTH: 7542
<212> TYPE: DNA
<213> ORGANISM: Artificial Sequence
<220> FEATURE:
<223> OTHER INFORMATION: Sequence put together from multiple organisms: Saccharomyces cerevisiae and Rhizopus oryzae

<400> SEQUENCE: 17
tcgagatctc ccgagtttat cattatcaat actgccattt caaagaatac gtaaataatt 60
aatagtagtg attttcctaa ctttatttag tcaaaaaatt ggccttttaa ttctgctgta 120
acccgtacat gcccaaaata gggggcgggt tacacagaat atataacatc ataggtgtct 180
gggtgaacag tttattcctg gcatccacta aatataatgg agcccgcttt ttttaagctg 240
gcatccagaa aaaaaaagaa tcccagcacc aaaatattgt tttcttcacc aaccatcagt 300
tcataggtcc attctcttag cgcaactaca cagaacaggg gcacaaacag gcaaaaaacg 360
ggcacaacct caatggagtg atgcaacctg cttggagtaa atgatgacac aaggcaattg 420
acctacgcat gtatctatct cattttctta caccttctat taccttctgc tctctctgat 480
ttggaaaaag ctgaaaaaaa aggttgaaac cagttccctg aaattattcc cctatttgac 540
taataagtat ataaagacgg taggtattga ttgtaattct gtaaatctat ttcttaaact 600
tcttaaattc tacttttata gttagtcttt tttttagttt taaaacacta agaacttagt 660
ttcgaataaa cacacataaa caaacaaatc tagaatgaag ttcatttcca ctttcttgac 720
cttcattttg gctgctgtct ctgtcaccgc tgcatctatt ccatctagtg catctgtaca 780
attggactcc tacaattacg atggttccac attttccggc aagatttatg tcaaaaacat 840
cgcttactct aaaaaggtta ctgttgtgta cgcagacggt tctgacaact ggaacaataa 900
cggcaacact attgctgcat cattttcagg cccaatctct ggatcaaatt acgaatactg 960
gacattctca gcatcagtga agggcataaa ggagttctac atcaaatacg aagtttcagg 1020
taagacatat tacgacaata acaactctgc aaactaccaa gtctcaactt ctaaacctac 1080
tacaactact gcagctacaa ccacaactac agctccatca acttctacaa caacccgtcc 1140

```
atctagttca gagcctgcca ccttccctac tggtaattct accatcagct cttggatcaa   1200
aaagcaggaa gatatttcca gattcgctat gcttagaaac atcaacccac ctggttctgc   1260
cacagggttt atcgccgcat cactctctac cgctggtcca gattactact acgcgtggac   1320
aagagatgcc gctttgacat ctaacgttat cgtttacgaa tacaacacca cattgtctgg   1380
gaataagaca attctaaacg tacttaagga ttacgtcaca ttcagtgtta agacacagtc   1440
tacttcaaca gtttgtaatt gccttggtga accaaagttc aatccagacg gcagtggtta   1500
cacaggtgct tggggtagac ctcaaaatga tggtcctgca gaaagagcga ctacatttgt   1560
tctgtttgcc gacagctact tgactcaaac taaggatgcc tcatacgtca ctggtacatt   1620
aaagccagca attttcaaag atctcgatta cgttgttaac gtctggagta acggatgttt   1680
cgatttatgg gaggaggtga acggagttca tttctacacc cttatggtta tgagaaaagg   1740
gctattgttg gggctgatt tcgcgaagag aaacggtgac tcaactagag cctcaactta   1800
ctcttctact gcttccacaa ttgctaacaa gatatcaagt ttctgggtta gctcaaacaa   1860
ctgggtgcaa gtatcccaat ctgtcacagg aggtgtaagt aaaaaggggt tagacgttag   1920
caccctgtta gctgcgaatc taggatcagt cgatgatgga tttttcactc caggttctga   1980
aaagatatta gctacagctg tggcagtcga agattccttt gccagtctat acccaatcaa   2040
caaaaacctt ccatcatact tggggaacgc tattggaaga taccctgaag atacatacaa   2100
cggtaatggt aactcacaag gcaatccttg gtttctggcg gttaccggct acgcagagtt   2160
gtactataga gcaattaagg aatggatttc taatggaggc gttacagtgt cctctatctc   2220
attgccattt ttcaaaaagt tcgatagctc tgcaacatcc ggtaaaaagt acaccgtagg   2280
tacttctgac ttcaacaatt tagcacaaaa cattgctctt gctgcagatc gtttcctatc   2340
tactgtacaa ctccatgcac caaacaatgg ttcattagca gaggaatttg atagaacaac   2400
aggtttttct accggcgcta gagatttaac atggtcccac gcctcattga taacagcatc   2460
ctatgccaaa gccggtgctc cagctgcata attaattaaa caggcccctt ttcctttgtc   2520
gatatcatgt aattagttat gtcacgctta cattcacgcc ctcctcccac atccgctcta   2580
accgaaaagg aaggagttag acaacctgaa gtctaggtcc ctatttattt ttttatagtt   2640
atgttagtat taagaacgtt atttatattt caaatttttc ttttttttct gtacaaacgc   2700
gtgtacgcat gtaacgggca gacgcggccg ccaccgcggt ggagctccaa ttcgccctat   2760
agtgagtcgt attacaattc actggccgtc gttttacaac gtcgtgactg ggaaaaccct   2820
ggcgttaccc aacttaatcg ccttgcagca catccccct tcgccagctg gcgtaatagc   2880
gaagaggccc gcaccgatcg cccttcccaa cagttgcgca gcctgaatgg cgaatggcgc   2940
gacgcgccct gtagcggcgc attaagcgcg gcgggtgtgg tggttacgcg cagcgtgacc   3000
gctacacttg ccagcgccct agcgcccgct cctttcgctt tcttcccttc ctttctcgcc   3060
acgttcgccg gctttccccg tcaagctcta aatcgggggc tccctttagg gttccgattt   3120
agtgctttac ggcacctcga ccccaaaaaa cttgattagg gtgatggttc acgtagtggg   3180
ccatcgccct gatagacggt ttttcgccct ttgacgttgg agtccacgtt ctttaatagt   3240
ggactcttgt tccaaactgg aacaacactc aaccctatct cggtctattc ttttgattta   3300
taagggattt tgccgatttc ggcctattgg ttaaaaaatg agctgattta acaaaaattt   3360
aacgcgaatt ttaacaaaat attaacgttt acaatttcct gatgcggtat tttctcctta   3420
cgcatctgtg cggtatttca caccgcaggg taataactga tataattaaa ttgaagctct   3480
```

```
aatttgtgag tttagtatac atgcatttac ttataataca gtttttttagt tttgctggcc   3540
gcatcttctc aaatatgctt cccagcctgc ttttctgtaa cgttcaccct ctaccttagc   3600
atcccttccc tttgcaaata gtcctcttcc aacaataata atgtcagatc ctgtagagac   3660
cacatcatcc acggttctat actgttgacc caatgcgtct cccttgtcat ctaaacccac   3720
accgggtgtc ataatcaacc aatcgtaacc ttcatctctt ccacccatgt ctctttgagc   3780
aataaagccg ataacaaaat ctttgtcgct cttcgcaatg tcaacagtac ccttagtata   3840
ttctccagta gatagggagc ccttgcatga caattctgct aacatcaaaa ggcctctagg   3900
ttcctttgtt acttcttctg ccgcctgctt caaaccgcta acaatacctg ggcccaccac   3960
accgtgtgca ttcgtaatgt ctgcccattc tgctattctg tatacacccg cagagtactg   4020
caatttgact gtattaccaa tgtcagcaaa ttttctgtct tcgaagagta aaaaattgta   4080
cttggcggat aatgccttta gcggcttaac tgtgccctcc atggaaaaat cagtcaagat   4140
atccacatgt gtttttagta aacaaatttt gggacctaat gcttcaacta actccagtaa   4200
ttccttggtg gtacgaacat ccaatgaagc acacaagttt gtttgctttt cgtgcatgat   4260
attaaatagc ttggcagcaa caggactagg atgagtagca gcacgttcct tatatgtagc   4320
tttcgacatg atttatcttc gtttcctgca ggtttttgtt ctgtgcagtt gggttaagaa   4380
tactgggcaa tttcatgttt cttcaacact acatatgcgt atatatacca atctaagtct   4440
gtgctccttc cttcgttctt ccttctgttc ggagattacc gaatcaaaaa aatttcaaag   4500
aaaccgaaat caaaaaaaag aataaaaaaa aaatgatgaa ttgaattgaa aagcgtggtg   4560
cactctcagt acaatctgct ctgatgccgc atagttaagc cagccccgac acccgccaac   4620
acccgctgac gcgccctgac gggcttgtct gctcccggca tccgcttaca gacaagctgt   4680
gaccgtctcc gggagctgca tgtgtcagag gttttcaccg tcatcaccga aacgcgcgag   4740
acgaaagggc ctcgtgatac gcctattttt ataggttaat gtcatgataa taatggtttc   4800
ttaggacgga tcgcttgcct gtaacttaca cgcgcctcgt atcttttaat gatggaataa   4860
tttgggaatt tactctgtgt ttatttattt ttatgttttg tatttggatt ttagaaagta   4920
aataaagaag gtagaagagt tacggaatga agaaaaaaaa ataaacaaag gtttaaaaaa   4980
tttcaacaaa aagcgtactt tacatatata tttattagac aagaaaagca gattaaatag   5040
atatacattc gattaacgat aagtaaaatg taaaatcaca ggattttcgt gtgtggtctt   5100
ctacacagac aagatgaaac aattcggcat taatacctga gagcaggaag agcaagataa   5160
aaggtagtat ttgttggcga tccccctaga gtcttttaca tcttcggaaa acaaaaacta   5220
ttttttcttt aatttctttt tttactttct atttttaatt tatatattta tattaaaaaa   5280
tttaaattat aattattttt atagcacgtg atgaaaagga cccaggtggc acttttcggg   5340
gaaatgtgcg cggaacccct atttgtttat ttttctaaat acattcaaat atgtatccgc   5400
tcatgagaca ataaccctga taaatgcttc aataatattg aaaaaggaag agtatgagta   5460
ttcaacattt ccgtgtcgcc cttattccct tttttgcggc attttgcctt cctgtttttg   5520
ctcacccaga aacgctggtg aaagtaaaag atgctgaaga tcagttgggt gcacgagtgg   5580
gttacatcga actggatctc aacagcggta agatccttga gagttttcgc cccgaagaac   5640
gttttccaat gatgagcact tttaaagttc tgctatgtgg cgcggtatta tcccgtattg   5700
acgccgggca agagcaactc ggtcgccgca tacactattc tcagaatgac ttggttgagt   5760
actcaccagt cacagaaaag catcttacgg atggcatgac agtaagagaa ttatgcagtg   5820
ctgccataac catgagtgat aacactgcgg ccaacttact tctgacaacg atcggaggac   5880
```

```
cgaaggagct aaccgctttt tttcacaaca tgggggatca tgtaactcgc cttgatcgtt   5940

gggaaccgga gctgaatgaa gccataccaa acgacgagcg tgacaccacg atgcctgtag   6000

caatggcaac aacgttgcgc aaactattaa ctggcgaact acttactcta gcttcccggc   6060

aacaattaat agactggatg gaggcggata aagttgcagg accacttctg cgctcggccc   6120

ttccggctgg ctggtttatt gctgataaat ctggagccgg tgagcgtggg tctcgcggta   6180

tcattgcagc actggggcca gatggtaagc cctcccgtat cgtagttatc tacacgacgg   6240

gcagtcaggc aactatggat gaacgaaata gacagatcgc tgagataggt gcctcactga   6300

ttaagcattg gtaactgtca gaccaagttt actcatatat actttagatt gatttaaaac   6360

ttcattttta atttaaaagg atctaggtga agatcctttt tgataatctc atgaccaaaa   6420

tcccttaacg tgagttttcg ttccactgag cgtcagaccc cgtagaaaag atcaaaggat   6480

cttcttgaga tccttttttt ctgcgcgtaa tctgctgctt gcaaacaaaa aaaccaccgc   6540

taccagcggt ggtttgtttg ccggatcaag agctaccaac tctttttccg aaggtaactg   6600

gcttcagcag agcgcagata ccaaatactg tccttctagt gtagccgtag ttaggccacc   6660

acttcaagaa ctctgtagca ccgcctacat acctcgctct gctaatcctg ttaccagtgg   6720

ctgctgccag tggcgataag tcgtgtctta ccgggttgga ctcaagacga tagttaccgg   6780

ataaggcgca gcggtcgggc tgaacggggg gttcgtgcac acagcccagc ttggagcgaa   6840

cgacctacac cgaactgaga tacctacagc gtgagcattg agaaagcgcc acgcttcccg   6900

aagggagaaa ggcggacagg tatccggtaa gcggcagggt cggaacagga gagcgcacga   6960

gggagcttcc agggggaaac gcctggtatc tttatagtcc tgtcgggttt cgccacctct   7020

gacttgagcg tcgatttttg tgatgctcgt caggggggcc gagcctatgg aaaaacgcca   7080

gcaacgcggc ctttttacgg ttcctggcct tttgctggcc ttttgctcac atgttctttc   7140

ctgcgttatc ccctgattct gtggataacc gtattaccgc ctttgagtga gctgataccg   7200

ctcgccgcag ccgaacgacc gagcgcagcg agtcagtgag cgaggaagcg gaagagcgcc   7260

caatacgcaa accgcctctc cccgcgcgtt ggccgattca ttaatgcagc tggcacgaca   7320

ggtttcccga ctggaaagcg ggcagtgagc gcaacgcaat taatgtgagt tacctcactc   7380

attaggcacc ccaggcttta cactttatgc ttccggctcc tatgttgtgt ggaattgtga   7440

gcggataaca atttcacaca ggaaacagct atgaccatga ttacgccaag ctcggaatta   7500

accctcacta aagggaacaa aagctgggta ccgggccccc cc                      7542
```

```
<210> SEQ ID NO 18
<211> LENGTH: 7560
<212> TYPE: DNA
<213> ORGANISM: Artificial Sequence
<220> FEATURE:
<223> OTHER INFORMATION: Sequence put together from multiple organisms:
      Saccharomyces cerevisiae and Rhizopus oryzae

<400> SEQUENCE: 18

atctcccgag tttatcatta tcaatactgc catttcaaag aatacgtaaa taattaatag     60

tagtgatttt cctaacttta tttagtcaaa aaattggcct tttaattctg ctgtaacccg    120

tacatgccca aaataggggg cgggttacac agaatatata acatcatagg tgtctgggtg    180

aacagtttat tcctggcatc cactaaatat aatggagccc gcttttttta agctggcatc    240

cagaaaaaaa aagaatccca gcaccaaaat attgttttct tcaccaacca tcagttcata    300

ggtccattct cttagcgcaa ctacacagaa caggggcaca aacaggcaaa aaacgggcac    360
```

-continued

```
aacctcaatg gagtgatgca acctgcttgg agtaaatgat gacacaaggc aattgaccta    420
cgcatgtatc tatctcattt tcttacacct tctattacct tctgctctct ctgatttgga    480
aaaagctgaa aaaaaaggtt gaaaccagtt ccctgaaatt attcccctat ttgactaata    540
agtatataaa gacggtaggt attgattgta attctgtaaa tctatttctt aaacttctta    600
aattctactt ttatagttag tctttttttt agttttaaaa cactaagaac ttagtttcga    660
ataaacacac ataaacaaac aaatctagaa tgcagttatt caatctacca ctgaaggtga    720
gtttcttctt ggtcttgtct tatttctcat tattggtttc tgccgcatct attccatcta    780
gtgcatctgt acaattggac tcctacaatt acgatggttc cacattttcc ggcaagattt    840
atgtcaaaaa catcgcttac tctaaaaagg ttactgttgt gtacgcagac ggttctgaca    900
actggaacaa taacggcaac actattgctg catcattttc aggcccaatc tctggatcaa    960
attacgaata ctggacattc tcagcatcag tgaagggcat aaaggagttc tacatcaaat   1020
acgaagtttc aggtaagaca tattacgaca ataacaactc tgcaaactac caagtctcaa   1080
cttctaaacc tactacaact actgcagcta caaccacaac tacagctcca tcaacttcta   1140
caacaacccg tccatctagt tcagagcctg ccaccttccc tactggtaat tctaccatca   1200
gctcttggat caaaaagcag gaagatattt ccagattcgc tatgcttaga aacatcaacc   1260
cacctggttc tgccacaggg tttatcgccg catcactctc taccgctggt ccagattact   1320
actacgcgtg gacaagagat gccgctttga catctaacgt tatcgtttac gaatacaaca   1380
ccacattgtc tgggaataag acaattctaa acgtacttaa ggattacgtc acattcagtg   1440
ttaagacaca gtctacttca acagtttgta attgccttgg tgaaccaaag ttcaatccag   1500
acggcagtgg ttacacaggt gcttggggta gacctcaaaa tgatggtcct gcagaaagag   1560
cgactacatt tgttctgttt gccgacagct acttgactca aactaaggat gcctcatacg   1620
tcactggtac attaaagcca gcaattttca aagatctcga ttacgttgtt aacgtctgga   1680
gtaacggatg tttcgattta tgggaggagg tgaacggagt tcatttctac acccttatgg   1740
ttatgagaaa agggctattg ttgggggctg atttcgcgaa gagaaacggt gactcaacta   1800
gagcctcaac ttactcttct actgcttcca caattgctaa caagatatca agtttctggg   1860
ttagctcaaa caactgggtg caagtatccc aatctgtcac aggaggtgta agtaaaaagg   1920
ggttagacgt tagcaccctg ttagctgcga atctaggatc agtcgatgat ggatttttca   1980
ctccaggttc tgaaaagata ttagctacag ctgtggcagt cgaagattcc tttgccagtc   2040
tatacccaat caacaaaaac cttccatcat acttggggaa cgctattgga agatacccctg   2100
aagatacata caacggtaat ggtaactcac aaggcaatcc ttggtttctg gcggttaccg   2160
gctacgcaga gttgtactat agagcaatta aggaatggat ttctaatgga ggcgttacag   2220
tgtcctctat ctcattgcca tttttcaaaa agttcgatag ctctgcaaca tccggtaaaa   2280
agtacaccgt aggtacttct gacttcaaca atttagcaca aaacattgct cttgctgcag   2340
atcgtttcct atctactgta caactccatg caccaaacaa tggttcatta gcagaggaat   2400
ttgatagaac aacaggtttt tctaccggcg ctagagattt aacatggtcc cacgcctcat   2460
tgataacagc atcctatgcc aaagccggtg ctccagctgc ataattaatt aaacaggccc   2520
cttttccttt gtcgatatca tgtaattagt tatgtcacgc ttacattcac gccctcctcc   2580
cacatccgct ctaaccgaaa aggaaggagt tagacaacct gaagtctagg tccctattta   2640
ttttttata gttatgttag tattaagaac gttatttata tttcaaattt ttcttttttt   2700
```

```
tctgtacaaa cgcgtgtacg catgtaacgg gcagacgcgg ccgccaccgc ggtggagctc   2760
caattcgccc tatagtgagt cgtattacaa ttcactggcc gtcgttttac aacgtcgtga   2820
ctgggaaaac cctggcgtta cccaacttaa tcgccttgca gcacatcccc ccttcgccag   2880
ctggcgtaat agcgaagagg cccgcaccga tcgcccttcc caacagttgc gcagcctgaa   2940
tggcgaatgg cgcgacgcgc cctgtagcgg cgcattaagc gcggcgggtg tggtggttac   3000
gcgcagcgtg accgctacac ttgccagcgc cctagcgccc gctcctttcg ctttcttccc   3060
ttcctttctc gccacgttcg ccggctttcc ccgtcaagct ctaaatcggg ggctcccttt   3120
agggttccga tttagtgctt tacggcacct cgaccccaaa aaacttgatt agggtgatgg   3180
ttcacgtagt gggccatcgc cctgatagac ggtttttcgc cctttgacgt tggagtccac   3240
gttctttaat agtggactct tgttccaaac tggaacaaca ctcaacccta tctcggtcta   3300
ttcttttgat ttataaggga ttttgccgat ttcggcctat tggttaaaaa atgagctgat   3360
ttaacaaaaa tttaacgcga attttaacaa aatattaacg tttacaattt cctgatgcgg   3420
tattttctcc ttacgcatct gtgcggtatt tcacaccgca gggtaataac tgatataatt   3480
aaattgaagc tctaatttgt gagtttagta tacatgcatt tacttataat acagtttttt   3540
agttttgctg gccgcatctt ctcaaatatg cttcccagcc tgcttttctg taacgttcac   3600
cctctacctt agcatccctt ccctttgcaa atagtcctct tccaacaata ataatgtcag   3660
atcctgtaga gaccacatca tccacggttc tatactgttg acccaatgcg tctcccttgt   3720
catctaaacc cacaccgggt gtcataatca accaatcgta accttcatct cttccaccca   3780
tgtctctttg agcaataaag ccgataacaa aatctttgtc gctcttcgca atgtcaacag   3840
tacccttagt atattctcca gtagataggg agcccttgca tgacaattct gctaacatca   3900
aaaggcctct aggttccttt gttacttctt ctgccgcctg cttcaaaccg ctaacaatac   3960
ctgggcccac cacaccgtgt gcattcgtaa tgtctgccca ttctgctatt ctgtatacac   4020
ccgcagagta ctgcaatttg actgtattac caatgtcagc aaattttctg tcttcgaaga   4080
gtaaaaaatt gtacttggcg gataatgcct ttagcggctt aactgtgccc tccatggaaa   4140
aatcagtcaa gatatccaca tgtgttttta gtaaacaaat tttgggacct aatgcttcaa   4200
ctaactccag taattccttg gtggtacgaa catccaatga agcacacaag tttgtttgct   4260
tttcgtgcat gatattaaat agcttggcag caacaggact aggatgagta gcagcacgtt   4320
ccttatatgt agctttcgac atgatttatc ttcgtttcct gcaggttttt gttctgtgca   4380
gttgggttaa gaatactggg caatttcatg tttcttcaac actacatatg cgtatatata   4440
ccaatctaag tctgtgctcc ttccttcgtt cttccttctg ttcggagatt accgaatcaa   4500
aaaaatttca aagaaaccga aatcaaaaaa aagaataaaa aaaaaatgat gaattgaatt   4560
gaaaagcgtg gtgcactctc agtacaatct gctctgatgc cgcatagtta agccagcccc   4620
gacacccgcc aacacccgct gacgcgccct gacgggcttg tctgctcccg gcatccgctt   4680
acagacaagc tgtgaccgtc tccgggagct gcatgtgtca gaggttttca ccgtcatcac   4740
cgaaacgcgc gagacgaaag ggcctcgtga tacgcctatt tttataggtt aatgtcatga   4800
taataatggt ttcttaggac ggatcgcttg cctgtaactt acacgcgcct cgtatctttt   4860
aatgatggaa taatttggga atttactctg tgtttattta tttttatgtt ttgtatttgg   4920
attttagaaa gtaaataaag aaggtagaag agttacggaa tgaagaaaaa aaaataaaca   4980
aaggtttaaa aaatttcaac aaaaagcgta ctttacatat atatttatta gacaagaaaa   5040
gcagattaaa tagatataca ttcgattaac gataagtaaa atgtaaaatc acaggatttt   5100
```

```
cgtgtgtggt cttctacaca gacaagatga aacaattcgg cattaatacc tgagagcagg   5160
aagagcaaga taaaaggtag tatttgttgg cgatccccct agagtctttt acatcttcgg   5220
aaaacaaaaa ctatttttc tttaatttct ttttttactt tctattttta atttatatat   5280
ttatattaaa aaatttaaat tataattatt tttatagcac gtgatgaaaa ggacccaggt   5340
ggcacttttc ggggaaatgt gcgcggaacc cctatttgtt tatttttcta aatacattca   5400
aatatgtatc cgctcatgag acaataaccc tgataaatgc ttcaataata ttgaaaaagg   5460
aagagtatga gtattcaaca tttccgtgtc gcccttattc cctttttgc ggcattttgc    5520
cttcctgttt ttgctcaccc agaaacgctg gtgaaagtaa aagatgctga agatcagttg   5580
ggtgcacgag tgggttacat cgaactggat ctcaacagcg gtaagatcct tgagagtttt   5640
cgccccgaag aacgttttcc aatgatgagc acttttaaag ttctgctatg tggcgcggta   5700
ttatcccgta ttgacgccgg gcaagagcaa ctcggtcgcc gcatacacta ttctcagaat   5760
gacttggttg agtactcacc agtcacagaa aagcatctta cggatggcat gacagtaaga   5820
gaattatgca gtgctgccat aaccatgagt gataacactg cggccaactt acttctgaca   5880
acgatcggag gaccgaagga gctaaccgct tttttcaca acatggggga tcatgtaact    5940
cgccttgatc gttgggaacc ggagctgaat gaagccatac caaacgacga gcgtgacacc   6000
acgatgcctg tagcaatggc aacaacgttg cgcaaactat taactggcga actacttact   6060
ctagcttccc ggcaacaatt aatagactgg atggaggcgg ataaagttgc aggaccactt   6120
ctgcgctcgg cccttccggc tggctggttt attgctgata aatctggagc cggtgagcgt   6180
gggtctcgcg gtatcattgc agcactgggg ccagatggta agccctcccg tatcgtagtt   6240
atctacacga cgggcagtca ggcaactatg gatgaacgaa atagacagat cgctgagata   6300
ggtgcctcac tgattaagca ttggtaactg tcagaccaag tttactcata tatactttag   6360
attgatttaa aacttcattt ttaatttaaa aggatctagg tgaagatcct ttttgataat   6420
ctcatgacca aaatccctta acgtgagttt tcgttccact gagcgtcaga ccccgtagaa   6480
aagatcaaag gatcttcttg agatcctttt tttctgcgcg taatctgctg cttgcaaaca   6540
aaaaaaccac cgctaccagc ggtggtttgt ttgccggatc aagagctacc aactcttttt   6600
ccgaaggtaa ctggcttcag cagagcgcag ataccaaata ctgtccttct agtgtagccg   6660
tagttaggcc accacttcaa gaactctgta gcaccgccta catacctcgc tctgctaatc   6720
ctgttaccag tggctgctgc cagtggcgat aagtcgtgtc ttaccgggtt ggactcaaga   6780
cgatagttac cggataaggc gcagcggtcg ggctgaacgg ggggttcgtg cacacagccc   6840
agcttggagc gaacgaccta caccgaactg agatacctac agcgtgagca ttgagaaagc   6900
gccacgcttc ccgaagggag aaaggcggac aggtatccgg taagcggcag ggtcggaaca   6960
ggagagcgca cgagggagct tccaggggg aacgcctggt atctttatag tcctgtcggg    7020
tttcgccacc tctgacttga gcgtcgattt ttgtgatgct cgtcaggggg gccgagccta   7080
tggaaaaacg ccagcaacgc ggccttttta cggttcctgg ccttttgctg gccttttgct   7140
cacatgttct ttcctgcgtt atcccctgat tctgtggata accgtattac cgcctttgag   7200
tgagctgata ccgctcgccg cagccgaacg accgagcgca gcgagtcagt gagcgaggaa   7260
gcggaagagc gcccaatacg caaaccgcct ctccccgcgc gttggccgat tcattaatgc   7320
agctggcacg acaggtttcc cgactggaaa gcgggcagtg agcgcaacgc aattaatgtg   7380
agttacctca ctcattaggc accccaggct ttacacttta tgcttccggc tcctatgttg   7440
```

```
tgtggaattg tgagcggata acaatttcac acaggaaaca gctatgacca tgattacgcc   7500

aagctcggaa ttaaccctca ctaaagggaa caaaagctgg gtaccgggcc cccctcgag   7560


<210> SEQ ID NO 19
<211> LENGTH: 7752
<212> TYPE: DNA
<213> ORGANISM: Artificial Sequence
<220> FEATURE:
<223> OTHER INFORMATION: Sequence put together from multiple organisms:
      Saccharomyces cerevisiae and Rhizopus oryzae

<400> SEQUENCE: 19

tcgagatctc ccgagtttat cattatcaat actgccattt caaagaatac gtaaataatt     60

aatagtagtg attttcctaa ctttatttag tcaaaaaatt ggccttttaa ttctgctgta    120

acccgtacat gcccaaaata gggggcgggt tacacagaat atataacatc ataggtgtct    180

gggtgaacag tttattcctg gcatccacta aatataatgg agcccgcttt ttttaagctg    240

gcatccagaa aaaaaaagaa tcccagcacc aaaatattgt tttcttcacc aaccatcagt    300

tcataggtcc attctcttag cgcaactaca cagaacaggg gcacaaacag gcaaaaaacg    360

ggcacaacct caatggagtg atgcaacctg cttggagtaa atgatgacac aaggcaattg    420

acctacgcat gtatctatct cattttctta caccttctat taccttctgc tctctctgat    480

ttggaaaaag ctgaaaaaaa aggttgaaac cagttccctg aaattattcc cctatttgac    540

taataagtat ataaagacgg taggtattga ttgtaattct gtaaatctat ttcttaaact    600

tcttaaattc tacttttata gttagtcttt tttttagttt taaaacacta agaacttagt    660

ttcgaataaa cacacataaa caaacaaatc tagaatgcgt ttcccaagta tcttcaccgc    720

tgttcttttc gctgcctctt ccgcactggc agctcctgtc aacaccacga ctgaggatga    780

gacagcacaa attcctgcgg aggctgtaat cggttacagt gacctggaag gcgattttga    840

cgttgctgtg ttgccgttct caaactctac taacaacgga cttcttttca taaacacgac    900

catagccagc attgcagcta aggaggaagg cgttagcctg gaaaagaggg aagcagaagc    960

cgcatctatt ccatctagtg catctgtaca attggactcc tacaattacg atggttccac   1020

attttccggc aagatttatg tcaaaaacat cgcttactct aaaaaggtta ctgttgtgta   1080

cgcagacggt tctgacaact ggaacaataa cggcaacact attgctgcat cattttcagg   1140

cccaatctct ggatcaaatt acgaatactg gacattctca gcatcagtga agggcataaa   1200

ggagttctac atcaaatacg aagtttcagg taagacatat tacgacaata acaactctgc   1260

aaactaccaa gtctcaactt ctaaacctac tacaactact gcagctacaa ccacaactac   1320

agctccatca acttctacaa caacccgtcc atctagttca gagcctgcca ccttccctac   1380

tggtaattct accatcagct cttggatcaa aaagcaggaa gatatttcca gattcgctat   1440

gcttagaaac atcaacccac ctggttctgc cacagggttt atcgccgcat cactctctac   1500

cgctggtcca gattactact acgcgtggac aagagatgcc gctttgacat ctaacgttat   1560

cgtttacgaa tacaacacca cattgtctgg gaataagaca attctaaacg tacttaagga   1620

ttacgtcaca ttcagtgtta agacacagtc tacttcaaca gtttgtaatt gccttggtga   1680

accaaagttc aatccagacg gcagtggtta cacaggtgct tggggtagac ctcaaaatga   1740

tggtcctgca gaaagagcga ctacatttgt tctgtttgcc gacagctact tgactcaaac   1800

taaggatgcc tcatacgtca ctggtacatt aaagccagca attttcaaag atctcgatta   1860

cgttgttaac gtctggagta acggatgttt cgatttatgg gaggaggtga acggagttca   1920
```

```
tttctacacc cttatggtta tgagaaaagg gctattgttg ggggctgatt tcgcgaagag   1980
aaacggtgac tcaactagag cctcaactta ctcttctact gcttccacaa ttgctaacaa   2040
gatatcaagt ttctgggtta gctcaaacaa ctgggtgcaa gtatcccaat ctgtcacagg   2100
aggtgtaagt aaaaaggggt tagacgttag caccctgtta gctgcgaatc taggatcagt   2160
cgatgatgga tttttcactc caggttctga aaagatatta gctacagctg tggcagtcga   2220
agattccttt gccagtctat acccaatcaa caaaaacctt ccatcatact tggggaacgc   2280
tattggaaga taccctgaag atacatacaa cggtaatggt aactcacaag gcaatccttg   2340
gtttctggcg gttaccggct acgcagagtt gtactataga gcaattaagg aatggatttc   2400
taatggaggc gttacagtgt cctctatctc attgccattt ttcaaaaagt tcgatagctc   2460
tgcaacatcc ggtaaaaagt acaccgtagg tacttctgac ttcaacaatt tagcacaaaa   2520
cattgctctt gctgcagatc gtttcctatc tactgtacaa ctccatgcac caaacaatgg   2580
ttcattagca gaggaatttg atagaacaac aggtttttct accggcgcta gagatttaac   2640
atggtcccac gcctcattga taacagcatc ctatgccaaa gccggtgctc cagctgcata   2700
attaattaaa caggcccctt ttcctttgtc gatatcatgt aattagttat gtcacgctta   2760
cattcacgcc ctcctcccac atccgctcta accgaaaagg aaggagttag acaacctgaa   2820
gtctaggtcc ctatttattt ttttatagtt atgttagtat taagaacgtt atttatattt   2880
caaatttttc ttttttttct gtacaaacgc gtgtacgcat gtaacgggca gacgcggccg   2940
ccaccgcggt ggagctccaa ttcgccctat agtgagtcgt attacaattc actggccgtc   3000
gttttacaac gtcgtgactg ggaaaaccct ggcgttaccc aacttaatcg ccttgcagca   3060
catccccct tcgccagctg gcgtaatagc gaagaggccc gcaccgatcg cccttcccaa   3120
cagttgcgca gcctgaatgg cgaatggcgc gacgcgccct gtagcggcgc attaagcgcg   3180
gcgggtgtgg tggttacgcg cagcgtgacc gctacacttg ccagcgccct agcgcccgct   3240
cctttcgctt tcttcccttc ctttctcgcc acgttcgccg gctttccccg tcaagctcta   3300
aatcgggggc tccctttagg gttccgattt agtgctttac ggcacctcga ccccaaaaaa   3360
cttgattagg gtgatggttc acgtagtggg ccatcgccct gatagacggt ttttcgccct   3420
ttgacgttgg agtccacgtt ctttaatagt ggactcttgt tccaaactgg aacaacactc   3480
aaccctatct cggtctattc ttttgattta taagggattt tgccgatttc ggcctattgg   3540
ttaaaaaatg agctgattta acaaaaattt aacgcgaatt ttaacaaaat attaacgttt   3600
acaatttcct gatgcggtat tttctcctta cgcatctgtg cggtatttca caccgcaggg   3660
taataactga tataattaaa ttgaagctct aatttgtgag tttagtatac atgcatttac   3720
ttataataca gtttttttagt tttgctggcc gcatcttctc aaatatgctt cccagcctgc   3780
ttttctgtaa cgttcaccct ctaccttagc atcccttccc tttgcaaata gtcctcttcc   3840
aacaataata atgtcagatc ctgtagagac cacatcatcc acggttctat actgttgacc   3900
caatgcgtct cccttgtcat ctaaacccac accgggtgtc ataatcaacc aatcgtaacc   3960
ttcatctctt ccacccatgt ctctttgagc aataaagccg ataacaaaat ctttgtcgct   4020
cttcgcaatg tcaacagtac ccttagtata ttctccagta gatagggagc ccttgcatga   4080
caattctgct aacatcaaaa ggcctctagg ttcctttgtt acttcttctg ccgcctgctt   4140
caaaccgcta acaatacctg ggcccaccac accgtgtgca ttcgtaatgt ctgcccattc   4200
tgctattctg tatacacccg cagagtactg caatttgact gtattaccaa tgtcagcaaa   4260
ttttctgtct tcgaagagta aaaaattgta cttggcggat aatgccttta gcggcttaac   4320
```

```
tgtgccctcc atggaaaaat cagtcaagat atccacatgt gtttttagta aacaaatttt   4380
gggacctaat gcttcaacta actccagtaa ttccttggtg gtacgaacat ccaatgaagc   4440
acacaagttt gtttgctttt cgtgcatgat attaaatagc ttggcagcaa caggactagg   4500
atgagtagca gcacgttcct tatatgtagc tttcgacatg atttatcttc gtttcctgca   4560
ggtttttgtt ctgtgcagtt gggttaagaa tactgggcaa tttcatgttt cttcaacact   4620
acatatgcgt atatatacca atctaagtct gtgctccttc cttcgttctt ccttctgttc   4680
ggagattacc gaatcaaaaa aatttcaaag aaaccgaaat caaaaaaaag aataaaaaaa   4740
aaatgatgaa ttgaattgaa aagcgtggtg cactctcagt acaatctgct ctgatgccgc   4800
atagttaagc cagccccgac acccgccaac acccgctgac gcgccctgac gggcttgtct   4860
gctcccggca tccgcttaca gacaagctgt gaccgtctcc gggagctgca tgtgtcagag   4920
gttttcaccg tcatcaccga aacgcgcgag acgaaagggc ctcgtgatac gcctattttt   4980
ataggttaat gtcatgataa taatggtttc ttaggacgga tcgcttgcct gtaacttaca   5040
cgcgcctcgt atcttttaat gatggaataa tttgggaatt tactctgtgt ttatttattt   5100
ttatgttttg tatttggatt ttagaaagta aataaagaag gtagaagagt tacggaatga   5160
agaaaaaaaa ataaacaaag gtttaaaaaa tttcaacaaa aagcgtactt tacatatata   5220
tttattagac aagaaaagca gattaaatag atatacattc gattaacgat aagtaaaatg   5280
taaaatcaca ggattttcgt gtgtggtctt ctacacagac aagatgaaac aattcggcat   5340
taatacctga gagcaggaag agcaagataa aaggtagtat ttgttggcga tccccctaga   5400
gtcttttaca tcttcggaaa acaaaaacta tttttcttt aatttctttt tttactttct   5460
atttttaatt tatatattta tattaaaaaa tttaaattat aattattttt atagcacgtg   5520
atgaaaagga cccaggtggc acttttcggg gaaatgtgcg cggaacccct atttgtttat   5580
ttttctaaat acattcaaat atgtatccgc tcatgagaca ataaccctga taaatgcttc   5640
aataatattg aaaaaggaag agtatgagta ttcaacattt ccgtgtcgcc cttattccct   5700
tttttgcggc attttgcctt cctgtttttg ctcacccaga aacgctggtg aaagtaaaag   5760
atgctgaaga tcagttgggt gcacgagtgg gttacatcga actggatctc aacagcggta   5820
agatccttga gagttttcgc cccgaagaac gttttccaat gatgagcact tttaaagttc   5880
tgctatgtgg cgcggtatta tcccgtattg acgccgggca agagcaactc ggtcgccgca   5940
tacactattc tcagaatgac ttggttgagt actcaccagt cacagaaaag catcttacgg   6000
atggcatgac agtaagagaa ttatgcagtg ctgccataac catgagtgat aacactgcgg   6060
ccaacttact tctgacaacg atcggaggac cgaaggagct aaccgctttt tttcacaaca   6120
tgggggatca tgtaactcgc cttgatcgtt gggaaccgga gctgaatgaa gccataccaa   6180
acgacgagcg tgacaccacg atgcctgtag caatggcaac aacgttgcgc aaactattaa   6240
ctggcgaact acttactcta gcttcccggc aacaattaat agactggatg gaggcggata   6300
aagttgcagg accacttctg cgctcggccc ttccggctgg ctggtttatt gctgataaat   6360
ctggagccgg tgagcgtggg tctcgcggta tcattgcagc actggggcca gatggtaagc   6420
cctcccgtat cgtagttatc tacacgacgg gcagtcaggc aactatggat gaacgaaata   6480
gacagatcgc tgagataggt gcctcactga ttaagcattg gtaactgtca gaccaagttt   6540
actcatatat actttagatt gatttaaaac ttcattttta atttaaaagg atctaggtga   6600
agatcctttt tgataatctc atgaccaaaa tcccttaacg tgagttttcg ttccactgag   6660
```

```
cgtcagaccc cgtagaaaag atcaaaggat cttcttgaga tcctttttt ctgcgcgtaa   6720

tctgctgctt gcaaacaaaa aaaccaccgc taccagcggt ggtttgtttg ccggatcaag   6780

agctaccaac tctttttccg aaggtaactg gcttcagcag agcgcagata ccaaatactg   6840

tccttctagt gtagccgtag ttaggccacc acttcaagaa ctctgtagca ccgcctacat   6900

acctcgctct gctaatcctg ttaccagtgg ctgctgccag tggcgataag tcgtgtctta   6960

ccgggttgga ctcaagacga tagttaccgg ataaggcgca gcggtcgggc tgaacggggg   7020

gttcgtgcac acagcccagc ttggagcgaa cgacctacac cgaactgaga tacctacagc   7080

gtgagcattg agaaagcgcc acgcttcccg aagggagaaa ggcggacagg tatccggtaa   7140

gcggcagggt cggaacagga gagcgcacga gggagcttcc agggggaaac gcctggtatc   7200

tttatagtcc tgtcgggttt cgccacctct gacttgagcg tcgatttttg tgatgctcgt   7260

caggggggcc gagcctatgg aaaaacgcca gcaacgcggc ctttttacgg ttcctggcct   7320

tttgctggcc ttttgctcac atgttctttc ctgcgttatc ccctgattct gtggataacc   7380

gtattaccgc ctttgagtga gctgataccg ctcgccgcag ccgaacgacc gagcgcagcg   7440

agtcagtgag cgaggaagcg gaagagcgcc caatacgcaa accgcctctc cccgcgcgtt   7500

ggccgattca ttaatgcagc tggcacgaca ggtttcccga ctggaaagcg ggcagtgagc   7560

gcaacgcaat taatgtgagt tacctcactc attaggcacc ccaggcttta cactttatgc   7620

ttccggctcc tatgttgtgt ggaattgtga gcggataaca atttcacaca ggaaacagct   7680

atgaccatga ttacgccaag ctcggaatta accctcacta aagggaacaa aagctgggta   7740

ccgggccccc cc                                                        7752
```

```
<210> SEQ ID NO 20
<211> LENGTH: 7668
<212> TYPE: DNA
<213> ORGANISM: Artificial Sequence
<220> FEATURE:
<223> OTHER INFORMATION: Sequence put together from multiple organisms:
      Saccharomyces cerevisiae and Rhizopus oryzae

<400> SEQUENCE: 20
```

```
tcgagatctc ccgagtttat cattatcaat actgccattt caaagaatac gtaaataatt     60

aatagtagtg attttcctaa ctttatttag tcaaaaaatt ggccttttaa ttctgctgta    120

acccgtacat gcccaaaata gggggcgggt tacacagaat atataacatc ataggtgtct    180

gggtgaacag tttattcctg gcatccacta aatataatgg agcccgcttt ttttaagctg    240

gcatccagaa aaaaaaagaa tcccagcacc aaaatattgt tttcttcacc aaccatcagt    300

tcataggtcc attctcttag cgcaactaca cagaacaggg gcacaaacag gcaaaaaacg    360

ggcacaacct caatggagtg atgcaacctg cttggagtaa atgatgacac aaggcaattg    420

acctacgcat gtatctatct cattttctta caccttctat taccttctgc tctctctgat    480

ttggaaaaag ctgaaaaaaa aggttgaaac cagttccctg aaattattcc cctatttgac    540

taataagtat ataaagacgg taggtattga ttgtaattct gtaaatctat ttcttaaact    600

tcttaaattc tacttttata gttagtcttt tttttagttt taaaacacta agaacttagt    660

ttcgaataaa cacacataaa caaacaaatc tagaatgcgt tttcccagca tctttactgc    720

tgtacttttt gccgcgagta gtgccctggc tgctccggtg aatactacaa ctgaagacga    780

attagagggg gatttcgatg tggccgttct accgttcagc gcgagcatag ctgcaaaaga    840

agaaggagtg agcttggaaa aaagggaggc tgaggcggca tctattccat ctagtgcatc    900
```

```
tgtacaattg gactcctaca attacgatgg ttccacattt tccggcaaga tttatgtcaa    960
aaacatcgct tactctaaaa aggttactgt tgtgtacgca gacggttctg acaactggaa   1020
caataacggc aacactattg ctgcatcatt ttcaggccca atctctggat caaattacga   1080
atactggaca ttctcagcat cagtgaaggg cataaaggag ttctacatca aatacgaagt   1140
ttcaggtaag acatattacg acaataacaa ctctgcaaac taccaagtct caacttctaa   1200
acctactaca actactgcag ctacaaccac aactacagct ccatcaactt ctacaacaac   1260
ccgtccatct agttcagagc ctgccacctt ccctactggt aattctacca tcagctcttg   1320
gatcaaaaag caggaagata tttccagatt cgctatgctt agaaacatca acccacctgg   1380
ttctgccaca gggtttatcg ccgcatcact ctctaccgct ggtccagatt actactacgc   1440
gtggacaaga gatgccgctt tgacatctaa cgttatcgtt tacgaataca acaccacatt   1500
gtctgggaat aagacaattc taaacgtact taaggattac gtcacattca gtgttaagac   1560
acagtctact tcaacagttt gtaattgcct tggtgaacca aagttcaatc cagacggcag   1620
tggttacaca ggtgcttggg gtagacctca aaatgatggt cctgcagaaa gagcgactac   1680
atttgttctg tttgccgaca gctacttgac tcaaactaag gatgcctcat acgtcactgg   1740
tacattaaag ccagcaattt tcaaagatct cgattacgtt gttaacgtct ggagtaacgg   1800
atgtttcgat ttatgggagg aggtgaacgg agttcatttc tacaccctta tggttatgag   1860
aaaagggcta ttgttggggg ctgatttcgc gaagagaaac ggtgactcaa ctagagcctc   1920
aacttactct tctactgctt ccacaattgc taacaagata tcaagtttct gggttagctc   1980
aaacaactgg gtgcaagtat cccaatctgt cacaggaggt gtaagtaaaa aggggttaga   2040
cgttagcacc ctgttagctg cgaatctagg atcagtcgat gatggatttt tcactccagg   2100
ttctgaaaag atattagcta cagctgtggc agtcgaagat tcctttgcca gtctataccc   2160
aatcaacaaa aaccttccat catacttggg gaacgctatt ggaagatacc ctgaagatac   2220
atacaacggt aatggtaact cacaaggcaa tccttggttt ctggcggtta ccggctacgc   2280
agagttgtac tatagagcaa ttaaggaatg gatttctaat ggaggcgtta cagtgtcctc   2340
tatctcattg ccatttttca aaaagttcga tagctctgca acatccggta aaaagtacac   2400
cgtaggtact tctgacttca acaatttagc acaaaacatt gctcttgctg cagatcgttt   2460
cctatctact gtacaactcc atgcaccaaa caatggttca ttagcagagg aatttgatag   2520
aacaacaggt ttttctaccg gcgctagaga tttaacatgg tcccacgcct cattgataac   2580
agcatcctat gccaaagccg gtgctccagc tgcataatta attaaacagg ccccttttcc   2640
tttgtcgata tcatgtaatt agttatgtca cgcttacatt cacgccctcc tcccacatcc   2700
gctctaaccg aaaaggaagg agttagacaa cctgaagtct aggtccctat ttattttttt   2760
atagttatgt tagtattaag aacgttattt atatttcaaa tttttctttt ttttctgtac   2820
aaacgcgtgt acgcatgtaa cgggcagacg cggccgccac cgcggtggag ctccaattcg   2880
ccctatagtg agtcgtatta caattcactg gccgtcgttt tacaacgtcg tgactgggaa   2940
aaccctggcg ttacccaact taatcgcctt gcagcacatc ccccctttcgc cagctggcgt   3000
aatagcgaag aggcccgcac cgatcgccct tcccaacagt tgcgcagcct gaatggcgaa   3060
tggcgcgacg cgccctgtag cggcgcatta agcgcggcgg gtgtggtggt tacgcgcagc   3120
gtgaccgcta cacttgccag cgccctagcg cccgctcctt tcgctttctt cccttccttt   3180
ctcgccacgt tcgccggctt tccccgtcaa gctctaaatc gggggctccc tttagggttc   3240
cgatttagtg ctttacggca cctcgacccc aaaaaacttg attagggtga tggttcacgt   3300
```

```
agtgggccat cgccctgata gacggttttt cgccctttga cgttggagtc cacgttcttt   3360
aatagtggac tcttgttcca aactggaaca acactcaacc ctatctcggt ctattctttt   3420
gatttataag ggattttgcc gatttcggcc tattggttaa aaaatgagct gatttaacaa   3480
aaatttaacg cgaattttaa caaaatatta acgtttacaa tttcctgatg cggtattttc   3540
tccttacgca tctgtgcggt atttcacacc gcagggtaat aactgatata attaaattga   3600
agctctaatt tgtgagttta gtatacatgc atttacttat aatacagttt tttagttttg   3660
ctggccgcat cttctcaaat atgcttccca gcctgctttt ctgtaacgtt caccctctac   3720
cttagcatcc cttccctttg caaatagtcc tcttccaaca ataataatgt cagatcctgt   3780
agagaccaca tcatccacgg ttctatactg ttgacccaat gcgtctccct tgtcatctaa   3840
acccacaccg ggtgtcataa tcaaccaatc gtaaccttca tctcttccac ccatgtctct   3900
ttgagcaata aagccgataa caaaatcttt gtcgctcttc gcaatgtcaa cagtaccctt   3960
agtatattct ccagtagata gggagccctt gcatgacaat tctgctaaca tcaaaaggcc   4020
tctaggttcc tttgttactt cttctgccgc ctgcttcaaa ccgctaacaa tacctgggcc   4080
caccacaccg tgtgcattcg taatgtctgc ccattctgct attctgtata cacccgcaga   4140
gtactgcaat ttgactgtat taccaatgtc agcaaatttt ctgtcttcga agagtaaaaa   4200
attgtacttg gcggataatg cctttagcgg cttaactgtg ccctccatgg aaaaatcagt   4260
caagatatcc acatgtgttt ttagtaaaca aattttggga cctaatgctt caactaactc   4320
cagtaattcc ttggtggtac gaacatccaa tgaagcacac aagtttgttt gcttttcgtg   4380
catgatatta aatagcttgg cagcaacagg actaggatga gtagcagcac gttccttata   4440
tgtagctttc gacatgattt atcttcgttt cctgcaggtt tttgttctgt gcagttgggt   4500
taagaatact gggcaatttc atgtttcttc aacactacat atgcgtatat ataccaatct   4560
aagtctgtgc tccttccttc gttcttcctt ctgttcggag attaccgaat caaaaaaatt   4620
tcaaagaaac cgaaatcaaa aaaaagaata aaaaaaaaat gatgaattga attgaaaagc   4680
gtggtgcact ctcagtacaa tctgctctga tgccgcatag ttaagccagc cccgacaccc   4740
gccaacaccc gctgacgcgc cctgacgggc ttgtctgctc ccggcatccg cttacagaca   4800
agctgtgacc gtctccggga gctgcatgtg tcagaggttt tcaccgtcat caccgaaacg   4860
cgcgagacga aagggcctcg tgatacgcct atttttatag gttaatgtca tgataataat   4920
ggtttcttag gacggatcgc ttgcctgtaa cttacacgcg cctcgtatct tttaatgatg   4980
gaataatttg ggaatttact ctgtgtttat ttatttttat gttttgtatt tggattttag   5040
aaagtaaata aagaaggtag aagagttacg gaatgaagaa aaaaaaataa acaaaggttt   5100
aaaaaatttc aacaaaaagc gtactttaca tatatattta ttagacaaga aaagcagatt   5160
aaatagatat acattcgatt aacgataagt aaaatgtaaa atcacaggat tttcgtgtgt   5220
ggtcttctac acagacaaga tgaaacaatt cggcattaat acctgagagc aggaagagca   5280
agataaaagg tagtatttgt tggcgatccc cctagagtct tttacatctt cggaaaacaa   5340
aaactatttt ttctttaatt tcttttttta ctttctattt ttaatttata tatttatatt   5400
aaaaaattta aattataatt atttttatag cacgtgatga aaaggaccca ggtggcactt   5460
ttcggggaaa tgtgcgcgga acccctattt gtttattttt ctaaatacat tcaaatatgt   5520
atccgctcat gagacaataa ccctgataaa tgcttcaata atattgaaaa aggaagagta   5580
tgagtattca acatttccgt gtcgccctta ttcccttttt tgcggcattt tgccttcctg   5640
```

```
tttttgctca cccagaaacg ctggtgaaag taaaagatgc tgaagatcag ttgggtgcac   5700

gagtgggtta catcgaactg gatctcaaca gcggtaagat ccttgagagt tttcgccccg   5760

aagaacgttt tccaatgatg agcactttta aagttctgct atgtggcgcg gtattatccc   5820

gtattgacgc cgggcaagag caactcggtc gccgcataca ctattctcag aatgacttgg   5880

ttgagtactc accagtcaca gaaaagcatc ttacggatgg catgacagta agagaattat   5940

gcagtgctgc cataaccatg agtgataaca ctgcggccaa cttacttctg acaacgatcg   6000

gaggaccgaa ggagctaacc gcttttttc acaacatggg ggatcatgta actcgccttg   6060

atcgttggga accggagctg aatgaagcca taccaaacga cgagcgtgac accacgatgc   6120

ctgtagcaat ggcaacaacg ttgcgcaaac tattaactgg cgaactactt actctagctt   6180

cccggcaaca attaatagac tggatggagg cggataaagt tgcaggacca cttctgcgct   6240

cggcccttcc ggctggctgg tttattgctg ataaatctgg agccggtgag cgtgggtctc   6300

gcggtatcat tgcagcactg gggccagatg gtaagccctc ccgtatcgta gttatctaca   6360

cgacgggcag tcaggcaact atggatgaac gaaatagaca gatcgctgag ataggtgcct   6420

cactgattaa gcattggtaa ctgtcagacc aagtttactc atatatactt tagattgatt   6480

taaaacttca tttttaattt aaaaggatct aggtgaagat cctttttgat aatctcatga   6540

ccaaaatccc ttaacgtgag ttttcgttcc actgagcgtc agaccccgta gaaaagatca   6600

aaggatcttc ttgagatcct ttttttctgc gcgtaatctg ctgcttgcaa acaaaaaaac   6660

caccgctacc agcggtggtt tgtttgccgg atcaagagct accaactctt tttccgaagg   6720

taactggctt cagcagagcg cagataccaa atactgtcct tctagtgtag ccgtagttag   6780

gccaccactt caagaactct gtagcaccgc ctacatacct cgctctgcta atcctgttac   6840

cagtggctgc tgccagtggc gataagtcgt gtcttaccgg gttggactca agacgatagt   6900

taccggataa ggcgcagcgg tcgggctgaa cggggggttc gtgcacacag cccagcttgg   6960

agcgaacgac ctacaccgaa ctgagatacc tacagcgtga gcattgagaa agcgccacgc   7020

ttcccgaagg gagaaaggcg gacaggtatc cggtaagcgg cagggtcgga acaggagagc   7080

gcacgaggga gcttccaggg ggaaacgcct ggtatcttta tagtcctgtc gggtttcgcc   7140

acctctgact tgagcgtcga tttttgtgat gctcgtcagg ggggccgagc ctatggaaaa   7200

acgccagcaa cgcggccttt ttacggttcc tggccttttg ctggcctttt gctcacatgt   7260

tctttcctgc gttatcccct gattctgtgg ataaccgtat taccgccttt gagtgagctg   7320

ataccgctcg ccgcagccga acgaccgagc gcagcgagtc agtgagcgag gaagcggaag   7380

agcgcccaat acgcaaaccg cctctccccg cgcgttggcc gattcattaa tgcagctggc   7440

acgacaggtt tcccgactgg aaagcgggca gtgagcgcaa cgcaattaat gtgagttacc   7500

tcactcatta ggcaccccag gctttacact ttatgcttcc ggctcctatg ttgtgtggaa   7560

ttgtgagcgg ataacaattt cacacaggaa acagctatga ccatgattac gccaagctcg   7620

gaattaaccc tcactaaagg gaacaaaagc tgggtaccgg gcccccc                 7668
```

```
<210> SEQ ID NO 21
<211> LENGTH: 7656
<212> TYPE: DNA
<213> ORGANISM: Artificial Sequence
<220> FEATURE:
<223> OTHER INFORMATION: Sequence put together from multiple organisms:
      Saccharomyces cerevisiae and Rhizopus oryzae

<400> SEQUENCE: 21
```

-continued

```
tcgagatctc ccgagtttat cattatcaat actgccattt caaagaatac gtaaataatt     60
aatagtagtg attttcctaa ctttatttag tcaaaaaatt ggccttttaa ttctgctgta    120
acccgtacat gcccaaaata gggggcgggt tacacagaat atataacatc ataggtgtct    180
gggtgaacag tttattcctg gcatccacta aatataatgg agcccgcttt ttttaagctg    240
gcatccagaa aaaaaaagaa tcccagcacc aaaatattgt ttcttcacc aaccatcagt     300
tcataggtcc attctcttag cgcaactaca cagaacaggg gcacaaacag gcaaaaaacg    360
ggcacaacct caatggagtg atgcaacctg cttggagtaa atgatgacac aaggcaattg    420
acctacgcat gtatctatct cattttctta caccttctat taccttctgc tctctctgat    480
ttggaaaaag ctgaaaaaaa aggttgaaac cagttccctg aaattattcc cctatttgac    540
taataagtat ataaagacgg taggtattga ttgtaattct gtaaatctat ttcttaaact    600
tcttaaattc tacttttata gttagtcttt tttttagttt taaaacacta agaacttagt    660
ttcgaataaa cacacataaa caaacaaatc tagaatgaga ttcccgtcca tattcacagc    720
cgtcttgttt gcggcatctt ctgcgttagc tgcgccagta aacacgacaa cggaagacga    780
acttgagggg gatttcgatg tggccgtact tcctttctcc gcatcaatcg cggcgaaaga    840
ggagggtgta tctttagaaa agagggcatc tattccatct agtgcatctg tacaattgga    900
ctcctacaat tacgatggtt ccacattttc cggcaagatt tatgtcaaaa acatcgctta    960
ctctaaaaag gttactgttg tgtacgcaga cggttctgac aactggaaca ataacggcaa   1020
cactattgct gcatcatttt caggcccaat ctctggatca aattacgaat actggacatt   1080
ctcagcatca gtgaagggca taaaggagtt ctacatcaaa tacgaagttt caggtaagac   1140
atattacgac aataacaact ctgcaaacta ccaagtctca acttctaaac ctactacaac   1200
tactgcagct acaaccacaa ctacagctcc atcaacttct acaacaaccc gtccatctag   1260
ttcagagcct gccaccttcc ctactggtaa ttctaccatc agctcttgga tcaaaaagca   1320
ggaagatatt tccagattcg ctatgcttag aaacatcaac ccacctggtt ctgccacagg   1380
gtttatcgcc gcatcactct ctaccgctgg tccagattac tactacgcgt ggacaagaga   1440
tgccgctttg acatctaacg ttatcgttta cgaatacaac accacattgt ctgggaataa   1500
gacaattcta aacgtactta aggattacgt cacattcagt gttaagacac agtctacttc   1560
aacagtttgt aattgccttg gtgaaccaaa gttcaatcca gacggcagtg gttacacagg   1620
tgcttggggt agacctcaaa atgatggtcc tgcagaaaga gcgactacat ttgttctgtt   1680
tgccgacagc tacttgactc aaactaagga tgcctcatac gtcactggta cattaaagcc   1740
agcaattttc aaagatctcg attacgttgt taacgtctgg agtaacggat gtttcgattt   1800
atgggaggag gtgaacggag ttcatttcta cacccttatg gttatgagaa aagggctatt   1860
gttgggggct gatttcgcga agagaaacgg tgactcaact agagcctcaa cttactcttc   1920
tactgcttcc acaattgcta acaagatatc aagtttctgg gttagctcaa acaactgggt   1980
gcaagtatcc caatctgtca caggaggtgt aagtaaaaag ggggttagacg ttagcaccct   2040
gttagctgcg aatctaggat cagtcgatga tggatttttc actccaggtt ctgaaaagat   2100
attagctaca gctgtggcag tcgaagattc ctttgccagt ctatacccaa tcaacaaaaa   2160
ccttccatca tacttgggga acgctattgg aagataccct gaagatacat acaacggtaa   2220
tggtaactca caaggcaatc cttggtttct ggcggttacc ggctacgcag agttgtacta   2280
tagagcaatt aaggaatgga tttctaatgg aggcgttaca gtgtcctcta tctcattgcc   2340
atttttcaaa aagttcgata gctctgcaac atccggtaaa aagtacaccg taggtacttc   2400
```

```
tgacttcaac aatttagcac aaaacattgc tcttgctgca gatcgtttcc tatctactgt   2460
acaactccat gcaccaaaca atggttcatt agcagaggaa tttgatagaa caacaggttt   2520
ttctaccggc gctagagatt taacatggtc ccacgcctca ttgataacag catcctatgc   2580
caaagccggt gctccagctg cataattaat taaacaggcc ccttttcctt tgtcgatatc   2640
atgtaattag ttatgtcacg cttacattca cgccctcctc ccacatccgc tctaaccgaa   2700
aaggaaggag ttagacaacc tgaagtctag gtccctattt atttttttat agttatgtta   2760
gtattaagaa cgttatttat atttcaaatt tttctttttt ttctgtacaa acgcgtgtac   2820
gcatgtaacg ggcagacgcg gccgccaccg cggtggagct ccaattcgcc ctatagtgag   2880
tcgtattaca attcactggc cgtcgtttta caacgtcgtg actgggaaaa ccctggcgtt   2940
acccaactta atcgccttgc agcacatccc cccttcgcca gctggcgtaa tagcgaagag   3000
gcccgcaccg atcgcccttc ccaacagttg cgcagcctga atggcgaatg gcgcgacgcg   3060
ccctgtagcg gcgcattaag cgcggcgggt gtggtggtta cgcgcagcgt gaccgctaca   3120
cttgccagcg ccctagcgcc cgctcctttc gctttcttcc cttcctttct cgccacgttc   3180
gccggctttc cccgtcaagc tctaaatcgg gggctccctt tagggttccg atttagtgct   3240
ttacggcacc tcgaccccaa aaaacttgat tagggtgatg gttcacgtag tgggccatcg   3300
ccctgataga cggtttttcg ccctttgacg ttggagtcca cgttctttaa tagtggactc   3360
ttgttccaaa ctggaacaac actcaaccct atctcggtct attcttttga tttataaggg   3420
attttgccga tttcggccta ttggttaaaa aatgagctga tttaacaaaa atttaacgcg   3480
aattttaaca aaatattaac gtttacaatt tcctgatgcg gtattttctc cttacgcatc   3540
tgtgcggtat ttcacaccgc agggtaataa ctgatataat taaattgaag ctctaatttg   3600
tgagtttagt atacatgcat ttacttataa tacagttttt tagttttgct ggccgcatct   3660
tctcaaatat gcttcccagc ctgcttttct gtaacgttca ccctctacct tagcatccct   3720
tccctttgca aatagtcctc ttccaacaat aataatgtca gatcctgtag agaccacatc   3780
atccacggtt ctatactgtt gacccaatgc gtctcccttg tcatctaaac ccacaccggg   3840
tgtcataatc aaccaatcgt aaccttcatc tcttccaccc atgtctcttt gagcaataaa   3900
gccgataaca aaatctttgt cgctcttcgc aatgtcaaca gtacccttag tatattctcc   3960
agtagatagg gagcccttgc atgacaattc tgctaacatc aaaaggcctc taggttcctt   4020
tgttacttct tctgccgcct gcttcaaacc gctaacaata cctgggccca ccacaccgtg   4080
tgcattcgta atgtctgccc attctgctat tctgtataca cccgcagagt actgcaattt   4140
gactgtatta ccaatgtcag caaattttct gtcttcgaag agtaaaaaat tgtacttggc   4200
ggataatgcc tttagcggct taactgtgcc ctccatggaa aaatcagtca agatatccac   4260
atgtgttttt agtaaacaaa ttttgggacc taatgcttca actaactcca gtaattcctt   4320
ggtggtacga acatccaatg aagcacacaa gtttgtttgc ttttcgtgca tgatattaaa   4380
tagcttggca gcaacaggac taggatgagt agcagcacgt tccttatatg tagctttcga   4440
catgatttat cttcgtttcc tgcaggtttt tgttctgtgc agttgggtta agaatactgg   4500
gcaatttcat gtttcttcaa cactacatat gcgtatatat accaatctaa gtctgtgctc   4560
cttccttcgt tcttccttct gttcggagat taccgaatca aaaaaatttc aaagaaaccg   4620
aaatcaaaaa aaagaataaa aaaaaaatga tgaattgaat tgaaaagcgt ggtgcactct   4680
cagtacaatc tgctctgatg ccgcatagtt aagccagccc cgacacccgc caacacccgc   4740
```

```
tgacgcgccc tgacgggctt gtctgctccc ggcatccgct tacagacaag ctgtgaccgt   4800
ctccgggagc tgcatgtgtc agaggttttc accgtcatca ccgaaacgcg cgagacgaaa   4860
gggcctcgtg atacgcctat ttttataggt taatgtcatg ataataatgg tttcttagga   4920
cggatcgctt gcctgtaact tacacgcgcc tcgtatcttt taatgatgga ataatttggg   4980
aatttactct gtgtttattt atttttatgt tttgtatttg gattttagaa agtaaataaa   5040
gaaggtagaa gagttacgga atgaagaaaa aaaaataaac aaaggtttaa aaaatttcaa   5100
caaaaagcgt actttacata tatatttatt agacaagaaa agcagattaa atagatatac   5160
attcgattaa cgataagtaa aatgtaaaat cacaggattt tcgtgtgtgg tcttctacac   5220
agacaagatg aaacaattcg gcattaatac ctgagagcag gaagagcaag ataaaaggta   5280
gtatttgttg gcgatccccc tagagtcttt tacatcttcg gaaaacaaaa actatttttt   5340
ctttaatttc tttttttact ttctattttt aatttatata tttatattaa aaaatttaaa   5400
ttataattat ttttatagca cgtgatgaaa aggacccagg tggcactttt cggggaaatg   5460
tgcgcggaac ccctatttgt ttatttttct aaatacattc aaatatgtat ccgctcatga   5520
gacaataacc ctgataaatg cttcaataat attgaaaaag gaagagtatg agtattcaac   5580
atttccgtgt cgcccttatt cccttttttg cggcattttg ccttcctgtt tttgctcacc   5640
cagaaacgct ggtgaaagta aaagatgctg aagatcagtt gggtgcacga gtgggttaca   5700
tcgaactgga tctcaacagc ggtaagatcc ttgagagttt tcgccccgaa gaacgttttc   5760
caatgatgag cacttttaaa gttctgctat gtggcgcggt attatcccgt attgacgccg   5820
ggcaagagca actcggtcgc cgcatacact attctcagaa tgacttggtt gagtactcac   5880
cagtcacaga aaagcatctt acggatggca tgacagtaag agaattatgc agtgctgcca   5940
taaccatgag tgataacact gcggccaact tacttctgac aacgatcgga ggaccgaagg   6000
agctaaccgc ttttttcac aacatggggg atcatgtaac tcgccttgat cgttgggaac   6060
cggagctgaa tgaagccata ccaaacgacg agcgtgacac cacgatgcct gtagcaatgg   6120
caacaacgtt gcgcaaacta ttaactggcg aactacttac tctagcttcc cggcaacaat   6180
taatagactg gatggaggcg gataaagttg caggaccact tctgcgctcg gcccttccgg   6240
ctggctggtt tattgctgat aaatctggag ccggtgagcg tgggtctcgc ggtatcattg   6300
cagcactggg gccagatggt aagccctccc gtatcgtagt tatctacacg acgggcagtc   6360
aggcaactat ggatgaacga aatagacaga tcgctgagat aggtgcctca ctgattaagc   6420
attggtaact gtcagaccaa gtttactcat atatacttta gattgattta aaacttcatt   6480
tttaatttaa aaggatctag gtgaagatcc tttttgataa tctcatgacc aaaatccctt   6540
aacgtgagtt ttcgttccac tgagcgtcag accccgtaga aaagatcaaa ggatcttctt   6600
gagatccttt ttttctgcgc gtaatctgct gcttgcaaac aaaaaaacca ccgctaccag   6660
cggtggtttg tttgccggat caagagctac caactctttt tccgaaggta actggcttca   6720
gcagagcgca gataccaaat actgtccttc tagtgtagcc gtagttaggc caccacttca   6780
agaactctgt agcaccgcct acatacctcg ctctgctaat cctgttacca gtggctgctg   6840
ccagtggcga taagtcgtgt cttaccgggt tggactcaag acgatagtta ccggataagg   6900
cgcagcggtc gggctgaacg gggggttcgt gcacacagcc cagcttggag cgaacgacct   6960
acaccgaact gagataccta cagcgtgagc attgagaaag cgccacgctt cccgaaggga   7020
gaaaggcgga caggtatccg gtaagcggca gggtcggaac aggagagcgc acgagggagc   7080
ttccaggggg gaacgcctgg tatctttata gtcctgtcgg gtttcgccac ctctgacttg   7140
```

agcgtcgatt tttgtgatgc tcgtcagggg ggccgagcct atggaaaaac gccagcaacg 7200
cggccttttt acggttcctg gccttttgct ggccttttgc tcacatgttc tttcctgcgt 7260
tatcccctga ttctgtggat aaccgtatta ccgcctttga gtgagctgat accgctcgcc 7320
gcagccgaac gaccgagcgc agcgagtcag tgagcgagga agcggaagag cgcccaatac 7380
gcaaaccgcc tctccccgcg cgttggccga ttcattaatg cagctggcac gacaggtttc 7440
ccgactggaa agcgggcagt gagcgcaacg caattaatgt gagttacctc actcattagg 7500
caccccaggc tttacacttt atgcttccgg ctcctatgtt gtgtggaatt gtgagcggat 7560
aacaatttca cacaggaaac agctatgacc atgattacgc caagctcgga attaaccctc 7620
actaaaggga acaaaagctg ggtaccgggc cccccc 7656

<210> SEQ ID NO 22
<211> LENGTH: 7542
<212> TYPE: DNA
<213> ORGANISM: Artificial Sequence
<220> FEATURE:
<223> OTHER INFORMATION: Sequence put together from multiple organisms: Saccharomyces cerevisiae and Rhizopus oryzae

<400> SEQUENCE: 22
tcgagatctc ccgagtttat cattatcaat actgccattt caaagaatac gtaaataatt 60
aatagtagtg attttcctaa ctttatttag tcaaaaaatt ggccttttaa ttctgctgta 120
acccgtacat gcccaaaata gggggcgggt tacacagaat atataacatc ataggtgtct 180
gggtgaacag tttattcctg gcatccacta aatataatgg agcccgcttt ttttaagctg 240
gcatccagaa aaaaaaagaa tcccagcacc aaaatattgt tttcttcacc aaccatcagt 300
tcataggtcc attctcttag cgcaactaca cagaacaggg gcacaaacag gcaaaaaacg 360
ggcacaacct caatggagtg atgcaacctg cttggagtaa atgatgacac aaggcaattg 420
acctacgcat gtatctatct cattttctta caccttctat taccttctgc tctctctgat 480
ttggaaaaag ctgaaaaaaa aggttgaaac cagttccctg aaattattcc cctatttgac 540
taataagtat ataaagacgg taggtattga ttgtaattct gtaaatctat ttcttaaact 600
tcttaaattc tacttttata gttagtcttt tttttagttt taaaacacta agaacttagt 660
ttcgaataaa cacacataaa caaacaaatc tagaatgagg tttccctcca tctttactgc 720
cgttttgttc gcggcttcca gcgcgttggc tgcatctatt ccatctagtg catctgtaca 780
attggactcc tacaattacg atggttccac attttccggc aagatttatg tcaaaaacat 840
cgcttactct aaaaaggtta ctgttgtgta cgcagacggt tctgacaact ggaacaataa 900
cggcaacact attgctgcat cattttcagg cccaatctct ggatcaaatt acgaatactg 960
gacattctca gcatcagtga agggcataaa ggagttctac atcaaatacg aagtttcagg 1020
taagacatat tacgacaata acaactctgc aaactaccaa gtctcaactt ctaaacctac 1080
tacaactact gcagctacaa ccacaactac agctccatca acttctacaa caacccgtcc 1140
atctagttca gagcctgcca ccttccctac tggtaattct accatcagct cttggatcaa 1200
aaagcaggaa gatatttcca gattcgctat gcttagaaac atcaacccac ctggttctgc 1260
cacagggttt atcgccgcat cactctctac cgctggtcca gattactact acgcgtggac 1320
aagagatgcc gctttgacat ctaacgttat cgtttacgaa tacaacacca cattgtctgg 1380
gaataagaca attctaaacg tacttaagga ttacgtcaca ttcagtgtta agacacagtc 1440
tacttcaaca gtttgtaatt gccttggtga accaaagttc aatccagacg gcagtggtta 1500

```
cacaggtgct tggggtagac ctcaaaatga tggtcctgca gaaagagcga ctacatttgt   1560
tctgtttgcc gacagctact tgactcaaac taaggatgcc tcatacgtca ctggtacatt   1620
aaagccagca attttcaaag atctcgatta cgttgttaac gtctggagta acggatgttt   1680
cgatttatgg gaggaggtga acggagttca tttctacacc cttatggtta tgagaaaagg   1740
gctattgttg ggggctgatt tcgcgaagag aaacggtgac tcaactagag cctcaactta   1800
ctcttctact gcttccacaa ttgctaacaa gatatcaagt ttctgggtta gctcaaacaa   1860
ctgggtgcaa gtatcccaat ctgtcacagg aggtgtaagt aaaaaggggt tagacgttag   1920
caccctgtta gctgcgaatc taggatcagt cgatgatgga tttttcactc caggttctga   1980
aaagatatta gctacagctg tggcagtcga agattccttt gccagtctat acccaatcaa   2040
caaaaacctt ccatcatact tggggaacgc tattggaaga taccctgaag atacatacaa   2100
cggtaatggt aactcacaag gcaatccttg gtttctggcg gttaccggct acgcagagtt   2160
gtactataga gcaattaagg aatggatttc taatggaggc gttacagtgt cctctatctc   2220
attgccattt ttcaaaaagt tcgatagctc tgcaacatcc ggtaaaaagt acaccgtagg   2280
tacttctgac ttcaacaatt tagcacaaaa cattgctctt gctgcagatc gtttcctatc   2340
tactgtacaa ctccatgcac caaacaatgg ttcattagca gaggaatttg atagaacaac   2400
aggtttttct accggcgcta gagatttaac atggtcccac gcctcattga taacagcatc   2460
ctatgccaaa gccggtgctc cagctgcata attaattaaa caggcccctt ttcctttgtc   2520
gatatcatgt aattagttat gtcacgctta cattcacgcc ctcctcccac atccgctcta   2580
accgaaaagg aaggagttag acaacctgaa gtctaggtcc ctatttattt ttttatagtt   2640
atgttagtat taagaacgtt atttatattt caaatttttc ttttttttct gtacaaacgc   2700
gtgtacgcat gtaacgggca gacgcggccg ccaccgcggt ggagctccaa ttcgccctat   2760
agtgagtcgt attacaattc actggccgtc gttttacaac gtcgtgactg ggaaaaccct   2820
ggcgttaccc aacttaatcg ccttgcagca catccccctt tcgccagctg gcgtaatagc   2880
gaagaggccc gcaccgatcg cccttcccaa cagttgcgca gcctgaatgg cgaatggcgc   2940
gacgcgccct gtagcggcgc attaagcgcg gcgggtgtgg tggttacgcg cagcgtgacc   3000
gctacacttg ccagcgccct agcgcccgct cctttcgctt tcttcccttc ctttctcgcc   3060
acgttcgccg gctttccccg tcaagctcta aatcgggggc tccctttagg gttccgattt   3120
agtgctttac ggcacctcga ccccaaaaaa cttgattagg gtgatggttc acgtagtggg   3180
ccatcgccct gatagacggt ttttcgccct ttgacgttgg agtccacgtt ctttaatagt   3240
ggactcttgt tccaaactgg aacaacactc aaccctatct cggtctattc ttttgattta   3300
taagggattt tgccgatttc ggcctattgg ttaaaaaatg agctgattta acaaaaattt   3360
aacgcgaatt ttaacaaaat attaacgttt acaatttcct gatgcggtat tttctcctta   3420
cgcatctgtg cggtatttca caccgcaggg taataactga tataattaaa ttgaagctct   3480
aatttgtgag tttagtatac atgcatttac ttataataca gtttttttagt tttgctggcc   3540
gcatcttctc aaatatgctt cccagcctgc ttttctgtaa cgttcaccct ctaccttagc   3600
atcccttccc tttgcaaata gtcctcttcc aacaataata atgtcagatc ctgtagagac   3660
cacatcatcc acggttctat actgttgacc caatgcgtct cccttgtcat ctaaacccac   3720
accgggtgtc ataatcaacc aatcgtaacc ttcatctctt ccacccatgt ctctttgagc   3780
aataaagccg ataacaaaat ctttgtcgct cttcgcaatg tcaacagtac ccttagtata   3840
```

```
ttctccagta gatagggagc ccttgcatga caattctgct aacatcaaaa ggcctctagg   3900
ttcctttgtt acttcttctg ccgcctgctt caaaccgcta acaatacctg ggcccaccac   3960
accgtgtgca ttcgtaatgt ctgcccattc tgctattctg tatacacccg cagagtactg   4020
caatttgact gtattaccaa tgtcagcaaa ttttctgtct tcgaagagta aaaaattgta   4080
cttggcggat aatgccttta gcggcttaac tgtgccctcc atggaaaaat cagtcaagat   4140
atccacatgt gtttttagta aacaaatttt gggacctaat gcttcaacta actccagtaa   4200
ttccttggtg gtacgaacat ccaatgaagc acacaagttt gtttgctttt cgtgcatgat   4260
attaaatagc ttggcagcaa caggactagg atgagtagca gcacgttcct tatatgtagc   4320
tttcgacatg atttatcttc gtttcctgca ggtttttgtt ctgtgcagtt gggttaagaa   4380
tactgggcaa tttcatgttt cttcaacact acatatgcgt atatatacca atctaagtct   4440
gtgctccttc cttcgttctt ccttctgttc ggagattacc gaatcaaaaa aatttcaaag   4500
aaaccgaaat caaaaaaaag aataaaaaaa aaatgatgaa ttgaattgaa aagcgtggtg   4560
cactctcagt acaatctgct ctgatgccgc atagttaagc cagccccgac acccgccaac   4620
acccgctgac gcgccctgac gggcttgtct gctcccggca tccgcttaca gacaagctgt   4680
gaccgtctcc gggagctgca tgtgtcagag gttttcaccg tcatcaccga aacgcgcgag   4740
acgaaagggc ctcgtgatac gcctattttt ataggttaat gtcatgataa taatggtttc   4800
ttaggacgga tcgcttgcct gtaacttaca cgcgcctcgt atcttttaat gatggaataa   4860
tttgggaatt tactctgtgt ttatttattt ttatgttttg tatttggatt ttagaaagta   4920
aataaagaag gtagaagagt tacggaatga agaaaaaaaa ataaacaaag gtttaaaaaa   4980
tttcaacaaa aagcgtactt tacatatata tttattagac aagaaaagca gattaaatag   5040
atatacattc gattaacgat aagtaaaatg taaaatcaca ggattttcgt gtgtggtctt   5100
ctacacagac aagatgaaac aattcggcat taatacctga gagcaggaag agcaagataa   5160
aaggtagtat ttgttggcga tccccctaga gtcttttaca tcttcggaaa acaaaaacta   5220
ttttttcttt aatttctttt tttactttct atttttaatt tatatattta tattaaaaaa   5280
tttaaattat aattattttt atagcacgtg atgaaaagga cccaggtggc acttttcggg   5340
gaaatgtgcg cggaacccct atttgtttat ttttctaaat acattcaaat atgtatccgc   5400
tcatgagaca ataaccctga taaatgcttc aataatattg aaaaaggaag agtatgagta   5460
ttcaacattt ccgtgtcgcc cttattccct tttttgcggc attttgcctt cctgtttttg   5520
ctcacccaga aacgctggtg aaagtaaaag atgctgaaga tcagttgggt gcacgagtgg   5580
gttacatcga actggatctc aacagcggta agatccttga gagttttcgc cccgaagaac   5640
gttttccaat gatgagcact tttaaagttc tgctatgtgg cgcggtatta tcccgtattg   5700
acgccgggca agagcaactc ggtcgccgca tacactattc tcagaatgac ttggttgagt   5760
actcaccagt cacagaaaag catcttacgg atggcatgac agtaagagaa ttatgcagtg   5820
ctgccataac catgagtgat aacactgcgg ccaacttact tctgacaacg atcggaggac   5880
cgaaggagct aaccgctttt ttcacaaca tgggggatca tgtaactcgc cttgatcgtt   5940
gggaaccgga gctgaatgaa gccataccaa acgacgagcg tgacaccacg atgcctgtag   6000
caatggcaac aacgttgcgc aaactattaa ctggcgaact acttactcta gcttcccggc   6060
aacaattaat agactggatg gaggcggata aagttgcagg accacttctg cgctcggccc   6120
ttccggctgg ctggtttatt gctgataaat ctggagccgg tgagcgtggg tctcgcggta   6180
tcattgcagc actggggcca gatggtaagc cctcccgtat cgtagttatc tacacgacgg   6240
```

```
gcagtcaggc aactatggat gaacgaaata gacagatcgc tgagataggt gcctcactga   6300

ttaagcattg gtaactgtca gaccaagttt actcatatat actttagatt gatttaaaac   6360

ttcattttta atttaaaagg atctaggtga agatcctttt tgataatctc atgaccaaaa   6420

tcccttaacg tgagttttcg ttccactgag cgtcagaccc cgtagaaaag atcaaaggat   6480

cttcttgaga tccttttttt ctgcgcgtaa tctgctgctt gcaaacaaaa aaaccaccgc   6540

taccagcggt ggtttgtttg ccggatcaag agctaccaac tctttttccg aaggtaactg   6600

gcttcagcag agcgcagata ccaaatactg tccttctagt gtagccgtag ttaggccacc   6660

acttcaagaa ctctgtagca ccgcctacat acctcgctct gctaatcctg ttaccagtgg   6720

ctgctgccag tggcgataag tcgtgtctta ccgggttgga ctcaagacga tagttaccgg   6780

ataaggcgca gcggtcgggc tgaacggggg gttcgtgcac acagcccagc ttggagcgaa   6840

cgacctacac cgaactgaga tacctacagc gtgagcattg agaaagcgcc acgcttcccg   6900

aagggagaaa ggcggacagg tatccggtaa gcggcagggt cggaacagga gagcgcacga   6960

gggagcttcc agggggaaac gcctggtatc tttatagtcc tgtcgggttt cgccacctct   7020

gacttgagcg tcgatttttg tgatgctcgt caggggggcc gagcctatgg aaaaacgcca   7080

gcaacgcggc ctttttacgg ttcctggcct tttgctggcc ttttgctcac atgttctttc   7140

ctgcgttatc ccctgattct gtggataacc gtattaccgc ctttgagtga gctgataccg   7200

ctcgccgcag ccgaacgacc gagcgcagcg agtcagtgag cgaggaagcg gaagagcgcc   7260

caatacgcaa accgcctctc cccgcgcgtt ggccgattca ttaatgcagc tggcacgaca   7320

ggtttcccga ctggaaagcg ggcagtgagc gcaacgcaat taatgtgagt tacctcactc   7380

attaggcacc ccaggcttta cactttatgc ttccggctcc tatgttgtgt ggaattgtga   7440

gcggataaca atttcacaca ggaaacagct atgaccatga ttacgccaag ctcggaatta   7500

accctcacta aagggaacaa aagctgggta ccgggccccc cc                      7542
```

```
<210> SEQ ID NO 23
<211> LENGTH: 7545
<212> TYPE: DNA
<213> ORGANISM: Artificial Sequence
<220> FEATURE:
<223> OTHER INFORMATION: Sequence put together from multiple organisms:
      Saccharomyces cerevisiae and Rhizopus oryzae

<400> SEQUENCE: 23
```

```
tcgagatctc ccgagtttat cattatcaat actgccattt caaagaatac gtaaataatt     60

aatagtagtg attttcctaa ctttatttag tcaaaaaatt ggccttttaa ttctgctgta    120

acccgtacat gcccaaaata gggggcgggt tacacagaat atataacatc ataggtgtct    180

gggtgaacag tttattcctg gcatccacta aatataatgg agcccgcttt ttttaagctg    240

gcatccagaa aaaaaagaa tcccagcacc aaaatattgt tttcttcacc aaccatcagt    300

tcataggtcc attctcttag cgcaactaca cagaacaggg gcacaaacag gcaaaaaacg    360

ggcacaacct caatggagtg atgcaacctg cttggagtaa atgatgacac aaggcaattg    420

acctacgcat gtatctatct cattttctta caccttctat taccttctgc tctctctgat    480

ttggaaaaag ctgaaaaaaa aggttgaaac cagttccctg aaattattcc cctatttgac    540

taataagtat ataaagacgg taggtattga ttgtaattct gtaaatctat ttcttaaact    600

tcttaaattc tacttttata gttagtcttt tttttagttt taaaacacta agaacttagt    660

ttcgaataaa cacacataaa caaacaaatc tagaatggtg gcctggtgga gtctgttcct    720
```

```
ttacgggtta caagtggctg cgcccgctct ggcagcatct attccatcta gtgcatctgt    780

acaattggac tcctacaatt acgatggttc cacattttcc ggcaagattt atgtcaaaaa    840

catcgcttac tctaaaaagg ttactgttgt gtacgcagac ggttctgaca actggaacaa    900

taacggcaac actattgctg catcattttc aggcccaatc tctggatcaa attacgaata    960

ctggacattc tcagcatcag tgaagggcat aaaggagttc tacatcaaat acgaagtttc   1020

aggtaagaca tattacgaca ataacaactc tgcaaactac caagtctcaa cttctaaacc   1080

tactacaact actgcagcta caaccacaac tacagctcca tcaacttcta caacaacccg   1140

tccatctagt tcagagcctg ccaccttccc tactggtaat tctaccatca gctcttggat   1200

caaaaagcag gaagatattt ccagattcgc tatgcttaga aacatcaacc cacctggttc   1260

tgccacaggg tttatcgccg catcactctc taccgctggt ccagattact actacgcgtg   1320

gacaagagat gccgctttga catctaacgt tatcgtttac gaatacaaca ccacattgtc   1380

tgggaataag acaattctaa acgtacttaa ggattacgtc acattcagtg ttaagacaca   1440

gtctacttca acagtttgta attgccttgg tgaaccaaag ttcaatccag acggcagtgg   1500

ttacacaggt gcttggggta gacctcaaaa tgatggtcct gcagaaagag cgactacatt   1560

tgttctgttt gccgacagct acttgactca aactaaggat gcctcatacg tcactggtac   1620

attaaagcca gcaattttca aagatctcga ttacgttgtt aacgtctgga gtaacggatg   1680

tttcgattta tgggaggagg tgaacggagt tcatttctac acccttatgg ttatgagaaa   1740

agggctattg ttgggggctg atttcgcgaa gagaaacggt gactcaacta gagcctcaac   1800

ttactcttct actgcttcca caattgctaa caagatatca agtttctggg ttagctcaaa   1860

caactgggtg caagtatccc aatctgtcac aggaggtgta agtaaaaagg ggttagacgt   1920

tagcaccctg ttagctgcga atctaggatc agtcgatgat ggatttttca ctccaggttc   1980

tgaaaagata ttagctacag ctgtggcagt cgaagattcc tttgccagtc tatacccaat   2040

caacaaaaac cttccatcat acttggggaa cgctattgga agataccctg aagatacata   2100

caacggtaat ggtaactcac aaggcaatcc ttggtttctg gcggttaccg gctacgcaga   2160

gttgtactat agagcaatta aggaatggat ttctaatgga ggcgttacag tgtcctctat   2220

ctcattgcca tttttcaaaa agttcgatag ctctgcaaca tccggtaaaa agtacaccgt   2280

aggtacttct gacttcaaca atttagcaca aaacattgct cttgctgcag atcgtttcct   2340

atctactgta caactccatg caccaaacaa tggttcatta gcagaggaat ttgatagaac   2400

aacaggtttt tctaccggcg ctagagattt aacatggtcc cacgcctcat tgataacagc   2460

atcctatgcc aaagccggtg ctccagctgc ataattaatt aaacaggccc cttttccttt   2520

gtcgatatca tgtaattagt tatgtcacgc ttacattcac gccctcctcc cacatccgct   2580

ctaaccgaaa aggaaggagt tagacaacct gaagtctagg tccctattta tttttttata   2640

gttatgttag tattaagaac gttatttata tttcaaattt ttcttttttt tctgtacaaa   2700

cgcgtgtacg catgtaacgg gcagacgcgg ccgccaccgc ggtggagctc caattcgccc   2760

tatagtgagt cgtattacaa ttcactggcc gtcgttttac aacgtcgtga ctgggaaaac   2820

cctggcgtta cccaacttaa tcgccttgca gcacatcccc ccttcgccag ctggcgtaat   2880

agcgaagagg cccgcaccga tcgcccttcc caacagttgc gcagcctgaa tggcgaatgg   2940

cgcgacgcgc cctgtagcgg cgcattaagc gcggcgggtg tggtggttac gcgcagcgtg   3000

accgctacac ttgccagcgc cctagcgccc gctcctttcg ctttcttccc ttcctttctc   3060
```

```
gccacgttcg ccggctttcc ccgtcaagct ctaaatcggg ggctcccttt agggttccga   3120
tttagtgctt tacggcacct cgaccccaaa aaacttgatt agggtgatgg ttcacgtagt   3180
gggccatcgc cctgatagac ggtttttcgc cctttgacgt tggagtccac gttctttaat   3240
agtggactct tgttccaaac tggaacaaca ctcaacccta tctcggtcta ttcttttgat   3300
ttataaggga ttttgccgat ttcggcctat tggttaaaaa atgagctgat ttaacaaaaa   3360
tttaacgcga attttaacaa aatattaacg tttacaattt cctgatgcgg tattttctcc   3420
ttacgcatct gtgcggtatt tcacaccgca gggtaataac tgatataatt aaattgaagc   3480
tctaatttgt gagtttagta tacatgcatt tacttataat acagtttttt agttttgctg   3540
gccgcatctt ctcaaatatg cttcccagcc tgcttttctg taacgttcac cctctacctt   3600
agcatccctt ccctttgcaa atagtcctct tccaacaata ataatgtcag atcctgtaga   3660
gaccacatca tccacggttc tatactgttg acccaatgcg tctcccttgt catctaaacc   3720
cacaccgggt gtcataatca accaatcgta accttcatct cttccaccca tgtctctttg   3780
agcaataaag ccgataacaa aatctttgtc gctcttcgca atgtcaacag tacccttagt   3840
atattctcca gtagataggg agcccttgca tgacaattct gctaacatca aaaggcctct   3900
aggttccttt gttacttctt ctgccgcctg cttcaaaccg ctaacaatac ctgggcccac   3960
cacaccgtgt gcattcgtaa tgtctgccca ttctgctatt ctgtatacac ccgcagagta   4020
ctgcaatttg actgtattac caatgtcagc aaattttctg tcttcgaaga gtaaaaaatt   4080
gtacttggcg gataatgcct ttagcggctt aactgtgccc tccatggaaa aatcagtcaa   4140
gatatccaca tgtgttttta gtaaacaaat tttgggacct aatgcttcaa ctaactccag   4200
taattccttg gtggtacgaa catccaatga agcacacaag tttgtttgct tttcgtgcat   4260
gatattaaat agcttggcag caacaggact aggatgagta gcagcacgtt ccttatatgt   4320
agctttcgac atgatttatc ttcgtttcct gcaggttttt gttctgtgca gttgggttaa   4380
gaatactggg caatttcatg tttcttcaac actacatatg cgtatatata ccaatctaag   4440
tctgtgctcc ttccttcgtt cttccttctg ttcggagatt accgaatcaa aaaaatttca   4500
aagaaaccga aatcaaaaaa aagaataaaa aaaaaatgat gaattgaatt gaaaagcgtg   4560
gtgcactctc agtacaatct gctctgatgc cgcatagtta agccagcccc gacacccgcc   4620
aacacccgct gacgcgccct gacgggcttg tctgctcccg gcatccgctt acagacaagc   4680
tgtgaccgtc tccgggagct gcatgtgtca gaggttttca ccgtcatcac cgaaacgcgc   4740
gagacgaaag ggcctcgtga tacgcctatt tttataggtt aatgtcatga taataatggt   4800
ttcttaggac ggatcgcttg cctgtaactt acacgcgcct cgtatctttt aatgatggaa   4860
taatttggga atttactctg tgtttattta tttttatgtt ttgtatttgg attttagaaa   4920
gtaaataaag aaggtagaag agttacggaa tgaagaaaaa aaaataaaca aaggtttaaa   4980
aaatttcaac aaaaagcgta ctttacatat atatttatta gacaagaaaa gcagattaaa   5040
tagatataca ttcgattaac gataagtaaa atgtaaaatc acaggatttt cgtgtgtggt   5100
cttctacaca gacaagatga aacaattcgg cattaatacc tgagagcagg aagagcaaga   5160
taaaaggtag tatttgttgg cgatccccct agagtctttt acatcttcgg aaaacaaaaa   5220
ctattttttc tttaatttct ttttttactt tctattttta atttatatat ttatattaaa   5280
aaatttaaat tataattatt tttatagcac gtgatgaaaa ggacccaggt ggcacttttc   5340
ggggaaatgt gcgcggaacc cctatttgtt tatttttcta aatacattca aatatgtatc   5400
cgctcatgag acaataaccc tgataaatgc ttcaataata ttgaaaaagg aagagtatga   5460
```

```
gtattcaaca tttccgtgtc gcccttattc ccttttttgc ggcattttgc cttcctgttt   5520
ttgctcaccc agaaacgctg gtgaaagtaa aagatgctga agatcagttg ggtgcacgag   5580
tgggttacat cgaactggat ctcaacagcg gtaagatcct tgagagtttt cgccccgaag   5640
aacgttttcc aatgatgagc acttttaaag ttctgctatg tggcgcggta ttatcccgta   5700
ttgacgccgg gcaagagcaa ctcggtcgcc gcatacacta ttctcagaat gacttggttg   5760
agtactcacc agtcacagaa aagcatctta cggatggcat gacagtaaga gaattatgca   5820
gtgctgccat aaccatgagt gataacactg cggccaactt acttctgaca acgatcggag   5880
gaccgaagga gctaaccgct tttttcaca acatgggga tcatgtaact cgccttgatc   5940
gttgggaacc ggagctgaat gaagccatac caaacgacga gcgtgacacc acgatgcctg   6000
tagcaatggc aacaacgttg cgcaaactat taactggcga actacttact ctagcttccc   6060
ggcaacaatt aatagactgg atggaggcgg ataaagttgc aggaccactt ctgcgctcgg   6120
cccttccggc tggctggttt attgctgata aatctggagc cggtgagcgt gggtctcgcg   6180
gtatcattgc agcactgggg ccagatggta agccctcccg tatcgtagtt atctacacga   6240
cgggcagtca ggcaactatg gatgaacgaa atagacagat cgctgagata ggtgcctcac   6300
tgattaagca ttggtaactg tcagaccaag tttactcata tatactttag attgatttaa   6360
aacttcattt ttaatttaaa aggatctagg tgaagatcct ttttgataat ctcatgacca   6420
aaatccctta acgtgagttt tcgttccact gagcgtcaga ccccgtagaa aagatcaaag   6480
gatcttcttg agatcctttt tttctgcgcg taatctgctg cttgcaaaca aaaaaaccac   6540
cgctaccagc ggtggtttgt ttgccggatc aagagctacc aactcttttt ccgaaggtaa   6600
ctggcttcag cagagcgcag ataccaaata ctgtccttct agtgtagccg tagttaggcc   6660
accacttcaa gaactctgta gcaccgccta catacctcgc tctgctaatc ctgttaccag   6720
tggctgctgc cagtggcgat aagtcgtgtc ttaccgggtt ggactcaaga cgatagttac   6780
cggataaggc gcagcggtcg ggctgaacgg ggggttcgtg cacacagccc agcttggagc   6840
gaacgaccta caccgaactg agatacctac agcgtgagca ttgagaaagc gccacgcttc   6900
ccgaagggag aaaggcggac aggtatccgg taagcggcag ggtcggaaca ggagagcgca   6960
cgagggagct tccaggggg aacgcctggt atctttatag tcctgtcggg tttcgccacc   7020
tctgacttga gcgtcgattt ttgtgatgct cgtcaggggg gccgagccta tggaaaaacg   7080
ccagcaacgc ggccttttta cggttcctgg ccttttgctg gccttttgct cacatgttct   7140
ttcctgcgtt atcccctgat tctgtggata accgtattac cgcctttgag tgagctgata   7200
ccgctcgccg cagccgaacg accgagcgca gcgagtcagt gagcgaggaa gcggaagagc   7260
gcccaatacg caaaccgcct ctccccgcgc gttggccgat tcattaatgc agctggcacg   7320
acaggtttcc cgactggaaa gcgggcagtg agcgcaacgc aattaatgtg agttacctca   7380
ctcattaggc accccaggct ttacacttta tgcttccggc tcctatgttg tgtggaattg   7440
tgagcggata acaatttcac acaggaaaca gctatgacca tgattacgcc aagctcggaa   7500
ttaaccctca ctaaagggaa caaaagctgg gtaccgggcc ccccc                   7545
```

<210> SEQ ID NO 24
<211> LENGTH: 7539
<212> TYPE: DNA
<213> ORGANISM: Artificial Sequence
<220> FEATURE:
<223> OTHER INFORMATION: Sequence put together from multiple organisms: Saccharomyces cerevisiae and Rhizopus oryzae

<400> SEQUENCE: 24

```
tcgagatctc ccgagtttat cattatcaat actgccattt caaagaatac gtaaataatt     60
aatagtagtg attttcctaa ctttatttag tcaaaaaatt ggccttttaa ttctgctgta    120
acccgtacat gcccaaaata gggggcgggt tacacagaat atataacatc ataggtgtct    180
gggtgaacag tttattcctg gcatccacta aatataatgg agcccgcttt ttttaagctg    240
gcatccagaa aaaaaaagaa tcccagcacc aaaatattgt ttttcttcacc aaccatcagt    300
tcataggtcc attctcttag cgcaactaca cagaacaggg gcacaaacag gcaaaaaacg    360
ggcacaacct caatggagtg atgcaacctg cttggagtaa atgatgacac aaggcaattg    420
acctacgcat gtatctatct cattttctta caccttctat taccttctgc tctctctgat    480
ttggaaaaag ctgaaaaaaa aggttgaaac cagttccctg aaattattcc cctatttgac    540
taataagtat ataaagacgg taggtattga ttgtaattct gtaaatctat ttcttaaact    600
tcttaaattc tacttttata gttagtcttt tttttagttt taaaacacta agaacttagt    660
ttcgaataaa cacacataaa caaacaaatc tagaatgagc tttaggagtc ttctggccct    720
tagtgggctg gtctgttctg gcttggcagc atctattcca tctagtgcat ctgtacaatt    780
ggactcctac aattacgatg gttccacatt ttccggcaag atttatgtca aaaacatcgc    840
ttactctaaa aaggttactg ttgtgtacgc agacggttct gacaactgga acaataacgg    900
caacactatt gctgcatcat tttcaggccc aatctctgga tcaaattacg aatactggac    960
attctcagca tcagtgaagg gcataaagga gttctacatc aaatacgaag tttcaggtaa   1020
gacatattac gacaataaca actctgcaaa ctaccaagtc tcaacttcta aacctactac   1080
aactactgca gctacaacca caactacagc tccatcaact tctacaacaa cccgtccatc   1140
tagttcagag cctgccacct tccctactgg taattctacc atcagctctt ggatcaaaaa   1200
gcaggaagat atttccagat tcgctatgct tagaaacatc aacccacctg gttctgccac   1260
agggtttatc gccgcatcac tctctaccgc tggtccagat tactactacg cgtggacaag   1320
agatgccgct ttgacatcta acgttatcgt ttacgaatac aacaccacat tgtctgggaa   1380
taagacaatt ctaaacgtac ttaaggatta cgtcacattc agtgttaaga cacagtctac   1440
ttcaacagtt tgtaattgcc ttggtgaacc aaagttcaat ccagacggca gtggttacac   1500
aggtgcttgg ggtagacctc aaaatgatgg tcctgcagaa agagcgacta catttgttct   1560
gtttgccgac agctacttga ctcaaactaa ggatgcctca tacgtcactg gtacattaaa   1620
gccagcaatt ttcaaagatc tcgattacgt tgttaacgtc tggagtaacg gatgtttcga   1680
tttatgggag gaggtgaacg gagttcattt ctacaccctt atggttatga gaaaagggct   1740
attgttgggg gctgatttcg cgaagagaaa cggtgactca actagagcct caacttactc   1800
ttctactgct tccacaattg ctaacaagat atcaagtttc tgggttagct caaacaactg   1860
ggtgcaagta tcccaatctg tcacaggagg tgtaagtaaa aaggggttag acgttagcac   1920
cctgttagct gcgaatctag gatcagtcga tgatggattt ttcactccag gttctgaaaa   1980
gatattagct acagctgtgg cagtcgaaga ttcctttgcc agtctatacc caatcaacaa   2040
aaaccttcca tcatacttgg ggaacgctat tggaagatac cctgaagata catacaacgg   2100
taatggtaac tcacaaggca atccttggtt tctggcggtt accggctacg cagagttgta   2160
ctatagagca attaaggaat ggatttctaa tggaggcgtt acagtgtcct ctatctcatt   2220
gccatttttc aaaaagttcg atagctctgc aacatccggt aaaaagtaca ccgtaggtac   2280
```

```
ttctgacttc aacaatttag cacaaaacat tgctcttgct gcagatcgtt tcctatctac   2340
tgtacaactc catgcaccaa acaatggttc attagcagag gaatttgata gaacaacagg   2400
tttttctacc ggcgctagag atttaacatg gtcccacgcc tcattgataa cagcatccta   2460
tgccaaagcc ggtgctccag ctgcataatt aattaaacag gccccttttc ctttgtcgat   2520
atcatgtaat tagttatgtc acgcttacat tcacgccctc ctcccacatc cgctctaacc   2580
gaaaaggaag gagttagaca acctgaagtc taggtcccta tttatttttt tatagttatg   2640
ttagtattaa gaacgttatt tatatttcaa atttttcttt tttttctgta caaacgcgtg   2700
tacgcatgta acgggcagac gcggccgcca ccgcggtgga gctccaattc gccctatagt   2760
gagtcgtatt acaattcact ggccgtcgtt ttacaacgtc gtgactggga aaaccctggc   2820
gttacccaac ttaatcgcct tgcagcacat ccccccttcg ccagctggcg taatagcgaa   2880
gaggcccgca ccgatcgccc ttcccaacag ttgcgcagcc tgaatggcga atggcgcgac   2940
gcgccctgta gcggcgcatt aagcgcggcg ggtgtggtgg ttacgcgcag cgtgaccgct   3000
acacttgcca gcgccctagc gcccgctcct ttcgctttct tcccttcctt tctcgccacg   3060
ttcgccggct ttccccgtca agctctaaat cgggggctcc ctttagggtt ccgatttagt   3120
gctttacggc acctcgaccc caaaaaactt gattagggtg atggttcacg tagtgggcca   3180
tcgccctgat agacggtttt tcgccctttg acgttggagt ccacgttctt taatagtgga   3240
ctcttgttcc aaactggaac aacactcaac cctatctcgg tctattcttt tgatttataa   3300
gggattttgc cgatttcggc ctattggtta aaaaatgagc tgatttaaca aaaatttaac   3360
gcgaatttta acaaaatatt aacgtttaca atttcctgat gcggtatttt ctccttacgc   3420
atctgtgcgg tatttcacac cgcagggtaa taactgatat aattaaattg aagctctaat   3480
ttgtgagttt agtatacatg catttactta taatacagtt ttttagtttt gctggccgca   3540
tcttctcaaa tatgcttccc agcctgcttt tctgtaacgt tcaccctcta ccttagcatc   3600
ccttcccttt gcaaatagtc ctcttccaac aataataatg tcagatcctg tagagaccac   3660
atcatccacg gttctatact gttgacccaa tgcgtctccc ttgtcatcta aacccacacc   3720
gggtgtcata atcaaccaat cgtaaccttc atctcttcca cccatgtctc tttgagcaat   3780
aaagccgata acaaaatctt tgtcgctctt cgcaatgtca acagtaccct tagtatattc   3840
tccagtagat agggagccct tgcatgacaa ttctgctaac atcaaaaggc ctctaggttc   3900
ctttgttact tcttctgccg cctgcttcaa accgctaaca atacctgggc ccaccacacc   3960
gtgtgcattc gtaatgtctg cccattctgc tattctgtat acacccgcag agtactgcaa   4020
tttgactgta ttaccaatgt cagcaaattt tctgtcttcg aagagtaaaa aattgtactt   4080
ggcggataat gcctttagcg gcttaactgt gccctccatg gaaaaatcag tcaagatatc   4140
cacatgtgtt tttagtaaac aaattttggg acctaatgct tcaactaact ccagtaattc   4200
cttggtggta cgaacatcca atgaagcaca caagtttgtt tgcttttcgt gcatgatatt   4260
aaatagcttg gcagcaacag gactaggatg agtagcagca cgttccttat atgtagcttt   4320
cgacatgatt tatcttcgtt tcctgcaggt ttttgttctg tgcagttggg ttaagaatac   4380
tgggcaattt catgtttctt caacactaca tatgcgtata tataccaatc taagtctgtg   4440
ctccttcctt cgttcttcct tctgttcgga gattaccgaa tcaaaaaaat ttcaaagaaa   4500
ccgaaatcaa aaaaaagaat aaaaaaaaaa tgatgaattg aattgaaaag cgtggtgcac   4560
tctcagtaca atctgctctg atgccgcata gttaagccag ccccgacacc cgccaacacc   4620
cgctgacgcg ccctgacggg cttgtctgct cccggcatcc gcttacagac aagctgtgac   4680
```

```
cgtctccggg agctgcatgt gtcagaggtt ttcaccgtca tcaccgaaac gcgcgagacg   4740
aaagggcctc gtgatacgcc tatttttata ggttaatgtc atgataataa tggtttctta   4800
ggacggatcg cttgcctgta acttacacgc gcctcgtatc ttttaatgat ggaataattt   4860
gggaatttac tctgtgttta tttattttta tgttttgtat ttggatttta gaaagtaaat   4920
aaagaaggta gaagagttac ggaatgaaga aaaaaaaata aacaaaggtt taaaaaattt   4980
caacaaaaag cgtactttac atatatattt attagacaag aaaagcagat taaatagata   5040
tacattcgat taacgataag taaaatgtaa aatcacagga ttttcgtgtg tggtcttcta   5100
cacagacaag atgaaacaat tcggcattaa tacctgagag caggaagagc aagataaaag   5160
gtagtatttg ttggcgatcc ccctagagtc ttttacatct tcggaaaaca aaaactattt   5220
tttctttaat ttcttttttt actttctatt tttaatttat atatttatat taaaaaattt   5280
aaattataat tatttttata gcacgtgatg aaaaggaccc aggtggcact tttcggggaa   5340
atgtgcgcgg aacccctatt tgtttatttt tctaaataca ttcaaatatg tatccgctca   5400
tgagacaata accctgataa atgcttcaat aatattgaaa aaggaagagt atgagtattc   5460
aacatttccg tgtcgccctt attccctttt ttgcggcatt ttgccttcct gtttttgctc   5520
acccagaaac gctggtgaaa gtaaaagatg ctgaagatca gttgggtgca cgagtgggtt   5580
acatcgaact ggatctcaac agcggtaaga tccttgagag ttttcgcccc gaagaacgtt   5640
ttccaatgat gagcactttt aaagttctgc tatgtggcgc ggtattatcc cgtattgacg   5700
ccgggcaaga gcaactcggt cgccgcatac actattctca gaatgacttg gttgagtact   5760
caccagtcac agaaaagcat cttacggatg gcatgacagt aagagaatta tgcagtgctg   5820
ccataaccat gagtgataac actgcggcca acttacttct gacaacgatc ggaggaccga   5880
aggagctaac cgcttttttt cacaacatgg gggatcatgt aactcgcctt gatcgttggg   5940
aaccggagct gaatgaagcc ataccaaacg acgagcgtga caccacgatg cctgtagcaa   6000
tggcaacaac gttgcgcaaa ctattaactg gcgaactact tactctagct tcccggcaac   6060
aattaataga ctggatggag gcggataaag ttgcaggacc acttctgcgc tcggcccttc   6120
cggctggctg gtttattgct gataaatctg gagccggtga gcgtgggtct cgcggtatca   6180
ttgcagcact ggggccagat ggtaagccct cccgtatcgt agttatctac acgacgggca   6240
gtcaggcaac tatggatgaa cgaaatagac agatcgctga gataggtgcc tcactgatta   6300
agcattggta actgtcagac caagtttact catatatact ttagattgat ttaaaacttc   6360
atttttaatt taaaaggatc taggtgaaga tcctttttga taatctcatg accaaaatcc   6420
cttaacgtga gttttcgttc cactgagcgt cagaccccgt agaaaagatc aaaggatctt   6480
cttgagatcc tttttttctg cgcgtaatct gctgcttgca aacaaaaaaa ccaccgctac   6540
cagcggtggt ttgtttgccg gatcaagagc taccaactct ttttccgaag gtaactggct   6600
tcagcagagc gcagatacca aatactgtcc ttctagtgta gccgtagtta ggccaccact   6660
tcaagaactc tgtagcaccg cctacatacc tcgctctgct aatcctgtta ccagtggctg   6720
ctgccagtgg cgataagtcg tgtcttaccg ggttggactc aagacgatag ttaccggata   6780
aggcgcagcg gtcgggctga acggggggtt cgtgcacaca gcccagcttg gagcgaacga   6840
cctacaccga actgagatac ctacagcgtg agcattgaga aagcgccacg cttcccgaag   6900
ggagaaaggc ggacaggtat ccggtaagcg gcagggtcgg aacaggagag cgcacgaggg   6960
agcttccagg ggggaacgcc tggtatcttt atagtcctgt cgggtttcgc cacctctgac   7020
```

```
ttgagcgtcg atttttgtga tgctcgtcag gggggccgag cctatggaaa aacgccagca   7080

acgcggcctt tttacggttc ctggcctttt gctggccttt tgctcacatg ttctttcctg   7140

cgttatcccc tgattctgtg gataaccgta ttaccgcctt tgagtgagct gataccgctc   7200

gccgcagccg aacgaccgag cgcagcgagt cagtgagcga ggaagcggaa gagcgcccaa   7260

tacgcaaacc gcctctcccc gcgcgttggc cgattcatta atgcagctgg cacgacaggt   7320

ttcccgactg gaaagcgggc agtgagcgca acgcaattaa tgtgagttac ctcactcatt   7380

aggcacccca ggctttacac tttatgcttc cggctcctat gttgtgtgga attgtgagcg   7440

gataacaatt tcacacagga aacagctatg accatgatta cgccaagctc ggaattaacc   7500

ctcactaaag ggaacaaaag ctgggtaccg ggccccccc                          7539
```

```
<210> SEQ ID NO 25
<211> LENGTH: 7533
<212> TYPE: DNA
<213> ORGANISM: Artificial Sequence
<220> FEATURE:
<223> OTHER INFORMATION: Sequence put together from multiple organisms:
      Saccharomyces cerevisiae and Rhizopus oryzae

<400> SEQUENCE: 25
```

```
tcgagatctc ccgagtttat cattatcaat actgccattt caaagaatac gtaaataatt     60

aatagtagtg attttcctaa ctttatttag tcaaaaaatt ggccttttaa ttctgctgta    120

acccgtacat gcccaaaata gggggcgggt tacacagaat atataacatc ataggtgtct    180

gggtgaacag tttattcctg gcatccacta aatataatgg agcccgcttt ttttaagctg    240

gcatccagaa aaaaaaagaa tcccagcacc aaaatattgt tttcttcacc aaccatcagt    300

tcataggtcc attctcttag cgcaactaca cagaacaggg gcacaaacag gcaaaaaacg    360

ggcacaacct caatggagtg atgcaacctg cttggagtaa atgatgacac aaggcaattg    420

acctacgcat gtatctatct cattttctta caccttctat taccttctgc tctctctgat    480

ttggaaaaag ctgaaaaaaa aggttgaaac cagttccctg aaattattcc cctatttgac    540

taataagtat ataaagacgg taggtattga ttgtaattct gtaaatctat ttcttaaact    600

tcttaaattc tacttttata gttagtcttt tttttagttt taaaacacta agaacttagt    660

ttcgaataaa cacacataaa caaacaaatc tagaatgaag ttggcatatt cattattgct    720

accgctggca ggtgtaagtg cagcatctat tccatctagt gcatctgtac aattggactc    780

ctacaattac gatggttcca cattttccgg caagatttat gtcaaaaaca tcgcttactc    840

taaaaaggtt actgttgtgt acgcagacgg ttctgacaac tggaacaata acggcaacac    900

tattgctgca tcattttcag gcccaatctc tggatcaaat tacgaatact ggacattctc    960

agcatcagtg aagggcataa aggagttcta catcaaatac gaagtttcag gtaagacata   1020

ttacgacaat aacaactctg caaactacca agtctcaact tctaaaccta ctacaactac   1080

tgcagctaca accacaacta cagctccatc aacttctaca acaacccgtc catctagttc   1140

agagcctgcc accttcccta ctggtaattc taccatcagc tcttggatca aaaagcagga   1200

agatatttcc agattcgcta tgcttagaaa catcaaccca cctggttctg ccacagggtt   1260

tatcgccgca tcactctcta ccgctggtcc agattactac tacgcgtgga caagagatgc   1320

cgctttgaca tctaacgtta tcgtttacga atacaacacc acattgtctg ggaataagac   1380

aattctaaac gtacttaagg attacgtcac attcagtgtt aagacacagt ctacttcaac   1440

agtttgtaat tgccttggtg aaccaaagtt caatccagac ggcagtggtt acacaggtgc   1500
```

```
ttggggtaga cctcaaaatg atggtcctgc agaaagagcg actacatttg ttctgtttgc   1560
cgacagctac ttgactcaaa ctaaggatgc ctcatacgtc actggtacat taaagccagc   1620
aattttcaaa gatctcgatt acgttgttaa cgtctggagt aacggatgtt tcgatttatg   1680
ggaggaggtg aacggagttc atttctacac ccttatggtt atgagaaaag ggctattgtt   1740
gggggctgat ttcgcgaaga gaaacggtga ctcaactaga gcctcaactt actcttctac   1800
tgcttccaca attgctaaca agatatcaag tttctgggtt agctcaaaca actgggtgca   1860
agtatcccaa tctgtcacag gaggtgtaag taaaaagggg ttagacgtta gcaccctgtt   1920
agctgcgaat ctaggatcag tcgatgatgg atttttcact ccaggttctg aaaagatatt   1980
agctacagct gtggcagtcg aagattcctt tgccagtcta tacccaatca acaaaaacct   2040
tccatcatac ttggggaacg ctattggaag ataccctgaa gatacataca acggtaatgg   2100
taactcacaa ggcaatcctt ggtttctggc ggttaccggc tacgcagagt tgtactatag   2160
agcaattaag gaatggattt ctaatggagg cgttacagtg tcctctatct cattgccatt   2220
tttcaaaaag ttcgatagct ctgcaacatc cggtaaaaag tacaccgtag gtacttctga   2280
cttcaacaat ttagcacaaa acattgctct tgctgcagat cgtttcctat ctactgtaca   2340
actccatgca ccaaacaatg gttcattagc agaggaattt gatagaacaa caggtttttc   2400
taccggcgct agagatttaa catggtccca cgcctcattg ataacagcat cctatgccaa   2460
agccggtgct ccagctgcat aattaattaa acaggcccct tttcctttgt cgatatcatg   2520
taattagtta tgtcacgctt acattcacgc cctcctccca catccgctct aaccgaaaag   2580
gaaggagtta gacaacctga agtctaggtc cctatttatt tttttatagt tatgttagta   2640
ttaagaacgt tatttatatt tcaaattttt cttttttttc tgtacaaacg cgtgtacgca   2700
tgtaacgggc agacgcggcc gccaccgcgg tggagctcca attcgcccta tagtgagtcg   2760
tattacaatt cactggccgt cgttttacaa cgtcgtgact gggaaaaccc tggcgttacc   2820
caacttaatc gccttgcagc acatccccct ttcgccagct ggcgtaatag cgaagaggcc   2880
cgcaccgatc gcccttccca acagttgcgc agcctgaatg gcgaatggcg cgacgcgccc   2940
tgtagcggcg cattaagcgc ggcgggtgtg gtggttacgc gcagcgtgac cgctacactt   3000
gccagcgccc tagcgcccgc tcctttcgct ttcttccctt cctttctcgc cacgttcgcc   3060
ggctttcccc gtcaagctct aaatcggggg ctccctttag ggttccgatt tagtgcttta   3120
cggcacctcg accccaaaaa acttgattag ggtgatggtt cacgtagtgg gccatcgccc   3180
tgatagacgg tttttcgccc tttgacgttg gagtccacgt tctttaatag tggactcttg   3240
ttccaaactg gaacaacact caaccctatc tcggtctatt cttttgattt ataagggatt   3300
ttgccgattt cggcctattg gttaaaaaat gagctgattt aacaaaaatt taacgcgaat   3360
tttaacaaaa tattaacgtt tacaatttcc tgatgcggta ttttctcctt acgcatctgt   3420
gcggtatttc acaccgcagg gtaataactg atataattaa attgaagctc taatttgtga   3480
gtttagtata catgcattta cttataatac agtttttttag ttttgctggc cgcatcttct   3540
caaatatgct tcccagcctg cttttctgta acgttcaccc tctaccttag catcccttcc   3600
ctttgcaaat agtcctcttc caacaataat aatgtcagat cctgtagaga ccacatcatc   3660
cacggttcta tactgttgac ccaatgcgtc tcccttgtca tctaaaccca caccgggtgt   3720
cataatcaac caatcgtaac cttcatctct tccacccatg tctctttgag caataaagcc   3780
gataacaaaa tctttgtcgc tcttcgcaat gtcaacagta cccttagtat attctccagt   3840
agatagggag cccttgcatg acaattctgc taacatcaaa aggcctctag gttcctttgt   3900
```

```
tacttcttct gccgcctgct tcaaaccgct aacaatacct gggcccacca caccgtgtgc   3960
attcgtaatg tctgcccatt ctgctattct gtatacaccc gcagagtact gcaatttgac   4020
tgtattacca atgtcagcaa atttctgtc ttcgaagagt aaaaaattgt acttggcgga   4080
taatgccttt agcggcttaa ctgtgccctc catggaaaaa tcagtcaaga tatccacatg   4140
tgtttttagt aaacaaattt tgggacctaa tgcttcaact aactccagta attccttggt   4200
ggtacgaaca tccaatgaag cacacaagtt tgtttgcttt tcgtgcatga tattaaatag   4260
cttggcagca acaggactag gatgagtagc agcacgttcc ttatatgtag ctttcgacat   4320
gatttatctt cgtttcctgc aggtttttgt tctgtgcagt tgggttaaga atactgggca   4380
atttcatgtt tcttcaacac tacatatgcg tatatatacc aatctaagtc tgtgctcctt   4440
ccttcgttct tccttctgtt cggagattac cgaatcaaaa aaatttcaaa gaaaccgaaa   4500
tcaaaaaaaa gaataaaaaa aaaatgatga attgaattga aaagcgtggt gcactctcag   4560
tacaatctgc tctgatgccg catagttaag ccagccccga cacccgccaa cacccgctga   4620
cgcgccctga cgggcttgtc tgctcccggc atccgcttac agacaagctg tgaccgtctc   4680
cgggagctgc atgtgtcaga ggttttcacc gtcatcaccg aaacgcgcga gacgaaaggg   4740
cctcgtgata cgcctatttt tataggttaa tgtcatgata ataatggttt cttaggacgg   4800
atcgcttgcc tgtaacttac acgcgcctcg tatcttttaa tgatggaata atttgggaat   4860
ttactctgtg tttatttatt tttatgtttt gtatttggat tttagaaagt aaataaagaa   4920
ggtagaagag ttacggaatg aagaaaaaaa aataaacaaa ggtttaaaaa atttcaacaa   4980
aaagcgtact ttacatatat atttattaga caagaaaagc agattaaata gatatacatt   5040
cgattaacga taagtaaaat gtaaaatcac aggattttcg tgtgtggtct tctacacaga   5100
caagatgaaa caattcggca ttaatacctg agagcaggaa gagcaagata aaaggtagta   5160
tttgttggcg atcccctag agtcttttac atcttcggaa aacaaaaact attttttctt   5220
taatttcttt ttttactttc tattttaat ttatatattt atattaaaaa atttaaatta   5280
taattatttt tatagcacgt gatgaaaagg acccaggtgg cacttttcgg ggaaatgtgc   5340
gcggaacccc tatttgttta tttttctaaa tacattcaaa tatgtatccg ctcatgagac   5400
aataaccctg ataaatgctt caataatatt gaaaaaggaa gagtatgagt attcaacatt   5460
tccgtgtcgc ccttattccc ttttttgcgg cattttgcct tcctgttttt gctcacccag   5520
aaacgctggt gaaagtaaaa gatgctgaag atcagttggg tgcacgagtg ggttacatcg   5580
aactggatct caacagcggt aagatccttg agagttttcg ccccgaagaa cgttttccaa   5640
tgatgagcac ttttaaagtt ctgctatgtg gcgcggtatt atcccgtatt gacgccgggc   5700
aagagcaact cggtcgccgc atacactatt ctcagaatga cttggttgag tactcaccag   5760
tcacagaaaa gcatcttacg gatggcatga cagtaagaga attatgcagt gctgccataa   5820
ccatgagtga taacactgcg gccaacttac ttctgacaac gatcggagga ccgaaggagc   5880
taaccgcttt ttttcacaac atgggggatc atgtaactcg ccttgatcgt tgggaaccgg   5940
agctgaatga agccatacca aacgacgagc gtgacaccac gatgcctgta gcaatggcaa   6000
caacgttgcg caaactatta actggcgaac tacttactct agcttcccgg caacaattaa   6060
tagactggat ggaggcggat aaagttgcag gaccacttct gcgctcggcc cttccggctg   6120
gctggtttat tgctgataaa tctggagccg gtgagcgtgg gtctcgcggt atcattgcag   6180
cactggggcc agatggtaag ccctcccgta tcgtagttat ctacacgacg ggcagtcagg   6240
```

caactatgga tgaacgaaat agacagatcg ctgagatagg tgcctcactg attaagcatt 6300
ggtaactgtc agaccaagtt tactcatata tactttagat tgatttaaaa cttcattttt 6360
aatttaaaag gatctaggtg aagatccttt ttgataatct catgaccaaa atcccttaac 6420
gtgagttttc gttccactga gcgtcagacc ccgtagaaaa gatcaaagga tcttcttgag 6480
atcctttttt tctgcgcgta atctgctgct tgcaaacaaa aaaaccaccg ctaccagcgg 6540
tggtttgttt gccggatcaa gagctaccaa ctctttttcc gaaggtaact ggcttcagca 6600
gagcgcagat accaaatact gtccttctag tgtagccgta gttaggccac cacttcaaga 6660
actctgtagc accgcctaca tacctcgctc tgctaatcct gttaccagtg gctgctgcca 6720
gtggcgataa gtcgtgtctt accgggttgg actcaagacg atagttaccg gataaggcgc 6780
agcggtcggg ctgaacgggg ggttcgtgca cacagcccag cttggagcga acgacctaca 6840
ccgaactgag atacctacag cgtgagcatt gagaaagcgc cacgcttccc gaagggagaa 6900
aggcggacag gtatccggta agcggcaggg tcggaacagg agagcgcacg agggagcttc 6960
caggggggaa cgcctggtat ctttatagtc ctgtcgggtt tcgccacctc tgacttgagc 7020
gtcgattttt gtgatgctcg tcaggggggc cgagcctatg gaaaaacgcc agcaacgcgg 7080
cctttttacg gttcctggcc ttttgctggc cttttgctca catgttcttt cctgcgttat 7140
cccctgattc tgtggataac cgtattaccg cctttgagtg agctgatacc gctcgccgca 7200
gccgaacgac cgagcgcagc gagtcagtga gcgaggaagc ggaagagcgc ccaatacgca 7260
aaccgcctct ccccgcgcgt tggccgattc attaatgcag ctggcacgac aggtttcccg 7320
actggaaagc gggcagtgag cgcaacgcaa ttaatgtgag ttacctcact cattaggcac 7380
cccaggcttt acactttatg cttccggctc ctatgttgtg tggaattgtg agcggataac 7440
aatttcacac aggaaacagc tatgaccatg attacgccaa gctcggaatt aaccctcact 7500
aaagggaaca aaagctgggt accgggcccc ccc 7533

<210> SEQ ID NO 26
<211> LENGTH: 7542
<212> TYPE: DNA
<213> ORGANISM: Artificial Sequence
<220> FEATURE:
<223> OTHER INFORMATION: Sequence put together from multiple organisms: Saccharomyces cerevisiae and Rhizopus oryzae

<400> SEQUENCE: 26
tcgagatctc ccgagtttat cattatcaat actgccattt caaagaatac gtaaataatt 60
aatagtagtg attttcctaa ctttatttag tcaaaaaatt ggccttttaa ttctgctgta 120
acccgtacat gcccaaaata gggggcgggt tacacagaat atataacatc ataggtgtct 180
gggtgaacag tttattcctg gcatccacta aatataatgg agcccgcttt ttttaagctg 240
gcatccagaa aaaaaaagaa tcccagcacc aaaatattgt tttcttcacc aaccatcagt 300
tcataggtcc attctcttag cgcaactaca cagaacaggg gcacaaacag gcaaaaaacg 360
ggcacaacct caatggagtg atgcaacctg cttggagtaa atgatgacac aaggcaattg 420
acctacgcat gtatctatct cattttctta caccttctat taccttctgc tctctctgat 480
ttggaaaaag ctgaaaaaaa aggttgaaac cagttccctg aaattattcc cctatttgac 540
taataagtat ataaagacgg taggtattga ttgtaattct gtaaatctat ttcttaaact 600
tcttaaattc tacttttata gttagtcttt tttttagttt taaaacacta agaacttagt 660
ttcgaataaa cacacataaa caaacaaatc tagaatgctt cttcaagcgt tcttgttttt 720

```
actggcaggg tttgctgcaa aaatttcagc cgcatctatt ccatctagtg catctgtaca    780

attggactcc tacaattacg atggttccac attttccggc aagatttatg tcaaaaacat    840

cgcttactct aaaaaggtta ctgttgtgta cgcagacggt tctgacaact ggaacaataa    900

cggcaacact attgctgcat cattttcagg cccaatctct ggatcaaatt acgaatactg    960

gacattctca gcatcagtga agggcataaa ggagttctac atcaaatacg aagtttcagg   1020

taagacatat tacgacaata acaactctgc aaactaccaa gtctcaactt ctaaacctac   1080

tacaactact gcagctacaa ccacaactac agctccatca acttctacaa caacccgtcc   1140

atctagttca gagcctgcca ccttccctac tggtaattct accatcagct cttggatcaa   1200

aaagcaggaa gatatttcca gattcgctat gcttagaaac atcaacccac ctggttctgc   1260

cacagggttt atcgccgcat cactctctac cgctggtcca gattactact acgcgtggac   1320

aagagatgcc gctttgacat ctaacgttat cgtttacgaa tacaacacca cattgtctgg   1380

gaataagaca attctaaacg tacttaagga ttacgtcaca ttcagtgtta agacacagtc   1440

tacttcaaca gtttgtaatt gccttggtga accaaagttc aatccagacg gcagtggtta   1500

cacaggtgct tggggtagac ctcaaaatga tggtcctgca gaaagagcga ctacatttgt   1560

tctgtttgcc gacagctact tgactcaaac taaggatgcc tcatacgtca ctggtacatt   1620

aaagccagca attttcaaag atctcgatta cgttgttaac gtctggagta acggatgttt   1680

cgatttatgg gaggaggtga acggagttca tttctacacc cttatggtta tgagaaaagg   1740

gctattgttg gggctgatt tcgcgaagag aaacggtgac tcaactagag cctcaactta    1800

ctcttctact gcttccacaa ttgctaacaa gatatcaagt ttctgggtta gctcaaacaa   1860

ctgggtgcaa gtatcccaat ctgtcacagg aggtgtaagt aaaaaggggt tagacgttag   1920

caccctgtta gctgcgaatc taggatcagt cgatgatgga tttttcactc caggttctga   1980

aaagatatta gctacagctg tggcagtcga agattccttt gccagtctat acccaatcaa   2040

caaaaacctt ccatcatact tggggaacgc tattggaaga taccctgaag atacatacaa   2100

cggtaatggt aactcacaag gcaatccttg gtttctggcg gttaccggct acgcagagtt   2160

gtactataga gcaattaagg aatggatttc taatggaggc gttacagtgt cctctatctc   2220

attgccattt ttcaaaaagt tcgatagctc tgcaacatcc ggtaaaaagt acaccgtagg   2280

tacttctgac ttcaacaatt tagcacaaaa cattgctctt gctgcagatc gtttcctatc   2340

tactgtacaa ctccatgcac caaacaatgg ttcattagca gaggaatttg atagaacaac   2400

aggtttttct accggcgcta gagatttaac atggtcccac gcctcattga taacagcatc   2460

ctatgccaaa gccggtgctc cagctgcata attaattaaa caggcccctt ttcctttgtc   2520

gatatcatgt aattagttat gtcacgctta cattcacgcc ctcctcccac atccgctcta   2580

accgaaaagg aaggagttag acaacctgaa gtctaggtcc ctatttattt ttttatagtt   2640

atgttagtat taagaacgtt atttatattt caaatttttc ttttttttct gtacaaacgc   2700

gtgtacgcat gtaacgggca gacgcggccg ccaccgcggt ggagctccaa ttcgccctat   2760

agtgagtcgt attacaattc actggccgtc gttttacaac gtcgtgactg ggaaaaccct   2820

ggcgttaccc aacttaatcg ccttgcagca catccccct tcgccagctg gcgtaatagc    2880

gaagaggccc gcaccgatcg cccttcccaa cagttgcgca gcctgaatgg cgaatggcgc   2940

gacgcgccct gtagcggcgc attaagcgcg gcgggtgtgg tggttacgcg cagcgtgacc   3000

gctacacttg ccagcgccct agcgcccgct cctttcgctt tcttcccttc ctttctcgcc   3060

acgttcgccg gctttccccg tcaagctcta aatcgggggc tccctttagg gttccgattt   3120
```

agtgctttac ggcacctcga ccccaaaaaa cttgattagg gtgatggttc acgtagtggg 3180
ccatcgccct gatagacggt ttttcgccct ttgacgttgg agtccacgtt ctttaatagt 3240
ggactcttgt tccaaactgg aacaacactc aaccctatct cggtctattc ttttgattta 3300
taagggattt tgccgatttc ggcctattgg ttaaaaaatg agctgattta acaaaaattt 3360
aacgcgaatt ttaacaaaat attaacgttt acaatttcct gatgcggtat tttctcctta 3420
cgcatctgtg cggtatttca caccgcaggg taataactga tataattaaa ttgaagctct 3480
aatttgtgag tttagtatac atgcatttac ttataataca gtttttttagt tttgctggcc 3540 gcatcttctc aaatatgctt cccagcctgc ttttctgtaa cgttcaccct ctaccttagc 3600
atcccttccc tttgcaaata gtcctcttcc aacaataata atgtcagatc ctgtagagac 3660
cacatcatcc acggttctat actgttgacc caatgcgtct cccttgtcat ctaaacccac 3720
accgggtgtc ataatcaacc aatcgtaacc ttcatctctt ccacccatgt ctctttgagc 3780
aataaagccg ataacaaaat ctttgtcgct cttcgcaatg tcaacagtac ccttagtata 3840
ttctccagta gatagggagc ccttgcatga caattctgct aacatcaaaa ggcctctagg 3900
ttcctttgtt acttcttctg ccgcctgctt caaaccgcta acaatacctg ggcccaccac 3960
accgtgtgca ttcgtaatgt ctgcccattc tgctattctg tatacacccg cagagtactg 4020
caatttgact gtattaccaa tgtcagcaaa ttttctgtct tcgaagagta aaaaattgta 4080
cttggcggat aatgccttta gcggcttaac tgtgccctcc atggaaaaat cagtcaagat 4140
atccacatgt gtttttagta aacaaatttt gggacctaat gcttcaacta actccagtaa 4200
ttccttggtg gtacgaacat ccaatgaagc acacaagttt gtttgctttt cgtgcatgat 4260
attaaatagc ttggcagcaa caggactagg atgagtagca gcacgttcct tatatgtagc 4320
tttcgacatg atttatcttc gtttcctgca ggtttttgtt ctgtgcagtt gggttaagaa 4380
tactgggcaa tttcatgttt cttcaacact acatatgcgt atatatacca atctaagtct 4440
gtgctccttc cttcgttctt ccttctgttc ggagattacc gaatcaaaaa aatttcaaag 4500
aaaccgaaat caaaaaaaag aataaaaaaa aaatgatgaa ttgaattgaa aagcgtggtg 4560
cactctcagt acaatctgct ctgatgccgc atagttaagc cagccccgac acccgccaac 4620
acccgctgac gcgccctgac gggcttgtct gctcccggca tccgcttaca gacaagctgt 4680
gaccgtctcc gggagctgca tgtgtcagag gttttcaccg tcatcaccga aacgcgcgag 4740
acgaaagggc ctcgtgatac gcctattttt ataggttaat gtcatgataa taatggtttc 4800
ttaggacgga tcgcttgcct gtaacttaca cgcgcctcgt atcttttaat gatggaataa 4860
tttgggaatt tactctgtgt ttatttattt ttatgttttg tatttggatt ttagaaagta 4920
aataaagaag gtagaagagt tacggaatga agaaaaaaaa ataaacaaag gtttaaaaaa 4980
tttcaacaaa aagcgtactt tacatatata tttattagac aagaaaagca gattaaatag 5040
atatacattc gattaacgat aagtaaaatg taaaatcaca ggattttcgt gtgtggtctt 5100
ctacacagac aagatgaaac aattcggcat taatacctga gagcaggaag agcaagataa 5160
aaggtagtat ttgttggcga tccccctaga gtcttttaca tcttcggaaa acaaaaacta 5220
ttttttcttt aatttctttt tttactttct atttttaatt tatatattta tattaaaaaa 5280
tttaaattat aattattttt atagcacgtg atgaaaagga cccaggtggc acttttcggg 5340
gaaatgtgcg cggaacccct atttgtttat ttttctaaat acattcaaat atgtatccgc 5400
tcatgagaca ataaccctga taaatgcttc aataatattg aaaaaggaag agtatgagta 5460

```
ttcaacattt ccgtgtcgcc cttattccct tttttgcggc attttgcctt cctgtttttg   5520
ctcacccaga aacgctggtg aaagtaaaag atgctgaaga tcagttgggt gcacgagtgg   5580
gttacatcga actggatctc aacagcggta agatccttga gagttttcgc cccgaagaac   5640
gttttccaat gatgagcact tttaaagttc tgctatgtgg cgcggtatta tcccgtattg   5700
acgccgggca agagcaactc ggtcgccgca tacactattc tcagaatgac ttggttgagt   5760
actcaccagt cacagaaaag catcttacgg atggcatgac agtaagagaa ttatgcagtg   5820
ctgccataac catgagtgat aacactgcgg ccaacttact tctgacaacg atcggaggac   5880
cgaaggagct aaccgctttt ttcacaaca tgggggatca tgtaactcgc cttgatcgtt    5940
gggaaccgga gctgaatgaa gccataccaa acgacgagcg tgacaccacg atgcctgtag   6000
caatggcaac aacgttgcgc aaactattaa ctggcgaact acttactcta gcttcccggc   6060
aacaattaat agactggatg gaggcggata aagttgcagg accacttctg cgctcggccc   6120
ttccggctgg ctggtttatt gctgataaat ctggagccgg tgagcgtggg tctcgcggta   6180
tcattgcagc actggggcca gatggtaagc cctcccgtat cgtagttatc tacacgacgg   6240
gcagtcaggc aactatggat gaacgaaata gacagatcgc tgagataggt gcctcactga   6300
ttaagcattg gtaactgtca gaccaagttt actcatatat actttagatt gatttaaaac   6360
ttcattttta atttaaaagg atctaggtga agatcctttt tgataatctc atgaccaaaa   6420
tcccttaacg tgagttttcg ttccactgag cgtcagaccc cgtagaaaag atcaaaggat   6480
cttcttgaga tccttttttt ctgcgcgtaa tctgctgctt gcaaacaaaa aaaccaccgc   6540
taccagcggt ggtttgtttg ccggatcaag agctaccaac tctttttccg aaggtaactg   6600
gcttcagcag agcgcagata ccaaatactg tccttctagt gtagccgtag ttaggccacc   6660
acttcaagaa ctctgtagca ccgcctacat acctcgctct gctaatcctg ttaccagtgg   6720
ctgctgccag tggcgataag tcgtgtctta ccgggttgga ctcaagacga tagttaccgg   6780
ataaggcgca gcggtcgggc tgaacggggg gttcgtgcac acagcccagc ttggagcgaa   6840
cgacctacac cgaactgaga tacctacagc gtgagcattg agaaagcgcc acgcttcccg   6900
aagggagaaa ggcggacagg tatccggtaa gcggcagggt cggaacagga gagcgcacga   6960
gggagcttcc agggggaaac gcctggtatc tttatagtcc tgtcgggttt cgccacctct   7020
gacttgagcg tcgatttttg tgatgctcgt caggggggcc gagcctatgg aaaaacgcca   7080
gcaacgcggc ctttttacgg ttcctggcct tttgctggcc ttttgctcac atgttctttc   7140
ctgcgttatc ccctgattct gtggataacc gtattaccgc ctttgagtga gctgataccg   7200
ctcgccgcag ccgaacgacc gagcgcagcg agtcagtgag cgaggaagcg gaagagcgcc   7260
caatacgcaa accgcctctc cccgcgcgtt ggccgattca ttaatgcagc tggcacgaca   7320
ggtttcccga ctggaaagcg ggcagtgagc gcaacgcaat taatgtgagt tacctcactc   7380
attaggcacc ccaggcttta cactttatgc ttccggctcc tatgttgtgt ggaattgtga   7440
gcggataaca atttcacaca ggaaacagct atgaccatga ttacgccaag ctcggaatta   7500
accctcacta aagggaacaa aagctgggta ccgggccccc cc                      7542
```

<210> SEQ ID NO 27
<211> LENGTH: 7563
<212> TYPE: DNA
<213> ORGANISM: Artificial Sequence
<220> FEATURE:
<223> OTHER INFORMATION: Sequence put together from multiple organisms: Saccharomyces cerevisiae and Rhizopus oryzae

<400> SEQUENCE: 27

```
tcgagatctc ccgagtttat cattatcaat actgccattt caaagaatac gtaaataatt     60
aatagtagtg attttcctaa ctttatttag tcaaaaaatt ggccttttaa ttctgctgta    120
acccgtacat gcccaaaata gggggcgggt tacacagaat atataacatc ataggtgtct    180
gggtgaacag tttattcctg gcatccacta aatataatgg agcccgcttt ttttaagctg    240
gcatccagaa aaaaaaagaa tcccagcacc aaaatattgt tttcttcacc aaccatcagt    300
tcataggtcc attctcttag cgcaactaca cagaacaggg gcacaaacag gcaaaaaacg    360
ggcacaacct caatggagtg atgcaacctg cttggagtaa atgatgacac aaggcaattg    420
acctacgcat gtatctatct cattttctta caccttctat taccttctgc tctctctgat    480
ttggaaaaag ctgaaaaaaa aggttgaaac cagttccctg aaattattcc cctatttgac    540
taataagtat ataaagacgg taggtattga ttgtaattct gtaaatctat ttcttaaact    600
tcttaaattc tacttttata gttagtcttt tttttagttt taaaacacta agaacttagt    660
ttcgaataaa cacacataaa caaacaaatc tagaatgacc aaaccaactc aggtgttggt    720
aaggtcagtg agtattctgt tcttcattac tttgcttcat ctggtcgtag ctgcatctat    780
tccatctagt gcatctgtac aattggactc ctacaattac gatggttcca cattttccgg    840
caagatttat gtcaaaaaca tcgcttactc taaaaaggtt actgttgtgt acgcagacgg    900
ttctgacaac tggaacaata acggcaacac tattgctgca tcattttcag gcccaatctc    960
tggatcaaat tacgaatact ggacattctc agcatcagtg aagggcataa aggagttcta   1020
catcaaatac gaagtttcag gtaagacata ttacgacaat aacaactctg caaactacca   1080
agtctcaact tctaaaccta ctacaactac tgcagctaca accacaacta cagctccatc   1140
aacttctaca acaacccgtc catctagttc agagcctgcc accttcccta ctggtaattc   1200
taccatcagc tcttggatca aaaagcagga agatatttcc agattcgcta tgcttagaaa   1260
catcaaccca cctggttctg ccacagggtt tatcgccgca tcactctcta ccgctggtcc   1320
agattactac tacgcgtgga caagagatgc cgctttgaca tctaacgtta tcgtttacga   1380
atacaacacc acattgtctg ggaataagac aattctaaac gtacttaagg attacgtcac   1440
attcagtgtt aagacacagt ctacttcaac agtttgtaat tgccttggtg aaccaaagtt   1500
caatccagac ggcagtggtt acacaggtgc ttggggtaga cctcaaaatg atggtcctgc   1560
agaaagagcg actacatttg ttctgtttgc cgacagctac ttgactcaaa ctaaggatgc   1620
ctcatacgtc actggtacat taaagccagc aattttcaaa gatctcgatt acgttgttaa   1680
cgtctggagt aacggatgtt tcgatttatg ggaggaggtg aacggagttc atttctacac   1740
ccttatggtt atgagaaaag ggctattgtt gggggctgat ttcgcgaaga gaaacggtga   1800
ctcaactaga gcctcaactt actcttctac tgcttccaca attgctaaca agatatcaag   1860
tttctgggtt agctcaaaca actgggtgca agtatcccaa tctgtcacag gaggtgtaag   1920
taaaaagggg ttagacgtta gcaccctgtt agctgcgaat ctaggatcag tcgatgatgg   1980
atttttcact ccaggttctg aaaagatatt agctacagct gtggcagtcg aagattcctt   2040
tgccagtcta tacccaatca acaaaaacct tccatcatac ttggggaacg ctattggaag   2100
ataccctgaa gatacataca acggtaatgg taactcacaa ggcaatcctt ggtttctggc   2160
ggttaccggc tacgcagagt tgtactatag agcaattaag gaatggattt ctaatggagg   2220
cgttacagtg tcctctatct cattgccatt tttcaaaaag ttcgatagct ctgcaacatc   2280
cggtaaaaag tacaccgtag gtacttctga cttcaacaat ttagcacaaa acattgctct   2340
```

```
tgctgcagat cgtttcctat ctactgtaca actccatgca ccaaacaatg gttcattagc   2400
agaggaattt gatagaacaa caggtttttc taccggcgct agagatttaa catggtccca   2460
cgcctcattg ataacagcat cctatgccaa agccggtgct ccagctgcat aattaattaa   2520
acaggcccct tttcctttgt cgatatcatg taattagtta tgtcacgctt acattcacgc   2580
cctcctccca catccgctct aaccgaaaag gaaggagtta gacaacctga agtctaggtc   2640
cctatttatt tttttatagt tatgttagta ttaagaacgt tatttatatt tcaaattttt   2700
cttttttttc tgtacaaacg cgtgtacgca tgtaacgggc agacgcggcc gccaccgcgg   2760
tggagctcca attcgcccta tagtgagtcg tattacaatt cactggccgt cgttttacaa   2820
cgtcgtgact gggaaaaccc tggcgttacc caacttaatc gccttgcagc acatcccccc   2880
ttcgccagct ggcgtaatag cgaagaggcc cgcaccgatc gcccttccca acagttgcgc   2940
agcctgaatg gcgaatggcg cgacgcgccc tgtagcggcg cattaagcgc ggcgggtgtg   3000
gtggttacgc gcagcgtgac cgctacactt gccagcgccc tagcgcccgc tcctttcgct   3060
ttcttccctt cctttctcgc cacgttcgcc ggctttcccc gtcaagctct aaatcggggg   3120
ctccctttag ggttccgatt tagtgcttta cggcacctcg accccaaaaa acttgattag   3180
ggtgatggtt cacgtagtgg gccatcgccc tgatagacgg tttttcgccc tttgacgttg   3240
gagtccacgt tctttaatag tggactcttg ttccaaactg gaacaacact caaccctatc   3300
tcggtctatt cttttgattt ataagggatt ttgccgattt cggcctattg gttaaaaaat   3360
gagctgattt aacaaaaatt taacgcgaat tttaacaaaa tattaacgtt tacaatttcc   3420
tgatgcggta ttttctcctt acgcatctgt gcggtatttc acaccgcagg gtaataactg   3480
atataattaa attgaagctc taatttgtga gtttagtata catgcattta cttataatac   3540
agtttttttag ttttgctggc cgcatcttct caaatatgct tcccagcctg cttttctgta   3600
acgttcaccc tctaccttag catcccttcc ctttgcaaat agtcctcttc caacaataat   3660
aatgtcagat cctgtagaga ccacatcatc cacggttcta tactgttgac ccaatgcgtc   3720
tcccttgtca tctaaaccca caccgggtgt cataatcaac caatcgtaac cttcatctct   3780
tccacccatg tctctttgag caataaagcc gataacaaaa tctttgtcgc tcttcgcaat   3840
gtcaacagta cccttagtat attctccagt agatagggag cccttgcatg acaattctgc   3900
taacatcaaa aggcctctag gttcctttgt tacttcttct gccgcctgct tcaaaccgct   3960
aacaatacct gggcccacca caccgtgtgc attcgtaatg tctgcccatt ctgctattct   4020
gtatacaccc gcagagtact gcaatttgac tgtattacca atgtcagcaa attttctgtc   4080
ttcgaagagt aaaaaattgt acttggcgga taatgccttt agcggcttaa ctgtgccctc   4140
catggaaaaa tcagtcaaga tatccacatg tgtttttagt aaacaaattt tgggacctaa   4200
tgcttcaact aactccagta attccttggt ggtacgaaca tccaatgaag cacacaagtt   4260
tgtttgcttt tcgtgcatga tattaaatag cttggcagca acaggactag gatgagtagc   4320
agcacgttcc ttatatgtag ctttcgacat gatttatctt cgtttcctgc aggtttttgt   4380
tctgtgcagt tgggttaaga atactgggca atttcatgtt tcttcaacac tacatatgcg   4440
tatatatacc aatctaagtc tgtgctcctt ccttcgttct tccttctgtt cggagattac   4500
cgaatcaaaa aaatttcaaa gaaaccgaaa tcaaaaaaaa gaataaaaaa aaaatgatga   4560
attgaattga aaagcgtggt gcactctcag tacaatctgc tctgatgccg catagttaag   4620
ccagccccga cacccgccaa cacccgctga cgcgccctga cgggcttgtc tgctcccggc   4680
```

```
atccgcttac agacaagctg tgaccgtctc cgggagctgc atgtgtcaga ggttttcacc   4740
gtcatcaccg aaacgcgcga gacgaaaggg cctcgtgata cgcctatttt tataggttaa   4800
tgtcatgata ataatggttt cttaggacgg atcgcttgcc tgtaacttac acgcgcctcg   4860
tatcttttaa tgatggaata atttgggaat ttactctgtg tttatttatt tttatgtttt   4920
gtatttggat tttagaaagt aaataaagaa ggtagaagag ttacggaatg aagaaaaaaa   4980
aataaacaaa ggtttaaaaa atttcaacaa aaagcgtact ttacatatat atttattaga   5040
caagaaaagc agattaaata gatatacatt cgattaacga taagtaaaat gtaaaatcac   5100
aggattttcg tgtgtggtct tctacacaga caagatgaaa caattcggca ttaatacctg   5160
agagcaggaa gagcaagata aaaggtagta tttgttggcg atccccctag agtcttttac   5220
atcttcggaa aacaaaaact atttttttctt taatttcttt ttttactttc tatttttaat   5280
ttatatattt atattaaaaa atttaaatta taattatttt tatagcacgt gatgaaaagg   5340
acccaggtgg cacttttcgg ggaaatgtgc gcggaacccc tatttgttta tttttctaaa   5400
tacattcaaa tatgtatccg ctcatgagac aataaccctg ataaatgctt caataatatt   5460
gaaaaaggaa gagtatgagt attcaacatt tccgtgtcgc ccttattccc ttttttgcgg   5520
cattttgcct tcctgttttt gctcacccag aaacgctggt gaaagtaaaa gatgctgaag   5580
atcagttggg tgcacgagtg ggttacatcg aactggatct caacagcggt aagatccttg   5640
agagttttcg ccccgaagaa cgttttccaa tgatgagcac ttttaaagtt ctgctatgtg   5700
gcgcggtatt atcccgtatt gacgccgggc aagagcaact cggtcgccgc atacactatt   5760
ctcagaatga cttggttgag tactcaccag tcacagaaaa gcatcttacg gatggcatga   5820
cagtaagaga attatgcagt gctgccataa ccatgagtga taacactgcg gccaacttac   5880
ttctgacaac gatcggagga ccgaaggagc taaccgcttt tttcacaac atgggggatc   5940
atgtaactcg ccttgatcgt tgggaaccgg agctgaatga agccatacca aacgacgagc   6000
gtgacaccac gatgcctgta gcaatggcaa caacgttgcg caaactatta actggcgaac   6060
tacttactct agcttcccgg caacaattaa tagactggat ggaggcggat aaagttgcag   6120
gaccacttct gcgctcggcc cttccggctg gctggtttat tgctgataaa tctggagccg   6180
gtgagcgtgg gtctcgcggt atcattgcag cactggggcc agatggtaag ccctcccgta   6240
tcgtagttat ctacacgacg gggagtcagg caactatgga tgaacgaaat agacagatcg   6300
ctgagatagg tgcctcactg attaagcatt ggtaactgtc agaccaagtt tactcatata   6360
tactttagat tgatttaaaa cttcattttt aatttaaaag gatctaggtg aagatccttt   6420
ttgataatct catgaccaaa atcccttaac gtgagttttc gttccactga gcgtcagacc   6480
ccgtagaaaa gatcaaagga tcttcttgag atcctttttt tctgcgcgta atctgctgct   6540
tgcaaacaaa aaaaccaccg ctaccagcgg tggtttgttt gccggatcaa gagctaccaa   6600
ctctttttcc gaaggtaact ggcttcagca gagcgcagat accaaatact gtccttctag   6660
tgtagccgta gttaggccac cacttcaaga actctgtagc accgcctaca tacctcgctc   6720
tgctaatcct gttaccagtg gctgctgcca gtggcgataa gtcgtgtctt accgggttgg   6780
actcaagacg atagttaccg gataaggcgc agcggtcggg ctgaacgggg ggttcgtgca   6840
cacagcccag cttggagcga acgacctaca ccgaactgag atacctacag cgtgagcatt   6900
gagaaagcgc cacgcttccc gaagggagaa aggcggacag gtatccggta agcggcaggg   6960
tcggaacagg agagcgcacg agggagcttc caggggggaa cgcctggtat ctttatagtc   7020
ctgtcgggtt tcgccacctc tgacttgagc gtcgattttt gtgatgctcg tcaggggggc   7080
```

```
cgagcctatg gaaaaacgcc agcaacgcgg cctttttacg gttcctggcc ttttgctggc   7140
cttttgctca catgttcttt cctgcgttat cccctgattc tgtggataac cgtattaccg   7200
cctttgagtg agctgatacc gctcgccgca gccgaacgac cgagcgcagc gagtcagtga   7260
gcgaggaagc ggaagagcgc ccaatacgca aaccgcctct ccccgcgcgt tggccgattc   7320
attaatgcag ctggcacgac aggtttcccg actggaaagc gggcagtgag cgcaacgcaa   7380
ttaatgtgag ttacctcact cattaggcac cccaggcttt acactttatg cttccggctc   7440
ctatgttgtg tggaattgtg agcggataac aatttcacac aggaaacagc tatgaccatg   7500
attacgccaa gctcggaatt aaccctcact aaagggaaca aaagctgggt accgggcccc   7560
ccc                                                                 7563
```

<210> SEQ ID NO 28
<211> LENGTH: 7539
<212> TYPE: DNA
<213> ORGANISM: Artificial Sequence
<220> FEATURE:
<223> OTHER INFORMATION: Sequence put together from multiple organisms: Saccharomyces cerevisiae and Rhizopus oryzae

<400> SEQUENCE: 28

```
tcgagatctc ccgagtttat cattatcaat actgccattt caaagaatac gtaaataatt     60
aatagtagtg attttcctaa ctttatttag tcaaaaaatt ggccttttaa ttctgctgta    120
acccgtacat gcccaaaata gggggcgggt tacacagaat atataacatc ataggtgtct    180
gggtgaacag tttattcctg gcatccacta aatataatgg agcccgcttt ttttaagctg    240
gcatccagaa aaaaaaagaa tcccagcacc aaaatattgt tttcttcacc aaccatcagt    300
tcataggtcc attctcttag cgcaactaca cagaacaggg gcacaaacag gcaaaaaacg    360
ggcacaacct caatggagtg atgcaacctg cttggagtaa atgatgacac aaggcaattg    420
acctacgcat gtatctatct cattttctta caccttctat taccttctgc tctctctgat    480
ttggaaaaag ctgaaaaaaa aggttgaaac cagttccctg aaattattcc cctatttgac    540
taataagtat ataaagacgg taggtattga ttgtaattct gtaaatctat ttcttaaact    600
tcttaaattc tacttttata gttagtcttt tttttagttt taaaacacta agaacttagt    660
ttcgaataaa cacacataaa caaacaaatc tagaatgaag tgggtaacat tcatctccct    720
tttgttctta ttttctagtg catacagcgc atctattcca tctagtgcat ctgtacaatt    780
ggactcctac aattacgatg gttccacatt ttccggcaag atttatgtca aaaacatcgc    840
ttactctaaa aaggttactg ttgtgtacgc agacggttct gacaactgga acaataacgg    900
caacactatt gctgcatcat tttcaggccc aatctctgga tcaaattacg aatactggac    960
attctcagca tcagtgaagg gcataaagga gttctacatc aaatacgaag tttcaggtaa   1020
gacatattac gacaataaca actctgcaaa ctaccaagtc tcaacttcta aacctactac   1080
aactactgca gctacaacca caactacagc tccatcaact tctacaacaa cccgtccatc   1140
tagttcagag cctgccacct tccctactgg taattctacc atcagctctt ggatcaaaaa   1200
gcaggaagat atttccagat tcgctatgct tagaaacatc aacccacctg gttctgccac   1260
agggtttatc gccgcatcac tctctaccgc tggtccagat tactactacg cgtggacaag   1320
agatgccgct ttgacatcta acgttatcgt ttacgaatac aacaccacat tgtctgggaa   1380
taagacaatt ctaaacgtac ttaaggatta cgtcacattc agtgttaaga cacagtctac   1440
ttcaacagtt tgtaattgcc ttggtgaacc aaagttcaat ccagacggca gtggttacac   1500
```

```
aggtgcttgg ggtagacctc aaaatgatgg tcctgcagaa agagcgacta catttgttct   1560
gtttgccgac agctacttga ctcaaactaa ggatgcctca tacgtcactg gtacattaaa   1620
gccagcaatt ttcaaagatc tcgattacgt tgttaacgtc tggagtaacg gatgtttcga   1680
tttatgggag gaggtgaacg gagttcattt ctacaccctt atggttatga gaaaagggct   1740
attgttgggg gctgatttcg cgaagagaaa cggtgactca actagagcct caacttactc   1800
ttctactgct tccacaattg ctaacaagat atcaagtttc tgggttagct caaacaactg   1860
ggtgcaagta tcccaatctg tcacaggagg tgtaagtaaa aaggggttag acgttagcac   1920
cctgttagct gcgaatctag gatcagtcga tgatggattt ttcactccag gttctgaaaa   1980
gatattagct acagctgtgg cagtcgaaga ttcctttgcc agtctatacc caatcaacaa   2040
aaaccttcca tcatacttgg ggaacgctat tggaagatac cctgaagata catacaacgg   2100
taatggtaac tcacaaggca atccttggtt tctggcggtt accggctacg cagagttgta   2160
ctatagagca attaaggaat ggatttctaa tggaggcgtt acagtgtcct ctatctcatt   2220
gccatttttc aaaaagttcg atagctctgc aacatccggt aaaaagtaca ccgtaggtac   2280
ttctgacttc aacaatttag cacaaaacat tgctcttgct gcagatcgtt tcctatctac   2340
tgtacaactc catgcaccaa acaatggttc attagcagag gaatttgata gaacaacagg   2400
tttttctacc ggcgctagag atttaacatg gtcccacgcc tcattgataa cagcatccta   2460
tgccaaagcc ggtgctccag ctgcataatt aattaaacag gccccttttc ctttgtcgat   2520
atcatgtaat tagttatgtc acgcttacat tcacgccctc ctcccacatc cgctctaacc   2580
gaaaaggaag gagttagaca acctgaagtc taggtcccta tttatttttt tatagttatg   2640
ttagtattaa gaacgttatt tatatttcaa atttttcttt tttttctgta caaacgcgtg   2700
tacgcatgta acgggcagac gcggccgcca ccgcggtgga gctccaattc gccctatagt   2760
gagtcgtatt acaattcact ggccgtcgtt ttacaacgtc gtgactggga aaaccctggc   2820
gttacccaac ttaatcgcct tgcagcacat ccccccttcg ccagctggcg taatagcgaa   2880
gaggcccgca ccgatcgccc ttcccaacag ttgcgcagcc tgaatggcga atggcgcgac   2940
gcgccctgta gcggcgcatt aagcgcggcg ggtgtggtgg ttacgcgcag cgtgaccgct   3000
acacttgcca gcgccctagc gcccgctcct ttcgctttct tcccttcctt tctcgccacg   3060
ttcgccggct ttccccgtca agctctaaat cgggggctcc ctttagggtt ccgatttagt   3120
gctttacggc acctcgaccc caaaaaactt gattagggtg atggttcacg tagtgggcca   3180
tcgccctgat agacggtttt tcgccctttg acgttggagt ccacgttctt taatagtgga   3240
ctcttgttcc aaactggaac aacactcaac cctatctcgg tctattcttt tgatttataa   3300
gggattttgc cgatttcggc ctattggtta aaaaatgagc tgatttaaca aaaatttaac   3360
gcgaatttta acaaaatatt aacgtttaca atttcctgat gcggtatttt ctccttacgc   3420
atctgtgcgg tatttcacac cgcagggtaa taactgatat aattaaattg aagctctaat   3480
ttgtgagttt agtatacatg catttactta taatacagtt ttttagtttt gctggccgca   3540
tcttctcaaa tatgcttccc agcctgcttt tctgtaacgt tcaccctcta ccttagcatc   3600
ccttcccttt gcaaatagtc ctcttccaac aataataatg tcagatcctg tagagaccac   3660
atcatccacg gttctatact gttgacccaa tgcgtctccc ttgtcatcta aacccacacc   3720
gggtgtcata atcaaccaat cgtaaccttc atctcttcca cccatgtctc tttgagcaat   3780
aaagccgata acaaaatctt tgtcgctctt cgcaatgtca acagtaccct tagtatattc   3840
```

```
tccagtagat agggagccct tgcatgacaa ttctgctaac atcaaaaggc ctctaggttc   3900
ctttgttact tcttctgccg cctgcttcaa accgctaaca atacctgggc ccaccacacc   3960
gtgtgcattc gtaatgtctg cccattctgc tattctgtat acacccgcag agtactgcaa   4020
tttgactgta ttaccaatgt cagcaaattt tctgtcttcg aagagtaaaa aattgtactt   4080
ggcggataat gcctttagcg gcttaactgt gccctccatg gaaaaatcag tcaagatatc   4140
cacatgtgtt tttagtaaac aaattttggg acctaatgct tcaactaact ccagtaattc   4200
cttggtggta cgaacatcca atgaagcaca caagtttgtt tgcttttcgt gcatgatatt   4260
aaatagcttg gcagcaacag gactaggatg agtagcagca cgttccttat atgtagcttt   4320
cgacatgatt tatcttcgtt tcctgcaggt ttttgttctg tgcagttggg ttaagaatac   4380
tgggcaattt catgtttctt caacactaca tatgcgtata tataccaatc taagtctgtg   4440
ctccttcctt cgttcttcct tctgttcgga gattaccgaa tcaaaaaaat ttcaaagaaa   4500
ccgaaatcaa aaaaaagaat aaaaaaaaaa tgatgaattg aattgaaaag cgtggtgcac   4560
tctcagtaca atctgctctg atgccgcata gttaagccag ccccgacacc cgccaacacc   4620
cgctgacgcg ccctgacggg cttgtctgct cccggcatcc gcttacagac aagctgtgac   4680
cgtctccggg agctgcatgt gtcagaggtt ttcaccgtca tcaccgaaac gcgcgagacg   4740
aaagggcctc gtgatacgcc tatttttata ggttaatgtc atgataataa tggtttctta   4800
ggacggatcg cttgcctgta acttacacgc gcctcgtatc ttttaatgat ggaataattt   4860
gggaatttac tctgtgttta tttattttta tgttttgtat ttggatttta gaaagtaaat   4920
aaagaaggta gaagagttac ggaatgaaga aaaaaaaata aacaaaggtt taaaaaattt   4980
caacaaaaag cgtactttac atatatattt attagacaag aaaagcagat taaatagata   5040
tacattcgat taacgataag taaaatgtaa aatcacagga ttttcgtgtg tggtcttcta   5100
cacagacaag atgaaacaat tcggcattaa tacctgagag caggaagagc aagataaaag   5160
gtagtatttg ttggcgatcc ccctagagtc ttttacatct tcggaaaaca aaaactattt   5220
tttctttaat ttcttttttt actttctatt tttaatttat atatttatat taaaaaattt   5280
aaattataat tatttttata gcacgtgatg aaaaggaccc aggtggcact tttcggggaa   5340
atgtgcgcgg aacccctatt tgtttatttt tctaaataca ttcaaatatg tatccgctca   5400
tgagacaata accctgataa atgcttcaat aatattgaaa aaggaagagt atgagtattc   5460
aacatttccg tgtcgccctt attccctttt ttgcggcatt ttgccttcct gtttttgctc   5520
acccagaaac gctggtgaaa gtaaaagatg ctgaagatca gttgggtgca cgagtgggtt   5580
acatcgaact ggatctcaac agcggtaaga tccttgagag ttttcgcccc gaagaacgtt   5640
ttccaatgat gagcactttt aaagttctgc tatgtggcgc ggtattatcc cgtattgacg   5700
ccgggcaaga gcaactcggt cgccgcatac actattctca gaatgacttg gttgagtact   5760
caccagtcac agaaaagcat cttacggatg gcatgacagt aagagaatta tgcagtgctg   5820
ccataaccat gagtgataac actgcggcca acttacttct gacaacgatc ggaggaccga   5880
aggagctaac cgcttttttt cacaacatgg gggatcatgt aactcgcctt gatcgttggg   5940
aaccggagct gaatgaagcc ataccaaacg acgagcgtga caccacgatg cctgtagcaa   6000
tggcaacaac gttgcgcaaa ctattaactg gcgaactact tactctagct tcccggcaac   6060
aattaataga ctggatggag gcggataaag ttgcaggacc acttctgcgc tcggcccttc   6120
cggctggctg gtttattgct gataaatctg gagccggtga gcgtgggtct cgcggtatca   6180
ttgcagcact ggggccagat ggtaagccct cccgtatcgt agttatctac acgacgggca   6240
```

```
gtcaggcaac tatggatgaa cgaaatagac agatcgctga gataggtgcc tcactgatta   6300

agcattggta actgtcagac caagtttact catatatact ttagattgat ttaaaacttc   6360

atttttaatt taaaaggatc taggtgaaga tcctttttga taatctcatg accaaaatcc   6420

cttaacgtga gttttcgttc cactgagcgt cagaccccgt agaaaagatc aaaggatctt   6480

cttgagatcc tttttttctg cgcgtaatct gctgcttgca aacaaaaaaa ccaccgctac   6540

cagcggtggt ttgtttgccg gatcaagagc taccaactct ttttccgaag gtaactggct   6600

tcagcagagc gcagatacca aatactgtcc ttctagtgta gccgtagtta ggccaccact   6660

tcaagaactc tgtagcaccg cctacatacc tcgctctgct aatcctgtta ccagtggctg   6720

ctgccagtgg cgataagtcg tgtcttaccg ggttggactc aagacgatag ttaccggata   6780

aggcgcagcg gtcgggctga acggggggtt cgtgcacaca gcccagcttg gagcgaacga   6840

cctacaccga actgagatac ctacagcgtg agcattgaga aagcgccacg cttcccgaag   6900

ggagaaaggc ggacaggtat ccggtaagcg gcagggtcgg aacaggagag cgcacgaggg   6960

agcttccagg gggaaacgcc tggtatcttt atagtcctgt cgggtttcgc cacctctgac   7020

ttgagcgtcg atttttgtga tgctcgtcag gggggcggag cctatggaaa aacgccagca   7080

acgcggcctt tttacggttc ctggcctttt gctggccttt tgctcacatg ttctttcctg   7140

cgttatcccc tgattctgtg gataaccgta ttaccgcctt tgagtgagct gataccgctc   7200

gccgcagccg aacgaccgag cgcagcgagt cagtgagcga ggaagcggaa gagcgcccaa   7260

tacgcaaacc gcctctcccc gcgcgttggc cgattcatta atgcagctgg cacgacaggt   7320

ttcccgactg gaaagcgggc agtgagcgca acgcaattaa tgtgagttac ctcactcatt   7380

aggcacccca ggctttacac tttatgcttc cggctcctat gttgtgtgga attgtgagcg   7440

gataacaatt tcacacagga aacagctatg accatgatta cgccaagctc ggaattaacc   7500

ctcactaaag ggaacaaaag ctgggtaccg ggccccccc                          7539
```

<210> SEQ ID NO 29
<211> LENGTH: 8086
<212> TYPE: DNA
<213> ORGANISM: Artificial Sequence
<220> FEATURE:
<223> OTHER INFORMATION: Sequence put together from multiple organisms: Saccharomyces cerevisiae and Saccharomyces mikatae

<400> SEQUENCE: 29

```
ccgggaaacc atccacttca cgagactgat ctcctctgcc ggaacaccgg gcatctccaa     60

cttataagtt ggagaaataa gagaatttca gattgagaga atgaaaaaaa aaaaaaaaga    120

cagaggagag cataaaaatg gggttcactt tttggtaaag ctatagcatg cctatcacat    180

ataaatagag tgccagtagc gactttttc acactcgaaa tactcttact actgctctct    240

tgttgttttt atcacttctt gtttcttctt ggtaaataga atatcaagct acaaaaagca    300

tacctcgagg ccagaaaaag gaagtgtttc cctccttctt gaattgatgt taccctcata    360

aagcacgtgg cctcttatcg agaaagaaat taccgtcgct cgtgatttgt ttgcaaaaag    420

aacaaaactg aaaaaaccca gacacgctcg acttcctgtc ttcctgttga ttgcagcttc    480

caatttcgtc acacaacaag gtcctagcga cggctcacag gttttgtaac aagcaatcga    540

aggttctgga atggcgggaa agggtttagt accacatgct atgatgccca ctgtgatctc    600

cagagcaaag ttcgttcgat cgtactgtta ctctctctct ttcaaacaga attgtccgaa    660

tcgtgtgaca acaacagcct gttctcacac actcttttct tctaaccaag gggtggttt    720
```

```
agtttagtag aacctcgtga aacttacatt tacatatata taaacttgca taaattggtc    780
aatgcaagaa atacatattt ggtcttttct aattcgtagt ttttcaagtt cttagatgct    840
ttctttttct ctttttaca gatcatcaag gaagtaatta tctacttttt acaagtctag    900
aatgactatc tcttctgctc acccagaaac tgaaccaaag tggtggaaag aggcaacttt    960
ttaccaaatc tacccagctt cattcaagga ctccaatgat gatggttggg gtgatatgaa   1020
aggtattgct tccaaattag aatacattaa ggaattaggt gccgatgcta tttggatttc   1080
tccattctat gattctccac aagacgatat gggttatgac atcgctaact atgaaaaggt   1140
ttggccaacc tatggcacta atgaggactg ttttgcatta attgagaaaa cccacaagtt   1200
gggcatgaag ttcattactg atcttgtcat taatcattgt tcatccgaac atgaatggtt   1260
caaggaatcc agatcctcca aaactaatcc aaaaagagat tggtttttct ggagaccacc   1320
taagggttat gatgctgaag gtaagccaat tccaccaaac aattggaagt cttactttgg   1380
tggttccgca tggaccttcg acgaaaagac ccaagagttt tacttgagat tattctgctc   1440
cacccaacca gatttgaact gggaaaatga agattgtaga aaagcaatct acgaatctgc   1500
agttggctat tggttagatc acggtgttga tggtttcaga attgatgttg gttcacttta   1560
ctcaaaggtt gttggtttgc cagatgcacc agttgttgat aaaaactcta catggcaatc   1620
ttctgaccca tacactctta atggtcctag aatccatgaa tttcatcaag agatgaacca   1680
gttcattaga aatagagtta aggatggtag agaaattatg accgttggtg aaatgcaaca   1740
tgcatctgat gaaactaaga gattatacac atcagcctcc cgtcacgaat tgtctgaatt   1800
attcaacttt tcacacacag acgttggcac atccccatta ttccgttata acttggttcc   1860
attcgaattg aaggactgga aaatcgcatt ggcagaattg tttagatata tcaatggtac   1920
tgattgttgg tctaccatct acttggaaaa ccacgaccaa ccaagatcca tcactagatt   1980
cggtgatgac tctcctaaaa accgtgtcat ttctggtaag ttactttctg tcttattatc   2040
cgccttaacc ggtactttgt acgtctatca aggccaggaa ttgggtcaaa ttaactttaa   2100
gaattggcca gtcgaaaagt atgaagatgt cgaaatcaga aacaactaca atgcaattaa   2160
ggaggaacat ggtgaaaatt cagaggaaat gaaaaagttt ttggaagcta ttgctcttat   2220
ttccagagat cacgctagaa ccccaatgca atggtcaaga gaggaaccta acgctggttt   2280
ctctggtcct tccgccaagc cttggtttta cttaaacgac tccttcagag aaggtattaa   2340
cgttgaagat gaaattaagg acccaaattc cgtccttaac ttctggaagg aagcattgaa   2400
gtttagaaag gcccataagg atattaccgt ttatggttat gactttgagt ttatcgattt   2460
ggataacaaa aagttattct cattcactaa aaagtataac aacaagacct tattcgctgc   2520
tttaaacttc tcttctgatg ctactgattt caaaattcct aatgacgatt cctctttcaa   2580
gttggagttt ggtaactacc caaagaagga agttgacgca tcttctcgta cattgaagcc   2640
ttgggaaggt agaatctaca tctccgagta acctgcaggt ttgccagctt actatccttc   2700
ttgaaaatat gcactctata tcttttagtt cttaattgca acacatagat ttgctgtata   2760
acgaatttta tgctattttt taaatttgga gttcagtgat aaaagtgtca cagcgaattt   2820
cctcacatgt agggaccgaa ttgtttacaa gttctctgta ccaccatgga gacatcaaaa   2880
attgaaaatc tatggaaaga tatggacggt agcaacaaga atatagcacg agccggcgac   2940
tagtaacggc cgccagtgtg ctggaattcg gccggccata acttcgtata atgtatgcta   3000
tacgaagtta tggcaacggt tcatcatctc atggatctgc acatgaacaa acaccagagt   3060
```

-continued

```
caaacgacgt tgaaattgag gctactgcgc caattgatga caatacagac gatgataaca   3120
aaccgaagtt atctgatgta gaaaaggatt agagatgcta agagatagtg atgatatttc   3180
ataaataatg taattctata tatgttaatt accttttttg cgaggcatat ttatggtgaa   3240
ggataagttt tgaccatcaa agaaggttaa tgtggctgtg gtttcagggt ccataaagct   3300
tttcaattca tctttttttt tttgttcttt tttttgattc cggtttcttt gaaatttttt   3360
tgattcggta atctccgagc agaaggaaga acgaaggaag gagcacagac ttagattggt   3420
atatatacgc atatgtggtg ttgaagaaac atgaaattgc ccagtattct taacccaact   3480
gcacagaaca aaaacctgca ggaaacgaag ataaatcatg tcgaaagcta catataagga   3540
acgtgctgct actcatccta gtcctgttgc tgccaagcta tttaatatca tgcacgaaaa   3600
gcaaacaaac ttgtgtgctt cattggatgt tcgtaccacc aaggaattac tggagttagt   3660
tgaagcatta ggtcccaaaa tttgtttact aaaaacacat gtggatatct tgactgattt   3720
ttccatggag ggcacagtta agccgctaaa ggcattatcc gccaagtaca atttttttact   3780
cttcgaagac agaaaatttg ctgacattgg taatacagtc aaattgcagt actctgcggg   3840
tgtatacaga atagcagaat gggcagacat tacgaatgcg cacggtgtgg tgggcccagg   3900
tattgttagc ggtttgaagc aggcggcgga agaagtaaca aaggaaccta gaggcctttt   3960
gatgttagca gaattgtcat gcaagggctc cctagctact ggagaatata ctaagggtac   4020
tgttgacatt gcgaagagcg acaaagattt tgttatcggc tttattgctc aaagagacat   4080
gggtggaaga gatgaaggtt acgattggtt gattatgaca cccggtgtgg gtttagatga   4140
caagggagac gcattgggtc aacagtatag agccgtggat gatgtggtct ctacaggatc   4200
tgacattatt attgttggaa gaggactatt tgcaaaggga agggatgcta aggtagaggg   4260
tgaacgttac agaaaagcag gctgggaagc atatttgaga agatgcggcc agcaaaacta   4320
aaaaactgta ttataagtaa atgcatgtat actaaactca caaattagag cttcaattta   4380
attatatcag ttattacccg ggaatctcgg tcgtaatgat tttataatg acgaaaaaaa    4440
aaaattggaa agaaaaagct tcatggcctt tataaaaagg aaccatccaa tacctcgcca   4500
gaaccaagta acagtatttt acggggcaca aatcaagaac aataagacag gactgtaaag   4560
atggacgcat tgaactccaa agaacaacaa gagttccaaa aagtagtgga acaaaagcaa   4620
atgaaggatt tcatgcgttt gataacttcg tataatgtat gctatacgaa gttatgcggc   4680
cgcctcgaga tctcccctaa accgtggaat atttcggata tccttttgtt gtttccgggt   4740
gtacaatatg gacttcctct tttctggcaa ccaaacccat acatcgggat tcctataata   4800
ccttcgttgg tctccctaac atgtaggtgg cggaggggag atatacaata gaacagatac   4860
cagacaagac ataatgggct aaacaagact acaccaatta cactgcctca ttgatggtgg   4920
tacataacga actaatactg tagccctaga cttgatagcc atcatcatat cgaagtttca   4980
ctaccctttt tccatttgcc atctattgaa gtaataatag gcgcatgcaa cttcttttct   5040
tttttttttct tttctctctc ccccgttgtt gtctcaccat atccgcaatg acaaaaaaat   5100
gatggaagac actaaaggaa aaaattaacg acaaagacag caccaacaga tgtcgttgtt   5160
ccagagctga tgggggggtat ctcgaagcac acgaaacttt ttccttcctt cattcacgca  5220
cactactctc taatgagcaa cggtatacgg ccttccttcc agttacttga atttgaaata   5280
aaaaaagttt gctgtcttgc tatcaagtat aaatagacct gcaattatta atcttttgtt   5340
tcctcgtcat tgttctcgtt ccctttcttc cttgtttctt tttctgcaca atatttcaag   5400
ctataccaag catacaatca actatctcat atacaatgaa gaacttcata tcactggtga   5460
```

```
acaagaaaaa gggtaccctg gatgatagga atagtagcgt tccggaatct tccagtggta   5520
taatacacca acgtggagct ttaaacactg aggattttga agaaggaaag aaagatggtg   5580
cattcgaatt gggtcacctc gaattcacca ccaattcagc ccaattgggt gattcagacg   5640
atgataatga taatgcaatt aagatagcga atgctgccac tgatgaagcc aatgaggcta   5700
atagtgaaga aaaaagcatg accttaaggc aagctttgag aaaatatcca aaggcagccc   5760
tatggtccat cttggtgtct actaccttag tcatggaagg ttatgatact gcgcttttga   5820
gtgcacttta tgcattaccg gttttccaga ggaaattcgg tactatgaat gcggaaggct   5880
cctacgaaat tacctcgcag tggcaaattg gtttgaacat gtgtgtcctt tgtggtgaaa   5940
tgattggttt acagatgacc acttacatgg tcgagttcat gggtaatcgt tacacaatga   6000
ttacggcgct cggcttgttg actgcttata tttttatcct ttactactgc aaaagtttgg   6060
ccatgatcgc tgtagggcaa attctgtctg ctatgccatg ggttgcttc  cagagtctgg   6120
ctgttaccta tgcttcggag gtttgccccc tagcgctgag atattacatg accagttact   6180
ccaatatttg ttggttgttt ggtcaaattt tcgcttctgg tatcatgaaa aactcccagg   6240
agaatttggg agactccgat ttaggctaca agttgccatt tgccttacaa tggatctggc   6300
ctgcaccttt gattattggt atcttctttg ctcctgagtc gccttggtgg ctggtgagaa   6360
agaataagat tgcggaggcc aaaaagtcct tgaatagaat cctgagcggc actgctgccg   6420
agagggagat tcaagtggat atcactttaa agcaaattga gatgaccatt gagaaggaga   6480
gacttctggc atctaaatca gggtcgttct tcaactgttt caaaggcgtt gatggaagaa   6540
gaacaaggct tgcgtgtttg acttgggttg ctcaaaacag tagtggtgcc gttttactag   6600
gttactcgac gtatttcttt gaaagggcag ggatggccac tgacaaggcg tttactttct   6660
cgcttatcca gtactgtcta ggtttagcag gcactctttg ttcctgggtg atatctggcc   6720
gtgttggtag atggagtatc ctggcttatg gtcttgcatt tcaaatggtg tgtctattca   6780
tcattggtgg aatggggttt gcatccggaa gcaatgccag taatggtgct ggtggtctac   6840
tgctggcttt atcgttcttt tacaacgctg gtatcggagc tgtcgtttac tgtattgtgg   6900
ctgaaattcc gtctgcagaa ttaaggacca aaactattgt aatggctcgt atttgctata   6960
atttgatggc cgtcatcaat gccattttaa cgccatatat gctgaacgtg agtgactgga   7020
actggggtgc taaaaccggc ctatactggg gtggtttcac tgcagtcact ttggcttggg   7080
ttatcattga tttgcctgag acaactggta gaacatttag cgaaattaat gagcttttca   7140
atcaaggtgt ccctgctaga aaatttgcat ctactgtagt tgatcctttc gggaagggac   7200
agcgtcaaaa tgattcgcaa gtggataacg tcattgacca gtcctcaagc gcaatgcagc   7260
aagagctaaa tgaagctaac gaattctaat taattaaaca ggcccctttt cctttgtcga   7320
tatcatgtaa ttagttatgt cacgcttaca ttcacgccct cctcccacat ccgctctaac   7380
cgaaaaggaa ggagttagac aacctgaagt ctaggtccct atttattttt ttatagttat   7440
gttagtatta agaacgttat ttatatttca aatttttctt ttttttctgt acaaacgcgt   7500
gtacgcatgt aacgggcaga cgaattcgat atcaagctta tcgataccgt cgacgcggat   7560
ctcttatgtc tttacgattt atagttttca ttatcaagta tgcctatatt agtatatagc   7620
atctttagat gacagtgttc gaagtttcac gaataaaaga taatattcta ctttttgctc   7680
ccaccgcgtt tgctagcacg agtgaacacc atccctcgcc tgtgagttgt acccattcct   7740
ctaaactgta gacatggtag cttcagcagt gttcgttatg tacggcatcc tccaacaaac   7800
```

```
agtcggttat agtttgtcct gctcctctga atcgtctccc tcgatatttc tcattttcct   7860

tcgcatgcca gcattgaaat gatcgaagtt caatgatgaa acggtaattc ttctgtcatt   7920

tactcatctc atctcatcaa gttatataat tctatacgga tgtaattttt cacttttcgt   7980

cttgacgtcc accctataat ttcaattatt gaaccctcac aaatgatgca ctgcaatgta   8040

cacaccctca tatagtttct cagggcttga tcagggttcc gtagag                  8086


<210> SEQ ID NO 30
<211> LENGTH: 8685
<212> TYPE: DNA
<213> ORGANISM: Artificial Sequence
<220> FEATURE:
<223> OTHER INFORMATION: Sequence put together from multiple organisms:
      Saccharomyces cerevisiae, Aspergillus nidulans, and Saccharomyces
      mikatae

<400> SEQUENCE: 30

ccgggaaacc atccacttca cgagactgat ctcctctgcc ggaacaccgg gcatctccaa     60

cttataagtt ggagaaataa gagaatttca gattgagaga atgaaaaaaa aaaaaaaaga    120

cagaggagag cataaaaatg gggttcactt tttggtaaag ctatagcatg cctatcacat    180

ataaatagag tgccagtagc gacttttttc acactcgaaa tactcttact actgctctct    240

tgttgttttt atcacttctt gtttcttctt ggtaaataga atatcaagct acaaaaagca    300

tacctcgagg ccagaaaaag gaagtgtttc cctccttctt gaattgatgt taccctcata    360

aagcacgtgg cctcttatcg agaaagaaat taccgtcgct cgtgatttgt ttgcaaaaag    420

aacaaaactg aaaaaaccca gacacgctcg acttcctgtc ttcctgttga ttgcagcttc    480

caatttcgtc acacaacaag gtcctagcga cggctcacag gttttgtaac aagcaatcga    540

aggttctgga atggcgggaa agggtttagt accacatgct atgatgccca ctgtgatctc    600

cagagcaaag ttcgttcgat cgtactgtta ctctctctct ttcaaacaga attgtccgaa    660

tcgtgtgaca acaacagcct gttctcacac actcttttct tctaaccaag gggtggttt    720

agtttagtag aacctcgtga aacttacatt tacatatata taaacttgca taaattggtc    780

aatgcaagaa atacatattt ggtcttttct aattcgtagt ttttcaagtt cttagatgct    840

ttctttttct cttttttaca gatcatcaag gaagtaatta tctacttttt acaagtctag    900

aatgactatc tcttctgctc acccagaaac tgaaccaaag tggtggaaag aggcaacttt    960

ttaccaaatc tacccagctt cattcaagga ctccaatgat gatggttggg gtgatatgaa   1020

aggtattgct tccaaattag aatacattaa ggaattaggt gccgatgcta tttggatttc   1080

tccattctat gattctccac aagacgatat gggttatgac atcgctaact atgaaaaggt   1140

ttggccaacc tatggcacta atgaggactg ttttgcatta attgagaaaa cccacaagtt   1200

gggcatgaag ttcattactg atcttgtcat taatcattgt tcatccgaac atgaatggtt   1260

caaggaatcc agatcctcca aaactaatcc aaaaagagat tggtttttct ggagaccacc   1320

taagggttat gatgctgaag gtaagccaat tccaccaaac aattggaagt cttactttgg   1380

tggttccgca tggaccttcg acgaaaagac ccaagagttt tacttgagat tattctgctc   1440

cacccaacca gatttgaact gggaaaatga agattgtaga aaagcaatct acgaatctgc   1500

agttggctat tggttagatc acggtgttga tggtttcaga attgatgttg gttcacttta   1560

ctcaaaggtt gttggtttgc cagatgcacc agttgttgat aaaaactcta catggcaatc   1620

ttctgaccca tacactctta atggtcctag aatccatgaa tttcatcaag agatgaacca   1680

gttcattaga aatagagtta aggatggtag agaaattatg accgttggtg aaatgcaaca   1740
```

```
tgcatctgat gaaactaaga gattatacac atcagcctcc cgtcacgaat tgtctgaatt   1800
attcaacttt tcacacacag acgttggcac atccccatta ttccgttata acttggttcc   1860
attcgaattg aaggactgga aaatcgcatt ggcagaattg tttagatata tcaatggtac   1920
tgattgttgg tctaccatct acttggaaaa ccacgaccaa ccaagatcca tcactagatt   1980
cggtgatgac tctcctaaaa accgtgtcat ttctggtaag ttactttctg tcttattatc   2040
cgccttaacc ggtactttgt acgtctatca aggccaggaa ttgggtcaaa ttaactttaa   2100
gaattggcca gtcgaaaagt atgaagatgt cgaaatcaga aacaactaca atgcaattaa   2160
ggaggaacat ggtgaaaatt cagaggaaat gaaaaagttt ttggaagcta ttgctcttat   2220
ttccagagat cacgctagaa ccccaatgca atggtcaaga gaggaaccta acgctggttt   2280
ctctggtcct tccgccaagc cttggtttta cttaaacgac tccttcagag aaggtattaa   2340
cgttgaagat gaaattaagg acccaaattc cgtccttaac ttctggaagg aagcattgaa   2400
gtttagaaag gcccataagg atattaccgt ttatggttat gactttgagt ttatcgattt   2460
ggataacaaa aagttattct cattcactaa aaagtataac aacaagacct tattcgctgc   2520
tttaaacttc tcttctgatg ctactgattt caaaattcct aatgacgatt cctctttcaa   2580
gttggagttt ggtaactacc caaagaagga agttgacgca tcttctcgta cattgaagcc   2640
ttgggaaggt agaatctaca tctccgagta acctgcaggt ttgccagctt actatccttc   2700
ttgaaaatat gcactctata tcttttagtt cttaattgca acacatagat ttgctgtata   2760
acgaatttta tgctattttt taaatttgga gttcagtgat aaaagtgtca cagcgaattt   2820
cctcacatgt agggaccgaa ttgtttacaa gttctctgta ccaccatgga gacatcaaaa   2880
attgaaaatc tatggaaaga tatggacggt agcaacaaga atatagcacg agccggcgac   2940
tagtaacggc cgccagtgtg ctggaattcg gccggccagg ccgcataact tcgtatagca   3000
tacattatac gaagttatcg cctgttaaga tataactgaa aaaagagggg aatttttaga   3060
tactgaaatg atattttaga ataaccagac tatatataag gataaattac aaaaaattaa   3120
ctaatagata agatttaaat ataaaagata tgcaactaga aaagtcttat caatctcctt   3180
atggagtgac gacgttaccc aacaatttac cgacttcttc ggcgatagcc aaagttctct   3240
cttcggacaa tcttctacca ataacttgaa cagcaacagg agcaccgtga taagcctctg   3300
ggtcgtattc ttcttgaacc aaagcatcca attcggaaac agctttaaaa gattcgttct   3360
tcttatcaat attcttatca gcgaaagtga ctgggacgac aacagaggtg aaatccaata   3420
agttaataac ggaggcgtaa ccgtagtatc tgaattgatc gtgtctgaca gcggcggtag   3480
gagtaattgg agcgataata gcgtccaatt ccttaccagc tttttcttca gcttcacgcc   3540
acttttccaa gtattccatt tgatagttcc acttttgtaa atgagtgtcc cacaattcgt   3600
tcatgttaac agccttaata tttgggttca acaagtcctt aatgttaggg atggctggct   3660
caccagaggc agaaatgtct ctcatgacgt cggcagaacc atcagcagca tagatgtggg   3720
aaatcaagtc atgaccgaaa tcatgcttgt atggagtcca tggagtaacg gtgtgaccag   3780
ccttggccaa agcggcaacg gtagtttcga caccacgtaa aattggtggg tgtggcaaga   3840
cgttaccgtc gaaattgtaa taaccaatgt tcaaaccacc attcttaatc ttagaggcaa   3900
tgatgtcaga ttcagattgt ctccatggca ttgggatgac cttagagtcg tacttccaag   3960
gttcttgacc caagacagat ttggtgaaca atctcaagtc ttcgacggag tgagtgatag   4020
gaccaacgac ggagtgaacg gtttcttgac cttccataga gttagccatt ttagcatatg   4080
```

```
gcaatctacc gtgagatggt ctcaaaccgt ataaaaagtt gaaagcagct gggactctaa   4140
tggaaccacc aatgtcagta ccgacaccaa taacaccacc tctaatacca acaatagcac   4200
cttcaccacc agaagaacca ccacaggacc aatttttgtt tcttggattg acagttctac   4260
caatgatgtt gttgacggtt tcacagacca tcaaggtttg tgggacagag gtcttaacgt   4320
agaaaacagc accagctttt ctcaacatgg tggttaagac ggaatcacct tcatcgtatt   4380
tgtttaacca ggaaatgtaa cccatggagg tttcgtaacc cttaacacgc aattggtcct   4440
ttaaagagat tggtaaaccg tgtaatggac caactggtct cttatgctta gcgtagtatt   4500
catctaattc tctagcttga gctaaagcag catctgggaa gaattcgtga gcacagttgg   4560
ttaattgttg agcaatagca gctctcttac aaaaagccaa agtgacttca acagaagtca   4620
actcaccagc ggccaacttg gagaccaaat cagcagcaga ggcttcggta atcttcaatt   4680
cagcctcaga caaaataccg gacttctttg ggaaatcaat aacggaatct tcggcaggca   4740
aagtttgaac cttccattcg tcaggaatgg ttttagccaa acgggcacgt ttgtcggcgg   4800
ccaattcttc ccaggattgt ggcattttgt aattaaaact tagattagat tgctatgctt   4860
tctttctaat gagcaagaag taaaaaaagt tgtaatagaa caagaaaaac gaaactgaaa   4920
cttgagaaat tgaagaccat ttattaactt aaatatcaat gggaggtcat cgaaagagaa   4980
aaaaatcaaa aaaaaaattt ttcaagaaaa agaaacgtga taaaaatttt tattgccttt   5040
ttcgacgaag aaaaagaaac gaggcggtct cttttttctt ttccaaacct ttagtacggg   5100
taattaacgc caccctagag gaagaaagag gggaaattta gtatgctgtg cttgggtgtt   5160
ttgaagtggt acggcgatgc gcggagtccg agaaaatctg gaagagtaaa aaaggagtag   5220
aaacattttg aagctatggt gtgtggggga tcacttgtgg gggattgggt gtgatgtaag   5280
gataacttcg tatagcatac attatacgaa gttatgcggc cgcgtctgcc cgttacatgc   5340
gtacacgcgt ttgtacagaa aaaaaagaaa aatttgaaat ataaataacg ttcttaatac   5400
taacataact ataaaaaaat aaatagggac ctagacttca ggttgtctaa ctccttcctt   5460
ttcggttaga gcggatgtgg gaggagggcg tgaatgtaag cgtgacataa ctaattacat   5520
gatatcgaca aaggaaaagg ggcctgttta attaattaga attcgttagc ttcatttagc   5580
tcttgctgca ttgcgcttga ggactggtca atgacgttat ccacttgcga atcattttga   5640
cgctgtccct tcccgaaagg atcaactaca gtagatgcaa attttctagc agggacacct   5700
tgattgaaaa gctcattaat ttcgctaaat gttctaccag ttgtctcagg caaatcaatg   5760
ataacccaag ccaaagtgac tgcagtgaaa ccaccccagt ataggccggt tttagcaccc   5820
cagttccagt cactcacgtt cagcatatat ggcgttaaaa tggcattgat gacggccatc   5880
aaattatagc aaatacgagc cattacaata gttttggtcc ttaattctgc agacggaatt   5940
tcagccacaa tacagtaaac gacagctccg ataccagcgt tgtaaaagaa cgataaagcc   6000
agcagtagac caccagcacc attactggca ttgcttccgg atgcaaaccc cattccacca   6060
atgatgaata gacacaccat ttgaaatgca agaccataag ccaggatact ccatctacca   6120
acacggccag atatcaccca ggaacaaaga gtgcctgcta aacctagaca gtactggata   6180
agcgagaaag taaacgcctt gtcagtggcc atccctgccc tttcaaagaa atacgtcgag   6240
taacctagta aaacggcacc actactgttt tgagcaaccc aagtcaaaca cgcaagcctt   6300
gttcttcttc catcaacgcc tttgaaacag ttgaagaacg accctgattt agatgccaga   6360
agtctctcct tctcaatggt catctcaatt tgctttaaag tgatatccac ttgaatctcc   6420
ctctcggcag cagtgccgct caggattcta ttcaaggact tttggcctc cgcaatctta   6480
```

```
ttctttctca ccagccacca aggcgactca ggagcaaaga agataccaat aatcaaaggt   6540
gcaggccaga tccattgtaa ggcaaatggc aacttgtagc ctaaatcgga gtctcccaaa   6600
ttctcctggg agtttttcat gataccagaa gcgaaaattt gaccaaacaa ccaacaaata   6660
ttggagtaac tggtcatgta atatctcagc gctagggggc aaacctccga agcataggta   6720
acagccagac tctggaagca accccatggc atagcagaca gaatttgccc tacagcgatc   6780
atggccaaac ttttgcagta gtaaaggata aaaatataag cagtcaacaa gccgagcgcc   6840
gtaatcattg tgtaacgatt acccatgaac tcgaccatgt aagtggtcat ctgtaaacca   6900
atcatttcac cacaaaggac acacatgttc aaaccaattt gccactgcga ggtaatttcg   6960
taggagcctt ccgcattcat agtaccgaat ttcctctgga aaaccggtaa tgcataaagt   7020
gcactcaaaa gcgcagtatc ataaccttcc atgactaagg tagtagacac caagatggac   7080
catagggctg cctttggata ttttctcaaa gcttgcctta aggtcatgct tttttcttca   7140
ctattagcct cattggcttc atcagtggca gcattcgcta tcttaattgc attatcatta   7200
tcatcgtctg aatcacccaa ttgggctgaa ttggtggtga attcgaggtg acccaattcg   7260
aatgcaccat ctttctttcc ttcttcaaaa tcctcagtgt ttaaagctcc acgttggtgt   7320
attataccac tggaagattc cggaacgcta ctattcctat catccagggt acccttttc    7380
ttgttcacca gtgatatgaa gttcttcatt gtatatgaga tagttgattg tatgcttggt   7440
atagcttgaa atattgtgca gaaaaagaaa caaggaagaa agggaacgag aacaatgacg   7500
aggaaacaaa agattaataa ttgcaggtct atttatactt gatagcaaga cagcaaactt   7560
tttttatttc aaattcaagt aactggaagg aaggccgtat accgttgctc attagagagt   7620
agtgtgcgtg aatgaaggaa ggaaaaagtt tcgtgtgctt cgagataccc cccatcagct   7680
ctggaacaac gacatctgtt ggtgctgtct ttgtcgttaa ttttttcctt tagtgtcttc   7740
catcattttt ttgtcattgc ggatatggtg agacaacaac gggggagaga gaaaagaaaa   7800
aaaaagaaaa gaagttgcat gcgcctatta ttacttcaat agatggcaaa tggaaaaagg   7860
gtagtgaaac ttcgatatga tgatggctat caagtctagg gctacagtat tagttcgtta   7920
tgtaccacca tcaatgaggc agtgtaattg gtgtagtctt gtttagccca ttatgtcttg   7980
tctggtatct gttctattgt atatctcccc tccgccacct acatgttagg gagaccaacg   8040
aaggtattat aggaatcccg atgtatgggt ttggttgcca gaaaagagga agtccatatt   8100
gtacacccgg aaacaacaaa aggatatccg aaatattcca cggtttaggt cgacgcggat   8160
ctcttatgtc tttacgattt atagttttca ttatcaagta tgcctatatt agtgtatagc   8220
atctttagat gacagtgttc gaagtttcac gaataaaaga taatattcta ctttttgctc   8280
ccaccgcgtt tgctagcacg agtgaacacc atccctcgcc tgtgagttgt acccattcct   8340
ctaaactgta gacatggtag cttcagcagt gttcgttatg tacggcatcc tccaacaaac   8400
agtcggttat agtttgtcct gctcctctga atcgtctccc tcgatatttc tcattttcct   8460
tcgcatgcca gcattgaaat gatcgaagtt caatgatgaa acggtaattc ttctgtcatt   8520
tactcatctc atctcatcaa gttatataat tctatacgga tgtaattttt cacttttcgt   8580
cttgacgtca ccctataatt tcaattgttg aaccctcaca aatgatgcac tgcaatgtac   8640
acaccctcat atagtttctc agggcttgat cagggttccg tagag                   8685
```

<210> SEQ ID NO 31
<211> LENGTH: 8719
<212> TYPE: DNA

```
<213> ORGANISM: Artificial Sequence
<220> FEATURE:
<223> OTHER INFORMATION: Synthetic sequence containing elements from
      Saccharomyces cerevisiae

<400> SEQUENCE: 31

atcacatagg aagcaacagg cgcgttggac ttttaatttt cgaggaccgc gaatccttac     60

atcacaccca atcccccaca agtgatcccc cacacaccat agcttcaaaa tgtttctact    120

ccttttttac tcttccagat tttctcggac tccgcgcatc gccgtaccac ttcaaaacac    180

ccaagcacag catactaaat ttcccctctt tcttcctcta gggtgtcgtt aattacccgt    240

actaaaggtt tggaaaagaa aaaagagacc gcctcgtttc tttttcttcg tcgaaaaagg    300

caataaaaat ttttatcacg tttctttttc ttgaaaattt ttttttttga tttttttctc    360

tttcgatgac ctcccattga tatttaagtt aataaacggt cttcaatttc tcaagtttca    420

gtttcatttt tcttgttcta ttacaacttt ttttacttct tgctcattag aaagaaagca    480

tagcaatcta atctaagttt taattacaaa tctagaatga gtgaatctcc aatgttcgct    540

gccaacggca tgccaaaggt aaatcaaggt gctgaagaag atgtcagaat tttaggttac    600

gacccattag cttctccagc tctccttcaa gtgcaaatcc cagccacacc aacttctttg    660

gaaactgcca agagaggtag aagagaagct atagatatta ttaccggtaa agacgacaga    720

gttcttgtca ttgtcggtcc ttgttccatc catgatcttg aagccgctca agaatacgct    780

ttgagattaa agaaattgtc agatgaatta aaaggtgatt tatccatcat tatgagagca    840

tacttggaga agccaagaac aaccgtcggc tggaaaggtc taattaatga ccctgatgtt    900

aacaacactt tcaacatcaa caagggtttg caatccgcta gacaattgtt tgtcaacttg    960

acaaatatcg gtttgccaat tggttctgaa atgcttgata ccatttctcc taaatacttg   1020

gctgatttgg tctccttcgg tgccattggt gccagaacca ccgaatctca actgcacaga   1080

gaattggcct ccggtttgtc tttcccagtt ggtttcaaga acggtaccga tggtacctta   1140

aatgttgctg tggatgcttg tcaagccgct gctcattctc accatttcat gggtgttact   1200

aagcatggtg ttgctgctat caccactact aagggtaacg aacactgctt cgttattcta   1260

agaggtggta aaaagggtac caactacgac gctaagtccg ttgcagaagc taaggctcaa   1320

ttgcctgccg gttccaacgg tctaatgatt gactactctc acggtaactc caataaggat   1380

ttcagaaacc aaccaaaggt caatgacgtt gtttgtgagc aaatcgctaa cggtgaaaac   1440

gccattaccg gtgtcatgat tgaatcaaac atcaacgaag gtaaccaagg catcccagcc   1500

gaaggtaaag ccggcttgaa atatggtgtt tccatcactg atgcttgtat aggttgggaa   1560

actactgaag acgtcttgag gaaattggct gctgctgtca gacaaagaag agaagttaac   1620

aagaaataga tgttttttta atgatatatg taacgtacat tctttcctct accactgcca   1680

attcggtatt atttaattgt gtttagcgct atttactaat taactagaaa ctcaattttt   1740

aaaggcaaag ctcgctgacc tttcactgat ttcgtggatg ttatactatc agttactctt   1800

ctgcaaaaaa aaattgagtc atatcgtagc tttgggatta tttttctctc tctccacggc   1860

taattaggtg atcatgaaaa aatgaaaaat tcatgagaaa agagtcagac atcgaaacat   1920

acataagttg atattccttt gatatcgacg actactcaat caggttttaa aagaaaagag   1980

gcagctattg aagtagcagt atccagttta ggttttttaa ttatttacaa gtaaagaaaa   2040

agagaatgcc ggtcgttcac ggcggccgcg ccagaaaaag gaagtgtttc cctccttctt   2100

gaattgatgt taccctcata aagcacgtgg cctcttatcg agaaagaaat taccgtcgct   2160
```

-continued

```
cgtgatttgt ttgcaaaaag aacaaaactg aaaaaaccca gacacgctcg acttcctgtc   2220

ttcctattga ttgcagcttc caatttcgtc acacaacaag gtcctagcga cggctcacag   2280

gttttgtaac aagcaatcga aggttctgga atggcgggaa agggtttagt accacatgct   2340

atgatgccca ctgtgatctc cagagcaaag ttcgttcgat cgtactgtta ctctctctct   2400

ttcaaacaga attgtccgaa tcgtgtgaca acaacagcct gttctcacac actcttttct   2460

tctaaccaag gggtggttt agtttagtag aacctcgtga aacttacatt tacatatata   2520

taaacttgca taaattggtc aatgcaagaa atacatattt ggtcttttct aattcgtagt   2580

ttttcaagtt cttagatgct ttctttttct ctttttaca gatcatcaac tctttttac   2640

agatcatcaa ggaagtaatt atctactttt tacaagaatt catgtctaat ttacttactg   2700

ttcaccaaaa cttgcctgca ttaccagttg acgcaacctc cgatgaagtc agaaagaacc   2760

ttatggatat gtttagagat agacaagctt tctccgaaca tacttggaaa atgttattat   2820

ccgtttgtag atcctgggcc gcttggtgta aacttaacaa tagaaaatgg tttcctgctg   2880

aaccagaaga cgtcagagat tacttacttt acttacaagc tagaggtttg gctgttaaaa   2940

ctatccaaca acacttaggt caattgaata tgttacacag aagatccggt ttaccaagac   3000

catccgattc caacgcagtt tcccttgtta tgagaagaat tagaaaagaa aatgttgacg   3060

ctggtgaaag agctaaacaa gcattagcat ttgaaagaac cgatttcgat caagttagat   3120

ccttaatgga aaattccgat agatgtcaag atattagaaa cttagctttc ttaggtattg   3180

cttacaacac attattaaga atcgctgaaa ttgctagaat tagagttaaa gatatttcaa   3240

gaaccgatgg cggtagaatg ttaatccaca ttggcagaac aaaaaacctta gtctccacag   3300

caggcgtcga aaaagcatta tcattaggtg ttactaaatt agttgaacgt tggatttccg   3360

tttccggtgt tgcagatgac ccaaacaact acttattctg tcgtgttaga aaaaatggtg   3420

ttgccgctcc ttccgctacc tcacaattat ccacaagagc attagaaggc atttttgaag   3480

ctacccacag acttatttat ggtgcaaaag acgattccgg tcaaagatat ttagcttggt   3540

ctggtcattc cgctagagtt ggtgccgcaa gagacatggc aagagctggt gtttctattc   3600

ctgaaattat gcaagccggt ggttggacta atgttaacat tgttatgaac tatatcagaa   3660

acttagattc cgaaacaggt gctatggtta gattacttga agacggtgat taagctagct   3720

aagatccgct ctaaccgaaa aggaaggagt tagacaacct gaagtctagg tccctattta   3780

ttttttata gttatgttag tattaagaac gttatttata tttcaaattt ttcttttttt   3840

tctgtacaga cgcgtgtacg catgtaacat tatactgaaa accttgcttg agaaggtttt   3900

gggacgctcg aaggagctcc aattcgccct atagtgagtc gtattacaat tcactggccg   3960

tcgttttaca acgtcgtgac tgggaaaacc ctggcgttac ccaacttaat cgccttgcag   4020

cacatccccc cttcgccagc tggcgtaata gcgaagaggc ccgcaccgat cgcccttccc   4080

aacagttgcg cagcctgaat ggcgaatggc gcgacgcgcc ctgtagcggc gcattaagcg   4140

cggcgggtgt ggtggttacg cgcagcgtga ccgctacact tgccagcgcc ctagcgcccg   4200

ctcctttcgc tttcttccct tcctttctcg ccacgttcgc cggctttccc cgtcaagctc   4260

taaatcgggg gctcccttta gggttccgat ttagtgcttt acggcacctc gaccccaaaa   4320

aacttgatta gggtgatggt tcacgtagtg ggccatcgcc ctgatagacg gtttttcgcc   4380

ctttgacgtt ggagtccacg ttctttaata gtggactctt gttccaaact ggaacaacac   4440

tcaaccctat ctcggtctat tcttttgatt tataagggat tttgccgatt tcggcctatt   4500

ggttaaaaaa tgagctgatt taacaaaaat ttaacgcgaa ttttaacaaa atattaacgt   4560
```

```
ttacaatttc ctgatgcggt attttctcct tacgcatctg tgcggtattt cacaccgcag   4620

ggtaataact gatataatta aattgaagct ctaatttgtg agtttagtat acatgcattt   4680

acttataata cagtttttta gttttgctgg ccgcatcttc tcaaatatgc ttcccagcct   4740

gcttttctgt aacgttcacc ctctacctta gcatcccttc cctttgcaaa tagtcctctt   4800

ccaacaataa taatgtcaga tcctgtagag accacatcat ccacggttct atactgttga   4860

cccaatgcgt ctcccttgtc atctaaaccc acaccgggtg tcataatcaa ccaatcgtaa   4920

ccttcatctc ttccacccat gtctctttga gcaataaagc cgataacaaa atctttgtcg   4980

ctcttcgcaa tgtcaacagt acccttagta tattctccag tagataggga gcccttgcat   5040

gacaattctg ctaacatcaa aaggcctcta ggttcctttg ttacttcttc tgccgcctgc   5100

ttcaaaccgc taacaatacc tgggcccacc acaccgtgtg cattcgtaat gtctgcccat   5160

tctgctattc tgtatacacc cgcagagtac tgcaatttga ctgtattacc aatgtcagca   5220

aattttctgt cttcgaagag taaaaaattg tacttggcgg ataatgcctt tagcggctta   5280

actgtgccct ccatggaaaa atcagtcaag atatccacat gtgtttttag taaacaaatt   5340

ttgggaccta atgcttcaac taactccagt aattccttgg tggtacgaac atccaatgaa   5400

gcacacaagt ttgtttgctt ttcgtgcatg atattaaata gcttggcagc aacaggacta   5460

ggatgagtag cagcacgttc cttatatgta gctttcgaca tgatttatct tcgtttcctg   5520

caggtttttg ttctgtgcag ttgggttaag aatactgggc aatttcatgt ttcttcaaca   5580

ctacatatgc gtatatatac caatctaagt ctgtgctcct tccttcgttc ttccttctgt   5640

tcggagatta ccgaatcaaa aaaatttcaa agaaaccgaa atcaaaaaaa agaataaaaa   5700

aaaaatgatg aattgaattg aaaagcgtgg tgcactctca gtacaatctg ctctgatgcc   5760

gcatagttaa gccagccccg acacccgcca acacccgctg acgcgccctg acgggcttgt   5820

ctgctcccgg catccgctta cagacaagct gtgaccgtct ccgggagctg catgtgtcag   5880

aggttttcac cgtcatcacc gaaacgcgcg agacgaaagg gcctcgtgat acgcctattt   5940

ttataggtta atgtcatgat aataatggtt tcttaggacg gatcgcttgc ctgtaactta   6000

cacgcgcctc gtatctttta atgatggaat aatttgggaa tttactctgt gtttatttat   6060

ttttatgttt tgtatttgga ttttagaaag taaataaaga aggtagaaga gttacggaat   6120

gaagaaaaaa aaataaacaa aggtttaaaa aatttcaaca aaaagcgtac tttacatata   6180

tatttattag acaagaaaag cagattaaat agatatacat tcgattaacg ataagtaaaa   6240

tgtaaaatca caggattttc gtgtgtggtc ttctacacag acaagatgaa acaattcggc   6300

attaatacct gagagcagga agagcaagat aaaaggtagt atttgttggc gatcccccta   6360

gagtctttta catcttcgga aaacaaaaac tatttttttct ttaatttctt tttttacttt   6420

ctatttttaa tttatatatt tatattaaaa aatttaaatt ataattattt ttatagcacg   6480

tgatgaaaag gacccaggtg gcacttttcg gggaaatgtg cgcggaaccc ctatttgttt   6540

atttttctaa atacattcaa atatgtatcc gctcatgaga caataaccct gataaatgct   6600

tcaataatat tgaaaaagga agagtatgag tattcaacat ttccgtgtcg cccttattcc   6660

cttttttgcg gcattttgcc ttcctgtttt tgctcaccca gaaacgctgg tgaaagtaaa   6720

agatgctgaa gatcagttgg gtgcacgagt gggttacatc gaactggatc tcaacagcgg   6780

taagatcctt gagagttttc gccccgaaga acgttttcca atgatgagca cttttaaagt   6840

tctgctatgt ggcgcggtat tatcccgtat tgacgccggg caagagcaac tcggtcgccg   6900
```

```
catacactat tctcagaatg acttggttga gtactcacca gtcacagaaa agcatcttac   6960

ggatggcatg acagtaagag aattatgcag tgctgccata accatgagtg ataacactgc   7020

ggccaactta cttctgacaa cgatcggagg accgaaggag ctaaccgctt ttttcacaa   7080

catgggggat catgtaactc gccttgatcg ttgggaaccg gagctgaatg aagccatacc   7140

aaacgacgag cgtgacacca cgatgcctgt agcaatggca acaacgttgc gcaaactatt   7200

aactggcgaa ctacttactc tagcttcccg gcaacaatta atagactgga tggaggcgga   7260

taaagttgca ggaccacttc tgcgctcggc ccttccggct ggctggttta ttgctgataa   7320

atctggagcc ggtgagcgtg ggtctcgcgg tatcattgca gcactggggc cagatggtaa   7380

gccctcccgt atcgtagtta tctacacgac gggcagtcag gcaactatgg atgaacgaaa   7440

tagacagatc gctgagatag gtgcctcact gattaagcat tggtaactgt cagaccaagt   7500

ttactcatat atactttaga ttgatttaaa acttcatttt taatttaaaa ggatctaggt   7560

gaagatcctt tttgataatc tcatgaccaa aatcccttaa cgtgagtttt cgttccactg   7620

agcgtcagac cccgtagaaa agatcaaagg atcttcttga gatccttttt ttctgcgcgt   7680

aatctgctgc ttgcaaacaa aaaaaccacc gctaccagcg gtggtttgtt tgccggatca   7740

agagctacca actctttttc cgaaggtaac tggcttcagc agagcgcaga taccaaatac   7800

tgtccttcta gtgtagccgt agttaggcca ccacttcaag aactctgtag caccgcctac   7860

atacctcgct ctgctaatcc tgttaccagt ggctgctgcc agtggcgata agtcgtgtct   7920

taccgggttg gactcaagac gatagttacc ggataaggcg cagcggtcgg gctgaacggg   7980

gggttcgtgc acacagccca gcttggagcg aacgacctac accgaactga gatacctaca   8040

gcgtgagcat tgagaaagcg ccacgcttcc cgaagggaga aaggcggaca ggtatccggt   8100

aagcggcagg gtcggaacag gagagcgcac gagggagctt ccagggggga acgcctggta   8160

tctttatagt cctgtcgggt ttcgccacct ctgacttgag cgtcgatttt tgtgatgctc   8220

gtcagggggg ccgagcctat ggaaaaacgc cagcaacgcg gcctttttac ggttcctggc   8280

cttttgctgg ccttttgctc acatgttctt tcctgcgtta tcccctgatt ctgtggataa   8340

ccgtattacc gcctttgagt gagctgatac cgctcgccgc agccgaacga ccgagcgcag   8400

cgagtcagtg agcgaggaag cggaagagcg cccaatacgc aaaccgcctc tccccgcgcg   8460

ttggccgatt cattaatgca gctggcacga caggtttccc gactggaaag cgggcagtga   8520

gcgcaacgca attaatgtga gttacctcac tcattaggca ccccaggctt tacactttat   8580

gcttccggct cctatgttgt gtggaattgt gagcggataa caatttcaca caggaaacag   8640

ctatgaccat gattacgcca agctcggaat taaccctcac taaagggaac aaaagctggg   8700

taccgggccc cccctcgag                                                 8719
```

<210> SEQ ID NO 32
<211> LENGTH: 5001
<212> TYPE: DNA
<213> ORGANISM: Artificial Sequence
<220> FEATURE:
<223> OTHER INFORMATION: Sequence put together from multiple organisms: Saccharomyces cerevisiae and Aspergillus shirousami

<400> SEQUENCE: 32

```
cagagcctct tatattcact ctgttcctcc atcgcctatt gagaaacgtt ggaataaaac     60

tctaaaaata tcatctagtt ggttagtttt tattttacca gtacattgtc acttgcggag    120

ggaggatgac ataaagattg agacgcagtc atttaatgaa gtttaaacgc aggtatttga    180
```

-continued

```
taaagtaata cgatattgaa tcatgacgta taaagtgaaa tgaacaaatg attacgtaaa    240
aaatgtcgat tttctcttga gagactccca tagcctctaa gaggccttct actacgttcc    300
atatatctaa gaatggggcc atatccagtg gaatcccagc aattatttaa ggatcaccta    360
tttctcagcc gatattttag caaaatcact accaatatca gggggcaata gttgatcgcc    420
tactttaaca aaaaatgttg ctcacgtatt aacacaggca acaaaaagga tattacgcaa    480
gaacgtagta tccacatgcc atcctccttg ttgcatcttt ttttttccga aatgattccc    540
tttcctgcac aacacgagat ctttcacgca tacatcggaa ggatcacccc ccactcaagt    600
cgttgcattg ctaacatgtg gcattctgcc cattttttc acgaaaattc tctctctata    660
atgaagaccc ttgtgccctg gactctgtaa tacttgaaac tacttcctca ataatcgctt    720
ggagacctac ccccacgctt ttcaaacaag gcgctagcaa aaagcctgcc gatatctcct    780
tgccccctcc ttctgttcga gagaactacg acccgaccaa taataatgtc atacaagaac    840
cgccaagaac caactgctga accttagatc tccaatactt cagttggagt atgtgaatat    900
ataagtacct ggtcgactaa tcttcttgca tcttttcgta ttcttacatc ctatgtcgct    960
aatacagttc ccgcatagag aagaaagcaa acaaaagtag tcactcgaga tctcccgagt   1020
ttatcattat caatactgcc atttcaaaga atacgtaaat aattaatagt agtgattttc   1080
ctaactttat ttagtcaaaa aattggcctt ttaattctgc tgtaacccgt acatgcccaa   1140
aataggggc gggttacaca gaatatataa catcataggt gtctgggtga acagtttatt   1200
cctggcatcc actaaatata atggagcccg cttttttaa gctggcatcc agaaaaaaaa    1260
agaatcccag caccaaaata ttgttttctt caccaaccat cagttcatag gtccattctc   1320
ttagcgcaac tacacagaac aggggcacaa acaggcaaaa aacgggcaca acctcaatgg   1380
agtgatgcaa cctgcttgga gtaaatgatg acacaaggca attgacctac gcatgtatct   1440
atctcatttt cttacacctt ctattacctt ctgctctctc tgatttggaa aaagctgaaa   1500
aaaaaggttg aaaccagttc cctgaaatta ttcccctatt tgactaataa gtatataaag   1560
acggtaggta ttgattgtaa ttctgtaaat ctatttctta aacttcttaa attctacttt   1620
tatagttagt cttttttta gtttaaaaca ccaagaactt agtttcgaat aaacacacat    1680
aaacaaacaa atctagaatg ttcaagtctg ttgtttactc tattttggct gcctctttgg   1740
ctaacgctag tgttatctct aagagagcaa cgttggatag ttggttatca aatgaagcaa   1800
ctgtcgctag aaccgcaatt ctaaacaata ttggagctga tggtgcatgg gttagcggtg   1860
cagactctgg tattgtggta gcctctccat ccacagataa tccagattat ttctatactt   1920
ggactagaga ttccggaata gttttgaaaa cgctggtgga tttgtttcgt aatggggaca   1980
ccgacttgtt atcaaccatt gagcattata tctccagtca agcaattatt caaggtgtct   2040
caaatccatc cggcgacttg agcagtgggg ggctgggaga acctaagttc aatgtggacg   2100
aaacggctta cgctggaagt tggggcagac cacagagaga cggaccagct ctaagagcaa   2160
cagccatgat tggattcggt cagtggctac tagacaatgg atacactagc gccgcgacag   2220
aaattgtttg gccactagtc aggaacgacc taagttacgt tgctcaatat tggaaccaaa   2280
ccgggtatga tctgtgggaa gaggttaatg gatctagttt cttcaccatc gcagttcagc   2340
atagagcttt ggttgaaggt agcgccttcg caacggcagt tgggagttca tgctcttggt   2400
gtgattcaca ggcaccacaa atcttatgtt atcttcagag cttttggacc ggttcctata   2460
ttctagccaa tttcgacagt tccagatccg gtaaggatac taacacttta cttggctcaa   2520
tacatacctt cgaccctgaa gctgggtgtg atgattctac attccaaccc tgttctccga   2580
```

gagcactggc caatcataaa gaagtggttg attcatttag aagtatttat acactaaatg 2640
acggattaag tgacagtgaa gccgtagccg tcggaagata tccagaagat tcctattaca 2700
atggtaatcc atggttctta tgtacacttg ctgctgctga acaattatat gacgcattgt 2760
atcaatggga taagcaaggc tctttagaaa ttaccgacgt aagtttagac ttctttaaag 2820
cattgtatag cggtgcagcc acgggtacat actcatcttc ttctagtacg tactcttcta 2880
ttgtttctgc ggtgaaaact tttgctgacg gctttgtttc tatcgtcgag acccatgccg 2940
ccagtaacgg ttctttatcc gaacaatttg acaagtccga tggcgatgag ttaagcgcaa 3000
gagatctaac ctggtcttat gccgcattac ttacagccaa caacagacgt aattccgttg 3060
taccaccatc ttggggtgaa acaagtgctt cttcagttcc gggcacctgc gcggccacaa 3120
gtgcatcagg aacttattca tcagtgactg taacatcttg gcctagtatt gtcgcaaccg 3180
gtggtacaac taccactgca actacgacgg gttctggagg agtcacttcc acaagcaaga 3240
ctacgactac tgcaagtaaa accagtacta ctacctcctc cactagctgt acgacaccca 3300
ccgccgtagc cgtcactttc gatttgactg ctacaaccac ctacggcgag aatatctact 3360
tggtgggatc aatctcacaa ctaggtgact gggagacttc cgacgggatc gctttgtcag 3420
cagataaata cacatcatct aacccaccat ggtatgtgac ggtcacttta cctgccgggg 3480
agtctttcga atacaagttt ataagggtag aatccgatga cagtgtggaa tgggaatctg 3540
atcctaatag agagtacaca gtgccacaag cttgtgggga atctacagcc acagttaccg 3600
atacatggag gtagttaatt aaacaggccc cttttccttt gtcgatatca tgtaattagt 3660
tatgtcacgc ttacattcac gccctcctcc cacatccgct ctaaccgaaa aggaaggagt 3720
tagacaacct gaagtctagg tccctattta tttttttata gttatgttag tattaagaac 3780
gttatttata tttcaaattt ttcttttttt tctgtacaaa cgcgtgtacg catgtaacgg 3840
gcagacggcc ggccataact tcgtataatg tatgctatac gaagttatgg caacggttca 3900
tcatctcatg gatctgcaca tgaacaaaca ccagagtcaa acgacgttga aattgaggct 3960
actgcgccaa ttgatgacaa tacagacgat gataacaaac cgaagttatc tgatgtagaa 4020
aaggattaga gatgctaaga gatagtgatg atatttcata aataatgtaa ttctatatat 4080
gttaattacc tttttttgcga ggcatattta tggtgaagga taagttttga ccatcaaaga 4140
aggttaatgt ggctgtggtt tcagggtcca taaagctttt caattcatct tttttttttt 4200
tgttcttttt tttgattccg gtttctttga aatttttttg attcggtaat ctccgagcag 4260
aaggaagaac gaaggaagga gcacagactt agattggtat atatacgcat atgtggtgtt 4320
gaagaaacat gaaattgccc agtattctta acccaactgc acagaacaaa aacctgcagg 4380
aaacgaagat aaatcatgtc gaaagctaca tataaggaac gtgctgctac tcatcctagt 4440
cctgttgctg ccaagctatt taatatcatg cacgaaaagc aaacaaactt gtgtgcttca 4500
ttggatgttc gtaccaccaa ggaattactg gagttagttg aagcattagg tcccaaaatt 4560
tgtttactaa aaacacatgt ggatatcttg actgattttt ccatggaggg cacagttaag 4620
ccgctaaagg cattatccgc caagtacaat tttttactct tcgaagacag aaaatttgct 4680
gacattggta atacagtcaa attgcagtac tctgcgggtg tatacagaat agcagaatgg 4740
gcagacatta cgaatgcaca cggtgtggtg ggcccaggta ttgttagcgg tttgaagcag 4800
gcggcggaag aagtaacaaa ggaacctaga ggccttttga tgttagcaga attgtcatgc 4860
aagggctccc tagctactgg agaatatact aagggtactg ttgacattgc gaagagcgac 4920

```
aaagattttg ttatcggctt tattgctcaa agagacatgg gtggaagaga tgaaggttac   4980

gattggttga ttatgacacg c                                             5001


<210> SEQ ID NO 33
<211> LENGTH: 5125
<212> TYPE: DNA
<213> ORGANISM: Artificial Sequence
<220> FEATURE:
<223> OTHER INFORMATION: Sequence put together from multiple organisms:
      Saccharomyces cerevisiae and Aspergillus  shirousami

<400> SEQUENCE: 33

ggccgctcca tggagggcac agttaagccg ctaaaggcat tatccgccaa gtacaatttt     60

ttactcttcg aagacagaaa atttgctgac attggtaata cagtcaaatt gcagtactct    120

gcgggtgtat acagaatagc agaatgggca gacattacga atgcacacgg tgtggtgggc    180

ccaggtattg ttagcggttt gaagcaggcg gcggaagaag taacaaagga acctagaggc    240

cttttgatgt tagcagaatt gtcatgcaag ggctccctag ctactggaga atatactaag    300

ggtactgttg acattgcgaa gagcgacaaa gattttgtta tcggctttat tgctcaaaga    360

gacatgggtg gaagagatga aggttacgat tggttgatta tgacacccgg tgtgggttta    420

gatgacaagg gagacgcatt gggtcaacag tatagaaccg tggatgatgt ggtctctaca    480

ggatctgaca ttattattgt tggaagagga ctatttgcaa agggaaggga tgctaaggta    540

gagggtgaac gttacagaaa agcaggctgg gaagcatatt tgagaagatg cggccagcaa    600

aactaaaaaa ctgtattata agtaaatgca tgtatactaa actcacaaat tagagcttca    660

atttaattat atcagttatt acccgggaat ctcggtcgta atgattttta taatgacgaa    720

aaaaaaaaaa ttggaaagaa aaagcttcat ggcctttata aaaaggaacc atccaatacc    780

tcgccagaac caagtaacag tattttacgg ggcacaaatc aagaacaata agacaggact    840

gtaaagatgg acgcattgaa ctccaaagaa caacaagagt tccaaaaagt agtggaacaa    900

aagcaaatga aggatttcat gcgtttgata acttcgtata atgtatgcta tacgaagtta    960

tctcgagatc tcccctaaac cgtggaatat ttcggatatc cttttgttgt ttccgggtgt   1020

acaatatgga cttcctcttt tctggcaacc aaacccatac atcgggattc ctataatacc   1080

ttcgttggtc tccctaacat gtaggtggcg gaggggagat atacaataga acagatacca   1140

gacaagacat aatgggctaa acaagactac accaattaca ctgcctcatt gatggtggta   1200

cataacgaac taatactgta gccctagact tgatagccat catcatatcg aagtttcact   1260

accctttttc catttgccat ctattgaagt aataataggc gcatgcaact tcttttcttt   1320

tttttctttt tctctctccc ccgttgttgt ctcaccatat ccgcaatgac aaaaaaaatga   1380

tggaagacac taaaggaaaa aattaacgac aaagacagca ccaacagatg tcgttgttcc   1440

agagctgatg aggggtatct cgaagcacac gaaacttttt ccttccttca ttcacgcaca   1500

ctactctcta atgagcaacg gtatacggcc ttccttccag ttacttgaat ttgaaataaa   1560

aaaaagtttg ctgtcttgct atcaagtata aatagacctg caattattaa tcttttgttt   1620

cctcgtcatt gttctcgttc cctttcttcc ttgtttcttt ttctgcacaa tatttcaagc   1680

tataccaagc atacaatcaa ctatctcata tacatctaga atgttcaaaa gcgtggttta   1740

ctccattttg gctgcatctt tggcaaatgc ctcagttatt tccaagcgtg ctacgttaga   1800

tagttggtta agtaatgagg caaccgtagc cagaaccgca atattgaaca atattggtgc   1860

cgatggggcc tgggttagcg gcgcagattc cggtatcgta gttgcaagcc cctccactga   1920
```

```
taaccccgat tacttctaca cttggactag ggactccggc atcgttttga agactctggt   1980
tgacttattt agaaatggcg atacggatct acttagcacg atagaacact atatcagttc   2040
ccaagctatt atacagggtg tttctaaccc cagtggagat ttatcaagcg gaggccttgg   2100
tgagcctaaa ttcaacgttg atgagactgc atatgcagga tcttggggca gaccacaaag   2160
agatggtcca gctttaagag ctactgccat gataggtttc gggcaatggt tgttggacaa   2220
tggatacact tcagcagcaa ctgaaatcgt ctggccgttg gtcagaaatg atttaagcta   2280
tgtcgctcag tattggaacc aaacaggcta cgatttgtgg gaagaggtca atggttcttc   2340
tttctttacc attgccgttc agcacagagc cctagtggaa ggttctgctt tcgcaacagc   2400
tgtggggtct tcttgctcat ggtgtgattc tcaagctcct cagatactgt gttatttaca   2460
gtcattctgg actggttcct acattcttgc taacttcgat tcttccagaa gcggcaaaga   2520
tactaacact ttgcttggca gcattcacac ttttgatccc gaagctgggt gcgacgattc   2580
tactttccaa ccatgttcac caagggcgct ggctaatcat aaggaagttg tcgattcttt   2640
tagatctatc tataccttga atgacggtct atcagattcc gaagccgtgg ctgtgggaag   2700
gtatcccgag gattcatact acaatggtaa cccatggttt ctttgcacat tggctgcagc   2760
ggaacaactg tatgatgctc tttaccaatg ggacaagcaa ggctctctgg agatcacaga   2820
tgttagtctg gatttcttta aggctttgta ctcaggtgca gccaccggta catatagctc   2880
ttcaagttca acctatagct ctatagtatc cgccgtgaag acctttgcag atggtttcgt   2940
tagcattgtt gaaacacacg ctgcatcaaa tggttcactg agtgaacagt ttgataaatc   3000
cgacggcgat gaattgagtg cgagagattt gacttggtct tatgcggctc ttcttactgc   3060
taacaataga cgtaatagtg ttgttccacc ctcttggggt gaaactagcg ctagtagtgt   3120
cccagggact tgcgcagcta caagtgcatc tggcacctac agctcagtga ctgttacatc   3180
ctggccaagt atagttgcta ccggtggcac tacaaccact gcaaccacta ctggtagcgg   3240
aggtgttact tcaacttcta aaaccacgac aactgcttct aagacgtcaa cgaccacatc   3300
ctcaacaagc tgtactacac ctacagcggt tgcagttaca ttcgacctaa ccgccacgac   3360
gacctacggg gaaaatatat atttggttgg aagtatctct caattagggg attgggaaac   3420
gtctgatgga attgccctaa gtgcagataa atatacatct tctaacccgc cttggtatgt   3480
taccgttaca ttgccagcag gcgaatcctt tgaatataaa ttcataagag tcgaatctga   3540
tgattctgtt gaatgggagt cagacccaaa tcgtgagtat actgtacctc aggcctgcgg   3600
tgaaagcaca gctactgtga ccgatacttg gaggtagtta attaatttac cagcttacta   3660
tccttcttga aaatatgcac tctatatctt ttagttctta attgcaacac atagatttgc   3720
tgtataacga attttatgct attttttttaa tttggagttc ggtgatgaaa gtgtcacagc   3780
gaatttcctc acatgtaggg accgaattgt ttacaagttc tctgtaccac catggagaca   3840
tcaaagattg aaaatctatg gaaagatatg gacggtagca acaagaatat agcacgagcc   3900
gcggagttca tttcgttact tttgatatcg ctcacaacta ttgcgaagcg cttcagtgaa   3960
aaaatcataa ggaaaagttg taaatattat tggtagtatt cgtttggtaa agtagagggg   4020
gtaatttttc ccctttattt tgttcataca ttcttaaatt gctttgcctc tccttttgga   4080
aagctatact tcggagcact gttgagcgaa ggctcaggcc ggccttatag cctagcttta   4140
aggctacttt aaaaactttt tatttattca tacacatata ttatcgaaca ttcgtataac   4200
ttaatatcat tcaaaaaaaa aaaaaaaaaa aaaagaaaac atatacacat atatatttat   4260
gtttatagag agagagagag aaaatttgaa tttttgaatc atttgcaaag ttatatgttt   4320
```

```
tatacattat ttattcattt tttttggtgt cgaggacatt gtgctgttca gagaaccact   4380

taaaatacgc atcgttctgt aaatatccac tttcattaaa aaccttattc acttctaact   4440

ttgccttcaa ctccttcttg gagttttctc cctttttttt ctgaacaagc tcaaccagat   4500

ataatggttc gttcttttcg aactttgtct ttacatatat ttcctccttt gtacctcttc   4560

tctttcccac ataaacagtc ccctttttcaa taaaacgaga gaaataccag aaaagtagcg   4620

agagaacaaa atatgcgcct accaaaagct tttgatacgt aacaatctga tctctctcaa   4680

atttttatc caagaagaaa ctcaaaccag ctacaacagc tatggaataa cctatgtaca   4740

atttagcatc gagtaaagcg tatgatctct cgtaatttaa tctcgcgaaa acagaaggta   4800

gggcttcatc taaagcttgg ttcaactccg ggattgaata tacattaata ggtttagcag   4860

aactcatctt gaacaggcgt ctcttttcct tacaataact tgtgcttttc cttctataat   4920

tccgtttcaa cgtgtacaat tgtcattttt tgtctggtat gattttgcag aactgaaaaa   4980

atctcttaaa tgttccgcct catcaagaag gcatattcct ttacaaaagt acattgatct   5040

tacaagaagc tagctaatgg tactatttaa aaaacaacta cactccatca atacataaaa   5100

ttgttatgat agacttgagg gacgg                                          5125
```

<210> SEQ ID NO 34
<211> LENGTH: 5384
<212> TYPE: DNA
<213> ORGANISM: Artificial Sequence
<220> FEATURE:
<223> OTHER INFORMATION: Sequence put together from multiple organisms: Saccharomyces cerevisiae, Aspergillus shirousami, and Aspergillus nidulans

<400> SEQUENCE: 34

```
cagagcctct tatattcact ctgttcctcc atcgcctatt gagaaacgtt ggaataaaac     60

tctaaaaata tcatctagtt ggttagtttt tattttacca gtacattgtc acttgcggag    120

ggaggatgac ataaagattg agacgcagtc atttaatgaa gtttaaacgc aggtatttga    180

taaagtaata cgatattgaa tcatgacgta taaagtgaaa tgaacaaatg attacgtaaa    240

aaatgtcgat ttctcttga gagactccca tagcctctaa gaggccttct actacgttcc    300

atatatctaa gaatggggcc atatccagtg gaatcccagc aattatttaa ggatcaccta    360

tttctcagcc gatattttag caaaatcact accaatatca gggggcaata gttgatcgcc    420

tactttaaca aaaaatgttg ctcacgtatt aacacaggca acaaaaagga tattacgcaa    480

gaacgtagta tccacatgcc atcctccttg ttgcatcttt ttttttccga aatgattccc    540

tttcctgcac aacacgagat ctttcacgca tacatcggaa ggatcacccc ccactcaagt    600

cgttgcattg ctaacatgtg gcattctgcc catttttttc acgaaaattc tctctctata    660

atgaagaccc ttgtgccctg gactctgtaa tacttgaaac tacttcctca ataatcgctt    720

ggagacctac ccccacgctt ttcaaacaag gcgctagcaa aaagcctgcc gatatctcct    780

tgccccctcc ttctgttcga gagaactacg acccgaccaa taataatgtc atacaagaac    840

cgccaagaac caactgctga accttagatc tccaatactt cagttggagt atgtgaatat    900

ataagtacct ggtcgactaa tcttcttgca tcttttcgta ttcttacatc ctatgtcgct    960

aatacagttc ccgcatagag aagaaagcaa acaaaagtag tcactcgaga tctcccgagt   1020

ttatcattat caatactgcc atttcaaaga atacgtaaat aattaatagt agtgattttc   1080

ctaactttat ttagtcaaaa aattggcctt ttaattctgc tgtaacccgt acatgcccaa   1140
```

-continued

```
aatagggggc gggttacaca gaatatataa catcataggt gtctgggtga acagtttatt   1200
cctggcatcc actaaatata atggagcccg cttttttttaa gctggcatcc agaaaaaaaa   1260
agaatcccag caccaaaata ttgttttctt caccaaccat cagttcatag gtccattctc   1320
ttagcgcaac tacacagaac aggggcacaa acaggcaaaa aacgggcaca acctcaatgg   1380
agtgatgcaa cctgcttgga gtaaatgatg acacaaggca attgacctac gcatgtatct   1440
atctcatttt cttacacctt ctattacctt ctgctctctc tgatttggaa aaagctgaaa   1500
aaaaaggttg aaaccagttc cctgaaatta ttcccctatt tgactaataa gtatataaag   1560
acggtaggta ttgattgtaa ttctgtaaat ctatttctta aacttcttaa attctacttt   1620
tatagttagt ctttttttta gtttaaaaca ccaagaactt agtttcgaat aaacacacat   1680
aaacaaacaa atctagaatg ttcaagtctg ttgtttactc tattttggct gcctctttgg   1740
ctaacgctag tgttatctct aagagagcaa cgttggatag ttggttatca aatgaagcaa   1800
ctgtcgctag aaccgcaatt ctaaacaata ttggagctga tggtgcatgg gttagcggtg   1860
cagactctgg tattgtggta gcctctccat ccacagataa tccagattat ttctatactt   1920
ggactagaga ttccggaata gttttgaaaa cgctggtgga tttgtttcgt aatggggaca   1980
ccgacttgtt atcaaccatt gagcattata tctccagtca agcaattatt caaggtgtct   2040
caaatccatc cggcgacttg agcagtgggg ggctgggaga acctaagttc aatgtggacg   2100
aaacggctta cgctggaagt tggggcagac cacagagaga cggaccagct ctaagagcaa   2160
cagccatgat tggattcggt cagtggctac tagacaatgg atacactagc gccgcgacag   2220
aaattgtttg gccactagtc aggaacgacc taagttacgt tgctcaatat tggaaccaaa   2280
ccgggtatga tctgtgggaa gaggttaatg gatctagttt cttcaccatc gcagttcagc   2340
atagagcttt ggttgaaggt agcgccttcg caacggcagt tgggagttca tgctcttggt   2400
gtgattcaca ggcaccacaa atcttatgtt atcttcagag cttttggacc ggttcctata   2460
ttctagccaa tttcgacagt tccagatccg gtaaggatac taacacttta cttggctcaa   2520
tacatacctt cgaccctgaa gctgggtgtg atgattctac attccaaccc tgttctccga   2580
gagcactggc caatcataaa gaagtggttg attcatttag aagtatttat acactaaatg   2640
acggattaag tgacagtgaa gccgtagccg tcggaagata tccagaagat tcctattaca   2700
atggtaatcc atggttctta tgtacacttg ctgctgctga acaattatat gacgcattgt   2760
atcaatggga taagcaaggc tctttagaaa ttaccgacgt aagtttagac ttctttaaag   2820
cattgtatag cggtgcagcc acgggtacat actcatcttc ttctagtacg tactcttcta   2880
ttgtttctgc ggtgaaaact tttgctgacg gctttgtttc tatcgtcgag acccatgccg   2940
ccagtaacgg ttctttatcc gaacaatttg acaagtccga tggcgatgag ttaagcgcaa   3000
gagatctaac ctggtcttat gccgcattac ttacagccaa caacagacgt aattccgttg   3060
taccaccatc ttggggtgaa acaagtgctt cttcagttcc gggcacctgc gcggccacaa   3120
gtgcatcagg aacttattca tcagtgactg taacatcttg gcctagtatt gtcgcaaccg   3180
gtggtacaac taccactgca actacgacgg gttctggagg agtcacttcc acaagcaaga   3240
ctacgactac tgcaagtaaa accagtacta ctacctcctc cactagctgt acgacaccca   3300
ccgccgtagc cgtcactttc gatttgactg ctacaaccac ctacggcgag aatatctact   3360
tggtgggatc aatctcacaa ctaggtgact gggagacttc cgacgggatc gctttgtcag   3420
cagataaata cacatcatct aacccaccat ggtatgtgac ggtcacttta cctgccgggg   3480
agtctttcga atacaagttt ataagggtag aatccgatga cagtgtggaa tgggaatctg   3540
```

```
atcctaatag agagtacaca gtgccacaag cttgtgggga atctacagcc acagttaccg   3600
atacatggag gtagttaatt aaacaggccc cttttccttt gtcgatatca tgtaattagt   3660
tatgtcacgc ttacattcac gccctcctcc cacatccgct ctaaccgaaa aggaaggagt   3720
tagacaacct gaagtctagg tccctattta tttttttata gttatgttag tattaagaac   3780
gttatttata tttcaaattt ttcttttttt tctgtacaaa cgcgtgtacg catgtaacgg   3840
gcagacggcc ggccataact tcgtataatg tatgctatac gaagttatcc ttacatcaca   3900
cccaatcccc cacaagtgat cccccacaca ccatagcttc aaaatgtttc tactcctttt   3960
ttactcttcc agattttctc ggactccgcg catcgccgta ccacttcaaa acacccaagc   4020
acagcatact aaatttcccc tctttcttcc tctagggtgg cgttaattac ccgtactaaa   4080
ggtttggaaa agaaaaaaga gaccgcctcg tttctttttc ttcgtcgaaa aaggcaataa   4140
aaatttttat cacgtttctt tttcttgaaa aatttttttt ttgatttttt tctctttcga   4200
tgacctccca ttgatattta agttaataaa tggtcttcaa tttctcaagt ttcagtttcg   4260
tttttcttgt tctattacaa cttttttac ttcttgctca ttagaaagaa agcatagcaa   4320
tctaatctaa gttttaatta caaaatgcca caatcctggg aagaattggc cgccgacaaa   4380
cgtgcccgtt tggctaaaac cattcctgac gaatggaagg ttcaaacttt gcctgccgaa   4440
gattccgtta ttgatttccc aaagaagtcc ggtattttgt ctgaggctga attgaagatt   4500
accgaagcct ctgctgctga tttggtctcc aagttggccg ctggtgagtt gacttctgtt   4560
gaagtcactt tggctttttg taagagagct gctattgctc aacaattaac caactgtgct   4620
cacgaattct tcccagatgc tgctttagct caagctagag aattagatga atactacgct   4680
aagcataaga gaccagttgg tccattacac ggtttaccaa tctctttaaa ggaccaattg   4740
cgtgttaagg gttacgaaac ctccatgggt tacatttcct ggttaaacaa atacgatgaa   4800
ggtgattccg tcttaaccac catgttgaga aaagctggtg ctgttttcta cgttaagacc   4860
tctgtcccac aaaccttgat ggtctgtgaa accgtcaaca acatcattgg tagaactgtc   4920
aatccaagaa acaaaaaattg gtcctgtggt ggttcttctg gtggtgaagg tgctattgtt   4980
ggtattagag gtggtgttat tggtgtcggt actgacattg gtggttccat tagagtccca   5040
gctgctttca actttttata cggtttgaga ccatctcacg gtagattgcc atatgctaaa   5100
atggctaact ctatggaagg tcaagaaacc gttcactccg tcgttggtcc tatcactcac   5160
tccgtcgaag acttgagatt gttcaccaaa tctgtcttgg gtcaagaacc ttggaagtac   5220
gactctaagg tcatccccat gccatggaga caatctgaat ctgacatcat tgcctctaag   5280
attaagaatg gtggtttgaa cattggttat tacaatttcg acggtaacgt cttgccacac   5340
ccaccaattt tacgtggtgt cgaaactacc gttgccgctt tggc                   5384
```

<210> SEQ ID NO 35
<211> LENGTH: 5533
<212> TYPE: DNA
<213> ORGANISM: Artificial Sequence
<220> FEATURE:
<223> OTHER INFORMATION: Sequence put together from multiple organisms: Saccharomyces cerevisiae, Aspergillus shirousami, and Aspergillus nidulans

<400> SEQUENCE: 35

```
ggccgcgaag gtgctattgt tggtattaga ggtggtgtta ttggtgtcgg tactgacatt     60
ggtggttcca ttagagtccc agctgctttc aactttttat acggtttgag accatctcac    120
```

-continued

```
ggtagattgc catatgctaa aatggctaac tctatggaag gtcaagaaac cgttcactcc    180
gtcgttggtc ctatcactca ctccgtcgaa gacttgagat tgttcaccaa atctgtcttg    240
ggtcaagaac cttggaagta cgactctaag gtcatcccaa tgccatggag acaatctgaa    300
tctgacatca ttgcctctaa gattaagaat ggtggtttga acattggtta ttacaatttc    360
gacggtaacg tcttgccaca cccaccaatt ttacgtggtg tcgaaactac cgttgccgct    420
ttggccaagg ctggtcacac cgttactcca tggactccat acaagcatga tttcggtcat    480
gacttgattt cccacatcta tgctgctgat ggttctgccg acgtcatgag agacatttct    540
gcctctggtg agccagccat ccctaacatt aaggacttgt tgaacccaaa tattaaggct    600
gttaacatga acgaattgtg ggacactcat ttacaaaagt ggaactatca aatggaatac    660
ttggaaaagt ggcgtgaagc tgaagaaaaa gctggtaagg aattggacgc tattatcgct    720
ccaattactc ctaccgccgc tgtcagacac gatcaattca gatactacgg ttacgcctcc    780
gttattaact tattggattt cacctctgtt gtcgtcccag tcactttcgc tgataagaat    840
attgataaga agaacgaatc ttttaaagct gtttccgaat tggatgcttt ggttcaagaa    900
gaatacgacc cagaggctta tcacggtgct cctgttgctg ttcaagttat tggtagaaga    960
ttgtccgaag agagaacttt ggctatcgcc gaagaagtcg gtaaattgtt gggtaacgtc   1020
gtcactccat aagcgaattt cttatgattt atgattttta ttattaaata agttataaaa   1080
aaaataagtg tatacaaatt ttaaagtgac tcttaggttt taaaacgaaa attcttattc   1140
ttgagtaact ctttcctgta ggtcaggttg ctttctcagg tatagcatga ggtcgctctt   1200
attgaccaca cctctaccgg catgccgagc aaatgcctgc aaatcgctcc ccatttcacc   1260
caattgtaga tatgctaact ccagcaatga gttgatgaat ctcggtgtgt attttatgtc   1320
ctcagaggac aacacataac ttcgtataat gtatgctata cgaagttatc tcgagatctc   1380
ccctaaaccg tggaatattt cggatatcct tttgttgttt ccgggtgtac aatatggact   1440
tcctcttttc tggcaaccaa acccatacat cgggattcct ataatacctt cgttggtctc   1500
cctaacatgt aggtggcgga ggggagatat acaatagaac agataccaga caagacataa   1560
tgggctaaac aagactacac caattacact gcctcattga tggtggtaca taacgaacta   1620
atactgtagc cctagacttg atagccatca tcatatcgaa gtttcactac cctttttcca   1680
tttgccatct attgaagtaa taataggcgc atgcaacttc ttttcttttt ttttcttttc   1740
tctctccccc gttgttgtct caccatatcc gcaatgacaa aaaaatgatg gaagacacta   1800
aaggaaaaaa ttaacgacaa agacagcacc aacagatgtc gttgttccag agctgatgag   1860
gggtatctcg aagcacacga aactttttcc ttccttcatt cacgcacact actctctaat   1920
gagcaacggt atacggcctt ccttccagtt acttgaattt gaaataaaaa aaagtttgct   1980
gtcttgctat caagtataaa tagacctgca attattaatc ttttgtttcc tcgtcattgt   2040
tctcgttccc tttcttcctt gtttcttttt ctgcacaata tttcaagcta taccaagcat   2100
acaatcaact atctcatata catctagaat gttcaaaagc gtggtttact ccattttggc   2160
tgcatctttg gcaaatgcct cagttatttc caagcgtgct acgttagata gttggttaag   2220
taatgaggca accgtagcca gaaccgcaat attgaacaat attggtgccg atggggcctg   2280
ggttagcggc gcagattccg gtatcgtagt tgcaagcccc tccactgata accccgatta   2340
cttctacact tggactaggg actccggcat cgttttgaag actctggttg acttatttag   2400
aaatggcgat acggatctac ttagcacgat agaacactat atcagttccc aagctattat   2460
acagggtgtt tctaacccca gtggagattt atcaagcgga ggccttggtg agcctaaatt   2520
```

caacgttgat gagactgcat atgcaggatc ttggggcaga ccacaaagag atggtccagc 2580
tttaagagct actgccatga taggtttcgg gcaatggttg ttggacaatg gatacacttc 2640
agcagcaact gaaatcgtct ggccgttggt cagaaatgat ttaagctatg tcgctcagta 2700
ttggaaccaa acaggctacg atttgtggga agaggtcaat ggttcttctt tctttaccat 2760
tgccgttcag cacagagccc tagtggaagg ttctgctttc gcaacagctg tggggtcttc 2820
ttgctcatgg tgtgattctc aagctcctca gatactgtgt tatttacagt cattctggac 2880
tggttcctac attcttgcta acttcgattc ttccagaagc ggcaaagata ctaacacttt 2940
gcttggcagc attcacactt ttgatcccga agctgggtgc gacgattcta ctttccaacc 3000
atgttcacca agggcgctgg ctaatcataa ggaagttgtc gattctttta gatctatcta 3060
taccttgaat gacggtctat cagattccga agccgtggct gtgggaaggt atcccgagga 3120
ttcatactac aatggtaacc catggtttct ttgcacattg gctgcagcgg aacaactgta 3180
tgatgctctt taccaatggg acaagcaagg ctctctggag atcacagatg ttagtctgga 3240
tttctttaag gctttgtact caggtgcagc caccggtaca tatagctctt caagttcaac 3300
ctatagctct atagtatccg ccgtgaagac ctttgcagat ggtttcgtta gcattgttga 3360
aacacacgct gcatcaaatg gttcactgag tgaacagttt gataaatccg acggcgatga 3420
attgagtgcg agagatttga cttggtctta tgcggctctt cttactgcta acaatagacg 3480
taatagtgtt gttccaccct cttggggtga aactagcgct agtagtgtcc cagggacttg 3540
cgcagctaca agtgcatctg gcacctacag ctcagtgact gttacatcct ggccaagtat 3600
agttgctacc ggtggcacta caaccactgc aaccactact ggtagcggag gtgttacttc 3660
aacttctaaa accacgacaa ctgcttctaa gacgtcaacg accacatcct caacaagctg 3720
tactacacct acagcggttg cagttacatt cgacctaacc gccacgacga cctacgggga 3780
aaatatatat ttggttggaa gtatctctca attaggggat tgggaaacgt ctgatggaat 3840
tgccctaagt gcagataaat atacatcttc taacccgcct tggtatgtta ccgttacatt 3900
gccagcaggc gaatcctttg aatataaatt cataagagtc gaatctgatg attctgttga 3960
atgggagtca gacccaaatc gtgagtatac tgtacctcag gcctgcggtg aaagcacagc 4020
tactgtgacc gatacttgga ggtagttaat taatttacca gcttactatc cttcttgaaa 4080
atatgcactc tatatctttt agttcttaat tgcaacacat agatttgctg tataacgaat 4140
tttatgctat ttttttaatt tggagttcgg tgatgaaagt gtcacagcga atttcctcac 4200
atgtagggac cgaattgttt acaagttctc tgtaccacca tggagacatc aaagattgaa 4260
aatctatgga aagatatgga cggtagcaac aagaatatag cacgagccgc ggagttcatt 4320
tcgttacttt tgatatcgct cacaactatt gcgaagcgct tcagtgaaaa aatcataagg 4380
aaaagttgta aatattattg gtagtattcg tttggtaaag tagagggggt aatttttccc 4440
ctttattttg ttcatacatt cttaaattgc tttgcctctc cttttggaaa gctatacttc 4500
ggagcactgt tgagcgaagg ctcaggccgg ccttatagcc tagctttaag gctactttaa 4560
aaactttttta tttattcata cacatatatt atcgaacatt cgtataactt aatatcattc 4620
aaaaaaaaaa aaaaaaaaaa aagaaaacat atacacatat atatttatgt ttatagagag 4680
agagagagaa aatttgaatt tttgaatcat ttgcaaagtt atatgtttta tacattattt 4740
attcattttt tttggtgtcg aggacattgt gctgttcaga gaaccactta aaatacgcat 4800
cgttctgtaa atatccactt tcattaaaaa ccttattcac ttctaacttt gccttcaact 4860

```
ccttcttgga gttttctccc tttttttttct gaacaagctc aaccagatat aatggttcgt   4920

tcttttcgaa ctttgtcttt acatatattt cctcctttgt acctcttctc tttcccacat   4980

aaacagtccc cttttcaata aaacgagaga aataccagaa aagtagcgag agaacaaaat   5040

atgcgcctac caaaagcttt tgatacgtaa caatctgatc tctctcaaat tttttatcca   5100

agaagaaact caaaccagct acaacagcta tggaataacc tatgtacaat ttagcatcga   5160

gtaaagcgta tgatctctcg taatttaatc tcgcgaaaac agaaggtagg gcttcatcta   5220

aagcttggtt caactccggg attgaatata cattaatagg tttagcagaa ctcatcttga   5280

acaggcgtct cttttcctta caataacttg tgcttttcct tctataattc cgtttcaacg   5340

tgtacaattg tcatttttttg tctggtatga ttttgcagaa ctgaaaaaat ctcttaaatg   5400

ttccgcctca tcaagaaggc atattccttt acaaaagtac attgatctta caagaagcta   5460

gctaatggta ctatttaaaa aacaactaca ctccatcaat acataaaatt gttatgatag   5520

acttgaggga cgg                                                       5533
```

<210> SEQ ID NO 36
<211> LENGTH: 4881
<212> TYPE: DNA
<213> ORGANISM: Artificial Sequence
<220> FEATURE:
<223> OTHER INFORMATION: Sequence put together from multiple organisms: Saccharomyces cerevisiae and Rhizopus oryzae

<400> SEQUENCE: 36

```
cagagcctct tatattcact ctgttcctcc atcgcctatt gagaaacgtt ggaataaaac     60

tctaaaaata tcatctagtt ggttagtttt tattttacca gtacattgtc acttgcggag    120

ggaggatgac ataaagattg agacgcagtc atttaatgaa gtttaaacgc aggtatttga    180

taaagtaata cgatattgaa tcatgacgta taaagtgaaa tgaacaaatg attacgtaaa    240

aaatgtcgat tttctcttga gagactccca tagcctctaa gaggccttct actacgttcc    300

atatatctaa gaatggggcc atatccagtg gaatcccagc aattatttaa ggatcaccta    360

tttctcagcc gatattttag caaaatcact accaatatca gggggcaata gttgatcgcc    420

tactttaaca aaaaatgttg ctcacgtatt aacacaggca acaaaaagga tattacgcaa    480

gaacgtagta tccacatgcc atcctccttg ttgcatcttt ttttttccga aatgattccc    540

tttcctgcac aacacgagat ctttcacgca tacatcggaa ggatcacccc ccactcaagt    600

cgttgcattg ctaacatgtg gcattctgcc catttttttc acgaaaattc tctctctata    660

atgaagaccc ttgtgccctg gactctgtaa tacttgaaac tacttcctca ataatcgctt    720

ggagacctac ccccacgctt ttcaaacaag gcgctagcaa aaagcctgcc gatatctcct    780

tgccccctcc ttctgttcga gagaactacg acccgaccaa taataatgtc atacaagaac    840

cgccaagaac caactgctga accttagatc tccaatactt cagttggagt atgtgaatat    900

ataagtacct ggtcgactaa tcttcttgca tcttttcgta ttcttacatc ctatgtcgct    960

aatacagttc ccgcatagag aagaaagcaa acaaaagtag tcactcgaga tctcccgagt   1020

ttatcattat caatactgcc atttcaaaga atacgtaaat aattaatagt agtgattttc   1080

ctaactttat ttagtcaaaa aattggcctt ttaattctgc tgtaacccgt acatgcccaa   1140

aatagggggc gggttacaca gaatatataa catcataggt gtctgggtga acagtttatt   1200

cctggcatcc actaaatata atggagcccg ctttttttaa gctggcatcc agaaaaaaaa   1260

agaatcccag caccaaaata ttgttttctt caccaaccat cagttcatag gtccattctc   1320
```

```
ttagcgcaac tacacagaac aggggcacaa acaggcaaaa aacgggcaca acctcaatgg   1380
agtgatgcaa cctgcttgga gtaaatgatg acacaaggca attgacctac gcatgtatct   1440
atctcatttt cttacacctt ctattacctt ctgctctctc tgatttggaa aaagctgaaa   1500
aaaaaggttg aaaccagttc cctgaaatta ttcccctatt tgactaataa gtatataaag   1560
acggtaggta ttgattgtaa ttctgtaaat ctatttctta aacttcttaa attctacttt   1620
tatagttagt cttttttttta gtttaaaaca ccaagaactt agtttcgaat aaacacacat   1680
aaacaaacaa atctagaatg aagttcattt ccactttctt gaccttcatt ttggctgctg   1740
tctctgtcac cgctgcatct attccatcta gtgcatctgt acaattggac tcctacaatt   1800
acgatggttc cacattttcc ggcaagattt atgtcaaaaa catcgcttac tctaaaaagg   1860
ttactgttgt gtacgcagac ggttctgaca actggaacaa taacggcaac actattgctg   1920
catcattttc aggcccaatc tctggatcaa attacgaata ctggacattc tcagcatcag   1980
tgaagggcat aaaggagttc tacatcaaat acgaagtttc aggtaagaca tattacgaca   2040
ataacaactc tgcaaactac caagtctcaa cttctaaacc tactacaact actgcagcta   2100
caaccacaac tacagctcca tcaacttcta caacaacccg tccatctagt tcagagcctg   2160
ccaccttccc tactggtaat tctaccatca gctcttggat caaaaagcag gaagatattt   2220
ccagattcgc tatgcttaga aacatcaacc cacctggttc tgccacaggg tttatcgccg   2280
catcactctc taccgctggt ccagattact actacgcgtg gacaagagat gccgctttga   2340
catctaacgt tatcgtttac gaatacaaca ccacattgtc tgggaataag acaattctaa   2400
acgtacttaa ggattacgtc acattcagtg ttaagacaca gtctacttca acagtttgta   2460
attgccttgg tgaaccaaag ttcaatccag acggcagtgg ttacacaggt gcttggggta   2520
gacctcaaaa tgatggtcct gcagaaagag cgactacatt tgttctgttt gccgacagct   2580
acttgactca aactaaggat gcctcatacg tcactggtac attaaagcca gcaattttca   2640
aagatctcga ttacgttgtt aacgtctgga gtaacggatg tttcgattta tgggaggagg   2700
tgaacggagt tcatttctac acccttatgg ttatgagaaa agggctattg ttgggggctg   2760
atttcgcgaa gagaaacggt gactcaacta gagcctcaac ttactcttct actgcttcca   2820
caattgctaa caagatatca agtttctggg ttagctcaaa caactgggtg caagtatccc   2880
aatctgtcac aggaggtgta agtaaaaagg ggttagacgt tagcaccctg ttagctgcga   2940
atctaggatc agtcgatgat ggatttttca ctccaggttc tgaaaagata ttagctacag   3000
ctgtggcagt cgaagattcc tttgccagtc tatacccaat caacaaaaac cttccatcat   3060
acttggggaa cgctattgga agataccctg aagatacata caacggtaat ggtaactcac   3120
aaggcaatcc ttggtttctg gcggttaccg gctacgcaga gttgtactat agagcaatta   3180
aggaatggat ttctaatgga ggcgttacag tgtcctctat ctcattgcca tttttcaaaa   3240
agttcgatag ctctgcaaca tccggtaaaa agtacaccgt aggtacttct gacttcaaca   3300
atttagcaca aaacattgct cttgctgcag atcgtttcct atctactgta caactccatg   3360
caccaaacaa tggttcatta gcagaggaat ttgatagaac aacaggtttt tctaccggcg   3420
ctagagattt aacatggtcc cacgcctcat tgataacagc atcctatgcc aaagccggtg   3480
ctccagctgc ataattaatt aaacaggccc cttttccttt gtcgatatca tgtaattagt   3540
tatgtcacgc ttacattcac gccctcctcc cacatccgct ctaaccgaaa aggaaggagt   3600
tagacaacct gaagtctagg tccctattta tttttttata gttatgttag tattaagaac   3660
gttatttata tttcaaattt ttcttttttt tctgtacaaa cgcgtgtacg catgtaacgg   3720
```

```
gcagacggcc ggccataact tcgtataatg tatgctatac gaagttatgg caacggttca   3780
tcatctcatg gatctgcaca tgaacaaaca ccagagtcaa acgacgttga aattgaggct   3840
actgcgccaa ttgatgacaa tacagacgat gataacaaac cgaagttatc tgatgtagaa   3900
aaggattaga gatgctaaga gatagtgatg atatttcata aataatgtaa ttctatatat   3960
gttaattacc tttttgcga ggcatattta tggtgaagga taagttttga ccatcaaaga    4020
aggttaatgt ggctgtggtt tcagggtcca taaagctttt caattcatct ttttttttt    4080
tgttcttttt tttgattccg gtttctttga aattttttg attcggtaat ctccgagcag    4140
aaggaagaac gaaggaagga gcacagactt agattggtat atatacgcat atgtggtgtt   4200
gaagaaacat gaaattgccc agtattctta acccaactgc acagaacaaa aacctgcagg   4260
aaacgaagat aaatcatgtc gaaagctaca tataaggaac gtgctgctac tcatcctagt   4320
cctgttgctg ccaagctatt taatatcatg cacgaaaagc aaacaaactt gtgtgcttca   4380
ttggatgttc gtaccaccaa ggaattactg gagttagttg aagcattagg tcccaaaatt   4440
tgtttactaa aaacacatgt ggatatcttg actgattttt ccatggaggg cacagttaag   4500
ccgctaaagg cattatccgc caagtacaat tttttactct tcgaagacag aaaatttgct   4560
gacattggta atacagtcaa attgcagtac tctgcgggtg tatacagaat agcagaatgg   4620
gcagacatta cgaatgcaca cggtgtggtg ggcccaggta ttgttagcgg tttgaagcag   4680
gcggcggaag aagtaacaaa ggaacctaga ggcctttga tgttagcaga attgtcatgc    4740
aagggctccc tagctactgg agaatatact aagggtactg ttgacattgc gaagagcgac   4800
aaagattttg ttatcggctt tattgctcaa agagacatgg gtggaagaga tgaaggttac   4860
gattggttga ttatgacacg c                                             4881
```

<210> SEQ ID NO 37
<211> LENGTH: 4921
<212> TYPE: DNA
<213> ORGANISM: Artificial Sequence
<220> FEATURE:
<223> OTHER INFORMATION: Sequence put together from multiple organisms: Saccharomyces cerevisiae and Rhizopus oryzae

<400> SEQUENCE: 37

```
ggccgctcca tggagggcac agttaagccg ctaaaggcat tatccgccaa gtacaatttt     60
ttactcttcg aagacagaaa atttgctgac attggtaata cagtcaaatt gcagtactct    120
gcgggtgtat acagaatagc agaatgggca gacattacga atgcacacgg tgtggtgggc    180
ccaggtattg ttagcggttt gaagcaggcg gcggaagaag taacaaagga acctagaggc    240
cttttgatgt tagcagaatt gtcatgcaag ggctccctag ctactggaga atatactaag    300
ggtactgttg acattgcgaa gagcgacaaa gattttgtta tcggctttat tgctcaaaga    360
gacatgggtg gaagagatga aggttacgat tggttgatta tgacacccgg tgtgggttta    420
gatgacaagg gagacgcatt gggtcaacag tatagaaccg tggatgatgt ggtctctaca    480
ggatctgaca ttattattgt tggaagagga ctatttgcaa agggaaggga tgctaaggta    540
gagggtgaac gttacagaaa agcaggctgg gaagcatatt tgagaagatg cggccagcaa    600
aactaaaaaa ctgtattata agtaaatgca tgtatactaa actcacaaat tagagcttca    660
atttaattat atcagttatt acccgggaat ctcggtcgta atgattttta taatgacgaa    720
aaaaaaaaaa ttggaaagaa aaagcttcat ggcctttata aaaaggaacc atccaatacc    780
tcgccagaac caagtaacag tattttacgg ggcacaaatc aagaacaata agacaggact    840
```

```
gtaaagatgg acgcattgaa ctccaaagaa caacaagagt tccaaaaagt agtggaacaa    900
aagcaaatga aggatttcat gcgtttgata acttcgtata atgtatgcta tacgaagtta    960
tctcgagatc tcccctaaac cgtggaatat ttcggatatc cttttgttgt ttccgggtgt   1020
acaatatgga cttcctcttt tctggcaacc aaacccatac atcgggattc ctataatacc   1080
ttcgttggtc tccctaacat gtaggtggcg gaggggagat atacaataga acagatacca   1140
gacaagacat aatgggctaa acaagactac accatttaca ctgcctcatt gatggtggta   1200
cataacgaac taatactgta gccctagact tgatagccat catcatatcg aagtttcact   1260
acccttttc catttgccat ctattgaagt aataataggc gcatgcaact tctttttttt    1320
tttttttttt ctctctcccc cgttgttgtc tcaccatatc cgcaatgaca aaaaaatgat   1380
ggaagacact aaaggaaaaa attaacgaca aagacagcac caacagatgt cgttgttcca   1440
gagctgatga ggggtatctc gaagcacacg aaactttttc cttccttcat tcacgcacac   1500
tactctctaa tgagcaacgg tatacggcct tccttccagt tacttgaatt tgaaataaaa   1560
aaaagtttgc tgtcttgcta tcaagtataa atagacctgc aattattaat cttttgtttc   1620
ctcgtcattg ttctcgttcc ctttcttcct tgtttctttt tctgcacaat atttcaagct   1680
ataccaagca tacaatcaac tatctcatat acatctagaa tgaagtttat ctccacgttt   1740
ttaaccttta tcctagcagc tgtcagcgtc accgccgcat caattccgag ttcagcatct   1800
gtacaacttg actcttacaa ttacgatggc agcactttct cagggaaaat ttatgtgaaa   1860
aacatagcat atagtaagaa ggttaccgtg gtatatgcag acggttctga taattggaat   1920
aataatggaa acactattgc cgccagtttt tccggcccaa tttctggttc caattacgag   1980
tattggacct tttctgcatc agtaaaaggc atcaaggaat tctatattaa gtacgaagtt   2040
tcaggtaaga catattacga taacaataac tcagcaaatt atcaagtctc tacatctaag   2100
cccacaacaa caactgctgc taccaccact acaaccgctc cttctaccag caccactacc   2160
agaccaagct ctagtgaacc ggctaccttt cctaccggaa acagtaccat ctcaagctgg   2220
atcaaaaagc aagaggacat aagtcgtttt gctatgttga ggaacattaa tcctccagga   2280
tccgcgaccg gtttcattgc agcatcacta agtactgccg ggcctgatta ttattatgct   2340
tggactagag acgctgcatt aacatcaaac gtgattgttt atgaatataa tacgaccctt   2400
tccggtaata aaacgatctt gaacgtatta aaagactatg tgacctttag tgtgaagacc   2460
caatctacat ctacagtgtg taattgtttg ggagaaccta aattcaatcc agacggttct   2520
gggtacactg gtgcctgggg tagacctcaa aacgacggtc cagcagaaag agcaacaacc   2580
tttgttctat ttgctgactc ttatttaacg caaacaaagg acgcctcata tgttacaggg   2640
accctaaaac cagcaatttt caaagacttg gattatgttg ttaatgtttg gagcaacgga   2700
tgttttgact tgtgggagga ggttaacggt gtacactttt atacattgat ggtgatgaga   2760
aaagggttgc tattgggagc agatttcgct aaaagaaatg gtgattctac aagagcgagc   2820
acatatagta gcaccgcttc aacaatcgcc aataaaatct catctttctg ggtatctagc   2880
aacaactggg tacaagtttc ccaaagtgtt accggcggtg tgtccaaaaa gggtttagac   2940
gttagcacac ttctagctgc taatttgggt agcgttgatg acgggttttt tactccaggt   3000
agtgagaaga tactggcaac cgcggtggcg gttgaagaca gctttgcttc attgtatcct   3060
ataaataaaa atctgccctc ttatctgggt aatgcaattg gcagataccc agaagatacc   3120
tacaatggta atggtaattc ccaggggaac ccatggtttt tggctgttac aggctacgca   3180
```

gaactttatt accgtgcaat caaggaatgg atttcaaatg gcggcgtcac tgtcagtagt 3240
ataagtttgc ccttttttaa gaaatttgat tcctcagcaa cgtctggtaa aaaatacacc 3300
gtaggtacta gtgatttcaa taatttggcc caaaatattg cgcttgctgc tgacaggttt 3360
cttagtaccg ttcagttgca cgctccaaat aatggctcat tggctgaaga atttgatcgt 3420
acgacaggtt tctccactgg tgctagggat ttgacttgga gtcatgcctc cttaatcaca 3480
gcaagctatg ctaaagctgg tgcacctgct gcttagttaa ttaatttacc agcttactat 3540
ccttcttgaa aatatgcact ctatatcttt tagttcttaa ttgcaacaca tagatttgct 3600
gtataacgaa ttttatgcta ttttttaat ttggagttcg gtgatgaaag tgtcacagcg 3660
aatttcctca catgtaggga ccgaattgtt tacaagttct ctgtaccacc atggagacat 3720
caaagattga aaatctatgg aaagatatgg acggtagcaa caagaatata gcacgagccg 3780
cggagttcat ttcgttactt ttgatatcgc tcacaactat tgcgaagcgc ttcagtgaaa 3840
aaatcataag gaaaagttgt aaatattatt ggtagtattc gtttggtaaa gtagaggggg 3900
taatttttcc cctttatttt gttcatacat tcttaaattg ctttgcctct ccttttggaa 3960
agctatactt cggagcactg ttgagcgaag gctcaggccg gccttatagc ctagctttaa 4020
ggctacttta aaaacttttt atttattcat acacatatat tatcgaacat tcgtataact 4080
taatatcatt caaaaaaaaa aaaaaaaaaa gaaaacatat acacatatat atttatgttt 4140
atagagagag agaaaaattg aatttttgaa tcatttgcaa agttatatgt tttatacatt 4200
atttattcat ttttttggt gtcgaggaca ttgtgctgtt cagagaacca cttaaaatac 4260
gcatcgttct gtaaatatcc actttcatta aaaaccttat tcacttctaa ctttgccttc 4320
aactccttct tggagttttc tccctttttt ttctgaacaa gctcaaccag atataatggt 4380
tcgttctttt cgaactttgt ctttacatat atttcctcct ttgtacctct tctctttccc 4440
acataaacag tccccttttc aataaaacga gagaaatacc agaaaagtag cgagagaaca 4500
aaatatgcgc ctaccaaaag cttttgatac gtaacaatct gatctctctc aaatttttta 4560
tccaagaaga aactcaaacc agctacaaca gctatggaat aacctatgta caatttagca 4620
tcgagtaaag cgtatgatct ctcgtaattt aatctcgcga aaacagaagg tagggcttca 4680
tctaaagctt ggttcaactc cgggattgaa tatacattaa taggtttagc agaactcatc 4740
ttgaacaggc gtctcttttc cttacaataa cttgtgcttt tccttctata attccgtttc 4800
aacgtgtaca attgtcattt tttgtctggt atgattttgc agaactgaaa aaatctctta 4860
aatgttccgc ctcatcaaga aggcatattc ctttacaaaa gtacattgat cttacaagaa 4920
g 4921

<210> SEQ ID NO 38
<211> LENGTH: 5264
<212> TYPE: DNA
<213> ORGANISM: Artificial Sequence
<220> FEATURE:
<223> OTHER INFORMATION: Sequence put together from multiple organisms: Saccharomyces cerevisiae, Rhizopus oryzae, and Aspergillus nidulans

<400> SEQUENCE: 38
cagagcctct tatattcact ctgttcctcc atcgcctatt gagaaacgtt ggaataaaac 60
tctaaaaata tcatctagtt ggttagtttt tattttacca gtacattgtc acttgcggag 120
ggaggatgac ataaagattg agacgcagtc atttaatgaa gtttaaacgc aggtatttga 180
taaagtaata cgatattgaa tcatgacgta taaagtgaaa tgaacaaatg attacgtaaa 240

```
aaatgtcgat tttctcttga gagactccca tagcctctaa gaggccttct actacgttcc    300
atatatctaa gaatggggcc atatccagtg gaatcccagc aattatttaa ggatcaccta    360
tttctcagcc gatattttag caaaatcact accaatatca gggggcaata gttgatcgcc    420
tactttaaca aaaaatgttg ctcacgtatt aacacaggca acaaaaagga tattacgcaa    480
gaacgtagta tccacatgcc atcctccttg ttgcatcttt ttttttccga aatgattccc    540
tttcctgcac aacacgagat ctttcacgca tacatcggaa ggatcacccc ccactcaagt    600
cgttgcattg ctaacatgtg gcattctgcc cattttttttc acgaaaattc tctctctata    660
atgaagaccc ttgtgccctg gactctgtaa tacttgaaac tacttcctca ataatcgctt    720
ggagacctac ccccacgctt ttcaaacaag gcgctagcaa aaagcctgcc gatatctcct    780
tgccccctcc ttctgttcga gagaactacg acccgaccaa taataatgtc atacaagaac    840
cgccaagaac caactgctga accttagatc tccaatactt cagttggagt atgtgaatat    900
ataagtacct ggtcgactaa tcttcttgca tcttttcgta ttcttacatc ctatgtcgct    960
aatacagttc ccgcatagag aagaaagcaa acaaaagtag tcactcgaga tctcccgagt   1020
ttatcattat caatactgcc atttcaaaga atacgtaaat aattaatagt agtgattttc   1080
ctaactttat ttagtcaaaa aattggcctt ttaattctgc tgtaacccgt acatgcccaa   1140
aatagggggc gggttacaca gaatatataa catcataggt gtctgggtga acagtttatt   1200
cctggcatcc actaaatata atggagcccg ctttttttaa gctggcatcc agaaaaaaaa   1260
agaatcccag caccaaaata ttgttttctt caccaaccat cagttcatag gtccattctc   1320
ttagcgcaac tacacagaac aggggcacaa acaggcaaaa aacgggcaca acctcaatgg   1380
agtgatgcaa cctgcttgga gtaaatgatg acacaaggca attgacctac gcatgtatct   1440
atctcatttt cttacacctt ctattacctt ctgctctctc tgatttggaa aaagctgaaa   1500
aaaaaggttg aaaccagttc cctgaaatta ttcccctatt tgactaataa gtatataaag   1560
acggtaggta ttgattgtaa ttctgtaaat ctatttctta aacttcttaa attctacttt   1620
tatagttagt cttttttttta gtttaaaaca ccaagaactt agtttcgaat aaacacacat   1680
aaacaaacaa atctagaatg aagttcattt ccactttctt gaccttcatt ttggctgctg   1740
tctctgtcac cgctgcatct attccatcta gtgcatctgt acaattggac tcctacaatt   1800
acgatggttc cacattttcc ggcaagattt atgtcaaaaa catcgcttac tctaaaaagg   1860
ttactgttgt gtacgcagac ggttctgaca actggaacaa taacggcaac actattgctg   1920
catcattttc aggcccaatc tctggatcaa attacgaata ctggacattc tcagcatcag   1980
tgaagggcat aaaggagttc tacatcaaat acgaagtttc aggtaagaca tattacgaca   2040
ataacaactc tgcaaactac caagtctcaa cttctaaacc tactacaact actgcagcta   2100
caaccacaac tacagctcca tcaacttcta caacaacccg tccatctagt tcagagcctg   2160
ccaccttccc tactggtaat tctaccatca gctcttggat caaaaagcag gaagatattt   2220
ccagattcgc tatgcttaga aacatcaacc cacctggttc tgccacaggg tttatcgccg   2280
catcactctc taccgctggt ccagattact actacgcgtg gacaagagat gccgctttga   2340
catctaacgt tatcgtttac gaatacaaca ccacattgtc tgggaataag acaattctaa   2400
acgtacttaa ggattacgtc acattcagtg ttaagacaca gtctacttca acagtttgta   2460
attgccttgg tgaaccaaag ttcaatccag acggcagtgg ttacacaggt gcttggggta   2520
gacctcaaaa tgatggtcct gcagaaagag cgactacatt tgttctgttt gccgacagct   2580
```

```
acttgactca aactaaggat gcctcatacg tcactggtac attaaagcca gcaattttca   2640
aagatctcga ttacgttgtt aacgtctgga gtaacggatg tttcgattta tgggaggagg   2700
tgaacggagt tcatttctac acccttatgg ttatgagaaa agggctattg ttgggggctg   2760
atttcgcgaa gagaaacggt gactcaacta gagcctcaac ttactcttct actgcttcca   2820
caattgctaa caagatatca agtttctggg ttagctcaaa caactgggtg caagtatccc   2880
aatctgtcac aggaggtgta agtaaaaagg ggttagacgt tagcaccctg ttagctgcga   2940
atctaggatc agtcgatgat ggatttttca ctccaggttc tgaaaagata ttagctacag   3000
ctgtggcagt cgaagattcc tttgccagtc tatacccaat caacaaaaac cttccatcat   3060
acttggggaa cgctattgga agataccctg aagatacata caacggtaat ggtaactcac   3120
aaggcaatcc ttggtttctg gcggttaccg gctacgcaga gttgtactat agagcaatta   3180
aggaatggat ttctaatgga ggcgttacag tgtcctctat ctcattgcca tttttcaaaa   3240
agttcgatag ctctgcaaca tccggtaaaa agtacaccgt aggtacttct gacttcaaca   3300
atttagcaca aaacattgct cttgctgcag atcgtttcct atctactgta caactccatg   3360
caccaaacaa tggttcatta gcagaggaat ttgatagaac aacaggtttt tctaccggcg   3420
ctagagattt aacatggtcc cacgcctcat tgataacagc atcctatgcc aaagccggtg   3480
ctccagctgc ataattaatt aaacaggccc cttttccttt gtcgatatca tgtaattagt   3540
tatgtcacgc ttacattcac gccctcctcc cacatccgct ctaaccgaaa aggaaggagt   3600
tagacaacct gaagtctagg tccctattta tttttttata gttatgttag tattaagaac   3660
gttatttata tttcaaattt ttcttttttt tctgtacaaa cgcgtgtacg catgtaacgg   3720
gcagacggcc ggccataact tcgtataatg tatgctatac gaagttatcc ttacatcaca   3780
cccaatcccc cacaagtgat cccccacaca ccatagcttc aaaatgtttc tactcctttt   3840
ttactcttcc agattttctc ggactccgcg catcgccgta ccacttcaaa acacccaagc   3900
acagcatact aaatttcccc tctttcttcc tctagggtgg cgttaattac ccgtactaaa   3960
ggtttggaaa agaaaaaaga gaccgcctcg tttctttttc ttcgtcgaaa aaggcaataa   4020
aaatttttat cacgtttctt tttcttgaaa aatttttttt ttgatttttt tctctttcga   4080
tgacctccca ttgatattta agttaataaa tggtcttcaa tttctcaagt ttcagtttcg   4140
tttttcttgt tctattacaa cttttttttac ttcttgctca ttagaaagaa agcatagcaa   4200
tctaatctaa gttttaatta caaaatgcca caatcctggg aagaattggc cgccgacaaa   4260
cgtgcccgtt tggctaaaac cattcctgac gaatggaagg ttcaaacttt gcctgccgaa   4320
gattccgtta ttgatttccc aaagaagtcc ggtattttgt ctgaggctga attgaagatt   4380
accgaagcct ctgctgctga tttggtctcc aagttggccg ctggtgagtt gacttctgtt   4440
gaagtcactt tggctttttg taagagagct gctattgctc aacaattaac caactgtgct   4500
cacgaattct tcccagatgc tgctttagct caagctagag aattagatga atactacgct   4560
aagcataaga gaccagttgg tccattacac ggtttaccaa tctctttaaa ggaccaattg   4620
cgtgttaagg gttacgaaac ctccatgggt tacatttcct ggttaaacaa atacgatgaa   4680
ggtgattccg tcttaaccac catgttgaga aaagctggtg ctgttttcta cgttaagacc   4740
tctgtcccac aaaccttgat ggtctgtgaa accgtcaaca acatcattgg tagaactgtc   4800
aatccaagaa acaaaaattg gtcctgtggt ggttcttctg gtggtgaagg tgctattgtt   4860
ggtattagag gtggtgttat tggtgtcggt actgacattg gtggttccat tagagtccca   4920
gctgctttca actttttata cggtttgaga ccatctcacg gtagattgcc atatgctaaa   4980
```

atggctaact ctatggaagg tcaagaaacc gttcactccg tcgttggtcc tatcactcac 5040
tccgtcgaag acttgagatt gttcaccaaa tctgtcttgg gtcaagaacc ttggaagtac 5100
gactctaagg tcatccccat gccatggaga caatctgaat ctgacatcat tgcctctaag 5160
attaagaatg gtggtttgaa cattggttat tacaatttcg acggtaacgt cttgccacac 5220
ccaccaattt tacgtggtgt cgaaactacc gttgccgctt tggc 5264

<210> SEQ ID NO 39
<211> LENGTH: 5337
<212> TYPE: DNA
<213> ORGANISM: Artificial Sequence
<220> FEATURE:
<223> OTHER INFORMATION: Sequence put together from multiple organisms: Saccharomyces cerevisiae, Rhizopus oryzae, and Aspergillus nidulans

<400> SEQUENCE: 39
ggccgcgaag gtgctattgt tggtattaga ggtggtgtta ttggtgtcgg tactgacatt 60
ggtggttcca ttagagtccc agctgctttc aactttttat acggtttgag accatctcac 120
ggtagattgc catatgctaa aatggctaac tctatggaag gtcaagaaac cgttcactcc 180
gtcgttggtc ctatcactca ctccgtcgaa gacttgagat tgttcaccaa atctgtcttg 240
ggtcaagaac cttggaagta cgactctaag gtcatcccaa tgccatggag acaatctgaa 300
tctgacatca ttgcctctaa gattaagaat ggtggtttga acattggtta ttacaatttc 360
gacggtaacg tcttgccaca cccaccaatt ttacgtggtg tcgaaactac cgttgccgct 420
ttggccaagg ctggtcacac cgttactcca tggactccat acaagcatga tttcggtcat 480
gacttgattt cccacatcta tgctgctgat ggttctgccg acgtcatgag agacatttct 540
gcctctggtg agccagccat ccctaacatt aaggacttgt tgaacccaaa tattaaggct 600
gttaacatga acgaattgtg ggacactcat ttacaaaagt ggaactatca aatggaatac 660
ttggaaaagt ggcgtgaagc tgaagaaaaa gctggtaagg aattggacgc tattatcgct 720
ccaattactc ctaccgccgc tgtcagacac gatcaattca gatactacgg ttacgcctcc 780
gttattaact tattggattt cacctctgtt gtcgtcccag tcactttcgc tgataagaat 840
attgataaga agaacgaatc ttttaaagct gtttccgaat tggatgcttt ggttcaagaa 900
gaatacgacc cagaggctta tcacggtgct cctgttgctg ttcaagttat tggtagaaga 960
ttgtccgaag agagaacttt ggctatcgcc gaagaagtcg gtaaattgtt gggtaacgtc 1020
gtcactccat aagcgaattt cttatgattt atgattttta ttattaaata agttataaaa 1080
aaaataagtg tatacaaatt ttaaagtgac tcttaggttt taaaacgaaa attcttattc 1140
ttgagtaact ctttcctgta ggtcaggttg ctttctcagg tatagcatga ggtcgctctt 1200
attgaccaca cctctaccgg catgccgagc aaatgcctgc aaatcgctcc ccatttcacc 1260
caattgtaga tatgctaact ccagcaatga gttgatgaat ctcggtgtgt attttatgtc 1320
ctcagaggac aacacataac ttcgtataat gtatgctata cgaagttatc tcgagatctc 1380
ccctaaaccg tggaatattt cggatatcct tttgttgttt ccgggtgtac aatatggact 1440
tcctcttttc tggcaaccaa acccatacat cgggattcct ataatacctt cgttggtctc 1500
cctaacatgt aggtggcgga ggggagatat acaatagaac agataccaga caagacataa 1560
tgggctaaac aagactacac caattacact gcctcattga tggtggtaca taacgaacta 1620
atactgtagc cctagacttg atagccatca tcatatcgaa gtttcactac ccttttttcca 1680

```
tttgccatct attgaagtaa taataggcgc atgcaacttc ttttcttttt ttttcttttc   1740
tctctccccc gttgttgtct caccatatcc gcaatgacaa aaaaatgatg gaagacacta   1800
aaggaaaaaa ttaacgacaa agacagcacc aacagatgtc gttgttccag agctgatgag   1860
gggtatctcg aagcacacga aactttttcc ttccttcatt cacgcacact actctctaat   1920
gagcaacggt atacggcctt ccttccagtt acttgaattt gaaataaaaa aaagtttgct   1980
gtcttgctat caagtataaa tagacctgca attattaatc ttttgtttcc tcgtcattgt   2040
tctcgttccc tttcttcctt gtttcttttt ctgcacaata tttcaagcta taccaagcat   2100
acaatcaact atctcatata catctagaat gaagtttatc tccacgtttt taacctttat   2160
cctagcagct gtcagcgtca ccgccgcatc aattccgagt tcagcatctg tacaacttga   2220
ctcttacaat tacgatggca gcactttctc agggaaaatt tatgtgaaaa acatagcata   2280
tagtaagaag gttaccgtgg tatatgcaga cggttctgat aattggaata ataatggaaa   2340
cactattgcc gccagttttt ccggcccaat ttctggttcc aattacgagt attggacctt   2400
ttctgcatca gtaaaaggca tcaaggaatt ctatattaag tacgaagttt caggtaagac   2460
atattacgat aacaataact cagcaaatta tcaagtctct acatctaagc ccacaacaac   2520
aactgctgct accaccacta caaccgctcc ttctaccagc accactacca gaccaagctc   2580
tagtgaaccg gctacctttc ctaccggaaa cagtaccatc tcaagctgga tcaaaaagca   2640
agaggacata agtcgttttg ctatgttgag gaacattaat cctccaggat ccgcgaccgg   2700
tttcattgca gcatcactaa gtactgccgg gcctgattat tattatgctt ggactagaga   2760
cgctgcatta acatcaaacg tgattgttta tgaatataat acgacccttt ccggtaataa   2820
aacgatcttg aacgtattaa aagactatgt gacctttagt gtgaagaccc aatctacatc   2880
tacagtgtgt aattgtttgg gagaacctaa attcaatcca gacggttctg ggtacactgg   2940
tgcctggggt agacctcaaa acgacggtcc agcagaaaga gcaacaacct ttgttctatt   3000
tgctgactct tatttaacgc aaacaaagga cgcctcatat gttacaggga ccctaaaacc   3060
agcaattttc aaagacttgg attatgttgt taatgtttgg agcaacggat gttttgactt   3120
gtgggaggag gttaacggtg tacactttta tacattgatg gtgatgagaa aagggttgct   3180
attgggagca gatttcgcta aaagaaatgg tgattctaca agagcgagca catatagtag   3240
caccgcttca acaatcgcca ataaaatctc atctttctgg gtatctagca acaactgggt   3300
acaagtttcc caaagtgtta ccggcggtgt gtccaaaaag ggtttagacg ttagcacact   3360
tctagctgct aatttgggta gcgttgatga cgggtttttt actccaggta gtgagaagat   3420
actggcaacc gcggtggcgg ttgaagacag ctttgcttca ttgtatccta taaataaaaa   3480
tctgccctct tatctgggta atgcaattgg cagataccca gaagatacct acaatggtaa   3540
tggtaattcc caggggaacc catggttttt ggctgttaca ggctacgcag aactttatta   3600
ccgtgcaatc aaggaatgga tttcaaatgg cggcgtcact gtcagtagta taagtttgcc   3660
ctttttaag aaatttgatt cctcagcaac gtctggtaaa aaatacaccg taggtactag   3720
tgatttcaat aatttggccc aaaatattgc gcttgctgct gacaggtttc ttagtaccgt   3780
tcagttgcac gctccaaata atggctcatt ggctgaagaa tttgatcgta cgacaggttt   3840
ctccactggt gctagggatt tgacttggag tcatgcctcc ttaatcacag caagctatgc   3900
taaagctggt gcacctgctg cttagttaat taatttacca gcttactatc cttcttgaaa   3960
atatgcactc tatatctttt agttcttaat tgcaacacat agatttgctg tataacgaat   4020
tttatgctat ttttttaatt tggagttcgg tgatgaaagt gtcacagcga atttcctcac   4080
```

```
atgtagggac cgaattgttt acaagttctc tgtaccacca tggagacatc aaagattgaa   4140

aatctatgga aagatatgga cggtagcaac aagaatatag cacgagccgc ggagttcatt   4200

tcgttacttt tgatatcgct cacaactatt gcgaagcgct tcagtgaaaa aatcataagg   4260

aaaagttgta aatattattg gtagtattcg tttggtaaag tagagggggt aatttttccc   4320

ctttattttg ttcatacatt cttaaattgc tttgcctctc cttttggaaa gctatacttc   4380

ggagcactgt tgagcgaagg ctcaggccgg ccttatagcc tagctttaag gctactttaa   4440

aaacttttta tttattcata cacatatatt atcgaacatt cgtataactt aatatcattc   4500

aaaaaaaaaa aaaaaaaaaa aagaaaacat atacacatat atatttatgt ttatagagag   4560

agagagagaa aatttgaatt tttgaatcat ttgcaaagtt atatgtttta tacattattt   4620

attcattttt tttggtgtcg aggacattgt gctgttcaga gaaccactta aaatacgcat   4680

cgttctgtaa atatccactt tcattaaaaa ccttattcac ttctaacttt gccttcaact   4740

ccttcttgga gttttctccc ttttttttct gaacaagctc aaccagatat aatggttcgt   4800

tcttttcgaa ctttgtcttt acatatattt cctcctttgt acctcttctc tttcccacat   4860

aaacagtccc cttttcaata aaacgagaga aataccagaa aagtagcgag agaacaaaat   4920

atgcgcctac caaaagcttt tgatacgtaa caatctgatc tctctcaaat tttttatcca   4980

agaagaaact caaaccagct acaacagcta tggaataacc tatgtacaat ttagcatcga   5040

gtaaagcgta tgatctctcg taatttaatc tcgcgaaaac agaaggtagg gcttcatcta   5100

aagcttggtt caactccggg attgaatata cattaatagg tttagcagaa ctcatcttga   5160

acaggcgtct cttttcctta caataacttg tgcttttcct tctataattc cgtttcaacg   5220

tgtacaattg tcatttttg tctggtatga ttttgcagaa ctgaaaaaat ctcttaaatg   5280

ttccgcctca tcaagaaggc atattccttt acaaaagtac attgatctta caagaag      5337
```

<210> SEQ ID NO 40
<211> LENGTH: 1684
<212> TYPE: DNA
<213> ORGANISM: Artificial Sequence
<220> FEATURE:
<223> OTHER INFORMATION: Synthetic sequence containing elements from Saccharomyces cerevisiae

<400> SEQUENCE: 40

```
ggccgccagt gtgatggata tctgcagaat tcgcccttgc tagcggcaac ggttcatcat     60

ctcatggatc tgcacatgaa caaacaccag agtcaaacga cgttgaaatt gaggctactg    120

cgccaattga tgacaataca gacgatgata acaaaccgaa gttatctgat gtagaaaagg    180

attagagatg ctaagagata gtgatgatat ttcataaata atgtaattct atatatgtta    240

attacctttt ttgcgaggca tatttatggt gaaggataag ttttgaccat caaagaaggt    300

taatgtggct gtggtttcag ggtccataaa gcttttcaat tcatcttttt ttttttttgtt    360

cttttttttg attccggttt ctttgaaatt tttttgattc ggtaatctcc gagcagaagg    420

aagaacgaag gaaggagcac agacttagat tggtatatat acgcatatgt ggtgttgaag    480

aaacatgaaa ttgcccagta ttcttaaccc aactgcacag aacaaaaacc tgcaggaaac    540

gaagataaat catgtcgaaa gctacatata aggaacgtgc tgctactcat cctagtcctg    600

ttgctgccaa gctatttaat atcatgcacg aaaagcaaac aaacttgtgt gcttcattgg    660

atgttcgtac caccaaggaa ttactggagt tagttgaagc attaggtccc aaaatttgtt    720

tactaaaaac acatgtggat atcttgactg atttttccat ggagggcaca gttaagccgc    780
```

```
taaaggcatt atccgccaag tacaattttt tactcttcga agacagaaaa tttgctgaca    840

ttggtaatac agtcaaattg cagtactctg cgggtgtata cagaatagca gaatgggcag    900

acattacgaa tgcacacggt gtggtgggcc caggtattgt tagcggtttg aagcaggcgg    960

cggaagaagt aacaaaggaa cctagaggcc ttttgatgtt agcagaattg tcatgcaagg   1020

gctccctagc tactggagaa tatactaagg gtactgttga cattgcgaag agcgacaaag   1080

attttgttat cggctttatt gctcaaagag acatgggtgg aagagatgaa ggttacgatt   1140

ggttgattat gacacccggt gtgggtttag atgacaaggg agacgcattg ggtcaacagt   1200

atagaaccgt ggatgatgtg gtctctacag gatctgacat tattattgtt ggaagaggac   1260

tatttgcaaa gggaagggat gctaaggtag agggtgaacg ttacagaaaa gcaggctggg   1320

aagcatattt gagaagatgc ggccagcaaa actaaaaaac tgtattataa gtaaatgcat   1380

gtatactaaa ctcacaaatt agagcttcaa tttaattata tcagttatta cccgggaatc   1440

tcggtcgtaa tgatttttat aatgacgaaa aaaaaaaaat tggaaagaaa aagcttcatg   1500

gcctttataa aaaggaacca tccaatacct cgccagaacc aagtaacagt attttacggg   1560

gcacaaatca agaacaataa gacaggactg taaagatgga cgcattgaac tccaaagaac   1620

aacaagagtt ccaaaaagta gtggaacaaa agcaaatgaa ggatttcatg cgtttgccgc   1680

gggc                                                                1684
```

<210> SEQ ID NO 41
<211> LENGTH: 497
<212> TYPE: PRT
<213> ORGANISM: Artificial Sequence
<220> FEATURE:
<223> OTHER INFORMATION: Synthetic sequence containing elements from Saccharomyces cerevisiae

<400> SEQUENCE: 41

```
Val Pro Val Glu Leu Asp Lys Arg Asn Thr Gly His Phe Gln Ala Tyr
1               5                   10                  15

Ser Gly Tyr Thr Val Ala Arg Ser Asn Phe Thr Gln Trp Ile His Glu
            20                  25                  30

Gln Pro Ala Val Ser Trp Tyr Tyr Leu Leu Gln Asn Ile Asp Tyr Pro
        35                  40                  45

Glu Gly Gln Phe Lys Ser Ala Lys Pro Gly Val Val Ala Ser Pro
    50                  55                  60

Ser Thr Ser Glu Pro Asp Tyr Phe Tyr Gln Trp Thr Arg Asp Thr Ala
65                  70                  75                  80

Ile Thr Phe Leu Ser Leu Ile Ala Glu Val Glu Asp His Ser Phe Ser
                85                  90                  95

Asn Thr Thr Leu Ala Lys Val Val Glu Tyr Tyr Ile Ser Asn Thr Tyr
            100                 105                 110

Thr Leu Gln Arg Val Ser Asn Pro Ser Gly Asn Phe Asp Ser Pro Asn
        115                 120                 125

His Asp Gly Leu Gly Glu Pro Lys Phe Asn Val Asp Asp Thr Ala Tyr
    130                 135                 140

Thr Ala Ser Trp Gly Arg Pro Gln Asn Asp Gly Pro Ala Leu Arg Ala
145                 150                 155                 160

Tyr Ala Ile Ser Arg Tyr Leu Asn Ala Val Ala Lys His Asn Asn Gly
                165                 170                 175

Lys Leu Leu Leu Ala Gly Gln Asn Gly Ile Pro Tyr Ser Ser Ala Ser
            180                 185                 190
```

```
Asp Ile Tyr Trp Lys Ile Ile Lys Pro Asp Leu Gln His Val Ser Thr
        195                 200                 205

His Trp Ser Thr Ser Gly Phe Asp Leu Trp Glu Glu Asn Gln Gly Thr
    210                 215                 220

His Phe Phe Thr Ala Leu Val Gln Leu Lys Ala Leu Ser Tyr Gly Ile
225                 230                 235                 240

Pro Leu Ser Lys Thr Tyr Asn Asp Pro Gly Phe Thr Ser Trp Leu Glu
                245                 250                 255

Lys Gln Lys Asp Ala Leu Asn Ser Tyr Ile Asn Ser Ser Gly Phe Val
            260                 265                 270

Asn Ser Gly Lys Lys His Ile Val Glu Ser Pro Gln Leu Ser Ser Arg
        275                 280                 285

Gly Gly Leu Asp Ser Ala Thr Tyr Ile Ala Ala Leu Ile Thr His Asp
    290                 295                 300

Ile Gly Asp Asp Asp Thr Tyr Thr Pro Phe Asn Val Asp Asn Ser Tyr
305                 310                 315                 320

Val Leu Asn Ser Leu Tyr Tyr Leu Leu Val Asp Asn Lys Asn Arg Tyr
                325                 330                 335

Lys Ile Asn Gly Asn Tyr Lys Ala Gly Ala Ala Val Gly Arg Tyr Pro
            340                 345                 350

Glu Asp Val Tyr Asn Gly Val Gly Thr Ser Glu Gly Asn Pro Trp Gln
        355                 360                 365

Leu Ala Thr Ala Tyr Ala Gly Gln Thr Phe Tyr Thr Leu Ala Tyr Asn
    370                 375                 380

Ser Leu Lys Asn Lys Lys Asn Leu Val Ile Glu Lys Leu Asn Tyr Asp
385                 390                 395                 400

Leu Tyr Asn Ser Phe Ile Ala Asp Leu Ser Lys Ile Asp Ser Ser Tyr
                405                 410                 415

Ala Ser Lys Asp Ser Leu Thr Leu Thr Tyr Gly Ser Asp Asn Tyr Lys
            420                 425                 430

Asn Val Ile Lys Ser Leu Leu Gln Phe Gly Asp Ser Phe Leu Lys Val
        435                 440                 445

Leu Leu Asp His Ile Asp Asp Asn Gly Gln Leu Thr Glu Glu Ile Asn
    450                 455                 460

Arg Tyr Thr Gly Phe Gln Ala Gly Ala Val Ser Leu Thr Trp Ser Ser
465                 470                 475                 480

Gly Ser Leu Leu Ser Ala Asn Arg Ala Arg Asn Lys Leu Ile Glu Leu
                485                 490                 495

Leu


<210> SEQ ID NO 42
<211> LENGTH: 579
<212> TYPE: PRT
<213> ORGANISM: Rhizopus oryzae

<400> SEQUENCE: 42

Ala Ser Ile Pro Ser Ser Ala Ser Val Gln Leu Asp Ser Tyr Asn Tyr
1               5                   10                  15

Asp Gly Ser Thr Phe Ser Gly Lys Ile Tyr Val Lys Asn Ile Ala Tyr
            20                  25                  30

Ser Lys Lys Val Thr Val Val Tyr Ala Asp Gly Ser Asp Asn Trp Asn
        35                  40                  45

Asn Asn Gly Asn Thr Ile Ala Ala Ser Phe Ser Gly Pro Ile Ser Gly
    50                  55                  60
```

```
Ser Asn Tyr Glu Tyr Trp Thr Phe Ser Ala Ser Val Lys Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser Lys Pro Thr Thr Thr
            100                 105                 110

Thr Ala Ala Thr Thr Thr Thr Thr Ala Pro Ser Thr Ser Thr Thr Thr
        115                 120                 125

Arg Pro Ser Ser Ser Glu Pro Ala Thr Phe Pro Thr Gly Asn Ser Thr
    130                 135                 140

Ile Ser Ser Trp Ile Lys Lys Gln Glu Asp Ile Ser Arg Phe Ala Met
145                 150                 155                 160

Leu Arg Asn Ile Asn Pro Pro Gly Ser Ala Thr Gly Phe Ile Ala Ala
                165                 170                 175

Ser Leu Ser Thr Ala Gly Pro Asp Tyr Tyr Tyr Ala Trp Thr Arg Asp
            180                 185                 190

Ala Ala Leu Thr Ser Asn Val Ile Val Tyr Glu Tyr Asn Thr Thr Leu
        195                 200                 205

Ser Gly Asn Lys Thr Ile Leu Asn Val Leu Lys Asp Tyr Val Thr Phe
    210                 215                 220

Ser Val Lys Thr Gln Ser Thr Ser Thr Val Cys Asn Cys Leu Gly Glu
225                 230                 235                 240

Pro Lys Phe Asn Pro Asp Gly Ser Gly Tyr Thr Gly Ala Trp Gly Arg
                245                 250                 255

Pro Gln Asn Asp Gly Pro Ala Glu Arg Ala Thr Thr Phe Val Leu Phe
            260                 265                 270

Ala Asp Ser Tyr Leu Thr Gln Thr Lys Asp Ala Ser Tyr Val Thr Gly
        275                 280                 285

Thr Leu Lys Pro Ala Ile Phe Lys Asp Leu Asp Tyr Val Val Asn Val
    290                 295                 300

Trp Ser Asn Gly Cys Phe Asp Leu Trp Glu Glu Val Asn Gly Val His
305                 310                 315                 320

Phe Tyr Thr Leu Met Val Met Arg Lys Gly Leu Leu Leu Gly Ala Asp
                325                 330                 335

Phe Ala Lys Arg Asn Gly Asp Ser Thr Arg Ala Ser Thr Tyr Ser Ser
            340                 345                 350

Thr Ala Ser Thr Ile Ala Asn Lys Ile Ser Ser Phe Trp Val Ser Ser
        355                 360                 365

Asn Asn Trp Val Gln Val Ser Gln Ser Val Thr Gly Gly Val Ser Lys
    370                 375                 380

Lys Gly Leu Asp Val Ser Thr Leu Leu Ala Ala Asn Leu Gly Ser Val
385                 390                 395                 400

Asp Asp Gly Phe Phe Thr Pro Gly Ser Glu Lys Ile Leu Ala Thr Ala
                405                 410                 415

Val Ala Val Glu Asp Ser Phe Ala Ser Leu Tyr Pro Ile Asn Lys Asn
            420                 425                 430

Leu Pro Ser Tyr Leu Gly Asn Ala Ile Gly Arg Tyr Pro Glu Asp Thr
        435                 440                 445

Tyr Asn Gly Asn Gly Asn Ser Gln Gly Asn Pro Trp Phe Leu Ala Val
    450                 455                 460

Thr Gly Tyr Ala Glu Leu Tyr Tyr Arg Ala Ile Lys Glu Trp Ile Ser
465                 470                 475                 480
```

```
Asn Gly Gly Val Thr Val Ser Ser Ile Ser Leu Pro Phe Phe Lys Lys
                485                 490                 495

Phe Asp Ser Ser Ala Thr Ser Gly Lys Lys Tyr Thr Val Gly Thr Ser
            500                 505                 510

Asp Phe Asn Asn Leu Ala Gln Asn Ile Ala Leu Ala Ala Asp Arg Phe
        515                 520                 525

Leu Ser Thr Val Gln Leu His Ala Pro Asn Asn Gly Ser Leu Ala Glu
    530                 535                 540

Glu Phe Asp Arg Thr Thr Gly Phe Ser Thr Gly Ala Arg Asp Leu Thr
545                 550                 555                 560

Trp Ser His Ala Ser Leu Ile Thr Ala Ser Tyr Ala Lys Ala Gly Ala
                565                 570                 575

Pro Ala Ala


<210> SEQ ID NO 43
<211> LENGTH: 621
<212> TYPE: PRT
<213> ORGANISM: Aspergillus shirousami

<400> SEQUENCE: 43

Ser Val Ile Ser Lys Arg Ala Thr Leu Asp Ser Trp Leu Ser Asn Glu
1               5                   10                  15

Ala Thr Val Ala Arg Thr Ala Ile Leu Asn Asn Ile Gly Ala Asp Gly
            20                  25                  30

Ala Trp Val Ser Gly Ala Asp Ser Gly Ile Val Val Ala Ser Pro Ser
        35                  40                  45

Thr Asp Asn Pro Asp Tyr Phe Tyr Thr Trp Thr Arg Asp Ser Gly Ile
    50                  55                  60

Val Leu Lys Thr Leu Val Asp Leu Phe Arg Asn Gly Asp Thr Asp Leu
65                  70                  75                  80

Leu Ser Thr Ile Glu His Tyr Ile Ser Ser Gln Ala Ile Ile Gln Gly
                85                  90                  95

Val Ser Asn Pro Ser Gly Asp Leu Ser Ser Gly Gly Leu Gly Glu Pro
            100                 105                 110

Lys Phe Asn Val Asp Glu Thr Ala Tyr Ala Gly Ser Trp Gly Arg Pro
        115                 120                 125

Gln Arg Asp Gly Pro Ala Leu Arg Ala Thr Ala Met Ile Gly Phe Gly
    130                 135                 140

Gln Trp Leu Leu Asp Asn Gly Tyr Thr Ser Ala Ala Thr Glu Ile Val
145                 150                 155                 160

Trp Pro Leu Val Arg Asn Asp Leu Ser Tyr Val Ala Gln Tyr Trp Asn
                165                 170                 175

Gln Thr Gly Tyr Asp Leu Trp Glu Glu Val Asn Gly Ser Ser Phe Phe
            180                 185                 190

Thr Ile Ala Val Gln His Arg Ala Leu Val Glu Gly Ser Ala Phe Ala
        195                 200                 205

Thr Ala Val Gly Ser Ser Cys Ser Trp Cys Asp Ser Gln Ala Pro Gln
    210                 215                 220

Ile Leu Cys Tyr Leu Gln Ser Phe Trp Thr Gly Ser Tyr Ile Leu Ala
225                 230                 235                 240

Asn Phe Asp Ser Ser Arg Ser Gly Lys Asp Thr Asn Thr Leu Leu Gly
                245                 250                 255

Ser Ile His Thr Phe Asp Pro Glu Ala Gly Cys Asp Asp Ser Thr Phe
            260                 265                 270
```

```
Gln Pro Cys Ser Pro Arg Ala Leu Ala Asn His Lys Glu Val Val Asp
        275                 280                 285

Ser Phe Arg Ser Ile Tyr Thr Leu Asn Asp Gly Leu Ser Asp Ser Glu
    290                 295                 300

Ala Val Ala Val Gly Arg Tyr Pro Glu Asp Ser Tyr Tyr Asn Gly Asn
305                 310                 315                 320

Pro Trp Phe Leu Cys Thr Leu Ala Ala Ala Glu Gln Leu Tyr Asp Ala
                325                 330                 335

Leu Tyr Gln Trp Asp Lys Gln Gly Ser Leu Glu Ile Thr Asp Val Ser
            340                 345                 350

Leu Asp Phe Phe Lys Ala Leu Tyr Ser Gly Ala Ala Thr Gly Thr Tyr
        355                 360                 365

Ser Ser Ser Ser Ser Thr Tyr Ser Ser Ile Val Ser Ala Val Lys Thr
    370                 375                 380

Phe Ala Asp Gly Phe Val Ser Ile Val Glu Thr His Ala Ala Ser Asn
385                 390                 395                 400

Gly Ser Leu Ser Glu Gln Phe Asp Lys Ser Asp Gly Asp Glu Leu Ser
                405                 410                 415

Ala Arg Asp Leu Thr Trp Ser Tyr Ala Ala Leu Leu Thr Ala Asn Asn
            420                 425                 430

Arg Arg Asn Ser Val Val Pro Pro Ser Trp Gly Glu Thr Ser Ala Ser
        435                 440                 445

Ser Val Pro Gly Thr Cys Ala Ala Thr Ser Ala Ser Gly Thr Tyr Ser
    450                 455                 460

Ser Val Thr Val Thr Ser Trp Pro Ser Ile Val Ala Thr Gly Gly Thr
465                 470                 475                 480

Thr Thr Thr Ala Thr Thr Thr Gly Ser Gly Gly Val Thr Ser Thr Ser
                485                 490                 495

Lys Thr Thr Thr Thr Ala Ser Lys Thr Ser Thr Thr Thr Ser Ser Thr
            500                 505                 510

Ser Cys Thr Thr Pro Thr Ala Val Ala Val Thr Phe Asp Leu Thr Ala
        515                 520                 525

Thr Thr Thr Tyr Gly Glu Asn Ile Tyr Leu Val Gly Ser Ile Ser Gln
    530                 535                 540

Leu Gly Asp Trp Glu Thr Ser Asp Gly Ile Ala Leu Ser Ala Asp Lys
545                 550                 555                 560

Tyr Thr Ser Ser Asn Pro Pro Trp Tyr Val Thr Val Thr Leu Pro Ala
                565                 570                 575

Gly Glu Ser Phe Glu Tyr Lys Phe Ile Arg Val Glu Ser Asp Asp Ser
            580                 585                 590

Val Glu Trp Glu Ser Asp Pro Asn Arg Glu Tyr Thr Val Pro Gln Ala
        595                 600                 605

Cys Gly Glu Ser Thr Ala Thr Val Thr Asp Thr Trp Arg
    610                 615                 620


<210> SEQ ID NO 44
<211> LENGTH: 616
<212> TYPE: PRT
<213> ORGANISM: Aspergillus terreus

<400> SEQUENCE: 44

Ala Pro Gln Leu Ala Pro Arg Ala Thr Thr Ser Leu Asp Ala Trp Leu
1               5                   10                  15

Ala Ser Glu Thr Thr Val Ala Leu Asp Gly Ile Leu Asp Asn Val Gly
            20                  25                  30
```

```
Ser Ser Gly Ala Tyr Ala Lys Ser Ala Lys Ser Gly Ile Val Ile Ala
        35                  40                  45

Ser Pro Ser Thr Ser Asp Pro Asp Tyr Tyr Tyr Thr Trp Thr Arg Asp
    50                  55                  60

Ala Ala Leu Thr Val Lys Ala Leu Ile Asp Leu Phe Arg Asn Gly Glu
65                  70                  75                  80

Thr Ser Leu Gln Thr Val Ile Met Glu Tyr Ile Ser Ser Gln Ala Tyr
                85                  90                  95

Leu Gln Thr Val Ser Asn Pro Ser Gly Ser Leu Ser Thr Gly Gly Leu
            100                 105                 110

Ala Glu Pro Lys Tyr Tyr Val Asp Glu Thr Ala Tyr Thr Gly Ser Trp
        115                 120                 125

Gly Arg Pro Gln Arg Asp Gly Pro Ala Leu Arg Ala Thr Ala Met Ile
    130                 135                 140

Asp Phe Gly Asn Trp Leu Ile Asp Asn Gly Tyr Ser Thr Tyr Ala Ser
145                 150                 155                 160

Ser Ile Val Trp Pro Ile Val Arg Asn Asp Leu Ser Tyr Val Ala Gln
                165                 170                 175

Tyr Trp Asn Gln Thr Gly Tyr Asp Leu Trp Glu Glu Val Asn Gly Ser
            180                 185                 190

Ser Phe Phe Thr Ile Ala Val Gln His Arg Ala Leu Val Glu Gly Ser
        195                 200                 205

Thr Phe Ala Ser Lys Val Gly Ala Ser Cys Ser Trp Cys Asp Ser Gln
    210                 215                 220

Ala Pro Gln Val Leu Cys Phe Leu Gln Arg Phe Trp Thr Gly Ser Tyr
225                 230                 235                 240

Ile Met Ala Asn Phe Gly Gly Gly Arg Ser Gly Lys Asp Ala Asn Thr
                245                 250                 255

Val Leu Gly Ser Ile His Thr Phe Asp Pro Asn Ala Gly Cys Asp Asp
            260                 265                 270

Thr Thr Phe Gln Pro Cys Ser Pro Arg Ala Leu Ala Asn His Lys Val
        275                 280                 285

Tyr Thr Asp Ser Phe Arg Ser Ile Tyr Ser Ile Asn Ser Gly Ile Ser
    290                 295                 300

Ser Gly Lys Ala Val Ala Val Gly Arg Tyr Pro Glu Asp Ser Tyr Tyr
305                 310                 315                 320

Asn Gly Asn Pro Trp Phe Leu Thr Thr Leu Ala Ala Ala Glu Gln Leu
                325                 330                 335

Tyr Asp Ala Ile Tyr Gln Trp Gln Lys Ile Gly Ser Ile Thr Ile Thr
            340                 345                 350

Asp Val Ser Leu Ala Phe Phe Lys Asp Leu Tyr Ser Ser Ala Ala Val
        355                 360                 365

Gly Thr Tyr Ala Ser Ser Ser Ser Ala Phe Thr Ser Ile Val Ser Ala
    370                 375                 380

Val Lys Thr Tyr Ala Asp Gly Tyr Met Ser Ile Val Gln Thr His Ala
385                 390                 395                 400

Met Thr Asn Gly Ser Leu Ser Glu Gln Phe Gly Lys Ser Asp Gly Phe
                405                 410                 415

Ser Leu Ser Ala Arg Asp Leu Thr Trp Ser Tyr Ala Ala Leu Leu Thr
            420                 425                 430

Ala Asn Leu Arg Arg Asn Ser Val Val Pro Pro Ser Trp Gly Glu Thr
        435                 440                 445
```

```
Thr Ala Thr Ser Val Pro Ser Val Cys Ser Ala Thr Ser Ala Thr Gly
    450                 455                 460

Thr Tyr Ser Thr Ala Thr Asn Thr Ala Trp Pro Ser Thr Leu Thr Ser
465                 470                 475                 480

Gly Thr Gly Ala Thr Thr Thr Thr Ser Lys Ala Thr Ser Ser Ser Thr
                485                 490                 495

Thr Thr Thr Ser Ser Ala Ser Ser Thr Thr Val Glu Cys Val Val Pro
            500                 505                 510

Thr Ala Val Ala Val Thr Phe Asp Glu Val Ala Thr Thr Thr Tyr Gly
        515                 520                 525

Glu Asn Val Tyr Val Val Gly Ser Ile Ser Gln Leu Gly Ser Trp Asp
    530                 535                 540

Thr Ser Lys Ala Val Ala Leu Ser Ala Ser Lys Tyr Thr Ser Ser Asn
545                 550                 555                 560

Asn Leu Trp Tyr Val Thr Val Thr Leu Pro Ala Gly Thr Thr Phe Gln
                565                 570                 575

Tyr Lys Phe Ile Arg Val Ser Ser Ser Gly Ser Val Thr Trp Glu Ser
            580                 585                 590

Asp Pro Asn Arg Ser Tyr Thr Val Pro Ser Ala Cys Gly Thr Ser Thr
        595                 600                 605

Ala Val Val Asn Thr Thr Trp Arg
    610                 615


<210> SEQ ID NO 45
<211> LENGTH: 586
<212> TYPE: PRT
<213> ORGANISM: Artificial Sequence
<220> FEATURE:
<223> OTHER INFORMATION: Sequence put together from multiple organisms:
      Saccharomyces cerevisiae and Saccharomycopsis fibuligera

<400> SEQUENCE: 45

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Val Pro Val Glu Leu Asp Lys
                85                  90                  95

Arg Asn Thr Gly His Phe Gln Ala Tyr Ser Gly Tyr Thr Val Ala Arg
            100                 105                 110

Ser Asn Phe Thr Gln Trp Ile His Glu Gln Pro Ala Val Ser Trp Tyr
        115                 120                 125

Tyr Leu Leu Gln Asn Ile Asp Tyr Pro Glu Gly Gln Phe Lys Ser Ala
    130                 135                 140

Lys Pro Gly Val Val Val Ala Ser Pro Ser Thr Ser Glu Pro Asp Tyr
145                 150                 155                 160

Phe Tyr Gln Trp Thr Arg Asp Thr Ala Ile Thr Phe Leu Ser Leu Ile
                165                 170                 175

Ala Glu Val Glu Asp His Ser Phe Ser Asn Thr Thr Leu Ala Lys Val
            180                 185                 190
```

```
Val Glu Tyr Tyr Ile Ser Asn Thr Tyr Thr Leu Gln Arg Val Ser Asn
        195                 200                 205

Pro Ser Gly Asn Phe Asp Ser Pro Asn His Asp Gly Leu Gly Glu Pro
    210                 215                 220

Lys Phe Asn Val Asp Asp Thr Ala Tyr Thr Ala Ser Trp Gly Arg Pro
225                 230                 235                 240

Gln Asn Asp Gly Pro Ala Leu Arg Ala Tyr Ala Ile Ser Arg Tyr Leu
                245                 250                 255

Asn Ala Val Ala Lys His Asn Asn Gly Lys Leu Leu Leu Ala Gly Gln
            260                 265                 270

Asn Gly Ile Pro Tyr Ser Ser Ala Ser Asp Ile Tyr Trp Lys Ile Ile
        275                 280                 285

Lys Pro Asp Leu Gln His Val Ser Thr His Trp Ser Thr Ser Gly Phe
    290                 295                 300

Asp Leu Trp Glu Glu Asn Gln Gly Thr His Phe Phe Thr Ala Leu Val
305                 310                 315                 320

Gln Leu Lys Ala Leu Ser Tyr Gly Ile Pro Leu Ser Lys Thr Tyr Asn
                325                 330                 335

Asp Pro Gly Phe Thr Ser Trp Leu Glu Lys Gln Lys Asp Ala Leu Asn
            340                 345                 350

Ser Tyr Ile Asn Ser Ser Gly Phe Val Asn Ser Gly Lys Lys His Ile
        355                 360                 365

Val Glu Ser Pro Gln Leu Ser Ser Arg Gly Gly Leu Asp Ser Ala Thr
    370                 375                 380

Tyr Ile Ala Ala Leu Ile Thr His Asp Ile Gly Asp Asp Asp Thr Tyr
385                 390                 395                 400

Thr Pro Phe Asn Val Asp Asn Ser Tyr Val Leu Asn Ser Leu Tyr Tyr
                405                 410                 415

Leu Leu Val Asp Asn Lys Asn Arg Tyr Lys Ile Asn Gly Asn Tyr Lys
            420                 425                 430

Ala Gly Ala Ala Val Gly Arg Tyr Pro Glu Asp Val Tyr Asn Gly Val
        435                 440                 445

Gly Thr Ser Glu Gly Asn Pro Trp Gln Leu Ala Thr Ala Tyr Ala Gly
    450                 455                 460

Gln Thr Phe Tyr Thr Leu Ala Tyr Asn Ser Leu Lys Asn Lys Lys Asn
465                 470                 475                 480

Leu Val Ile Glu Lys Leu Asn Tyr Asp Leu Tyr Asn Ser Phe Ile Ala
                485                 490                 495

Asp Leu Ser Lys Ile Asp Ser Ser Tyr Ala Ser Lys Asp Ser Leu Thr
            500                 505                 510

Leu Thr Tyr Gly Ser Asp Asn Tyr Lys Asn Val Ile Lys Ser Leu Leu
        515                 520                 525

Gln Phe Gly Asp Ser Phe Leu Lys Val Leu Leu Asp His Ile Asp Asp
    530                 535                 540

Asn Gly Gln Leu Thr Glu Glu Ile Asn Arg Tyr Thr Gly Phe Gln Ala
545                 550                 555                 560

Gly Ala Val Ser Leu Thr Trp Ser Ser Gly Ser Leu Leu Ser Ala Asn
                565                 570                 575

Arg Ala Arg Asn Lys Leu Ile Glu Leu Leu
            580                 585
```

<210> SEQ ID NO 46
<211> LENGTH: 558

```
<212> TYPE: PRT
<213> ORGANISM: Artificial Sequence
<220> FEATURE:
<223> OTHER INFORMATION: Sequence put together from multiple organisms:
      Saccharomyces cerevisiae and Saccharomycopsis fibuligera

<400> SEQUENCE: 46

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Leu Glu Gly
            20                  25                  30

Asp Phe Asp Val Ala Val Leu Pro Phe Ser Ala Ser Ile Ala Ala Lys
        35                  40                  45

Glu Glu Gly Val Ser Leu Glu Lys Arg Glu Ala Glu Ala Val Pro Val
    50                  55                  60

Glu Leu Asp Lys Arg Asn Thr Gly His Phe Gln Ala Tyr Ser Gly Tyr
65                  70                  75                  80

Thr Val Ala Arg Ser Asn Phe Thr Gln Trp Ile His Glu Gln Pro Ala
                85                  90                  95

Val Ser Trp Tyr Tyr Leu Leu Gln Asn Ile Asp Tyr Pro Glu Gly Gln
            100                 105                 110

Phe Lys Ser Ala Lys Pro Gly Val Val Val Ala Ser Pro Ser Thr Ser
        115                 120                 125

Glu Pro Asp Tyr Phe Tyr Gln Trp Thr Arg Asp Thr Ala Ile Thr Phe
    130                 135                 140

Leu Ser Leu Ile Ala Glu Val Glu Asp His Ser Phe Ser Asn Thr Thr
145                 150                 155                 160

Leu Ala Lys Val Val Glu Tyr Tyr Ile Ser Asn Thr Tyr Thr Leu Gln
                165                 170                 175

Arg Val Ser Asn Pro Ser Gly Asn Phe Asp Ser Pro Asn His Asp Gly
            180                 185                 190

Leu Gly Glu Pro Lys Phe Asn Val Asp Asp Thr Ala Tyr Thr Ala Ser
        195                 200                 205

Trp Gly Arg Pro Gln Asn Asp Gly Pro Ala Leu Arg Ala Tyr Ala Ile
    210                 215                 220

Ser Arg Tyr Leu Asn Ala Val Ala Lys His Asn Asn Gly Lys Leu Leu
225                 230                 235                 240

Leu Ala Gly Gln Asn Gly Ile Pro Tyr Ser Ser Ala Ser Asp Ile Tyr
                245                 250                 255

Trp Lys Ile Ile Lys Pro Asp Leu Gln His Val Ser Thr His Trp Ser
            260                 265                 270

Thr Ser Gly Phe Asp Leu Trp Glu Glu Asn Gln Gly Thr His Phe Phe
        275                 280                 285

Thr Ala Leu Val Gln Leu Lys Ala Leu Ser Tyr Gly Ile Pro Leu Ser
    290                 295                 300

Lys Thr Tyr Asn Asp Pro Gly Phe Thr Ser Trp Leu Glu Lys Gln Lys
305                 310                 315                 320

Asp Ala Leu Asn Ser Tyr Ile Asn Ser Ser Gly Phe Val Asn Ser Gly
                325                 330                 335

Lys Lys His Ile Val Glu Ser Pro Gln Leu Ser Ser Arg Gly Gly Leu
            340                 345                 350

Asp Ser Ala Thr Tyr Ile Ala Ala Leu Ile Thr His Asp Ile Gly Asp
        355                 360                 365

Asp Asp Thr Tyr Thr Pro Phe Asn Val Asp Asn Ser Tyr Val Leu Asn
    370                 375                 380
```

```
Ser Leu Tyr Tyr Leu Leu Val Asp Asn Lys Asn Arg Tyr Lys Ile Asn
385                 390                 395                 400

Gly Asn Tyr Lys Ala Gly Ala Ala Val Gly Arg Tyr Pro Glu Asp Val
                405                 410                 415

Tyr Asn Gly Val Gly Thr Ser Glu Gly Asn Pro Trp Gln Leu Ala Thr
            420                 425                 430

Ala Tyr Ala Gly Gln Thr Phe Tyr Thr Leu Ala Tyr Asn Ser Leu Lys
        435                 440                 445

Asn Lys Lys Asn Leu Val Ile Glu Lys Leu Asn Tyr Asp Leu Tyr Asn
    450                 455                 460

Ser Phe Ile Ala Asp Leu Ser Lys Ile Asp Ser Ser Tyr Ala Ser Lys
465                 470                 475                 480

Asp Ser Leu Thr Leu Thr Tyr Gly Ser Asp Asn Tyr Lys Asn Val Ile
                485                 490                 495

Lys Ser Leu Leu Gln Phe Gly Asp Ser Phe Leu Lys Val Leu Leu Asp
            500                 505                 510

His Ile Asp Asp Asn Gly Gln Leu Thr Glu Glu Ile Asn Arg Tyr Thr
        515                 520                 525

Gly Phe Gln Ala Gly Ala Val Ser Leu Thr Trp Ser Ser Gly Ser Leu
    530                 535                 540

Leu Ser Ala Asn Arg Ala Arg Asn Lys Leu Ile Glu Leu Leu
545                 550                 555
```

<210> SEQ ID NO 47
<211> LENGTH: 516
<212> TYPE: PRT
<213> ORGANISM: Artificial Sequence
<220> FEATURE:
<223> OTHER INFORMATION: Sequence put together from multiple organisms: An and Saccharomycopsis fibuligera

<400> SEQUENCE: 47

```
Met Arg Phe Pro Ser Ile Phe Thr Ala Val Leu Phe Ala Ala Ser Ser
1               5                   10                  15

Ala Leu Ala Val Pro Val Glu Leu Asp Lys Arg Asn Thr Gly His Phe
            20                  25                  30

Gln Ala Tyr Ser Gly Tyr Thr Val Ala Arg Ser Asn Phe Thr Gln Trp
        35                  40                  45

Ile His Glu Gln Pro Ala Val Ser Trp Tyr Tyr Leu Leu Gln Asn Ile
    50                  55                  60

Asp Tyr Pro Glu Gly Gln Phe Lys Ser Ala Lys Pro Gly Val Val Val
65                  70                  75                  80

Ala Ser Pro Ser Thr Ser Glu Pro Asp Tyr Phe Tyr Gln Trp Thr Arg
                85                  90                  95

Asp Thr Ala Ile Thr Phe Leu Ser Leu Ile Ala Glu Val Glu Asp His
            100                 105                 110

Ser Phe Ser Asn Thr Thr Leu Ala Lys Val Val Glu Tyr Tyr Ile Ser
        115                 120                 125

Asn Thr Tyr Thr Leu Gln Arg Val Ser Asn Pro Ser Gly Asn Phe Asp
    130                 135                 140

Ser Pro Asn His Asp Gly Leu Gly Glu Pro Lys Phe Asn Val Asp Asp
145                 150                 155                 160

Thr Ala Tyr Thr Ala Ser Trp Gly Arg Pro Gln Asn Asp Gly Pro Ala
                165                 170                 175

Leu Arg Ala Tyr Ala Ile Ser Arg Tyr Leu Asn Ala Val Ala Lys His
```

```
            180                 185                 190

Asn Asn Gly Lys Leu Leu Leu Ala Gly Gln Asn Gly Ile Pro Tyr Ser
        195                 200                 205

Ser Ala Ser Asp Ile Tyr Trp Lys Ile Ile Lys Pro Asp Leu Gln His
    210                 215                 220

Val Ser Thr His Trp Ser Thr Ser Gly Phe Asp Leu Trp Glu Glu Asn
225                 230                 235                 240

Gln Gly Thr His Phe Phe Thr Ala Leu Val Gln Leu Lys Ala Leu Ser
                245                 250                 255

Tyr Gly Ile Pro Leu Ser Lys Thr Tyr Asn Asp Pro Gly Phe Thr Ser
            260                 265                 270

Trp Leu Glu Lys Gln Lys Asp Ala Leu Asn Ser Tyr Ile Asn Ser Ser
        275                 280                 285

Gly Phe Val Asn Ser Gly Lys Lys His Ile Val Glu Ser Pro Gln Leu
    290                 295                 300

Ser Ser Arg Gly Gly Leu Asp Ser Ala Thr Tyr Ile Ala Ala Leu Ile
305                 310                 315                 320

Thr His Asp Ile Gly Asp Asp Asp Thr Tyr Thr Pro Phe Asn Val Asp
                325                 330                 335

Asn Ser Tyr Val Leu Asn Ser Leu Tyr Tyr Leu Leu Val Asp Asn Lys
            340                 345                 350

Asn Arg Tyr Lys Ile Asn Gly Asn Tyr Lys Ala Gly Ala Ala Val Gly
        355                 360                 365

Arg Tyr Pro Glu Asp Val Tyr Asn Gly Val Gly Thr Ser Glu Gly Asn
    370                 375                 380

Pro Trp Gln Leu Ala Thr Ala Tyr Ala Gly Gln Thr Phe Tyr Thr Leu
385                 390                 395                 400

Ala Tyr Asn Ser Leu Lys Asn Lys Lys Asn Leu Val Ile Glu Lys Leu
                405                 410                 415

Asn Tyr Asp Leu Tyr Asn Ser Phe Ile Ala Asp Leu Ser Lys Ile Asp
            420                 425                 430

Ser Ser Tyr Ala Ser Lys Asp Ser Leu Thr Leu Thr Tyr Gly Ser Asp
        435                 440                 445

Asn Tyr Lys Asn Val Ile Lys Ser Leu Leu Gln Phe Gly Asp Ser Phe
    450                 455                 460

Leu Lys Val Leu Leu Asp His Ile Asp Asp Asn Gly Gln Leu Thr Glu
465                 470                 475                 480

Glu Ile Asn Arg Tyr Thr Gly Phe Gln Ala Gly Ala Val Ser Leu Thr
                485                 490                 495

Trp Ser Ser Gly Ser Leu Leu Ser Ala Asn Arg Ala Arg Asn Lys Leu
            500                 505                 510

Ile Glu Leu Leu
        515


<210> SEQ ID NO 48
<211> LENGTH: 516
<212> TYPE: PRT
<213> ORGANISM: Artificial Sequence
<220> FEATURE:
<223> OTHER INFORMATION: Sequence put together from multiple organisms:
      Saccharomyces cerevisiae and Saccharomycopsis fibuligera

<400> SEQUENCE: 48

Met Leu Leu Gln Ala Phe Leu Phe Leu Leu Ala Gly Phe Ala Ala Lys
1               5                   10                  15
```

```
Ile Ser Ala Val Pro Val Glu Leu Asp Lys Arg Asn Thr Gly His Phe
            20                  25                  30

Gln Ala Tyr Ser Gly Tyr Thr Val Ala Arg Ser Asn Phe Thr Gln Trp
        35                  40                  45

Ile His Glu Gln Pro Ala Val Ser Trp Tyr Tyr Leu Leu Gln Asn Ile
    50                  55                  60

Asp Tyr Pro Glu Gly Gln Phe Lys Ser Ala Lys Pro Gly Val Val Val
65                  70                  75                  80

Ala Ser Pro Ser Thr Ser Glu Pro Asp Tyr Phe Tyr Gln Trp Thr Arg
                85                  90                  95

Asp Thr Ala Ile Thr Phe Leu Ser Leu Ile Ala Glu Val Glu Asp His
            100                 105                 110

Ser Phe Ser Asn Thr Thr Leu Ala Lys Val Val Glu Tyr Tyr Ile Ser
        115                 120                 125

Asn Thr Tyr Thr Leu Gln Arg Val Ser Asn Pro Ser Gly Asn Phe Asp
    130                 135                 140

Ser Pro Asn His Asp Gly Leu Gly Glu Pro Lys Phe Asn Val Asp Asp
145                 150                 155                 160

Thr Ala Tyr Thr Ala Ser Trp Gly Arg Pro Gln Asn Asp Gly Pro Ala
                165                 170                 175

Leu Arg Ala Tyr Ala Ile Ser Arg Tyr Leu Asn Ala Val Ala Lys His
            180                 185                 190

Asn Asn Gly Lys Leu Leu Leu Ala Gly Gln Asn Gly Ile Pro Tyr Ser
        195                 200                 205

Ser Ala Ser Asp Ile Tyr Trp Lys Ile Ile Lys Pro Asp Leu Gln His
    210                 215                 220

Val Ser Thr His Trp Ser Thr Ser Gly Phe Asp Leu Trp Glu Glu Asn
225                 230                 235                 240

Gln Gly Thr His Phe Phe Thr Ala Leu Val Gln Leu Lys Ala Leu Ser
                245                 250                 255

Tyr Gly Ile Pro Leu Ser Lys Thr Tyr Asn Asp Pro Gly Phe Thr Ser
            260                 265                 270

Trp Leu Glu Lys Gln Lys Asp Ala Leu Asn Ser Tyr Ile Asn Ser Ser
        275                 280                 285

Gly Phe Val Asn Ser Gly Lys Lys His Ile Val Glu Ser Pro Gln Leu
    290                 295                 300

Ser Ser Arg Gly Gly Leu Asp Ser Ala Thr Tyr Ile Ala Ala Leu Ile
305                 310                 315                 320

Thr His Asp Ile Gly Asp Asp Asp Thr Tyr Thr Pro Phe Asn Val Asp
                325                 330                 335

Asn Ser Tyr Val Leu Asn Ser Leu Tyr Tyr Leu Leu Val Asp Asn Lys
            340                 345                 350

Asn Arg Tyr Lys Ile Asn Gly Asn Tyr Lys Ala Gly Ala Ala Val Gly
        355                 360                 365

Arg Tyr Pro Glu Asp Val Tyr Asn Gly Val Gly Thr Ser Glu Gly Asn
    370                 375                 380

Pro Trp Gln Leu Ala Thr Ala Tyr Ala Gly Gln Thr Phe Tyr Thr Leu
385                 390                 395                 400

Ala Tyr Asn Ser Leu Lys Asn Lys Lys Asn Leu Val Ile Glu Lys Leu
                405                 410                 415

Asn Tyr Asp Leu Tyr Asn Ser Phe Ile Ala Asp Leu Ser Lys Ile Asp
            420                 425                 430

Ser Ser Tyr Ala Ser Lys Asp Ser Leu Thr Leu Thr Tyr Gly Ser Asp
```

```
        435                 440                 445

Asn Tyr Lys Asn Val Ile Lys Ser Leu Leu Gln Phe Gly Asp Ser Phe
    450                 455                 460

Leu Lys Val Leu Leu Asp His Ile Asp Asp Asn Gly Gln Leu Thr Glu
465                 470                 475                 480

Glu Ile Asn Arg Tyr Thr Gly Phe Gln Ala Gly Ala Val Ser Leu Thr
                485                 490                 495

Trp Ser Ser Gly Ser Leu Leu Ser Ala Asn Arg Ala Arg Asn Lys Leu
            500                 505                 510

Ile Glu Leu Leu
        515


<210> SEQ ID NO 49
<211> LENGTH: 523
<212> TYPE: PRT
<213> ORGANISM: Artificial Sequence
<220> FEATURE:
<223> OTHER INFORMATION: Sequence put together from multiple organisms:
      Gallus gallus and Saccharomycopsis fibuligera

<400> SEQUENCE: 49

Met Leu Gly Lys Asn Asp Pro Met Cys Leu Val Leu Val Leu Leu Gly
1               5                   10                  15

Leu Thr Ala Leu Leu Gly Ile Cys Gln Gly Val Pro Val Glu Leu Asp
            20                  25                  30

Lys Arg Asn Thr Gly His Phe Gln Ala Tyr Ser Gly Tyr Thr Val Ala
        35                  40                  45

Arg Ser Asn Phe Thr Gln Trp Ile His Glu Gln Pro Ala Val Ser Trp
    50                  55                  60

Tyr Tyr Leu Leu Gln Asn Ile Asp Tyr Pro Glu Gly Gln Phe Lys Ser
65                  70                  75                  80

Ala Lys Pro Gly Val Val Val Ala Ser Pro Ser Thr Ser Glu Pro Asp
                85                  90                  95

Tyr Phe Tyr Gln Trp Thr Arg Asp Thr Ala Ile Thr Phe Leu Ser Leu
            100                 105                 110

Ile Ala Glu Val Glu Asp His Ser Phe Ser Asn Thr Thr Leu Ala Lys
        115                 120                 125

Val Val Glu Tyr Tyr Ile Ser Asn Thr Tyr Thr Leu Gln Arg Val Ser
    130                 135                 140

Asn Pro Ser Gly Asn Phe Asp Ser Pro Asn His Asp Gly Leu Gly Glu
145                 150                 155                 160

Pro Lys Phe Asn Val Asp Asp Thr Ala Tyr Thr Ala Ser Trp Gly Arg
                165                 170                 175

Pro Gln Asn Asp Gly Pro Ala Leu Arg Ala Tyr Ala Ile Ser Arg Tyr
            180                 185                 190

Leu Asn Ala Val Ala Lys His Asn Asn Gly Lys Leu Leu Leu Ala Gly
        195                 200                 205

Gln Asn Gly Ile Pro Tyr Ser Ser Ala Ser Asp Ile Tyr Trp Lys Ile
    210                 215                 220

Ile Lys Pro Asp Leu Gln His Val Ser Thr His Trp Ser Thr Ser Gly
225                 230                 235                 240

Phe Asp Leu Trp Glu Glu Asn Gln Gly Thr His Phe Phe Thr Ala Leu
                245                 250                 255

Val Gln Leu Lys Ala Leu Ser Tyr Gly Ile Pro Leu Ser Lys Thr Tyr
            260                 265                 270
```

```
Asn Asp Pro Gly Phe Thr Ser Trp Leu Glu Lys Gln Lys Asp Ala Leu
        275                 280                 285

Asn Ser Tyr Ile Asn Ser Ser Gly Phe Val Asn Ser Gly Lys Lys His
    290                 295                 300

Ile Val Glu Ser Pro Gln Leu Ser Ser Arg Gly Gly Leu Asp Ser Ala
305                 310                 315                 320

Thr Tyr Ile Ala Ala Leu Ile Thr His Asp Ile Gly Asp Asp Asp Thr
                325                 330                 335

Tyr Thr Pro Phe Asn Val Asp Asn Ser Tyr Val Leu Asn Ser Leu Tyr
            340                 345                 350

Tyr Leu Leu Val Asp Asn Lys Asn Arg Tyr Lys Ile Asn Gly Asn Tyr
        355                 360                 365

Lys Ala Gly Ala Ala Val Gly Arg Tyr Pro Glu Asp Val Tyr Asn Gly
    370                 375                 380

Val Gly Thr Ser Glu Gly Asn Pro Trp Gln Leu Ala Thr Ala Tyr Ala
385                 390                 395                 400

Gly Gln Thr Phe Tyr Thr Leu Ala Tyr Asn Ser Leu Lys Asn Lys Lys
                405                 410                 415

Asn Leu Val Ile Glu Lys Leu Asn Tyr Asp Leu Tyr Asn Ser Phe Ile
            420                 425                 430

Ala Asp Leu Ser Lys Ile Asp Ser Ser Tyr Ala Ser Lys Asp Ser Leu
        435                 440                 445

Thr Leu Thr Tyr Gly Ser Asp Asn Tyr Lys Asn Val Ile Lys Ser Leu
    450                 455                 460

Leu Gln Phe Gly Asp Ser Phe Leu Lys Val Leu Leu Asp His Ile Asp
465                 470                 475                 480

Asp Asn Gly Gln Leu Thr Glu Glu Ile Asn Arg Tyr Thr Gly Phe Gln
                485                 490                 495

Ala Gly Ala Val Ser Leu Thr Trp Ser Ser Gly Ser Leu Leu Ser Ala
            500                 505                 510

Asn Arg Ala Arg Asn Lys Leu Ile Glu Leu Leu
        515                 520


<210> SEQ ID NO 50
<211> LENGTH: 515
<212> TYPE: PRT
<213> ORGANISM: Artificial Sequence
<220> FEATURE:
<223> OTHER INFORMATION: Sequence put together from multiple organisms:
      Homo sapiens and Saccharomycopsis fibuligera

<400> SEQUENCE: 50

Met Lys Trp Val Thr Phe Ile Ser Leu Leu Phe Leu Phe Ser Ser Ala
1               5                   10                  15

Tyr Ser Val Pro Val Glu Leu Asp Lys Arg Asn Thr Gly His Phe Gln
            20                  25                  30

Ala Tyr Ser Gly Tyr Thr Val Ala Arg Ser Asn Phe Thr Gln Trp Ile
        35                  40                  45

His Glu Gln Pro Ala Val Ser Trp Tyr Tyr Leu Leu Gln Asn Ile Asp
    50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Phe Leu Ser Leu Ile Ala Glu Val Glu Asp His Ser
            100                 105                 110
```

```
Phe Ser Asn Thr Thr Leu Ala Lys Val Val Glu Tyr Tyr Ile Ser Asn
        115                 120                 125

Thr Tyr Thr Leu Gln Arg Val Ser Asn Pro Ser Gly Asn Phe Asp Ser
    130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
            180                 185                 190

Asn Gly Lys Leu Leu Leu Ala Gly Gln Asn Gly Ile Pro Tyr Ser Ser
        195                 200                 205

Ala Ser Asp Ile Tyr Trp Lys Ile Ile Lys Pro Asp Leu Gln His Val
    210                 215                 220

Ser Thr His Trp Ser Thr Ser Gly Phe Asp Leu Trp Glu Glu Asn Gln
225                 230                 235                 240

Gly Thr His Phe Phe Thr Ala Leu Val Gln Leu Lys Ala Leu Ser Tyr
                245                 250                 255

Gly Ile Pro Leu Ser Lys Thr Tyr Asn Asp Pro Gly Phe Thr Ser Trp
            260                 265                 270

Leu Glu Lys Gln Lys Asp Ala Leu Asn Ser Tyr Ile Asn Ser Ser Gly
        275                 280                 285

Phe Val Asn Ser Gly Lys Lys His Ile Val Glu Ser Pro Gln Leu Ser
    290                 295                 300

Ser Arg Gly Gly Leu Asp Ser Ala Thr Tyr Ile Ala Ala Leu Ile Thr
305                 310                 315                 320

His Asp Ile Gly Asp Asp Asp Thr Tyr Thr Pro Phe Asn Val Asp Asn
                325                 330                 335

Ser Tyr Val Leu Asn Ser Leu Tyr Tyr Leu Leu Val Asp Asn Lys Asn
            340                 345                 350

Arg Tyr Lys Ile Asn Gly Asn Tyr Lys Ala Gly Ala Ala Val Gly Arg
        355                 360                 365

Tyr Pro Glu Asp Val Tyr Asn Gly Val Gly Thr Ser Glu Gly Asn Pro
    370                 375                 380

Trp Gln Leu Ala Thr Ala Tyr Ala Gly Gln Thr Phe Tyr Thr Leu Ala
385                 390                 395                 400

Tyr Asn Ser Leu Lys Asn Lys Lys Asn Leu Val Ile Glu Lys Leu Asn
                405                 410                 415

Tyr Asp Leu Tyr Asn Ser Phe Ile Ala Asp Leu Ser Lys Ile Asp Ser
            420                 425                 430

Ser Tyr Ala Ser Lys Asp Ser Leu Thr Leu Thr Tyr Gly Ser Asp Asn
        435                 440                 445

Tyr Lys Asn Val Ile Lys Ser Leu Leu Gln Phe Gly Asp Ser Phe Leu
    450                 455                 460

Lys Val Leu Leu Asp His Ile Asp Asp Asn Gly Gln Leu Thr Glu Glu
465                 470                 475                 480

Ile Asn Arg Tyr Thr Gly Phe Gln Ala Gly Ala Val Ser Leu Thr Trp
                485                 490                 495

Ser Ser Gly Ser Leu Leu Ser Ala Asn Arg Ala Arg Asn Lys Leu Ile
            500                 505                 510

Glu Leu Leu
        515
```

<210> SEQ ID NO 51
<211> LENGTH: 516
<212> TYPE: PRT
<213> ORGANISM: Artificial Sequence
<220> FEATURE:
<223> OTHER INFORMATION: Sequence put together from multiple organisms:
Saccharomyces cerevisiae and Saccharomycopsis fibuligera

<400> SEQUENCE: 51

```
Met Arg Phe Pro Ser Ile Phe Thr Ala Val Leu Phe Ala Ala Ser Ser
1               5                   10                  15

Ala Leu Ala Val Pro Val Glu Leu Asp Lys Arg Asn Thr Gly His Phe
            20                  25                  30

Gln Ala Tyr Ser Gly Tyr Thr Val Ala Arg Ser Asn Phe Thr Gln Trp
        35                  40                  45

Ile His Glu Gln Pro Ala Val Ser Trp Tyr Tyr Leu Leu Gln Asn Ile
    50                  55                  60

Asp Tyr Pro Glu Gly Gln Phe Lys Ser Ala Lys Pro Gly Val Val Val
65                  70                  75                  80

Ala Ser Pro Ser Thr Ser Glu Pro Asp Tyr Phe Tyr Gln Trp Thr Arg
                85                  90                  95

Asp Thr Ala Ile Thr Phe Leu Ser Leu Ile Ala Glu Val Glu Asp His
            100                 105                 110

Ser Phe Ser Asn Thr Thr Leu Ala Lys Val Val Glu Tyr Tyr Ile Ser
        115                 120                 125

Asn Thr Tyr Thr Leu Gln Arg Val Ser Asn Pro Ser Gly Asn Phe Asp
    130                 135                 140

Ser Pro Asn His Asp Gly Leu Gly Glu Pro Lys Phe Asn Val Asp Asp
145                 150                 155                 160

Thr Ala Tyr Thr Ala Ser Trp Gly Arg Pro Gln Asn Asp Gly Pro Ala
                165                 170                 175

Leu Arg Ala Tyr Ala Ile Ser Arg Tyr Leu Asn Ala Val Ala Lys His
            180                 185                 190

Asn Asn Gly Lys Leu Leu Leu Ala Gly Gln Asn Gly Ile Pro Tyr Ser
        195                 200                 205

Ser Ala Ser Asp Ile Tyr Trp Lys Ile Ile Lys Pro Asp Leu Gln His
    210                 215                 220

Val Ser Thr His Trp Ser Thr Ser Gly Phe Asp Leu Trp Glu Glu Asn
225                 230                 235                 240

Gln Gly Thr His Phe Phe Thr Ala Leu Val Gln Leu Lys Ala Leu Ser
                245                 250                 255

Tyr Gly Ile Pro Leu Ser Lys Thr Tyr Asn Asp Pro Gly Phe Thr Ser
            260                 265                 270

Trp Leu Glu Lys Gln Lys Asp Ala Leu Asn Ser Tyr Ile Asn Ser Ser
        275                 280                 285

Gly Phe Val Asn Ser Gly Lys Lys His Ile Val Glu Ser Pro Gln Leu
    290                 295                 300

Ser Ser Arg Gly Gly Leu Asp Ser Ala Thr Tyr Ile Ala Ala Leu Ile
305                 310                 315                 320

Thr His Asp Ile Gly Asp Asp Asp Thr Tyr Thr Pro Phe Asn Val Asp
                325                 330                 335

Asn Ser Tyr Val Leu Asn Ser Leu Tyr Tyr Leu Leu Val Asp Asn Lys
            340                 345                 350

Asn Arg Tyr Lys Ile Asn Gly Asn Tyr Lys Ala Gly Ala Ala Val Gly
        355                 360                 365
```

```
Arg Tyr Pro Glu Asp Val Tyr Asn Gly Val Gly Thr Ser Glu Gly Asn
    370                 375                 380

Pro Trp Gln Leu Ala Thr Ala Tyr Ala Gly Gln Thr Phe Tyr Thr Leu
385                 390                 395                 400

Ala Tyr Asn Ser Leu Lys Asn Lys Lys Asn Leu Val Ile Glu Lys Leu
                405                 410                 415

Asn Tyr Asp Leu Tyr Asn Ser Phe Ile Ala Asp Leu Ser Lys Ile Asp
            420                 425                 430

Ser Ser Tyr Ala Ser Lys Asp Ser Leu Thr Leu Thr Tyr Gly Ser Asp
        435                 440                 445

Asn Tyr Lys Asn Val Ile Lys Ser Leu Leu Gln Phe Gly Asp Ser Phe
    450                 455                 460

Leu Lys Val Leu Leu Asp His Ile Asp Asp Asn Gly Gln Leu Thr Glu
465                 470                 475                 480

Glu Ile Asn Arg Tyr Thr Gly Phe Gln Ala Gly Ala Val Ser Leu Thr
                485                 490                 495

Trp Ser Ser Gly Ser Leu Leu Ser Ala Asn Arg Ala Arg Asn Lys Leu
            500                 505                 510

Ile Glu Leu Leu
        515


<210> SEQ ID NO 52
<211> LENGTH: 668
<212> TYPE: PRT
<213> ORGANISM: Artificial Sequence
<220> FEATURE:
<223> OTHER INFORMATION: Sequence put together from multiple organisms:
      Saccharomyces cerevisiae and Rhizopus oryzae

<400> SEQUENCE: 52

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ala Ser Ile Pro Ser Ser Ala
                85                  90                  95

Ser Val Gln Leu Asp Ser Tyr Asn Tyr Asp Gly Ser Thr Phe Ser Gly
            100                 105                 110

Lys Ile Tyr Val Lys Asn Ile Ala Tyr Ser Lys Lys Val Thr Val Val
        115                 120                 125

Tyr Ala Asp Gly Ser Asp Asn Trp Asn Asn Asn Gly Asn Thr Ile Ala
    130                 135                 140

Ala Ser Phe Ser Gly Pro Ile Ser Gly Ser Asn Tyr Glu Tyr Trp Thr
145                 150                 155                 160

Phe Ser Ala Ser Val Lys Gly Ile Lys Glu Phe Tyr Ile Lys Tyr Glu
                165                 170                 175

Val Ser Gly Lys Thr Tyr Tyr Asp Asn Asn Asn Ser Ala Asn Tyr Gln
            180                 185                 190

Val Ser Thr Ser Lys Pro Thr Thr Thr Thr Ala Ala Thr Thr Thr Thr
```

```
        195                 200                 205

Thr Ala Pro Ser Thr Ser Thr Thr Thr Arg Pro Ser Ser Ser Glu Pro
    210                 215                 220

Ala Thr Phe Pro Thr Gly Asn Ser Thr Ile Ser Ser Trp Ile Lys Lys
225                 230                 235                 240

Gln Glu Asp Ile Ser Arg Phe Ala Met Leu Arg Asn Ile Asn Pro Pro
                245                 250                 255

Gly Ser Ala Thr Gly Phe Ile Ala Ala Ser Leu Ser Thr Ala Gly Pro
            260                 265                 270

Asp Tyr Tyr Tyr Ala Trp Thr Arg Asp Ala Ala Leu Thr Ser Asn Val
        275                 280                 285

Ile Val Tyr Glu Tyr Asn Thr Thr Leu Ser Gly Asn Lys Thr Ile Leu
    290                 295                 300

Asn Val Leu Lys Asp Tyr Val Thr Phe Ser Val Lys Thr Gln Ser Thr
305                 310                 315                 320

Ser Thr Val Cys Asn Cys Leu Gly Glu Pro Lys Phe Asn Pro Asp Gly
                325                 330                 335

Ser Gly Tyr Thr Gly Ala Trp Gly Arg Pro Gln Asn Asp Gly Pro Ala
            340                 345                 350

Glu Arg Ala Thr Thr Phe Val Leu Phe Ala Asp Ser Tyr Leu Thr Gln
        355                 360                 365

Thr Lys Asp Ala Ser Tyr Val Thr Gly Thr Leu Lys Pro Ala Ile Phe
    370                 375                 380

Lys Asp Leu Asp Tyr Val Val Asn Val Trp Ser Asn Gly Cys Phe Asp
385                 390                 395                 400

Leu Trp Glu Glu Val Asn Gly Val His Phe Tyr Thr Leu Met Val Met
                405                 410                 415

Arg Lys Gly Leu Leu Leu Gly Ala Asp Phe Ala Lys Arg Asn Gly Asp
            420                 425                 430

Ser Thr Arg Ala Ser Thr Tyr Ser Ser Thr Ala Ser Thr Ile Ala Asn
        435                 440                 445

Lys Ile Ser Ser Phe Trp Val Ser Ser Asn Asn Trp Val Gln Val Ser
    450                 455                 460

Gln Ser Val Thr Gly Gly Val Ser Lys Lys Gly Leu Asp Val Ser Thr
465                 470                 475                 480

Leu Leu Ala Ala Asn Leu Gly Ser Val Asp Asp Gly Phe Phe Thr Pro
                485                 490                 495

Gly Ser Glu Lys Ile Leu Ala Thr Ala Val Ala Val Glu Asp Ser Phe
            500                 505                 510

Ala Ser Leu Tyr Pro Ile Asn Lys Asn Leu Pro Ser Tyr Leu Gly Asn
        515                 520                 525

Ala Ile Gly Arg Tyr Pro Glu Asp Thr Tyr Asn Gly Asn Gly Asn Ser
    530                 535                 540

Gln Gly Asn Pro Trp Phe Leu Ala Val Thr Gly Tyr Ala Glu Leu Tyr
545                 550                 555                 560

Tyr Arg Ala Ile Lys Glu Trp Ile Ser Asn Gly Gly Val Thr Val Ser
                565                 570                 575

Ser Ile Ser Leu Pro Phe Phe Lys Lys Phe Asp Ser Ser Ala Thr Ser
            580                 585                 590

Gly Lys Lys Tyr Thr Val Gly Thr Ser Asp Phe Asn Asn Leu Ala Gln
        595                 600                 605

Asn Ile Ala Leu Ala Ala Asp Arg Phe Leu Ser Thr Val Gln Leu His
    610                 615                 620
```

```
Ala Pro Asn Asn Gly Ser Leu Ala Glu Glu Phe Asp Arg Thr Thr Gly
625                 630                 635                 640

Phe Ser Thr Gly Ala Arg Asp Leu Thr Trp Ser His Ala Ser Leu Ile
                645                 650                 655

Thr Ala Ser Tyr Ala Lys Ala Gly Ala Pro Ala Ala
            660                 665


<210> SEQ ID NO 53
<211> LENGTH: 640
<212> TYPE: PRT
<213> ORGANISM: Artificial Sequence
<220> FEATURE:
<223> OTHER INFORMATION: Sequence put together from multiple organisms:
      Saccharomyces cerevisiae and Rhizopus oryzae

<400> SEQUENCE: 53

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Leu Glu Gly
            20                  25                  30

Asp Phe Asp Val Ala Val Leu Pro Phe Ser Ala Ser Ile Ala Ala Lys
        35                  40                  45

Glu Glu Gly Val Ser Leu Glu Lys Arg Glu Ala Glu Ala Ala Ser Ile
    50                  55                  60

Pro Ser Ser Ala Ser Val Gln Leu Asp Ser Tyr Asn Tyr Asp Gly Ser
65                  70                  75                  80

Thr Phe Ser Gly Lys Ile Tyr Val Lys Asn Ile Ala Tyr Ser Lys Lys
                85                  90                  95

Val Thr Val Val Tyr Ala Asp Gly Ser Asp Asn Trp Asn Asn Asn Gly
            100                 105                 110

Asn Thr Ile Ala Ala Ser Phe Ser Gly Pro Ile Ser Gly Ser Asn Tyr
        115                 120                 125

Glu Tyr Trp Thr Phe Ser Ala Ser Val Lys Gly Ile Lys Glu Phe Tyr
    130                 135                 140

Ile Lys Tyr Glu Val Ser Gly Lys Thr Tyr Tyr Asp Asn Asn Asn Ser
145                 150                 155                 160

Ala Asn Tyr Gln Val Ser Thr Ser Lys Pro Thr Thr Thr Thr Ala Ala
                165                 170                 175

Thr Thr Thr Thr Thr Ala Pro Ser Thr Ser Thr Thr Thr Arg Pro Ser
            180                 185                 190

Ser Ser Glu Pro Ala Thr Phe Pro Thr Gly Asn Ser Thr Ile Ser Ser
        195                 200                 205

Trp Ile Lys Lys Gln Glu Asp Ile Ser Arg Phe Ala Met Leu Arg Asn
    210                 215                 220

Ile Asn Pro Pro Gly Ser Ala Thr Gly Phe Ile Ala Ala Ser Leu Ser
225                 230                 235                 240

Thr Ala Gly Pro Asp Tyr Tyr Tyr Ala Trp Thr Arg Asp Ala Ala Leu
                245                 250                 255

Thr Ser Asn Val Ile Val Tyr Glu Tyr Asn Thr Thr Leu Ser Gly Asn
            260                 265                 270

Lys Thr Ile Leu Asn Val Leu Lys Asp Tyr Val Thr Phe Ser Val Lys
        275                 280                 285

Thr Gln Ser Thr Ser Thr Val Cys Asn Cys Leu Gly Glu Pro Lys Phe
    290                 295                 300

Asn Pro Asp Gly Ser Gly Tyr Thr Gly Ala Trp Gly Arg Pro Gln Asn
```

```
305                 310                 315                 320

Asp Gly Pro Ala Glu Arg Ala Thr Thr Phe Val Leu Phe Ala Asp Ser
                325                 330                 335

Tyr Leu Thr Gln Thr Lys Asp Ala Ser Tyr Val Thr Gly Thr Leu Lys
            340                 345                 350

Pro Ala Ile Phe Lys Asp Leu Asp Tyr Val Val Asn Val Trp Ser Asn
        355                 360                 365

Gly Cys Phe Asp Leu Trp Glu Glu Val Asn Gly Val His Phe Tyr Thr
    370                 375                 380

Leu Met Val Met Arg Lys Gly Leu Leu Leu Gly Ala Asp Phe Ala Lys
385                 390                 395                 400

Arg Asn Gly Asp Ser Thr Arg Ala Ser Thr Tyr Ser Ser Thr Ala Ser
                405                 410                 415

Thr Ile Ala Asn Lys Ile Ser Ser Phe Trp Val Ser Ser Asn Asn Trp
            420                 425                 430

Val Gln Val Ser Gln Ser Val Thr Gly Gly Val Ser Lys Lys Gly Leu
        435                 440                 445

Asp Val Ser Thr Leu Leu Ala Ala Asn Leu Gly Ser Val Asp Asp Gly
    450                 455                 460

Phe Phe Thr Pro Gly Ser Glu Lys Ile Leu Ala Thr Ala Val Ala Val
465                 470                 475                 480

Glu Asp Ser Phe Ala Ser Leu Tyr Pro Ile Asn Lys Asn Leu Pro Ser
                485                 490                 495

Tyr Leu Gly Asn Ala Ile Gly Arg Tyr Pro Glu Asp Thr Tyr Asn Gly
            500                 505                 510

Asn Gly Asn Ser Gln Gly Asn Pro Trp Phe Leu Ala Val Thr Gly Tyr
        515                 520                 525

Ala Glu Leu Tyr Tyr Arg Ala Ile Lys Glu Trp Ile Ser Asn Gly Gly
    530                 535                 540

Val Thr Val Ser Ser Ile Ser Leu Pro Phe Phe Lys Lys Phe Asp Ser
545                 550                 555                 560

Ser Ala Thr Ser Gly Lys Lys Tyr Thr Val Gly Thr Ser Asp Phe Asn
                565                 570                 575

Asn Leu Ala Gln Asn Ile Ala Leu Ala Ala Asp Arg Phe Leu Ser Thr
            580                 585                 590

Val Gln Leu His Ala Pro Asn Asn Gly Ser Leu Ala Glu Glu Phe Asp
        595                 600                 605

Arg Thr Thr Gly Phe Ser Thr Gly Ala Arg Asp Leu Thr Trp Ser His
    610                 615                 620

Ala Ser Leu Ile Thr Ala Ser Tyr Ala Lys Ala Gly Ala Pro Ala Ala
625                 630                 635                 640


<210> SEQ ID NO 54
<211> LENGTH: 598
<212> TYPE: PRT
<213> ORGANISM: Artificial Sequence
<220> FEATURE:
<223> OTHER INFORMATION: Sequence put together from multiple organisms:
      Aspergillus nidulans and Rhizopus oryzae

<400> SEQUENCE: 54

Met Arg Phe Pro Ser Ile Phe Thr Ala Val Leu Phe Ala Ala Ser Ser
1               5                   10                  15

Ala Leu Ala Ala Ser Ile Pro Ser Ser Ala Ser Val Gln Leu Asp Ser
            20                  25                  30
```

```
Tyr Asn Tyr Asp Gly Ser Thr Phe Ser Gly Lys Ile Tyr Val Lys Asn
        35                  40                  45

Ile Ala Tyr Ser Lys Lys Val Thr Val Val Tyr Ala Asp Gly Ser Asp
    50                  55                  60

Asn Trp Asn Asn Asn Gly Asn Thr Ile Ala Ala Ser Phe Ser Gly Pro
65                  70                  75                  80

Ile Ser Gly Ser Asn Tyr Glu Tyr Trp Thr Phe Ser Ala Ser Val Lys
                85                  90                  95

Gly Ile Lys Glu Phe Tyr Ile Lys Tyr Glu Val Ser Gly Lys Thr Tyr
            100                 105                 110

Tyr Asp Asn Asn Asn Ser Ala Asn Tyr Gln Val Ser Thr Ser Lys Pro
        115                 120                 125

Thr Thr Thr Thr Ala Ala Thr Thr Thr Thr Thr Ala Pro Ser Thr Ser
    130                 135                 140

Thr Thr Thr Arg Pro Ser Ser Ser Glu Pro Ala Thr Phe Pro Thr Gly
145                 150                 155                 160

Asn Ser Thr Ile Ser Ser Trp Ile Lys Lys Gln Glu Asp Ile Ser Arg
                165                 170                 175

Phe Ala Met Leu Arg Asn Ile Asn Pro Pro Gly Ser Ala Thr Gly Phe
            180                 185                 190

Ile Ala Ala Ser Leu Ser Thr Ala Gly Pro Asp Tyr Tyr Tyr Ala Trp
        195                 200                 205

Thr Arg Asp Ala Ala Leu Thr Ser Asn Val Ile Val Tyr Glu Tyr Asn
    210                 215                 220

Thr Thr Leu Ser Gly Asn Lys Thr Ile Leu Asn Val Leu Lys Asp Tyr
225                 230                 235                 240

Val Thr Phe Ser Val Lys Thr Gln Ser Thr Ser Thr Val Cys Asn Cys
                245                 250                 255

Leu Gly Glu Pro Lys Phe Asn Pro Asp Gly Ser Gly Tyr Thr Gly Ala
            260                 265                 270

Trp Gly Arg Pro Gln Asn Asp Gly Pro Ala Glu Arg Ala Thr Thr Phe
        275                 280                 285

Val Leu Phe Ala Asp Ser Tyr Leu Thr Gln Thr Lys Asp Ala Ser Tyr
    290                 295                 300

Val Thr Gly Thr Leu Lys Pro Ala Ile Phe Lys Asp Leu Asp Tyr Val
305                 310                 315                 320

Val Asn Val Trp Ser Asn Gly Cys Phe Asp Leu Trp Glu Glu Val Asn
                325                 330                 335

Gly Val His Phe Tyr Thr Leu Met Val Met Arg Lys Gly Leu Leu Leu
            340                 345                 350

Gly Ala Asp Phe Ala Lys Arg Asn Gly Asp Ser Thr Arg Ala Ser Thr
        355                 360                 365

Tyr Ser Ser Thr Ala Ser Thr Ile Ala Asn Lys Ile Ser Ser Phe Trp
    370                 375                 380

Val Ser Ser Asn Asn Trp Val Gln Val Ser Gln Ser Val Thr Gly Gly
385                 390                 395                 400

Val Ser Lys Lys Gly Leu Asp Val Ser Thr Leu Leu Ala Ala Asn Leu
                405                 410                 415

Gly Ser Val Asp Asp Gly Phe Phe Thr Pro Gly Ser Glu Lys Ile Leu
            420                 425                 430

Ala Thr Ala Val Ala Val Glu Asp Ser Phe Ala Ser Leu Tyr Pro Ile
        435                 440                 445

Asn Lys Asn Leu Pro Ser Tyr Leu Gly Asn Ala Ile Gly Arg Tyr Pro
```

```
    450                 455                 460

Glu Asp Thr Tyr Asn Gly Asn Gly Asn Ser Gln Gly Asn Pro Trp Phe
465                 470                 475                 480

Leu Ala Val Thr Gly Tyr Ala Glu Leu Tyr Tyr Arg Ala Ile Lys Glu
                485                 490                 495

Trp Ile Ser Asn Gly Gly Val Thr Val Ser Ser Ile Ser Leu Pro Phe
            500                 505                 510

Phe Lys Lys Phe Asp Ser Ser Ala Thr Ser Gly Lys Lys Tyr Thr Val
        515                 520                 525

Gly Thr Ser Asp Phe Asn Asn Leu Ala Gln Asn Ile Ala Leu Ala Ala
    530                 535                 540

Asp Arg Phe Leu Ser Thr Val Gln Leu His Ala Pro Asn Asn Gly Ser
545                 550                 555                 560

Leu Ala Glu Glu Phe Asp Arg Thr Thr Gly Phe Ser Thr Gly Ala Arg
                565                 570                 575

Asp Leu Thr Trp Ser His Ala Ser Leu Ile Thr Ala Ser Tyr Ala Lys
            580                 585                 590

Ala Gly Ala Pro Ala Ala
        595


<210> SEQ ID NO 55
<211> LENGTH: 598
<212> TYPE: PRT
<213> ORGANISM: Artificial Sequence
<220> FEATURE:
<223> OTHER INFORMATION: Sequence put together from multiple organisms:
      Saccharomyces cerevisiae and Rhizopus oryzae

<400> SEQUENCE: 55

Met Leu Leu Gln Ala Phe Leu Phe Leu Leu Ala Gly Phe Ala Ala Lys
1               5                   10                  15

Ile Ser Ala Ala Ser Ile Pro Ser Ser Ala Ser Val Gln Leu Asp Ser
            20                  25                  30

Tyr Asn Tyr Asp Gly Ser Thr Phe Ser Gly Lys Ile Tyr Val Lys Asn
        35                  40                  45

Ile Ala Tyr Ser Lys Lys Val Thr Val Val Tyr Ala Asp Gly Ser Asp
    50                  55                  60

Asn Trp Asn Asn Asn Gly Asn Thr Ile Ala Ala Ser Phe Ser Gly Pro
65                  70                  75                  80

Ile Ser Gly Ser Asn Tyr Glu Tyr Trp Thr Phe Ser Ala Ser Val Lys
                85                  90                  95

Gly Ile Lys Glu Phe Tyr Ile Lys Tyr Glu Val Ser Gly Lys Thr Tyr
            100                 105                 110

Tyr Asp Asn Asn Asn Ser Ala Asn Tyr Gln Val Ser Thr Ser Lys Pro
        115                 120                 125

Thr Thr Thr Thr Ala Ala Thr Thr Thr Thr Thr Ala Pro Ser Thr Ser
    130                 135                 140

Thr Thr Thr Arg Pro Ser Ser Ser Glu Pro Ala Thr Phe Pro Thr Gly
145                 150                 155                 160

Asn Ser Thr Ile Ser Ser Trp Ile Lys Lys Gln Glu Asp Ile Ser Arg
                165                 170                 175

Phe Ala Met Leu Arg Asn Ile Asn Pro Pro Gly Ser Ala Thr Gly Phe
            180                 185                 190

Ile Ala Ala Ser Leu Ser Thr Ala Gly Pro Asp Tyr Tyr Tyr Ala Trp
        195                 200                 205
```

```
Thr Arg Asp Ala Ala Leu Thr Ser Asn Val Ile Val Tyr Glu Tyr Asn
    210                 215                 220

Thr Thr Leu Ser Gly Asn Lys Thr Ile Leu Asn Val Leu Lys Asp Tyr
225                 230                 235                 240

Val Thr Phe Ser Val Lys Thr Gln Ser Thr Ser Thr Val Cys Asn Cys
                245                 250                 255

Leu Gly Glu Pro Lys Phe Asn Pro Asp Gly Ser Gly Tyr Thr Gly Ala
            260                 265                 270

Trp Gly Arg Pro Gln Asn Asp Gly Pro Ala Glu Arg Ala Thr Thr Phe
        275                 280                 285

Val Leu Phe Ala Asp Ser Tyr Leu Thr Gln Thr Lys Asp Ala Ser Tyr
    290                 295                 300

Val Thr Gly Thr Leu Lys Pro Ala Ile Phe Lys Asp Leu Asp Tyr Val
305                 310                 315                 320

Val Asn Val Trp Ser Asn Gly Cys Phe Asp Leu Trp Glu Glu Val Asn
                325                 330                 335

Gly Val His Phe Tyr Thr Leu Met Val Met Arg Lys Gly Leu Leu Leu
            340                 345                 350

Gly Ala Asp Phe Ala Lys Arg Asn Gly Asp Ser Thr Arg Ala Ser Thr
        355                 360                 365

Tyr Ser Ser Thr Ala Ser Thr Ile Ala Asn Lys Ile Ser Ser Phe Trp
    370                 375                 380

Val Ser Ser Asn Asn Trp Val Gln Val Ser Gln Ser Val Thr Gly Gly
385                 390                 395                 400

Val Ser Lys Lys Gly Leu Asp Val Ser Thr Leu Leu Ala Ala Asn Leu
                405                 410                 415

Gly Ser Val Asp Asp Gly Phe Phe Thr Pro Gly Ser Glu Lys Ile Leu
            420                 425                 430

Ala Thr Ala Val Ala Val Glu Asp Ser Phe Ala Ser Leu Tyr Pro Ile
        435                 440                 445

Asn Lys Asn Leu Pro Ser Tyr Leu Gly Asn Ala Ile Gly Arg Tyr Pro
    450                 455                 460

Glu Asp Thr Tyr Asn Gly Asn Gly Asn Ser Gln Gly Asn Pro Trp Phe
465                 470                 475                 480

Leu Ala Val Thr Gly Tyr Ala Glu Leu Tyr Tyr Arg Ala Ile Lys Glu
                485                 490                 495

Trp Ile Ser Asn Gly Gly Val Thr Val Ser Ser Ile Ser Leu Pro Phe
            500                 505                 510

Phe Lys Lys Phe Asp Ser Ser Ala Thr Ser Gly Lys Lys Tyr Thr Val
        515                 520                 525

Gly Thr Ser Asp Phe Asn Asn Leu Ala Gln Asn Ile Ala Leu Ala Ala
    530                 535                 540

Asp Arg Phe Leu Ser Thr Val Gln Leu His Ala Pro Asn Asn Gly Ser
545                 550                 555                 560

Leu Ala Glu Glu Phe Asp Arg Thr Thr Gly Phe Ser Thr Gly Ala Arg
                565                 570                 575

Asp Leu Thr Trp Ser His Ala Ser Leu Ile Thr Ala Ser Tyr Ala Lys
            580                 585                 590

Ala Gly Ala Pro Ala Ala
        595
```

<210> SEQ ID NO 56
<211> LENGTH: 605
<212> TYPE: PRT

```
<213> ORGANISM: Artificial Sequence
<220> FEATURE:
<223> OTHER INFORMATION: Sequence put together from multiple organisms:
      Gallus gallus and Rhizopus oryzae

<400> SEQUENCE: 56

Met Leu Gly Lys Asn Asp Pro Met Cys Leu Val Leu Val Leu Leu Gly
1               5                   10                  15

Leu Thr Ala Leu Leu Gly Ile Cys Gln Gly Ala Ser Ile Pro Ser Ser
            20                  25                  30

Ala Ser Val Gln Leu Asp Ser Tyr Asn Tyr Asp Gly Ser Thr Phe Ser
        35                  40                  45

Gly Lys Ile Tyr Val Lys Asn Ile Ala Tyr Ser Lys Lys Val Thr Val
    50                  55                  60

Val Tyr Ala Asp Gly Ser Asp Asn Trp Asn Asn Asn Gly Asn Thr Ile
65                  70                  75                  80

Ala Ala Ser Phe Ser Gly Pro Ile Ser Gly Ser Asn Tyr Glu Tyr Trp
                85                  90                  95

Thr Phe Ser Ala Ser Val Lys Gly Ile Lys Glu Phe Tyr Ile Lys Tyr
            100                 105                 110

Glu Val Ser Gly Lys Thr Tyr Tyr Asp Asn Asn Asn Ser Ala Asn Tyr
        115                 120                 125

Gln Val Ser Thr Ser Lys Pro Thr Thr Thr Thr Ala Ala Thr Thr Thr
    130                 135                 140

Thr Thr Ala Pro Ser Thr Ser Thr Thr Thr Arg Pro Ser Ser Ser Glu
145                 150                 155                 160

Pro Ala Thr Phe Pro Thr Gly Asn Ser Thr Ile Ser Ser Trp Ile Lys
                165                 170                 175

Lys Gln Glu Asp Ile Ser Arg Phe Ala Met Leu Arg Asn Ile Asn Pro
            180                 185                 190

Pro Gly Ser Ala Thr Gly Phe Ile Ala Ala Ser Leu Ser Thr Ala Gly
        195                 200                 205

Pro Asp Tyr Tyr Tyr Ala Trp Thr Arg Asp Ala Ala Leu Thr Ser Asn
    210                 215                 220

Val Ile Val Tyr Glu Tyr Asn Thr Thr Leu Ser Gly Asn Lys Thr Ile
225                 230                 235                 240

Leu Asn Val Leu Lys Asp Tyr Val Thr Phe Ser Val Lys Thr Gln Ser
                245                 250                 255

Thr Ser Thr Val Cys Asn Cys Leu Gly Glu Pro Lys Phe Asn Pro Asp
            260                 265                 270

Gly Ser Gly Tyr Thr Gly Ala Trp Gly Arg Pro Gln Asn Asp Gly Pro
        275                 280                 285

Ala Glu Arg Ala Thr Thr Phe Val Leu Phe Ala Asp Ser Tyr Leu Thr
    290                 295                 300

Gln Thr Lys Asp Ala Ser Tyr Val Thr Gly Thr Leu Lys Pro Ala Ile
305                 310                 315                 320

Phe Lys Asp Leu Asp Tyr Val Val Asn Val Trp Ser Asn Gly Cys Phe
                325                 330                 335

Asp Leu Trp Glu Glu Val Asn Gly Val His Phe Tyr Thr Leu Met Val
            340                 345                 350

Met Arg Lys Gly Leu Leu Leu Gly Ala Asp Phe Ala Lys Arg Asn Gly
        355                 360                 365

Asp Ser Thr Arg Ala Ser Thr Tyr Ser Ser Thr Ala Ser Thr Ile Ala
    370                 375                 380
```

```
Asn Lys Ile Ser Ser Phe Trp Val Ser Ser Asn Asn Trp Val Gln Val
385                 390                 395                 400

Ser Gln Ser Val Thr Gly Gly Val Ser Lys Lys Gly Leu Asp Val Ser
                405                 410                 415

Thr Leu Leu Ala Ala Asn Leu Gly Ser Val Asp Asp Gly Phe Phe Thr
            420                 425                 430

Pro Gly Ser Glu Lys Ile Leu Ala Thr Ala Val Ala Val Glu Asp Ser
        435                 440                 445

Phe Ala Ser Leu Tyr Pro Ile Asn Lys Asn Leu Pro Ser Tyr Leu Gly
    450                 455                 460

Asn Ala Ile Gly Arg Tyr Pro Glu Asp Thr Tyr Asn Gly Asn Gly Asn
465                 470                 475                 480

Ser Gln Gly Asn Pro Trp Phe Leu Ala Val Thr Gly Tyr Ala Glu Leu
                485                 490                 495

Tyr Tyr Arg Ala Ile Lys Glu Trp Ile Ser Asn Gly Gly Val Thr Val
            500                 505                 510

Ser Ser Ile Ser Leu Pro Phe Phe Lys Lys Phe Asp Ser Ser Ala Thr
        515                 520                 525

Ser Gly Lys Lys Tyr Thr Val Gly Thr Ser Asp Phe Asn Asn Leu Ala
    530                 535                 540

Gln Asn Ile Ala Leu Ala Ala Asp Arg Phe Leu Ser Thr Val Gln Leu
545                 550                 555                 560

His Ala Pro Asn Asn Gly Ser Leu Ala Glu Glu Phe Asp Arg Thr Thr
                565                 570                 575

Gly Phe Ser Thr Gly Ala Arg Asp Leu Thr Trp Ser His Ala Ser Leu
            580                 585                 590

Ile Thr Ala Ser Tyr Ala Lys Ala Gly Ala Pro Ala Ala
        595                 600                 605


<210> SEQ ID NO 57
<211> LENGTH: 597
<212> TYPE: PRT
<213> ORGANISM: Artificial Sequence
<220> FEATURE:
<223> OTHER INFORMATION: Sequence put together from multiple organisms:
      Homo sapiens and Rhizopus oryzae

<400> SEQUENCE: 57

Met Lys Trp Val Thr Phe Ile Ser Leu Leu Phe Leu Phe Ser Ser Ala
1               5                   10                  15

Tyr Ser Ala Ser Ile Pro Ser Ser Ala Ser Val Gln Leu Asp Ser Tyr
            20                  25                  30

Asn Tyr Asp Gly Ser Thr Phe Ser Gly Lys Ile Tyr Val Lys Asn Ile
        35                  40                  45

Ala Tyr Ser Lys Lys Val Thr Val Val Tyr Ala Asp Gly Ser Asp Asn
    50                  55                  60

Trp Asn Asn Asn Gly Asn Thr Ile Ala Ala Ser Phe Ser Gly Pro Ile
65                  70                  75                  80

Ser Gly Ser Asn Tyr Glu Tyr Trp Thr Phe Ser Ala Ser Val Lys Gly
                85                  90                  95

Ile Lys Glu Phe Tyr Ile Lys Tyr Glu Val Ser Gly Lys Thr Tyr Tyr
            100                 105                 110

Asp Asn Asn Asn Ser Ala Asn Tyr Gln Val Ser Thr Ser Lys Pro Thr
        115                 120                 125

Thr Thr Thr Ala Ala Thr Thr Thr Thr Thr Ala Pro Ser Thr Ser Thr
    130                 135                 140
```

```
Thr Thr Arg Pro Ser Ser Ser Glu Pro Ala Thr Phe Pro Thr Gly Asn
145                 150                 155                 160

Ser Thr Ile Ser Ser Trp Ile Lys Lys Gln Glu Asp Ile Ser Arg Phe
                165                 170                 175

Ala Met Leu Arg Asn Ile Asn Pro Pro Gly Ser Ala Thr Gly Phe Ile
            180                 185                 190

Ala Ala Ser Leu Ser Thr Ala Gly Pro Asp Tyr Tyr Tyr Ala Trp Thr
        195                 200                 205

Arg Asp Ala Ala Leu Thr Ser Asn Val Ile Val Tyr Glu Tyr Asn Thr
    210                 215                 220

Thr Leu Ser Gly Asn Lys Thr Ile Leu Asn Val Leu Lys Asp Tyr Val
225                 230                 235                 240

Thr Phe Ser Val Lys Thr Gln Ser Thr Ser Thr Val Cys Asn Cys Leu
                245                 250                 255

Gly Glu Pro Lys Phe Asn Pro Asp Gly Ser Gly Tyr Thr Gly Ala Trp
            260                 265                 270

Gly Arg Pro Gln Asn Asp Gly Pro Ala Glu Arg Ala Thr Thr Phe Val
        275                 280                 285

Leu Phe Ala Asp Ser Tyr Leu Thr Gln Thr Lys Asp Ala Ser Tyr Val
    290                 295                 300

Thr Gly Thr Leu Lys Pro Ala Ile Phe Lys Asp Leu Asp Tyr Val Val
305                 310                 315                 320

Asn Val Trp Ser Asn Gly Cys Phe Asp Leu Trp Glu Glu Val Asn Gly
                325                 330                 335

Val His Phe Tyr Thr Leu Met Val Met Arg Lys Gly Leu Leu Leu Gly
            340                 345                 350

Ala Asp Phe Ala Lys Arg Asn Gly Asp Ser Thr Arg Ala Ser Thr Tyr
        355                 360                 365

Ser Ser Thr Ala Ser Thr Ile Ala Asn Lys Ile Ser Ser Phe Trp Val
    370                 375                 380

Ser Ser Asn Asn Trp Val Gln Val Ser Gln Ser Val Thr Gly Gly Val
385                 390                 395                 400

Ser Lys Lys Gly Leu Asp Val Ser Thr Leu Leu Ala Ala Asn Leu Gly
                405                 410                 415

Ser Val Asp Asp Gly Phe Phe Thr Pro Gly Ser Glu Lys Ile Leu Ala
            420                 425                 430

Thr Ala Val Ala Val Glu Asp Ser Phe Ala Ser Leu Tyr Pro Ile Asn
        435                 440                 445

Lys Asn Leu Pro Ser Tyr Leu Gly Asn Ala Ile Gly Arg Tyr Pro Glu
    450                 455                 460

Asp Thr Tyr Asn Gly Asn Gly Asn Ser Gln Gly Asn Pro Trp Phe Leu
465                 470                 475                 480

Ala Val Thr Gly Tyr Ala Glu Leu Tyr Tyr Arg Ala Ile Lys Glu Trp
                485                 490                 495

Ile Ser Asn Gly Gly Val Thr Val Ser Ser Ile Ser Leu Pro Phe Phe
            500                 505                 510

Lys Lys Phe Asp Ser Ser Ala Thr Ser Gly Lys Lys Tyr Thr Val Gly
        515                 520                 525

Thr Ser Asp Phe Asn Asn Leu Ala Gln Asn Ile Ala Leu Ala Ala Asp
    530                 535                 540

Arg Phe Leu Ser Thr Val Gln Leu His Ala Pro Asn Asn Gly Ser Leu
545                 550                 555                 560
```

```
Ala Glu Glu Phe Asp Arg Thr Thr Gly Phe Ser Thr Gly Ala Arg Asp
                565                 570                 575

Leu Thr Trp Ser His Ala Ser Leu Ile Thr Ala Ser Tyr Ala Lys Ala
            580                 585                 590

Gly Ala Pro Ala Ala
        595


<210> SEQ ID NO 58
<211> LENGTH: 598
<212> TYPE: PRT
<213> ORGANISM: Artificial Sequence
<220> FEATURE:
<223> OTHER INFORMATION: Sequence put together from multiple organisms:
      Saccharomyces cerevisiae and Rhizopus oryzae

<400> SEQUENCE: 58

Met Arg Phe Pro Ser Ile Phe Thr Ala Val Leu Phe Ala Ala Ser Ser
1               5                   10                  15

Ala Leu Ala Ala Ser Ile Pro Ser Ser Ala Ser Val Gln Leu Asp Ser
            20                  25                  30

Tyr Asn Tyr Asp Gly Ser Thr Phe Ser Gly Lys Ile Tyr Val Lys Asn
        35                  40                  45

Ile Ala Tyr Ser Lys Lys Val Thr Val Val Tyr Ala Asp Gly Ser Asp
    50                  55                  60

Asn Trp Asn Asn Asn Gly Asn Thr Ile Ala Ala Ser Phe Ser Gly Pro
65                  70                  75                  80

Ile Ser Gly Ser Asn Tyr Glu Tyr Trp Thr Phe Ser Ala Ser Val Lys
                85                  90                  95

Gly Ile Lys Glu Phe Tyr Ile Lys Tyr Glu Val Ser Gly Lys Thr Tyr
            100                 105                 110

Tyr Asp Asn Asn Asn Ser Ala Asn Tyr Gln Val Ser Thr Ser Lys Pro
        115                 120                 125

Thr Thr Thr Thr Ala Ala Thr Thr Thr Thr Thr Ala Pro Ser Thr Ser
    130                 135                 140

Thr Thr Thr Arg Pro Ser Ser Ser Glu Pro Ala Thr Phe Pro Thr Gly
145                 150                 155                 160

Asn Ser Thr Ile Ser Ser Trp Ile Lys Lys Gln Glu Asp Ile Ser Arg
                165                 170                 175

Phe Ala Met Leu Arg Asn Ile Asn Pro Pro Gly Ser Ala Thr Gly Phe
            180                 185                 190

Ile Ala Ala Ser Leu Ser Thr Ala Gly Pro Asp Tyr Tyr Tyr Ala Trp
        195                 200                 205

Thr Arg Asp Ala Ala Leu Thr Ser Asn Val Ile Val Tyr Glu Tyr Asn
    210                 215                 220

Thr Thr Leu Ser Gly Asn Lys Thr Ile Leu Asn Val Leu Lys Asp Tyr
225                 230                 235                 240

Val Thr Phe Ser Val Lys Thr Gln Ser Thr Ser Thr Val Cys Asn Cys
                245                 250                 255

Leu Gly Glu Pro Lys Phe Asn Pro Asp Gly Ser Gly Tyr Thr Gly Ala
            260                 265                 270

Trp Gly Arg Pro Gln Asn Asp Gly Pro Ala Glu Arg Ala Thr Thr Phe
        275                 280                 285

Val Leu Phe Ala Asp Ser Tyr Leu Thr Gln Thr Lys Asp Ala Ser Tyr
    290                 295                 300

Val Thr Gly Thr Leu Lys Pro Ala Ile Phe Lys Asp Leu Asp Tyr Val
305                 310                 315                 320
```

```
Val Asn Val Trp Ser Asn Gly Cys Phe Asp Leu Trp Glu Glu Val Asn
                325                 330                 335

Gly Val His Phe Tyr Thr Leu Met Val Met Arg Lys Gly Leu Leu Leu
            340                 345                 350

Gly Ala Asp Phe Ala Lys Arg Asn Gly Asp Ser Thr Arg Ala Ser Thr
        355                 360                 365

Tyr Ser Ser Thr Ala Ser Thr Ile Ala Asn Lys Ile Ser Ser Phe Trp
    370                 375                 380

Val Ser Ser Asn Asn Trp Val Gln Val Ser Gln Ser Val Thr Gly Gly
385                 390                 395                 400

Val Ser Lys Lys Gly Leu Asp Val Ser Thr Leu Leu Ala Ala Asn Leu
                405                 410                 415

Gly Ser Val Asp Asp Gly Phe Phe Thr Pro Gly Ser Glu Lys Ile Leu
            420                 425                 430

Ala Thr Ala Val Ala Val Glu Asp Ser Phe Ala Ser Leu Tyr Pro Ile
        435                 440                 445

Asn Lys Asn Leu Pro Ser Tyr Leu Gly Asn Ala Ile Gly Arg Tyr Pro
    450                 455                 460

Glu Asp Thr Tyr Asn Gly Asn Gly Asn Ser Gln Gly Asn Pro Trp Phe
465                 470                 475                 480

Leu Ala Val Thr Gly Tyr Ala Glu Leu Tyr Tyr Arg Ala Ile Lys Glu
                485                 490                 495

Trp Ile Ser Asn Gly Gly Val Thr Val Ser Ser Ile Ser Leu Pro Phe
            500                 505                 510

Phe Lys Lys Phe Asp Ser Ser Ala Thr Ser Gly Lys Lys Tyr Thr Val
        515                 520                 525

Gly Thr Ser Asp Phe Asn Asn Leu Ala Gln Asn Ile Ala Leu Ala Ala
    530                 535                 540

Asp Arg Phe Leu Ser Thr Val Gln Leu His Ala Pro Asn Asn Gly Ser
545                 550                 555                 560

Leu Ala Glu Glu Phe Asp Arg Thr Thr Gly Phe Ser Thr Gly Ala Arg
                565                 570                 575

Asp Leu Thr Trp Ser His Ala Ser Leu Ile Thr Ala Ser Tyr Ala Lys
            580                 585                 590

Ala Gly Ala Pro Ala Ala
        595


<210> SEQ ID NO 59
<211> LENGTH: 710
<212> TYPE: PRT
<213> ORGANISM: Artificial Sequence
<220> FEATURE:
<223> OTHER INFORMATION: Sequence put together from multiple organisms:
      Saccharomyces cerevisiae and Aspergillus shirousami

<400> SEQUENCE: 59

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
```

```
65                  70                  75                  80

Ser Leu Glu Lys Arg Glu Ala Glu Ala Ser Val Ile Ser Lys Arg Ala
                85                  90                  95

Thr Leu Asp Ser Trp Leu Ser Asn Glu Ala Thr Val Ala Arg Thr Ala
            100                 105                 110

Ile Leu Asn Asn Ile Gly Ala Asp Gly Ala Trp Val Ser Gly Ala Asp
        115                 120                 125

Ser Gly Ile Val Val Ala Ser Pro Ser Thr Asp Asn Pro Asp Tyr Phe
    130                 135                 140

Tyr Thr Trp Thr Arg Asp Ser Gly Ile Val Leu Lys Thr Leu Val Asp
145                 150                 155                 160

Leu Phe Arg Asn Gly Asp Thr Asp Leu Leu Ser Thr Ile Glu His Tyr
                165                 170                 175

Ile Ser Ser Gln Ala Ile Ile Gln Gly Val Ser Asn Pro Ser Gly Asp
            180                 185                 190

Leu Ser Ser Gly Gly Leu Gly Glu Pro Lys Phe Asn Val Asp Glu Thr
        195                 200                 205

Ala Tyr Ala Gly Ser Trp Gly Arg Pro Gln Arg Asp Gly Pro Ala Leu
    210                 215                 220

Arg Ala Thr Ala Met Ile Gly Phe Gly Gln Trp Leu Leu Asp Asn Gly
225                 230                 235                 240

Tyr Thr Ser Ala Ala Thr Glu Ile Val Trp Pro Leu Val Arg Asn Asp
                245                 250                 255

Leu Ser Tyr Val Ala Gln Tyr Trp Asn Gln Thr Gly Tyr Asp Leu Trp
            260                 265                 270

Glu Glu Val Asn Gly Ser Ser Phe Phe Thr Ile Ala Val Gln His Arg
        275                 280                 285

Ala Leu Val Glu Gly Ser Ala Phe Ala Thr Ala Val Gly Ser Ser Cys
    290                 295                 300

Ser Trp Cys Asp Ser Gln Ala Pro Gln Ile Leu Cys Tyr Leu Gln Ser
305                 310                 315                 320

Phe Trp Thr Gly Ser Tyr Ile Leu Ala Asn Phe Asp Ser Ser Arg Ser
                325                 330                 335

Gly Lys Asp Thr Asn Thr Leu Leu Gly Ser Ile His Thr Phe Asp Pro
            340                 345                 350

Glu Ala Gly Cys Asp Asp Ser Thr Phe Gln Pro Cys Ser Pro Arg Ala
        355                 360                 365

Leu Ala Asn His Lys Glu Val Val Asp Ser Phe Arg Ser Ile Tyr Thr
    370                 375                 380

Leu Asn Asp Gly Leu Ser Asp Ser Glu Ala Val Ala Val Gly Arg Tyr
385                 390                 395                 400

Pro Glu Asp Ser Tyr Tyr Asn Gly Asn Pro Trp Phe Leu Cys Thr Leu
                405                 410                 415

Ala Ala Ala Glu Gln Leu Tyr Asp Ala Leu Tyr Gln Trp Asp Lys Gln
            420                 425                 430

Gly Ser Leu Glu Ile Thr Asp Val Ser Leu Asp Phe Phe Lys Ala Leu
        435                 440                 445

Tyr Ser Gly Ala Ala Thr Gly Thr Tyr Ser Ser Ser Ser Ser Thr Tyr
    450                 455                 460

Ser Ser Ile Val Ser Ala Val Lys Thr Phe Ala Asp Gly Phe Val Ser
465                 470                 475                 480

Ile Val Glu Thr His Ala Ala Ser Asn Gly Ser Leu Ser Glu Gln Phe
                485                 490                 495
```

```
Asp Lys Ser Asp Gly Asp Glu Leu Ser Ala Arg Asp Leu Thr Trp Ser
            500                 505                 510

Tyr Ala Ala Leu Leu Thr Ala Asn Asn Arg Arg Asn Ser Val Val Pro
        515                 520                 525

Pro Ser Trp Gly Glu Thr Ser Ala Ser Ser Val Pro Gly Thr Cys Ala
    530                 535                 540

Ala Thr Ser Ala Ser Gly Thr Tyr Ser Ser Val Thr Val Thr Ser Trp
545                 550                 555                 560

Pro Ser Ile Val Ala Thr Gly Gly Thr Thr Thr Thr Ala Thr Thr Thr
                565                 570                 575

Gly Ser Gly Gly Val Thr Ser Thr Ser Lys Thr Thr Thr Thr Ala Ser
            580                 585                 590

Lys Thr Ser Thr Thr Thr Ser Ser Thr Ser Cys Thr Thr Pro Thr Ala
        595                 600                 605

Val Ala Val Thr Phe Asp Leu Thr Ala Thr Thr Thr Tyr Gly Glu Asn
    610                 615                 620

Ile Tyr Leu Val Gly Ser Ile Ser Gln Leu Gly Asp Trp Glu Thr Ser
625                 630                 635                 640

Asp Gly Ile Ala Leu Ser Ala Asp Lys Tyr Thr Ser Ser Asn Pro Pro
                645                 650                 655

Trp Tyr Val Thr Val Thr Leu Pro Ala Gly Glu Ser Phe Glu Tyr Lys
            660                 665                 670

Phe Ile Arg Val Glu Ser Asp Asp Ser Val Glu Trp Glu Ser Asp Pro
        675                 680                 685

Asn Arg Glu Tyr Thr Val Pro Gln Ala Cys Gly Glu Ser Thr Ala Thr
    690                 695                 700

Val Thr Asp Thr Trp Arg
705                 710


<210> SEQ ID NO 60
<211> LENGTH: 682
<212> TYPE: PRT
<213> ORGANISM: Artificial Sequence
<220> FEATURE:
<223> OTHER INFORMATION: Sequence put together from multiple organisms:
      Saccharomyces cerevisiae and Aspergillus shirousami

<400> SEQUENCE: 60

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Leu Glu Gly
            20                  25                  30

Asp Phe Asp Val Ala Val Leu Pro Phe Ser Ala Ser Ile Ala Ala Lys
        35                  40                  45

Glu Glu Gly Val Ser Leu Glu Lys Arg Glu Ala Glu Ala Ser Val Ile
    50                  55                  60

Ser Lys Arg Ala Thr Leu Asp Ser Trp Leu Ser Asn Glu Ala Thr Val
65                  70                  75                  80

Ala Arg Thr Ala Ile Leu Asn Asn Ile Gly Ala Asp Gly Ala Trp Val
                85                  90                  95

Ser Gly Ala Asp Ser Gly Ile Val Val Ala Ser Pro Ser Thr Asp Asn
            100                 105                 110

Pro Asp Tyr Phe Tyr Thr Trp Thr Arg Asp Ser Gly Ile Val Leu Lys
        115                 120                 125

Thr Leu Val Asp Leu Phe Arg Asn Gly Asp Thr Asp Leu Leu Ser Thr
```

```
    130                 135                 140

Ile Glu His Tyr Ile Ser Ser Gln Ala Ile Ile Gln Gly Val Ser Asn
145                 150                 155                 160

Pro Ser Gly Asp Leu Ser Ser Gly Gly Leu Gly Glu Pro Lys Phe Asn
                165                 170                 175

Val Asp Glu Thr Ala Tyr Ala Gly Ser Trp Gly Arg Pro Gln Arg Asp
            180                 185                 190

Gly Pro Ala Leu Arg Ala Thr Ala Met Ile Gly Phe Gly Gln Trp Leu
        195                 200                 205

Leu Asp Asn Gly Tyr Thr Ser Ala Ala Thr Glu Ile Val Trp Pro Leu
    210                 215                 220

Val Arg Asn Asp Leu Ser Tyr Val Ala Gln Tyr Trp Asn Gln Thr Gly
225                 230                 235                 240

Tyr Asp Leu Trp Glu Glu Val Asn Gly Ser Ser Phe Phe Thr Ile Ala
                245                 250                 255

Val Gln His Arg Ala Leu Val Glu Gly Ser Ala Phe Ala Thr Ala Val
            260                 265                 270

Gly Ser Ser Cys Ser Trp Cys Asp Ser Gln Ala Pro Gln Ile Leu Cys
        275                 280                 285

Tyr Leu Gln Ser Phe Trp Thr Gly Ser Tyr Ile Leu Ala Asn Phe Asp
    290                 295                 300

Ser Ser Arg Ser Gly Lys Asp Thr Asn Thr Leu Leu Gly Ser Ile His
305                 310                 315                 320

Thr Phe Asp Pro Glu Ala Gly Cys Asp Asp Ser Thr Phe Gln Pro Cys
                325                 330                 335

Ser Pro Arg Ala Leu Ala Asn His Lys Glu Val Val Asp Ser Phe Arg
            340                 345                 350

Ser Ile Tyr Thr Leu Asn Asp Gly Leu Ser Asp Ser Glu Ala Val Ala
        355                 360                 365

Val Gly Arg Tyr Pro Glu Asp Ser Tyr Tyr Asn Gly Asn Pro Trp Phe
    370                 375                 380

Leu Cys Thr Leu Ala Ala Ala Glu Gln Leu Tyr Asp Ala Leu Tyr Gln
385                 390                 395                 400

Trp Asp Lys Gln Gly Ser Leu Glu Ile Thr Asp Val Ser Leu Asp Phe
                405                 410                 415

Phe Lys Ala Leu Tyr Ser Gly Ala Ala Thr Gly Thr Tyr Ser Ser Ser
            420                 425                 430

Ser Ser Thr Tyr Ser Ser Ile Val Ser Ala Val Lys Thr Phe Ala Asp
        435                 440                 445

Gly Phe Val Ser Ile Val Glu Thr His Ala Ala Ser Asn Gly Ser Leu
    450                 455                 460

Ser Glu Gln Phe Asp Lys Ser Asp Gly Asp Glu Leu Ser Ala Arg Asp
465                 470                 475                 480

Leu Thr Trp Ser Tyr Ala Ala Leu Leu Thr Ala Asn Asn Arg Arg Asn
                485                 490                 495

Ser Val Val Pro Pro Ser Trp Gly Glu Thr Ser Ala Ser Ser Val Pro
            500                 505                 510

Gly Thr Cys Ala Ala Thr Ser Ala Ser Gly Thr Tyr Ser Ser Val Thr
        515                 520                 525

Val Thr Ser Trp Pro Ser Ile Val Ala Thr Gly Gly Thr Thr Thr Thr
    530                 535                 540

Ala Thr Thr Thr Gly Ser Gly Gly Val Thr Ser Thr Ser Lys Thr Thr
545                 550                 555                 560
```

```
Thr Thr Ala Ser Lys Thr Ser Thr Thr Thr Ser Ser Thr Ser Cys Thr
                565                 570                 575

Thr Pro Thr Ala Val Ala Val Thr Phe Asp Leu Thr Ala Thr Thr Thr
            580                 585                 590

Tyr Gly Glu Asn Ile Tyr Leu Val Gly Ser Ile Ser Gln Leu Gly Asp
        595                 600                 605

Trp Glu Thr Ser Asp Gly Ile Ala Leu Ser Ala Asp Lys Tyr Thr Ser
    610                 615                 620

Ser Asn Pro Pro Trp Tyr Val Thr Val Thr Leu Pro Ala Gly Glu Ser
625                 630                 635                 640

Phe Glu Tyr Lys Phe Ile Arg Val Glu Ser Asp Asp Ser Val Glu Trp
                645                 650                 655

Glu Ser Asp Pro Asn Arg Glu Tyr Thr Val Pro Gln Ala Cys Gly Glu
            660                 665                 670

Ser Thr Ala Thr Val Thr Asp Thr Trp Arg
        675                 680
```

<210> SEQ ID NO 61
<211> LENGTH: 640
<212> TYPE: PRT
<213> ORGANISM: Artificial Sequence
<220> FEATURE:
<223> OTHER INFORMATION: Sequence put together from multiple organisms: Aspergillus nidulans and Aspergillus shirousami

<400> SEQUENCE: 61

```
Met Arg Phe Pro Ser Ile Phe Thr Ala Val Leu Phe Ala Ala Ser Ser
1               5                   10                  15

Ala Leu Ala Ser Val Ile Ser Lys Arg Ala Thr Leu Asp Ser Trp Leu
            20                  25                  30

Ser Asn Glu Ala Thr Val Ala Arg Thr Ala Ile Leu Asn Asn Ile Gly
        35                  40                  45

Ala Asp Gly Ala Trp Val Ser Gly Ala Asp Ser Gly Ile Val Val Ala
    50                  55                  60

Ser Pro Ser Thr Asp Asn Pro Asp Tyr Phe Tyr Thr Trp Thr Arg Asp
65                  70                  75                  80

Ser Gly Ile Val Leu Lys Thr Leu Val Asp Leu Phe Arg Asn Gly Asp
                85                  90                  95

Thr Asp Leu Leu Ser Thr Ile Glu His Tyr Ile Ser Ser Gln Ala Ile
            100                 105                 110

Ile Gln Gly Val Ser Asn Pro Ser Gly Asp Leu Ser Ser Gly Gly Leu
        115                 120                 125

Gly Glu Pro Lys Phe Asn Val Asp Glu Thr Ala Tyr Ala Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Ala Ala Thr
                165                 170                 175

Glu Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
```

```
225                 230                 235                 240

Ala Pro Gln Ile Leu Cys Tyr Leu Gln Ser Phe Trp Thr Gly Ser Tyr
                245                 250                 255

Ile Leu Ala Asn Phe Asp Ser Ser Arg Ser Gly Lys Asp Thr Asn Thr
            260                 265                 270

Leu Leu Gly Ser Ile His Thr Phe Asp Pro Glu Ala Gly Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Ser Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Ile Thr
        355                 360                 365

Asp Val Ser Leu Asp Phe Phe Lys Ala Leu Tyr Ser Gly Ala Ala Thr
    370                 375                 380

Gly Thr Tyr Ser Ser Ser Ser Ser Thr Tyr Ser Ser Ile Val Ser Ala
385                 390                 395                 400

Val Lys Thr Phe Ala Asp Gly Phe Val Ser Ile Val Glu Thr His Ala
                405                 410                 415

Ala Ser Asn Gly Ser Leu Ser Glu Gln Phe Asp Lys Ser Asp Gly Asp
            420                 425                 430

Glu Leu Ser Ala Arg Asp Leu Thr Trp Ser Tyr Ala Ala Leu Leu Thr
        435                 440                 445

Ala Asn Asn Arg Arg Asn Ser Val Val Pro Pro Ser Trp Gly Glu Thr
    450                 455                 460

Ser Ala Ser Ser Val Pro Gly Thr Cys Ala Ala Thr Ser Ala Ser Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Thr Thr Gly Ser Gly Gly Val Thr
            500                 505                 510

Ser Thr Ser Lys Thr Thr Thr Thr Ala Ser Lys Thr Ser Thr Thr Thr
        515                 520                 525

Ser Ser Thr Ser Cys Thr Thr Pro Thr Ala Val Ala Val Thr Phe Asp
    530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Ser Asn Pro Pro Trp Tyr Val Thr Val Thr
            580                 585                 590

Leu Pro Ala Gly Glu Ser Phe Glu Tyr Lys Phe Ile Arg Val Glu Ser
        595                 600                 605

Asp Asp Ser Val Glu Trp Glu Ser Asp Pro Asn Arg Glu Tyr Thr Val
    610                 615                 620

Pro Gln Ala Cys Gly Glu Ser Thr Ala Thr Val Thr Asp Thr Trp Arg
625                 630                 635                 640
```

<210> SEQ ID NO 62

<211> LENGTH: 640
<212> TYPE: PRT
<213> ORGANISM: Artificial Sequence
<220> FEATURE:
<223> OTHER INFORMATION: Sequence put together from multiple organisms: Saccharomyces cerevisiae and Aspergillus shirousami

<400> SEQUENCE: 62

```
Met Leu Leu Gln Ala Phe Leu Phe Leu Leu Ala Gly Phe Ala Ala Lys
1               5                   10                  15

Ile Ser Ala Ser Val Ile Ser Lys Arg Ala Thr Leu Asp Ser Trp Leu
            20                  25                  30

Ser Asn Glu Ala Thr Val Ala Arg Thr Ala Ile Leu Asn Asn Ile Gly
        35                  40                  45

Ala Asp Gly Ala Trp Val Ser Gly Ala Asp Ser Gly Ile Val Val Ala
    50                  55                  60

Ser Pro Ser Thr Asp Asn Pro Asp Tyr Phe Tyr Thr Trp Thr Arg Asp
65                  70                  75                  80

Ser Gly Ile Val Leu Lys Thr Leu Val Asp Leu Phe Arg Asn Gly Asp
                85                  90                  95

Thr Asp Leu Leu Ser Thr Ile Glu His Tyr Ile Ser Ser Gln Ala Ile
            100                 105                 110

Ile Gln Gly Val Ser Asn Pro Ser Gly Asp Leu Ser Ser Gly Gly Leu
        115                 120                 125

Gly Glu Pro Lys Phe Asn Val Asp Glu Thr Ala Tyr Ala Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Ala Ala Thr
                165                 170                 175

Glu Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Gln Ile Leu Cys Tyr Leu Gln Ser Phe Trp Thr Gly Ser Tyr
                245                 250                 255

Ile Leu Ala Asn Phe Asp Ser Ser Arg Ser Gly Lys Asp Thr Asn Thr
            260                 265                 270

Leu Leu Gly Ser Ile His Thr Phe Asp Pro Glu Ala Gly Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Ser Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Ile Thr
        355                 360                 365

Asp Val Ser Leu Asp Phe Phe Lys Ala Leu Tyr Ser Gly Ala Ala Thr
```

```
    370                 375                 380

Gly Thr Tyr Ser Ser Ser Ser Ser Thr Tyr Ser Ser Ile Val Ser Ala
385                 390                 395                 400

Val Lys Thr Phe Ala Asp Gly Phe Val Ser Ile Val Glu Thr His Ala
                405                 410                 415

Ala Ser Asn Gly Ser Leu Ser Glu Gln Phe Asp Lys Ser Asp Gly Asp
            420                 425                 430

Glu Leu Ser Ala Arg Asp Leu Thr Trp Ser Tyr Ala Ala Leu Leu Thr
        435                 440                 445

Ala Asn Asn Arg Arg Asn Ser Val Val Pro Pro Ser Trp Gly Glu Thr
    450                 455                 460

Ser Ala Ser Ser Val Pro Gly Thr Cys Ala Ala Thr Ser Ala Ser Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Thr Thr Gly Ser Gly Gly Val Thr
            500                 505                 510

Ser Thr Ser Lys Thr Thr Thr Thr Ala Ser Lys Thr Ser Thr Thr Thr
        515                 520                 525

Ser Ser Thr Ser Cys Thr Thr Pro Thr Ala Val Ala Val Thr Phe Asp
    530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Ser Asn Pro Pro Trp Tyr Val Thr Val Thr
            580                 585                 590

Leu Pro Ala Gly Glu Ser Phe Glu Tyr Lys Phe Ile Arg Val Glu Ser
        595                 600                 605

Asp Asp Ser Val Glu Trp Glu Ser Asp Pro Asn Arg Glu Tyr Thr Val
    610                 615                 620

Pro Gln Ala Cys Gly Glu Ser Thr Ala Thr Val Thr Asp Thr Trp Arg
625                 630                 635                 640


<210> SEQ ID NO 63
<211> LENGTH: 647
<212> TYPE: PRT
<213> ORGANISM: Artificial Sequence
<220> FEATURE:
<223> OTHER INFORMATION: Sequence put together from multiple organisms:
      Gallus gallus and Aspergillus shirousami

<400> SEQUENCE: 63

Met Leu Gly Lys Asn Asp Pro Met Cys Leu Val Leu Val Leu Leu Gly
1               5                   10                  15

Leu Thr Ala Leu Leu Gly Ile Cys Gln Gly Ser Val Ile Ser Lys Arg
            20                  25                  30

Ala Thr Leu Asp Ser Trp Leu Ser Asn Glu Ala Thr Val Ala Arg Thr
        35                  40                  45

Ala Ile Leu Asn Asn Ile Gly Ala Asp Gly Ala Trp Val Ser Gly Ala
    50                  55                  60

Asp Ser Gly Ile Val Val Ala Ser Pro Ser Thr Asp Asn Pro Asp Tyr
65                  70                  75                  80

Phe Tyr Thr Trp Thr Arg Asp Ser Gly Ile Val Leu Lys Thr Leu Val
                85                  90                  95
```

```
Asp Leu Phe Arg Asn Gly Asp Thr Asp Leu Leu Ser Thr Ile Glu His
            100                 105                 110

Tyr Ile Ser Ser Gln Ala Ile Ile Gln Gly Val Ser Asn Pro Ser Gly
        115                 120                 125

Asp Leu Ser Ser Gly Gly Leu Gly Glu Pro Lys Phe Asn Val Asp Glu
    130                 135                 140

Thr Ala Tyr Ala Gly Ser Trp Gly Arg Pro Gln Arg Asp Gly Pro Ala
145                 150                 155                 160

Leu Arg Ala Thr Ala Met Ile Gly Phe Gly Gln Trp Leu Leu Asp Asn
                165                 170                 175

Gly Tyr Thr Ser Ala Ala Thr Glu Ile Val Trp Pro Leu Val Arg Asn
            180                 185                 190

Asp Leu Ser Tyr Val Ala Gln Tyr Trp Asn Gln Thr Gly Tyr Asp Leu
        195                 200                 205

Trp Glu Glu Val Asn Gly Ser Ser Phe Phe Thr Ile Ala Val Gln His
    210                 215                 220

Arg Ala Leu Val Glu Gly Ser Ala Phe Ala Thr Ala Val Gly Ser Ser
225                 230                 235                 240

Cys Ser Trp Cys Asp Ser Gln Ala Pro Gln Ile Leu Cys Tyr Leu Gln
                245                 250                 255

Ser Phe Trp Thr Gly Ser Tyr Ile Leu Ala Asn Phe Asp Ser Ser Arg
            260                 265                 270

Ser Gly Lys Asp Thr Asn Thr Leu Leu Gly Ser Ile His Thr Phe Asp
        275                 280                 285

Pro Glu Ala Gly Cys Asp Asp Ser Thr Phe Gln Pro Cys Ser Pro Arg
    290                 295                 300

Ala Leu Ala Asn His Lys Glu Val Val Asp Ser Phe Arg Ser Ile Tyr
305                 310                 315                 320

Thr Leu Asn Asp Gly Leu Ser Asp Ser Glu Ala Val Ala Val Gly Arg
                325                 330                 335

Tyr Pro Glu Asp Ser Tyr Tyr Asn Gly Asn Pro Trp Phe Leu Cys Thr
            340                 345                 350

Leu Ala Ala Ala Glu Gln Leu Tyr Asp Ala Leu Tyr Gln Trp Asp Lys
        355                 360                 365

Gln Gly Ser Leu Glu Ile Thr Asp Val Ser Leu Asp Phe Phe Lys Ala
    370                 375                 380

Leu Tyr Ser Gly Ala Ala Thr Gly Thr Tyr Ser Ser Ser Ser Ser Thr
385                 390                 395                 400

Tyr Ser Ser Ile Val Ser Ala Val Lys Thr Phe Ala Asp Gly Phe Val
                405                 410                 415

Ser Ile Val Glu Thr His Ala Ala Ser Asn Gly Ser Leu Ser Glu Gln
            420                 425                 430

Phe Asp Lys Ser Asp Gly Asp Glu Leu Ser Ala Arg Asp Leu Thr Trp
        435                 440                 445

Ser Tyr Ala Ala Leu Leu Thr Ala Asn Asn Arg Arg Asn Ser Val Val
    450                 455                 460

Pro Pro Ser Trp Gly Glu Thr Ser Ala Ser Ser Val Pro Gly Thr Cys
465                 470                 475                 480

Ala Ala Thr Ser Ala Ser Gly Thr Tyr Ser Ser Val Thr Val Thr Ser
                485                 490                 495

Trp Pro Ser Ile Val Ala Thr Gly Gly Thr Thr Thr Thr Ala Thr Thr
            500                 505                 510

Thr Gly Ser Gly Gly Val Thr Ser Thr Ser Lys Thr Thr Thr Thr Ala
```

```
        515                 520                 525

Ser Lys Thr Ser Thr Thr Thr Ser Ser Thr Ser Cys Thr Thr Pro Thr
    530                 535                 540

Ala Val Ala Val Thr Phe Asp Leu Thr Ala Thr Thr Thr Tyr Gly Glu
545                 550                 555                 560

Asn Ile Tyr Leu Val Gly Ser Ile Ser Gln Leu Gly Asp Trp Glu Thr
                565                 570                 575

Ser Asp Gly Ile Ala Leu Ser Ala Asp Lys Tyr Thr Ser Ser Asn Pro
            580                 585                 590

Pro Trp Tyr Val Thr Val Thr Leu Pro Ala Gly Glu Ser Phe Glu Tyr
        595                 600                 605

Lys Phe Ile Arg Val Glu Ser Asp Asp Ser Val Glu Trp Glu Ser Asp
    610                 615                 620

Pro Asn Arg Glu Tyr Thr Val Pro Gln Ala Cys Gly Glu Ser Thr Ala
625                 630                 635                 640

Thr Val Thr Asp Thr Trp Arg
                645


<210> SEQ ID NO 64
<211> LENGTH: 639
<212> TYPE: PRT
<213> ORGANISM: Artificial Sequence
<220> FEATURE:
<223> OTHER INFORMATION: Sequence put together from multiple organisms:
      Homo sapiens and Aspergillus shirousami

<400> SEQUENCE: 64

Met Lys Trp Val Thr Phe Ile Ser Leu Leu Phe Leu Phe Ser Ser Ala
1               5                   10                  15

Tyr Ser Ser Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Ile Val Leu Lys Thr Leu Val Asp Leu Phe Arg Asn Gly Asp Thr
                85                  90                  95

Asp Leu Leu Ser Thr Ile Glu His Tyr Ile Ser Ser Gln Ala Ile Ile
            100                 105                 110

Gln Gly Val Ser Asn Pro Ser Gly Asp Leu Ser Ser Gly Gly Leu Gly
        115                 120                 125

Glu Pro Lys Phe Asn Val Asp Glu Thr Ala Tyr Ala Gly Ser Trp Gly
    130                 135                 140

Arg Pro Gln Arg Asp Gly Pro Ala Leu Arg Ala Thr Ala Met Ile Gly
145                 150                 155                 160

Phe Gly Gln Trp Leu Leu Asp Asn Gly Tyr Thr Ser Ala Ala Thr Glu
                165                 170                 175

Ile Val Trp Pro Leu Val Arg Asn Asp Leu Ser Tyr Val Ala Gln Tyr
            180                 185                 190

Trp Asn Gln Thr Gly Tyr Asp Leu Trp Glu Glu Val Asn Gly Ser Ser
        195                 200                 205

Phe Phe Thr Ile Ala Val Gln His Arg Ala Leu Val Glu Gly Ser Ala
    210                 215                 220
```

```
Phe Ala Thr Ala Val Gly Ser Ser Cys Ser Trp Cys Asp Ser Gln Ala
225                 230                 235                 240

Pro Gln Ile Leu Cys Tyr Leu Gln Ser Phe Trp Thr Gly Ser Tyr Ile
                245                 250                 255

Leu Ala Asn Phe Asp Ser Ser Arg Ser Gly Lys Asp Thr Asn Thr Leu
            260                 265                 270

Leu Gly Ser Ile His Thr Phe Asp Pro Glu Ala Gly Cys Asp Asp Ser
        275                 280                 285

Thr Phe Gln Pro Cys Ser Pro Arg Ala Leu Ala Asn His Lys Glu Val
    290                 295                 300

Val Asp Ser Phe Arg Ser Ile Tyr Thr Leu Asn Asp Gly Leu Ser Asp
305                 310                 315                 320

Ser Glu Ala Val Ala Val Gly Arg Tyr Pro Glu Asp Ser Tyr Tyr Asn
                325                 330                 335

Gly Asn Pro Trp Phe Leu Cys Thr Leu Ala Ala Ala Glu Gln Leu Tyr
            340                 345                 350

Asp Ala Leu Tyr Gln Trp Asp Lys Gln Gly Ser Leu Glu Ile Thr Asp
        355                 360                 365

Val Ser Leu Asp Phe Phe Lys Ala Leu Tyr Ser Gly Ala Ala Thr Gly
    370                 375                 380

Thr Tyr Ser Ser Ser Ser Ser Thr Tyr Ser Ser Ile Val Ser Ala Val
385                 390                 395                 400

Lys Thr Phe Ala Asp Gly Phe Val Ser Ile Val Glu Thr His Ala Ala
                405                 410                 415

Ser Asn Gly Ser Leu Ser Glu Gln Phe Asp Lys Ser Asp Gly Asp Glu
            420                 425                 430

Leu Ser Ala Arg Asp Leu Thr Trp Ser Tyr Ala Ala Leu Leu Thr Ala
        435                 440                 445

Asn Asn Arg Arg Asn Ser Val Val Pro Pro Ser Trp Gly Glu Thr Ser
    450                 455                 460

Ala Ser Ser Val Pro Gly Thr Cys Ala Ala Thr Ser Ala Ser Gly Thr
465                 470                 475                 480

Tyr Ser Ser Val Thr Val Thr Ser Trp Pro Ser Ile Val Ala Thr Gly
                485                 490                 495

Gly Thr Thr Thr Thr Ala Thr Thr Thr Gly Ser Gly Gly Val Thr Ser
            500                 505                 510

Thr Ser Lys Thr Thr Thr Thr Ala Ser Lys Thr Ser Thr Thr Thr Ser
        515                 520                 525

Ser Thr Ser Cys Thr Thr Pro Thr Ala Val Ala Val Thr Phe Asp Leu
    530                 535                 540

Thr Ala Thr Thr Thr Tyr Gly Glu Asn Ile Tyr Leu Val Gly Ser Ile
545                 550                 555                 560

Ser Gln Leu Gly Asp Trp Glu Thr Ser Asp Gly Ile Ala Leu Ser Ala
                565                 570                 575

Asp Lys Tyr Thr Ser Ser Asn Pro Pro Trp Tyr Val Thr Val Thr Leu
            580                 585                 590

Pro Ala Gly Glu Ser Phe Glu Tyr Lys Phe Ile Arg Val Glu Ser Asp
        595                 600                 605

Asp Ser Val Glu Trp Glu Ser Asp Pro Asn Arg Glu Tyr Thr Val Pro
    610                 615                 620

Gln Ala Cys Gly Glu Ser Thr Ala Thr Val Thr Asp Thr Trp Arg
625                 630                 635
```

```
<210> SEQ ID NO 65
<211> LENGTH: 640
<212> TYPE: PRT
<213> ORGANISM: Artificial Sequence
<220> FEATURE:
<223> OTHER INFORMATION: Sequence put together from multiple organisms:
      Saccharomyces cerevisiae and Aspergillus shirousami

<400> SEQUENCE: 65

Met Arg Phe Pro Ser Ile Phe Thr Ala Val Leu Phe Ala Ala Ser Ser
1               5                   10                  15

Ala Leu Ala Ser Val Ile Ser Lys Arg Ala Thr Leu Asp Ser Trp Leu
            20                  25                  30

Ser Asn Glu Ala Thr Val Ala Arg Thr Ala Ile Leu Asn Asn Ile Gly
        35                  40                  45

Ala Asp Gly Ala Trp Val Ser Gly Ala Asp Ser Gly Ile Val Val Ala
    50                  55                  60

Ser Pro Ser Thr Asp Asn Pro Asp Tyr Phe Tyr Thr Trp Thr Arg Asp
65                  70                  75                  80

Ser Gly Ile Val Leu Lys Thr Leu Val Asp Leu Phe Arg Asn Gly Asp
                85                  90                  95

Thr Asp Leu Leu Ser Thr Ile Glu His Tyr Ile Ser Ser Gln Ala Ile
            100                 105                 110

Ile Gln Gly Val Ser Asn Pro Ser Gly Asp Leu Ser Ser Gly Gly Leu
        115                 120                 125

Gly Glu Pro Lys Phe Asn Val Asp Glu Thr Ala Tyr Ala Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Ala Ala Thr
                165                 170                 175

Glu Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Gln Ile Leu Cys Tyr Leu Gln Ser Phe Trp Thr Gly Ser Tyr
                245                 250                 255

Ile Leu Ala Asn Phe Asp Ser Ser Arg Ser Gly Lys Asp Thr Asn Thr
            260                 265                 270

Leu Leu Gly Ser Ile His Thr Phe Asp Pro Glu Ala Gly Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Ser Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Ile Thr
        355                 360                 365
```

```
Asp Val Ser Leu Asp Phe Phe Lys Ala Leu Tyr Ser Gly Ala Ala Thr
    370                 375                 380

Gly Thr Tyr Ser Ser Ser Ser Ser Thr Tyr Ser Ser Ile Val Ser Ala
385                 390                 395                 400

Val Lys Thr Phe Ala Asp Gly Phe Val Ser Ile Val Glu Thr His Ala
                405                 410                 415

Ala Ser Asn Gly Ser Leu Ser Glu Gln Phe Asp Lys Ser Asp Gly Asp
            420                 425                 430

Glu Leu Ser Ala Arg Asp Leu Thr Trp Ser Tyr Ala Ala Leu Leu Thr
        435                 440                 445

Ala Asn Asn Arg Arg Asn Ser Val Val Pro Pro Ser Trp Gly Glu Thr
    450                 455                 460

Ser Ala Ser Ser Val Pro Gly Thr Cys Ala Ala Thr Ser Ala Ser Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Thr Thr Gly Ser Gly Gly Val Thr
            500                 505                 510

Ser Thr Ser Lys Thr Thr Thr Thr Ala Ser Lys Thr Ser Thr Thr Thr
        515                 520                 525

Ser Ser Thr Ser Cys Thr Thr Pro Thr Ala Val Ala Val Thr Phe Asp
    530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Ser Asn Pro Pro Trp Tyr Val Thr Val Thr
            580                 585                 590

Leu Pro Ala Gly Glu Ser Phe Glu Tyr Lys Phe Ile Arg Val Glu Ser
        595                 600                 605

Asp Asp Ser Val Glu Trp Glu Ser Asp Pro Asn Arg Glu Tyr Thr Val
    610                 615                 620

Pro Gln Ala Cys Gly Glu Ser Thr Ala Thr Val Thr Asp Thr Trp Arg
625                 630                 635                 640
```

<210> SEQ ID NO 66
<211> LENGTH: 705
<212> TYPE: PRT
<213> ORGANISM: Artificial Sequence
<220> FEATURE:
<223> OTHER INFORMATION: Sequence put together from multiple organisms: Saccharomyces cerevisiae and Aspergillus terreus

<400> SEQUENCE: 66

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ala Pro Gln Leu Ala Pro Arg
                85                  90                  95
```

```
Ala Thr Thr Ser Leu Asp Ala Trp Leu Ala Ser Glu Thr Thr Val Ala
            100                 105                 110

Leu Asp Gly Ile Leu Asp Asn Val Gly Ser Ser Gly Ala Tyr Ala Lys
        115                 120                 125

Ser Ala Lys Ser Gly Ile Val Ile Ala Ser Pro Ser Thr Ser Asp Pro
    130                 135                 140

Asp Tyr Tyr Tyr Thr Trp Thr Arg Asp Ala Ala Leu Thr Val Lys Ala
145                 150                 155                 160

Leu Ile Asp Leu Phe Arg Asn Gly Glu Thr Ser Leu Gln Thr Val Ile
                165                 170                 175

Met Glu Tyr Ile Ser Ser Gln Ala Tyr Leu Gln Thr Val Ser Asn Pro
            180                 185                 190

Ser Gly Ser Leu Ser Thr Gly Gly Leu Ala Glu Pro Lys Tyr Tyr Val
        195                 200                 205

Asp Glu Thr Ala Tyr Thr Gly Ser Trp Gly Arg Pro Gln Arg Asp Gly
    210                 215                 220

Pro Ala Leu Arg Ala Thr Ala Met Ile Asp Phe Gly Asn Trp Leu Ile
225                 230                 235                 240

Asp Asn Gly Tyr Ser Thr Tyr Ala Ser Ser Ile Val Trp Pro Ile Val
                245                 250                 255

Arg Asn Asp Leu Ser Tyr Val Ala Gln Tyr Trp Asn Gln Thr Gly Tyr
            260                 265                 270

Asp Leu Trp Glu Glu Val Asn Gly Ser Ser Phe Phe Thr Ile Ala Val
        275                 280                 285

Gln His Arg Ala Leu Val Glu Gly Ser Thr Phe Ala Ser Lys Val Gly
    290                 295                 300

Ala Ser Cys Ser Trp Cys Asp Ser Gln Ala Pro Gln Val Leu Cys Phe
305                 310                 315                 320

Leu Gln Arg Phe Trp Thr Gly Ser Tyr Ile Met Ala Asn Phe Gly Gly
                325                 330                 335

Gly Arg Ser Gly Lys Asp Ala Asn Thr Val Leu Gly Ser Ile His Thr
            340                 345                 350

Phe Asp Pro Asn Ala Gly Cys Asp Asp Thr Thr Phe Gln Pro Cys Ser
        355                 360                 365

Pro Arg Ala Leu Ala Asn His Lys Val Tyr Thr Asp Ser Phe Arg Ser
    370                 375                 380

Ile Tyr Ser Ile Asn Ser Gly Ile Ser Ser Gly Lys Ala Val Ala Val
385                 390                 395                 400

Gly Arg Tyr Pro Glu Asp Ser Tyr Tyr Asn Gly Asn Pro Trp Phe Leu
                405                 410                 415

Thr Thr Leu Ala Ala Ala Glu Gln Leu Tyr Asp Ala Ile Tyr Gln Trp
            420                 425                 430

Gln Lys Ile Gly Ser Ile Thr Ile Thr Asp Val Ser Leu Ala Phe Phe
        435                 440                 445

Lys Asp Leu Tyr Ser Ser Ala Ala Val Gly Thr Tyr Ala Ser Ser Ser
    450                 455                 460

Ser Ala Phe Thr Ser Ile Val Ser Ala Val Lys Thr Tyr Ala Asp Gly
465                 470                 475                 480

Tyr Met Ser Ile Val Gln Thr His Ala Met Thr Asn Gly Ser Leu Ser
                485                 490                 495

Glu Gln Phe Gly Lys Ser Asp Gly Phe Ser Leu Ser Ala Arg Asp Leu
            500                 505                 510
```

```
Thr Trp Ser Tyr Ala Ala Leu Leu Thr Ala Asn Leu Arg Arg Asn Ser
        515                 520                 525

Val Val Pro Pro Ser Trp Gly Glu Thr Thr Ala Thr Ser Val Pro Ser
    530                 535                 540

Val Cys Ser Ala Thr Ser Ala Thr Gly Thr Tyr Ser Thr Ala Thr Asn
545                 550                 555                 560

Thr Ala Trp Pro Ser Thr Leu Thr Ser Gly Thr Gly Ala Thr Thr Thr
                565                 570                 575

Thr Ser Lys Ala Thr Ser Ser Ser Thr Thr Thr Thr Ser Ser Ala Ser
            580                 585                 590

Ser Thr Thr Val Glu Cys Val Val Pro Thr Ala Val Ala Val Thr Phe
        595                 600                 605

Asp Glu Val Ala Thr Thr Thr Tyr Gly Glu Asn Val Tyr Val Val Gly
    610                 615                 620

Ser Ile Ser Gln Leu Gly Ser Trp Asp Thr Ser Lys Ala Val Ala Leu
625                 630                 635                 640

Ser Ala Ser Lys Tyr Thr Ser Ser Asn Asn Leu Trp Tyr Val Thr Val
                645                 650                 655

Thr Leu Pro Ala Gly Thr Thr Phe Gln Tyr Lys Phe Ile Arg Val Ser
            660                 665                 670

Ser Ser Gly Ser Val Thr Trp Glu Ser Asp Pro Asn Arg Ser Tyr Thr
        675                 680                 685

Val Pro Ser Ala Cys Gly Thr Ser Thr Ala Val Val Asn Thr Thr Trp
    690                 695                 700

Arg
705


<210> SEQ ID NO 67
<211> LENGTH: 677
<212> TYPE: PRT
<213> ORGANISM: Artificial Sequence
<220> FEATURE:
<223> OTHER INFORMATION: Sequence put together from multiple organisms:
      Saccharomyces cerevisiae and Aspergillus terreus

<400> SEQUENCE: 67

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Leu Glu Gly
            20                  25                  30

Asp Phe Asp Val Ala Val Leu Pro Phe Ser Ala Ser Ile Ala Ala Lys
        35                  40                  45

Glu Glu Gly Val Ser Leu Glu Lys Arg Glu Ala Glu Ala Ala Pro Gln
    50                  55                  60

Leu Ala Pro Arg Ala Thr Thr Ser Leu Asp Ala Trp Leu Ala Ser Glu
65                  70                  75                  80

Thr Thr Val Ala Leu Asp Gly Ile Leu Asp Asn Val Gly Ser Ser Gly
                85                  90                  95

Ala Tyr Ala Lys Ser Ala Lys Ser Gly Ile Val Ile Ala Ser Pro Ser
            100                 105                 110

Thr Ser Asp Pro Asp Tyr Tyr Tyr Thr Trp Thr Arg Asp Ala Ala Leu
        115                 120                 125

Thr Val Lys Ala Leu Ile Asp Leu Phe Arg Asn Gly Glu Thr Ser Leu
    130                 135                 140

Gln Thr Val Ile Met Glu Tyr Ile Ser Ser Gln Ala Tyr Leu Gln Thr
145                 150                 155                 160
```

```
Val Ser Asn Pro Ser Gly Ser Leu Ser Thr Gly Gly Leu Ala Glu Pro
                165                 170                 175

Lys Tyr Tyr Val Asp Glu Thr Ala Tyr Thr Gly Ser Trp Gly Arg Pro
            180                 185                 190

Gln Arg Asp Gly Pro Ala Leu Arg Ala Thr Ala Met Ile Asp Phe Gly
        195                 200                 205

Asn Trp Leu Ile Asp Asn Gly Tyr Ser Thr Tyr Ala Ser Ser Ile Val
    210                 215                 220

Trp Pro Ile Val Arg Asn Asp Leu Ser Tyr Val Ala Gln Tyr Trp Asn
225                 230                 235                 240

Gln Thr Gly Tyr Asp Leu Trp Glu Glu Val Asn Gly Ser Ser Phe Phe
                245                 250                 255

Thr Ile Ala Val Gln His Arg Ala Leu Val Glu Gly Ser Thr Phe Ala
            260                 265                 270

Ser Lys Val Gly Ala Ser Cys Ser Trp Cys Asp Ser Gln Ala Pro Gln
        275                 280                 285

Val Leu Cys Phe Leu Gln Arg Phe Trp Thr Gly Ser Tyr Ile Met Ala
    290                 295                 300

Asn Phe Gly Gly Gly Arg Ser Gly Lys Asp Ala Asn Thr Val Leu Gly
305                 310                 315                 320

Ser Ile His Thr Phe Asp Pro Asn Ala Gly Cys Asp Asp Thr Thr Phe
                325                 330                 335

Gln Pro Cys Ser Pro Arg Ala Leu Ala Asn His Lys Val Tyr Thr Asp
            340                 345                 350

Ser Phe Arg Ser Ile Tyr Ser Ile Asn Ser Gly Ile Ser Ser Gly Lys
        355                 360                 365

Ala Val Ala Val Gly Arg Tyr Pro Glu Asp Ser Tyr Tyr Asn Gly Asn
    370                 375                 380

Pro Trp Phe Leu Thr Thr Leu Ala Ala Ala Glu Gln Leu Tyr Asp Ala
385                 390                 395                 400

Ile Tyr Gln Trp Gln Lys Ile Gly Ser Ile Thr Ile Thr Asp Val Ser
                405                 410                 415

Leu Ala Phe Phe Lys Asp Leu Tyr Ser Ser Ala Ala Val Gly Thr Tyr
            420                 425                 430

Ala Ser Ser Ser Ser Ala Phe Thr Ser Ile Val Ser Ala Val Lys Thr
        435                 440                 445

Tyr Ala Asp Gly Tyr Met Ser Ile Val Gln Thr His Ala Met Thr Asn
    450                 455                 460

Gly Ser Leu Ser Glu Gln Phe Gly Lys Ser Asp Gly Phe Ser Leu Ser
465                 470                 475                 480

Ala Arg Asp Leu Thr Trp Ser Tyr Ala Ala Leu Leu Thr Ala Asn Leu
                485                 490                 495

Arg Arg Asn Ser Val Val Pro Pro Ser Trp Gly Glu Thr Thr Ala Thr
            500                 505                 510

Ser Val Pro Ser Val Cys Ser Ala Thr Ser Ala Thr Gly Thr Tyr Ser
        515                 520                 525

Thr Ala Thr Asn Thr Ala Trp Pro Ser Thr Leu Thr Ser Gly Thr Gly
    530                 535                 540

Ala Thr Thr Thr Thr Ser Lys Ala Thr Ser Ser Ser Thr Thr Thr Thr
545                 550                 555                 560

Ser Ser Ala Ser Ser Thr Thr Val Glu Cys Val Val Pro Thr Ala Val
                565                 570                 575
```

```
Ala Val Thr Phe Asp Glu Val Ala Thr Thr Thr Tyr Gly Glu Asn Val
            580                 585                 590

Tyr Val Val Gly Ser Ile Ser Gln Leu Gly Ser Trp Asp Thr Ser Lys
        595                 600                 605

Ala Val Ala Leu Ser Ala Ser Lys Tyr Thr Ser Ser Asn Asn Leu Trp
    610                 615                 620

Tyr Val Thr Val Thr Leu Pro Ala Gly Thr Thr Phe Gln Tyr Lys Phe
625                 630                 635                 640

Ile Arg Val Ser Ser Ser Gly Ser Val Thr Trp Glu Ser Asp Pro Asn
                645                 650                 655

Arg Ser Tyr Thr Val Pro Ser Ala Cys Gly Thr Ser Thr Ala Val Val
            660                 665                 670

Asn Thr Thr Trp Arg
        675
```

<210> SEQ ID NO 68
<211> LENGTH: 635
<212> TYPE: PRT
<213> ORGANISM: Artificial Sequence
<220> FEATURE:
<223> OTHER INFORMATION: Sequence put together from multiple organisms: Aspergillus nidulans and Aspergillus terreus

<400> SEQUENCE: 68

```
Met Arg Phe Pro Ser Ile Phe Thr Ala Val Leu Phe Ala Ala Ser Ser
1               5                   10                  15

Ala Leu Ala Ala Pro Gln Leu Ala Pro Arg Ala Thr Thr Ser Leu Asp
            20                  25                  30

Ala Trp Leu Ala Ser Glu Thr Thr Val Ala Leu Asp Gly Ile Leu Asp
        35                  40                  45

Asn Val Gly Ser Ser Gly Ala Tyr Ala Lys Ser Ala Lys Ser Gly Ile
    50                  55                  60

Val Ile Ala Ser Pro Ser Thr Ser Asp Pro Asp Tyr Tyr Tyr Thr Trp
65                  70                  75                  80

Thr Arg Asp Ala Ala Leu Thr Val Lys Ala Leu Ile Asp Leu Phe Arg
                85                  90                  95

Asn Gly Glu Thr Ser Leu Gln Thr Val Ile Met Glu Tyr Ile Ser Ser
            100                 105                 110

Gln Ala Tyr Leu Gln Thr Val Ser Asn Pro Ser Gly Ser Leu Ser Thr
        115                 120                 125

Gly Gly Leu Ala Glu Pro Lys Tyr Tyr Val Asp Glu Thr Ala Tyr Thr
    130                 135                 140

Gly Ser Trp Gly Arg Pro Gln Arg Asp Gly Pro Ala Leu Arg Ala Thr
145                 150                 155                 160

Ala Met Ile Asp Phe Gly Asn Trp Leu Ile Asp Asn Gly Tyr Ser Thr
                165                 170                 175

Tyr Ala Ser Ser Ile Val Trp Pro Ile Val Arg Asn Asp Leu Ser Tyr
            180                 185                 190

Val Ala Gln Tyr Trp Asn Gln Thr Gly Tyr Asp Leu Trp Glu Glu Val
        195                 200                 205

Asn Gly Ser Ser Phe Phe Thr Ile Ala Val Gln His Arg Ala Leu Val
    210                 215                 220

Glu Gly Ser Thr Phe Ala Ser Lys Val Gly Ala Ser Cys Ser Trp Cys
225                 230                 235                 240

Asp Ser Gln Ala Pro Gln Val Leu Cys Phe Leu Gln Arg Phe Trp Thr
                245                 250                 255
```

```
Gly Ser Tyr Ile Met Ala Asn Phe Gly Gly Gly Arg Ser Gly Lys Asp
            260                 265                 270

Ala Asn Thr Val Leu Gly Ser Ile His Thr Phe Asp Pro Asn Ala Gly
        275                 280                 285

Cys Asp Asp Thr Thr Phe Gln Pro Cys Ser Pro Arg Ala Leu Ala Asn
    290                 295                 300

His Lys Val Tyr Thr Asp Ser Phe Arg Ser Ile Tyr Ser Ile Asn Ser
305                 310                 315                 320

Gly Ile Ser Ser Gly Lys Ala Val Ala Val Gly Arg Tyr Pro Glu Asp
                325                 330                 335

Ser Tyr Tyr Asn Gly Asn Pro Trp Phe Leu Thr Thr Leu Ala Ala Ala
            340                 345                 350

Glu Gln Leu Tyr Asp Ala Ile Tyr Gln Trp Gln Lys Ile Gly Ser Ile
        355                 360                 365

Thr Ile Thr Asp Val Ser Leu Ala Phe Phe Lys Asp Leu Tyr Ser Ser
    370                 375                 380

Ala Ala Val Gly Thr Tyr Ala Ser Ser Ser Ser Ala Phe Thr Ser Ile
385                 390                 395                 400

Val Ser Ala Val Lys Thr Tyr Ala Asp Gly Tyr Met Ser Ile Val Gln
                405                 410                 415

Thr His Ala Met Thr Asn Gly Ser Leu Ser Glu Gln Phe Gly Lys Ser
            420                 425                 430

Asp Gly Phe Ser Leu Ser Ala Arg Asp Leu Thr Trp Ser Tyr Ala Ala
        435                 440                 445

Leu Leu Thr Ala Asn Leu Arg Arg Asn Ser Val Val Pro Pro Ser Trp
    450                 455                 460

Gly Glu Thr Thr Ala Thr Ser Val Pro Ser Val Cys Ser Ala Thr Ser
465                 470                 475                 480

Ala Thr Gly Thr Tyr Ser Thr Ala Thr Asn Thr Ala Trp Pro Ser Thr
                485                 490                 495

Leu Thr Ser Gly Thr Gly Ala Thr Thr Thr Thr Ser Lys Ala Thr Ser
            500                 505                 510

Ser Ser Thr Thr Thr Thr Ser Ser Ala Ser Ser Thr Thr Val Glu Cys
        515                 520                 525

Val Val Pro Thr Ala Val Ala Val Thr Phe Asp Glu Val Ala Thr Thr
    530                 535                 540

Thr Tyr Gly Glu Asn Val Tyr Val Val Gly Ser Ile Ser Gln Leu Gly
545                 550                 555                 560

Ser Trp Asp Thr Ser Lys Ala Val Ala Leu Ser Ala Ser Lys Tyr Thr
                565                 570                 575

Ser Ser Asn Asn Leu Trp Tyr Val Thr Val Thr Leu Pro Ala Gly Thr
            580                 585                 590

Thr Phe Gln Tyr Lys Phe Ile Arg Val Ser Ser Ser Gly Ser Val Thr
        595                 600                 605

Trp Glu Ser Asp Pro Asn Arg Ser Tyr Thr Val Pro Ser Ala Cys Gly
    610                 615                 620

Thr Ser Thr Ala Val Val Asn Thr Thr Trp Arg
625                 630                 635
```

<210> SEQ ID NO 69
<211> LENGTH: 635
<212> TYPE: PRT
<213> ORGANISM: Artificial Sequence
<220> FEATURE:

<223> OTHER INFORMATION: Sequence put together from multiple organisms: Saccharomyces cerevisiae and Aspergillus terreus

<400> SEQUENCE: 69

```
Met Leu Leu Gln Ala Phe Leu Phe Leu Leu Ala Gly Phe Ala Ala Lys
1               5                   10                  15

Ile Ser Ala Ala Pro Gln Leu Ala Pro Arg Ala Thr Thr Ser Leu Asp
            20                  25                  30

Ala Trp Leu Ala Ser Glu Thr Thr Val Ala Leu Asp Gly Ile Leu Asp
        35                  40                  45

Asn Val Gly Ser Ser Gly Ala Tyr Ala Lys Ser Ala Lys Ser Gly Ile
    50                  55                  60

Val Ile Ala Ser Pro Ser Thr Ser Asp Pro Asp Tyr Tyr Tyr Thr Trp
65                  70                  75                  80

Thr Arg Asp Ala Ala Leu Thr Val Lys Ala Leu Ile Asp Leu Phe Arg
                85                  90                  95

Asn Gly Glu Thr Ser Leu Gln Thr Val Ile Met Glu Tyr Ile Ser Ser
            100                 105                 110

Gln Ala Tyr Leu Gln Thr Val Ser Asn Pro Ser Gly Ser Leu Ser Thr
        115                 120                 125

Gly Gly Leu Ala Glu Pro Lys Tyr Tyr Val Asp Glu Thr Ala Tyr Thr
    130                 135                 140

Gly Ser Trp Gly Arg Pro Gln Arg Asp Gly Pro Ala Leu Arg Ala Thr
145                 150                 155                 160

Ala Met Ile Asp Phe Gly Asn Trp Leu Ile Asp Asn Gly Tyr Ser Thr
                165                 170                 175

Tyr Ala Ser Ser Ile Val Trp Pro Ile Val Arg Asn Asp Leu Ser Tyr
            180                 185                 190

Val Ala Gln Tyr Trp Asn Gln Thr Gly Tyr Asp Leu Trp Glu Glu Val
        195                 200                 205

Asn Gly Ser Ser Phe Phe Thr Ile Ala Val Gln His Arg Ala Leu Val
    210                 215                 220

Glu Gly Ser Thr Phe Ala Ser Lys Val Gly Ala Ser Cys Ser Trp Cys
225                 230                 235                 240

Asp Ser Gln Ala Pro Gln Val Leu Cys Phe Leu Gln Arg Phe Trp Thr
                245                 250                 255

Gly Ser Tyr Ile Met Ala Asn Phe Gly Gly Gly Arg Ser Gly Lys Asp
            260                 265                 270

Ala Asn Thr Val Leu Gly Ser Ile His Thr Phe Asp Pro Asn Ala Gly
        275                 280                 285

Cys Asp Asp Thr Thr Phe Gln Pro Cys Ser Pro Arg Ala Leu Ala Asn
    290                 295                 300

His Lys Val Tyr Thr Asp Ser Phe Arg Ser Ile Tyr Ser Ile Asn Ser
305                 310                 315                 320

Gly Ile Ser Ser Gly Lys Ala Val Ala Val Gly Arg Tyr Pro Glu Asp
                325                 330                 335

Ser Tyr Tyr Asn Gly Asn Pro Trp Phe Leu Thr Thr Leu Ala Ala Ala
            340                 345                 350

Glu Gln Leu Tyr Asp Ala Ile Tyr Gln Trp Gln Lys Ile Gly Ser Ile
        355                 360                 365

Thr Ile Thr Asp Val Ser Leu Ala Phe Phe Lys Asp Leu Tyr Ser Ser
    370                 375                 380

Ala Ala Val Gly Thr Tyr Ala Ser Ser Ser Ser Ala Phe Thr Ser Ile
385                 390                 395                 400
```

```
Val Ser Ala Val Lys Thr Tyr Ala Asp Gly Tyr Met Ser Ile Val Gln
                405                 410                 415

Thr His Ala Met Thr Asn Gly Ser Leu Ser Glu Gln Phe Gly Lys Ser
            420                 425                 430

Asp Gly Phe Ser Leu Ser Ala Arg Asp Leu Thr Trp Ser Tyr Ala Ala
        435                 440                 445

Leu Leu Thr Ala Asn Leu Arg Arg Asn Ser Val Val Pro Pro Ser Trp
    450                 455                 460

Gly Glu Thr Thr Ala Thr Ser Val Pro Ser Val Cys Ser Ala Thr Ser
465                 470                 475                 480

Ala Thr Gly Thr Tyr Ser Thr Ala Thr Asn Thr Ala Trp Pro Ser Thr
                485                 490                 495

Leu Thr Ser Gly Thr Gly Ala Thr Thr Thr Thr Ser Lys Ala Thr Ser
            500                 505                 510

Ser Ser Thr Thr Thr Thr Ser Ser Ala Ser Ser Thr Thr Val Glu Cys
        515                 520                 525

Val Val Pro Thr Ala Val Ala Val Thr Phe Asp Glu Val Ala Thr Thr
    530                 535                 540

Thr Tyr Gly Glu Asn Val Tyr Val Val Gly Ser Ile Ser Gln Leu Gly
545                 550                 555                 560

Ser Trp Asp Thr Ser Lys Ala Val Ala Leu Ser Ala Ser Lys Tyr Thr
                565                 570                 575

Ser Ser Asn Asn Leu Trp Tyr Val Thr Val Thr Leu Pro Ala Gly Thr
            580                 585                 590

Thr Phe Gln Tyr Lys Phe Ile Arg Val Ser Ser Ser Gly Ser Val Thr
        595                 600                 605

Trp Glu Ser Asp Pro Asn Arg Ser Tyr Thr Val Pro Ser Ala Cys Gly
    610                 615                 620

Thr Ser Thr Ala Val Val Asn Thr Thr Trp Arg
625                 630                 635
```

<210> SEQ ID NO 70
<211> LENGTH: 642
<212> TYPE: PRT
<213> ORGANISM: Artificial Sequence
<220> FEATURE:
<223> OTHER INFORMATION: Sequence put together from multiple organisms: Gallus gallus and Aspergillus terreus

<400> SEQUENCE: 70

```
Met Leu Gly Lys Asn Asp Pro Met Cys Leu Val Leu Val Leu Leu Gly
1               5                   10                  15

Leu Thr Ala Leu Leu Gly Ile Cys Gln Gly Ala Pro Gln Leu Ala Pro
            20                  25                  30

Arg Ala Thr Thr Ser Leu Asp Ala Trp Leu Ala Ser Glu Thr Thr Val
        35                  40                  45

Ala Leu Asp Gly Ile Leu Asp Asn Val Gly Ser Ser Gly Ala Tyr Ala
    50                  55                  60

Lys Ser Ala Lys Ser Gly Ile Val Ile Ala Ser Pro Ser Thr Ser Asp
65                  70                  75                  80

Pro Asp Tyr Tyr Tyr Thr Trp Thr Arg Asp Ala Ala Leu Thr Val Lys
                85                  90                  95

Ala Leu Ile Asp Leu Phe Arg Asn Gly Glu Thr Ser Leu Gln Thr Val
            100                 105                 110

Ile Met Glu Tyr Ile Ser Ser Gln Ala Tyr Leu Gln Thr Val Ser Asn
```

```
        115                 120                 125

Pro Ser Gly Ser Leu Ser Thr Gly Gly Leu Ala Glu Pro Lys Tyr Tyr
    130                 135                 140

Val Asp Glu Thr Ala Tyr Thr Gly Ser Trp Gly Arg Pro Gln Arg Asp
145                 150                 155                 160

Gly Pro Ala Leu Arg Ala Thr Ala Met Ile Asp Phe Gly Asn Trp Leu
                165                 170                 175

Ile Asp Asn Gly Tyr Ser Thr Tyr Ala Ser Ser Ile Val Trp Pro Ile
            180                 185                 190

Val Arg Asn Asp Leu Ser Tyr Val Ala Gln Tyr Trp Asn Gln Thr Gly
        195                 200                 205

Tyr Asp Leu Trp Glu Glu Val Asn Gly Ser Ser Phe Phe Thr Ile Ala
    210                 215                 220

Val Gln His Arg Ala Leu Val Glu Gly Ser Thr Phe Ala Ser Lys Val
225                 230                 235                 240

Gly Ala Ser Cys Ser Trp Cys Asp Ser Gln Ala Pro Gln Val Leu Cys
                245                 250                 255

Phe Leu Gln Arg Phe Trp Thr Gly Ser Tyr Ile Met Ala Asn Phe Gly
            260                 265                 270

Gly Gly Arg Ser Gly Lys Asp Ala Asn Thr Val Leu Gly Ser Ile His
        275                 280                 285

Thr Phe Asp Pro Asn Ala Gly Cys Asp Asp Thr Thr Phe Gln Pro Cys
    290                 295                 300

Ser Pro Arg Ala Leu Ala Asn His Lys Val Tyr Thr Asp Ser Phe Arg
305                 310                 315                 320

Ser Ile Tyr Ser Ile Asn Ser Gly Ile Ser Ser Gly Lys Ala Val Ala
                325                 330                 335

Val Gly Arg Tyr Pro Glu Asp Ser Tyr Tyr Asn Gly Asn Pro Trp Phe
            340                 345                 350

Leu Thr Thr Leu Ala Ala Ala Glu Gln Leu Tyr Asp Ala Ile Tyr Gln
        355                 360                 365

Trp Gln Lys Ile Gly Ser Ile Thr Ile Thr Asp Val Ser Leu Ala Phe
    370                 375                 380

Phe Lys Asp Leu Tyr Ser Ser Ala Ala Val Gly Thr Tyr Ala Ser Ser
385                 390                 395                 400

Ser Ser Ala Phe Thr Ser Ile Val Ser Ala Val Lys Thr Tyr Ala Asp
                405                 410                 415

Gly Tyr Met Ser Ile Val Gln Thr His Ala Met Thr Asn Gly Ser Leu
            420                 425                 430

Ser Glu Gln Phe Gly Lys Ser Asp Gly Phe Ser Leu Ser Ala Arg Asp
        435                 440                 445

Leu Thr Trp Ser Tyr Ala Ala Leu Leu Thr Ala Asn Leu Arg Arg Asn
    450                 455                 460

Ser Val Val Pro Pro Ser Trp Gly Glu Thr Thr Ala Thr Ser Val Pro
465                 470                 475                 480

Ser Val Cys Ser Ala Thr Ser Ala Thr Gly Thr Tyr Ser Thr Ala Thr
                485                 490                 495

Asn Thr Ala Trp Pro Ser Thr Leu Thr Ser Gly Thr Gly Ala Thr Thr
            500                 505                 510

Thr Thr Ser Lys Ala Thr Ser Ser Ser Thr Thr Thr Thr Ser Ser Ala
        515                 520                 525

Ser Ser Thr Thr Val Glu Cys Val Val Pro Thr Ala Val Ala Val Thr
    530                 535                 540
```

Phe Asp Glu Val Ala Thr Thr Thr Tyr Gly Glu Asn Val Tyr Val Val
545 550 555 560

Gly Ser Ile Ser Gln Leu Gly Ser Trp Asp Thr Ser Lys Ala Val Ala
565 570 575

Leu Ser Ala Ser Lys Tyr Thr Ser Ser Asn Asn Leu Trp Tyr Val Thr
580 585 590

Val Thr Leu Pro Ala Gly Thr Thr Phe Gln Tyr Lys Phe Ile Arg Val
595 600 605

Ser Ser Ser Gly Ser Val Thr Trp Glu Ser Asp Pro Asn Arg Ser Tyr
610 615 620

Thr Val Pro Ser Ala Cys Gly Thr Ser Thr Ala Val Val Asn Thr Thr
625 630 635 640

Trp Arg

<210> SEQ ID NO 71
<211> LENGTH: 634
<212> TYPE: PRT
<213> ORGANISM: Artificial Sequence
<220> FEATURE:
<223> OTHER INFORMATION: Sequence put together from multiple organisms:
Homo sapiens and Aspergillus terreus

<400> SEQUENCE: 71

Met Lys Trp Val Thr Phe Ile Ser Leu Leu Phe Leu Phe Ser Ser Ala
1 5 10 15

Tyr Ser Ala Pro Gln Leu Ala Pro Arg Ala Thr Thr Ser Leu Asp Ala
20 25 30

Trp Leu Ala Ser Glu Thr Thr Val Ala Leu Asp Gly Ile Leu Asp Asn
35 40 45

Val Gly Ser Ser Gly Ala Tyr Ala Lys Ser Ala Lys Ser Gly Ile Val
50 55 60

Ile Ala Ser Pro Ser Thr Ser Asp Pro Asp Tyr Tyr Tyr Thr Trp Thr
65 70 75 80

Arg Asp Ala Ala Leu Thr Val Lys Ala Leu Ile Asp Leu Phe Arg Asn
85 90 95

Gly Glu Thr Ser Leu Gln Thr Val Ile Met Glu Tyr Ile Ser Ser Gln
100 105 110

Ala Tyr Leu Gln Thr Val Ser Asn Pro Ser Gly Ser Leu Ser Thr Gly
115 120 125

Gly Leu Ala Glu Pro Lys Tyr Tyr Val Asp Glu Thr Ala Tyr Thr Gly
130 135 140

Ser Trp Gly Arg Pro Gln Arg Asp Gly Pro Ala Leu Arg Ala Thr Ala
145 150 155 160

Met Ile Asp Phe Gly Asn Trp Leu Ile Asp Asn Gly Tyr Ser Thr Tyr
165 170 175

Ala Ser Ser Ile Val Trp Pro Ile Val Arg Asn Asp Leu Ser Tyr Val
180 185 190

Ala Gln Tyr Trp Asn Gln Thr Gly Tyr Asp Leu Trp Glu Glu Val Asn
195 200 205

Gly Ser Ser Phe Phe Thr Ile Ala Val Gln His Arg Ala Leu Val Glu
210 215 220

Gly Ser Thr Phe Ala Ser Lys Val Gly Ala Ser Cys Ser Trp Cys Asp
225 230 235 240

Ser Gln Ala Pro Gln Val Leu Cys Phe Leu Gln Arg Phe Trp Thr Gly
245 250 255

```
Ser Tyr Ile Met Ala Asn Phe Gly Gly Gly Arg Ser Gly Lys Asp Ala
            260                 265                 270

Asn Thr Val Leu Gly Ser Ile His Thr Phe Asp Pro Asn Ala Gly Cys
        275                 280                 285

Asp Asp Thr Thr Phe Gln Pro Cys Ser Pro Arg Ala Leu Ala Asn His
    290                 295                 300

Lys Val Tyr Thr Asp Ser Phe Arg Ser Ile Tyr Ser Ile Asn Ser Gly
305                 310                 315                 320

Ile Ser Ser Gly Lys Ala Val Ala Val Gly Arg Tyr Pro Glu Asp Ser
                325                 330                 335

Tyr Tyr Asn Gly Asn Pro Trp Phe Leu Thr Thr Leu Ala Ala Ala Glu
            340                 345                 350

Gln Leu Tyr Asp Ala Ile Tyr Gln Trp Gln Lys Ile Gly Ser Ile Thr
        355                 360                 365

Ile Thr Asp Val Ser Leu Ala Phe Phe Lys Asp Leu Tyr Ser Ser Ala
    370                 375                 380

Ala Val Gly Thr Tyr Ala Ser Ser Ser Ser Ala Phe Thr Ser Ile Val
385                 390                 395                 400

Ser Ala Val Lys Thr Tyr Ala Asp Gly Tyr Met Ser Ile Val Gln Thr
                405                 410                 415

His Ala Met Thr Asn Gly Ser Leu Ser Glu Gln Phe Gly Lys Ser Asp
            420                 425                 430

Gly Phe Ser Leu Ser Ala Arg Asp Leu Thr Trp Ser Tyr Ala Ala Leu
        435                 440                 445

Leu Thr Ala Asn Leu Arg Arg Asn Ser Val Val Pro Pro Ser Trp Gly
    450                 455                 460

Glu Thr Thr Ala Thr Ser Val Pro Ser Val Cys Ser Ala Thr Ser Ala
465                 470                 475                 480

Thr Gly Thr Tyr Ser Thr Ala Thr Asn Thr Ala Trp Pro Ser Thr Leu
                485                 490                 495

Thr Ser Gly Thr Gly Ala Thr Thr Thr Thr Ser Lys Ala Thr Ser Ser
            500                 505                 510

Ser Thr Thr Thr Thr Ser Ser Ala Ser Ser Thr Thr Val Glu Cys Val
        515                 520                 525

Val Pro Thr Ala Val Ala Val Thr Phe Asp Glu Val Ala Thr Thr Thr
    530                 535                 540

Tyr Gly Glu Asn Val Tyr Val Val Gly Ser Ile Ser Gln Leu Gly Ser
545                 550                 555                 560

Trp Asp Thr Ser Lys Ala Val Ala Leu Ser Ala Ser Lys Tyr Thr Ser
                565                 570                 575

Ser Asn Asn Leu Trp Tyr Val Thr Val Thr Leu Pro Ala Gly Thr Thr
            580                 585                 590

Phe Gln Tyr Lys Phe Ile Arg Val Ser Ser Ser Gly Ser Val Thr Trp
        595                 600                 605

Glu Ser Asp Pro Asn Arg Ser Tyr Thr Val Pro Ser Ala Cys Gly Thr
    610                 615                 620

Ser Thr Ala Val Val Asn Thr Thr Trp Arg
625                 630
```

<210> SEQ ID NO 72
<211> LENGTH: 635
<212> TYPE: PRT
<213> ORGANISM: Artificial Sequence
<220> FEATURE:

<223> OTHER INFORMATION: Sequence put together from multiple organisms: Saccharomyces cerevisiae and Aspergillus terreus

<400> SEQUENCE: 72

```
Met Arg Phe Pro Ser Ile Phe Thr Ala Val Leu Phe Ala Ala Ser Ser
1               5                   10                  15

Ala Leu Ala Ala Pro Gln Leu Ala Pro Arg Ala Thr Thr Ser Leu Asp
            20                  25                  30

Ala Trp Leu Ala Ser Glu Thr Thr Val Ala Leu Asp Gly Ile Leu Asp
        35                  40                  45

Asn Val Gly Ser Ser Gly Ala Tyr Ala Lys Ser Ala Lys Ser Gly Ile
    50                  55                  60

Val Ile Ala Ser Pro Ser Thr Ser Asp Pro Asp Tyr Tyr Tyr Thr Trp
65                  70                  75                  80

Thr Arg Asp Ala Ala Leu Thr Val Lys Ala Leu Ile Asp Leu Phe Arg
                85                  90                  95

Asn Gly Glu Thr Ser Leu Gln Thr Val Ile Met Glu Tyr Ile Ser Ser
            100                 105                 110

Gln Ala Tyr Leu Gln Thr Val Ser Asn Pro Ser Gly Ser Leu Ser Thr
        115                 120                 125

Gly Gly Leu Ala Glu Pro Lys Tyr Tyr Val Asp Glu Thr Ala Tyr Thr
    130                 135                 140

Gly Ser Trp Gly Arg Pro Gln Arg Asp Gly Pro Ala Leu Arg Ala Thr
145                 150                 155                 160

Ala Met Ile Asp Phe Gly Asn Trp Leu Ile Asp Asn Gly Tyr Ser Thr
                165                 170                 175

Tyr Ala Ser Ser Ile Val Trp Pro Ile Val Arg Asn Asp Leu Ser Tyr
            180                 185                 190

Val Ala Gln Tyr Trp Asn Gln Thr Gly Tyr Asp Leu Trp Glu Glu Val
        195                 200                 205

Asn Gly Ser Ser Phe Phe Thr Ile Ala Val Gln His Arg Ala Leu Val
    210                 215                 220

Glu Gly Ser Thr Phe Ala Ser Lys Val Gly Ala Ser Cys Ser Trp Cys
225                 230                 235                 240

Asp Ser Gln Ala Pro Gln Val Leu Cys Phe Leu Gln Arg Phe Trp Thr
                245                 250                 255

Gly Ser Tyr Ile Met Ala Asn Phe Gly Gly Gly Arg Ser Gly Lys Asp
            260                 265                 270

Ala Asn Thr Val Leu Gly Ser Ile His Thr Phe Asp Pro Asn Ala Gly
        275                 280                 285

Cys Asp Asp Thr Thr Phe Gln Pro Cys Ser Pro Arg Ala Leu Ala Asn
    290                 295                 300

His Lys Val Tyr Thr Asp Ser Phe Arg Ser Ile Tyr Ser Ile Asn Ser
305                 310                 315                 320

Gly Ile Ser Ser Gly Lys Ala Val Ala Val Gly Arg Tyr Pro Glu Asp
                325                 330                 335

Ser Tyr Tyr Asn Gly Asn Pro Trp Phe Leu Thr Thr Leu Ala Ala Ala
            340                 345                 350

Glu Gln Leu Tyr Asp Ala Ile Tyr Gln Trp Gln Lys Ile Gly Ser Ile
        355                 360                 365

Thr Ile Thr Asp Val Ser Leu Ala Phe Phe Lys Asp Leu Tyr Ser Ser
    370                 375                 380

Ala Ala Val Gly Thr Tyr Ala Ser Ser Ser Ser Ala Phe Thr Ser Ile
385                 390                 395                 400
```

```
Val Ser Ala Val Lys Thr Tyr Ala Asp Gly Tyr Met Ser Ile Val Gln
                405                 410                 415

Thr His Ala Met Thr Asn Gly Ser Leu Ser Glu Gln Phe Gly Lys Ser
            420                 425                 430

Asp Gly Phe Ser Leu Ser Ala Arg Asp Leu Thr Trp Ser Tyr Ala Ala
        435                 440                 445

Leu Leu Thr Ala Asn Leu Arg Arg Asn Ser Val Val Pro Pro Ser Trp
    450                 455                 460

Gly Glu Thr Thr Ala Thr Ser Val Pro Ser Val Cys Ser Ala Thr Ser
465                 470                 475                 480

Ala Thr Gly Thr Tyr Ser Thr Ala Thr Asn Thr Ala Trp Pro Ser Thr
                485                 490                 495

Leu Thr Ser Gly Thr Gly Ala Thr Thr Thr Thr Ser Lys Ala Thr Ser
            500                 505                 510

Ser Ser Thr Thr Thr Thr Ser Ser Ala Ser Ser Thr Thr Val Glu Cys
        515                 520                 525

Val Val Pro Thr Ala Val Ala Val Thr Phe Asp Glu Val Ala Thr Thr
    530                 535                 540

Thr Tyr Gly Glu Asn Val Tyr Val Val Gly Ser Ile Ser Gln Leu Gly
545                 550                 555                 560

Ser Trp Asp Thr Ser Lys Ala Val Ala Leu Ser Ala Ser Lys Tyr Thr
                565                 570                 575

Ser Ser Asn Asn Leu Trp Tyr Val Thr Val Thr Leu Pro Ala Gly Thr
            580                 585                 590

Thr Phe Gln Tyr Lys Phe Ile Arg Val Ser Ser Ser Gly Ser Val Thr
        595                 600                 605

Trp Glu Ser Asp Pro Asn Arg Ser Tyr Thr Val Pro Ser Ala Cys Gly
    610                 615                 620

Thr Ser Thr Ala Val Val Asn Thr Thr Trp Arg
625                 630                 635
```

<210> SEQ ID NO 73
<211> LENGTH: 90
<212> TYPE: PRT
<213> ORGANISM: Saccharomyces cerevisiae

<400> SEQUENCE: 73

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ser
                85                  90
```

<210> SEQ ID NO 74
<211> LENGTH: 61
<212> TYPE: PRT
<213> ORGANISM: Saccharomyces cerevisiae

<400> SEQUENCE: 74

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Leu Glu Gly
            20                  25                  30

Asp Phe Asp Val Ala Val Leu Pro Phe Ser Ala Ser Ile Ala Ala Lys
        35                  40                  45

Glu Glu Gly Val Ser Leu Glu Lys Arg Glu Ala Glu Ala
    50                  55                  60


<210> SEQ ID NO 75
<211> LENGTH: 19
<212> TYPE: PRT
<213> ORGANISM: Saccharomyces cerevisiae

<400> SEQUENCE: 75

Met Leu Leu Gln Ala Phe Leu Phe Leu Leu Ala Gly Phe Ala Ala Lys
1               5                   10                  15

Ile Ser Ala


<210> SEQ ID NO 76
<211> LENGTH: 26
<212> TYPE: PRT
<213> ORGANISM: Gallus gallus

<400> SEQUENCE: 76

Met Leu Gly Lys Asn Asp Pro Met Cys Leu Val Leu Val Leu Leu Gly
1               5                   10                  15

Leu Thr Ala Leu Leu Gly Ile Cys Gln Gly
            20                  25


<210> SEQ ID NO 77
<211> LENGTH: 20
<212> TYPE: PRT
<213> ORGANISM: Saccharomyces cerevisiae

<400> SEQUENCE: 77

Met Val Ala Trp Trp Ser Leu Phe Leu Tyr Gly Leu Gln Val Ala Ala
1               5                   10                  15

Pro Ala Leu Ala
            20


<210> SEQ ID NO 78
<211> LENGTH: 18
<212> TYPE: PRT
<213> ORGANISM: Homo sapiens

<400> SEQUENCE: 78

Met Lys Trp Val Thr Phe Ile Ser Leu Leu Phe Leu Phe Ser Ser Ala
1               5                   10                  15

Tyr Ser


<210> SEQ ID NO 79
<211> LENGTH: 617
<212> TYPE: PRT
<213> ORGANISM: Saccharomyces mikatae

<400> SEQUENCE: 79

Met Lys Asn Phe Ile Ser Leu Val Asn Lys Lys Lys Gly Thr Leu Asp
1               5                   10                  15

Asp Arg Asn Ser Ser Val Pro Glu Ser Ser Ser Gly Ile Ile His Gln
```

```
            20                  25                  30

Arg Gly Ala Leu Asn Thr Glu Asp Phe Glu Glu Gly Lys Lys Asp Gly
        35                  40                  45

Ala Phe Glu Leu Gly His Leu Glu Phe Thr Thr Asn Ser Ala Gln Leu
    50                  55                  60

Gly Asp Ser Asp Asp Asp Asn Asp Asn Ala Ile Lys Ile Ala Asn Ala
65                  70                  75                  80

Ala Thr Asp Glu Ala Asn Glu Ala Asn Ser Glu Glu Lys Ser Met Thr
                85                  90                  95

Leu Arg Gln Ala Leu Arg Lys Tyr Pro Lys Ala Ala Leu Trp Ser Ile
            100                 105                 110

Leu Val Ser Thr Thr Leu Val Met Glu Gly Tyr Asp Thr Ala Leu Leu
        115                 120                 125

Ser Ala Leu Tyr Ala Leu Pro Val Phe Gln Arg Lys Phe Gly Thr Met
    130                 135                 140

Asn Ala Glu Gly Ser Tyr Glu Ile Thr Ser Gln Trp Gln Ile Gly Leu
145                 150                 155                 160

Asn Met Cys Val Leu Cys Gly Glu Met Ile Gly Leu Gln Met Thr Thr
                165                 170                 175

Tyr Met Val Glu Phe Met Gly Asn Arg Tyr Thr Met Ile Thr Ala Leu
            180                 185                 190

Gly Leu Leu Thr Ala Tyr Ile Phe Ile Leu Tyr Tyr Cys Lys Ser Leu
        195                 200                 205

Ala Met Ile Ala Val Gly Gln Ile Leu Ser Ala Met Pro Trp Gly Cys
    210                 215                 220

Phe Gln Ser Leu Ala Val Thr Tyr Ala Ser Glu Val Cys Pro Leu Ala
225                 230                 235                 240

Leu Arg Tyr Tyr Met Thr Ser Tyr Ser Asn Ile Cys Trp Leu Phe Gly
                245                 250                 255

Gln Ile Phe Ala Ser Gly Ile Met Lys Asn Ser Gln Glu Asn Leu Gly
            260                 265                 270

Asp Ser Asp Leu Gly Tyr Lys Leu Pro Phe Ala Leu Gln Trp Ile Trp
        275                 280                 285

Pro Ala Pro Leu Ile Ile Gly Ile Phe Phe Ala Pro Glu Ser Pro Trp
    290                 295                 300

Trp Leu Val Arg Lys Asn Lys Ile Ala Glu Ala Lys Lys Ser Leu Asn
305                 310                 315                 320

Arg Ile Leu Ser Gly Thr Ala Ala Glu Arg Glu Ile Gln Val Asp Ile
                325                 330                 335

Thr Leu Lys Gln Ile Glu Met Thr Ile Glu Lys Glu Arg Leu Leu Ala
            340                 345                 350

Ser Lys Ser Gly Ser Phe Phe Asn Cys Phe Lys Gly Val Asp Gly Arg
        355                 360                 365

Arg Thr Arg Leu Ala Cys Leu Thr Trp Val Ala Gln Asn Ser Ser Gly
    370                 375                 380

Ala Val Leu Leu Gly Tyr Ser Thr Tyr Phe Phe Glu Arg Ala Gly Met
385                 390                 395                 400

Ala Thr Asp Lys Ala Phe Thr Phe Ser Leu Ile Gln Tyr Cys Leu Gly
                405                 410                 415

Leu Ala Gly Thr Leu Cys Ser Trp Val Ile Ser Gly Arg Val Gly Arg
            420                 425                 430

Trp Ser Ile Leu Ala Tyr Gly Leu Ala Phe Gln Met Val Cys Leu Phe
        435                 440                 445
```

```
Ile Ile Gly Gly Met Gly Phe Ala Ser Gly Ser Asn Ala Ser Asn Gly
    450                 455                 460

Ala Gly Gly Leu Leu Leu Ala Leu Ser Phe Phe Tyr Asn Ala Gly Ile
465                 470                 475                 480

Gly Ala Val Val Tyr Cys Ile Val Ala Glu Ile Pro Ser Ala Glu Leu
                485                 490                 495

Arg Thr Lys Thr Ile Val Met Ala Arg Ile Cys Tyr Asn Leu Met Ala
            500                 505                 510

Val Ile Asn Ala Ile Leu Thr Pro Tyr Met Leu Asn Val Ser Asp Trp
        515                 520                 525

Asn Trp Gly Ala Lys Thr Gly Leu Tyr Trp Gly Gly Phe Thr Ala Val
    530                 535                 540

Thr Leu Ala Trp Val Ile Ile Asp Leu Pro Glu Thr Thr Gly Arg Thr
545                 550                 555                 560

Phe Ser Glu Ile Asn Glu Leu Phe Asn Gln Gly Val Pro Ala Arg Lys
                565                 570                 575

Phe Ala Ser Thr Val Val Asp Pro Phe Gly Lys Gly Gln Arg Gln Asn
            580                 585                 590

Asp Ser Gln Val Asp Asn Val Ile Asp Gln Ser Ser Ser Ala Met Gln
        595                 600                 605

Gln Glu Leu Asn Glu Ala Asn Glu Phe
    610                 615


<210> SEQ ID NO 80
<211> LENGTH: 19
<212> TYPE: PRT
<213> ORGANISM: Saccharomyces cerevisiae

<400> SEQUENCE: 80

Met Lys Phe Ile Ser Thr Phe Leu Thr Phe Ile Leu Ala Ala Val Ser
1               5                   10                  15

Val Thr Ala


<210> SEQ ID NO 81
<211> LENGTH: 17
<212> TYPE: PRT
<213> ORGANISM: Saccharomyces cerevisiae

<400> SEQUENCE: 81

Met Phe Lys Ser Val Val Tyr Ser Ile Leu Ala Ala Ser Leu Ala Asn
1               5                   10                  15

Ala


<210> SEQ ID NO 82
<211> LENGTH: 6
<212> TYPE: PRT
<213> ORGANISM: Artificial Sequence
<220> FEATURE:
<223> OTHER INFORMATION: Synthetic sequence

<400> SEQUENCE: 82

Ala Val Leu Phe Ala Ala
1               5


<210> SEQ ID NO 83
<211> LENGTH: 6
<212> TYPE: PRT
<213> ORGANISM: Artificial Sequence
<220> FEATURE:
```

```
<223> OTHER INFORMATION: Synthetic sequence

<400> SEQUENCE: 83

Ala Phe Leu Phe Leu Leu
1               5


<210> SEQ ID NO 84
<211> LENGTH: 6
<212> TYPE: PRT
<213> ORGANISM: Artificial Sequence
<220> FEATURE:
<223> OTHER INFORMATION: Synthetic sequence

<400> SEQUENCE: 84

Leu Val Leu Val Leu Leu
1               5


<210> SEQ ID NO 85
<211> LENGTH: 5
<212> TYPE: PRT
<213> ORGANISM: Artificial Sequence
<220> FEATURE:
<223> OTHER INFORMATION: Synthetic sequence

<400> SEQUENCE: 85

Leu Leu Phe Leu Phe
1               5


<210> SEQ ID NO 86
<211> LENGTH: 6
<212> TYPE: PRT
<213> ORGANISM: Artificial Sequence
<220> FEATURE:
<223> OTHER INFORMATION: Synthetic sequence

<400> SEQUENCE: 86

Phe Ile Leu Ala Ala Val
1               5
```

ENGINEERED YEAST STRAINS WITH SIGNAL SEQUENCE-MODIFIED GLUCOAMYLASE POLYPEPTIDES AND ENHANCED ETHANOL PRODUCTION

CROSS-REFERENCE TO RELATED APPLICATIONS

This application is a national phase application of PCT/US2017/045493, filed Aug. 4, 2017, entitled LEADER-MODIFIED GLUCOAMYLASE POLYPEPTIDES AND ENGINEERED YEAST STRAINS HAVING ENHANCED BIOPRODUCT PRODUCTION, which claims the benefit of U.S. Provisional Patent Application No. 62/371,681, filed Aug. 5, 2016, entitled LEADER-MODIFIED GLUCOAMYLASE POLYPEPTIDES AND ENGINEERED YEAST STRAINS HAVING ENHANCED BIOPRODUCT PRODUCTION, each of which is hereby incorporated by reference herein in its entirety.

SEQUENCE LISTING

The entire contents of the ASCII text file entitled "N00485_ST25.txt," created on Sep. 14, 2017, and having a size of 447 kilobytes, is incorporated herein by reference in its entirety.

FIELD OF THE INVENTION

The current invention relates to modified glucoamylase (GA) enzymes, microorganisms expressing these enzymes, and fermentations methods for producing ethanol.

BACKGROUND

Ethanol production by fermentation is a well know industrial process. However increasing ethanol yields can be technically difficult. There are various factors that make it challenging for microorganisms to grow in fermentation conditions designed for increased ethanol production. For example, the fermentation medium may have higher substrate concentrations to promote ethanol production, but these conditions can have a negative impact on cell growth. Also, increased ethanol concentration and accumulation of undesirable byproducts can also be detrimental to cell health. Yeast strains have been selected for tolerance to these conditions, which can result in improved ethanol yields. In particular, the ethanol tolerant strains of the yeast *Saccharomyces cerevisiae* have been used in industrial settings as a workhorse microorganism for producing ethanol.

Molecular techniques have led to the identification of genes that are associated with ethanol tolerance. For example, Kajiwara (Appl Microbiol Biotechnol. 2000; 53:568-74.) reports that overexpression of the OLE1 gene which is involved in unsaturated fatty acid (UFA) synthesis resulted in higher unsaturated fatty acid levels in the cell and higher ethanol production. Other research has found that accumulation of trehalose by disruption of the trehalose-hydrolyzing enzyme, acid trehalase (ATH) (Kim et al., Appl Environ Microbiol. 1996; 62:1563-1569) or accumulation of proline L-proline by a strain carrying a PRO1 gamma-glutamyl kinase mutation (Takagi, et al., Appl Environ Microbiol. 2005; 71:8656-8662.) improves ethanol tolerance in yeast. Ergosterol is closely associated with ethanol tolerance of *Saccharomyces cerevisiae* (Inoue, et al., Biosci Biotechnol Biochem. 2000; 64:229-236). While advancements have been made in this area, use of genetically modified strains that demonstrate ethanol tolerance may not alone be sufficient to provide desired levels of ethanol during a fermentation process.

In addition to the genetic profile of the fermentation microorganism, the components of the fermentation medium can have a significant impact on ethanol production. In fermentation processes, a carbohydrate or carbohydrate mixture is present in the medium. Starch is a widely available and inexpensive carbohydrate source. It is available from a wide variety of plant sources such as corn, wheat, rice, barley, and the like. Many organisms are not capable of metabolizing starch directly, or else metabolize it slowly and inefficiently.

Accordingly, it is common to treat starch before feeding it into the fermentation process, in order to break it down into monosaccharides that the organism can ferment easily. Usually, starch is hydrolyzed to form a mixture containing mainly glucose (i.e., dextrose). However, the pre-treatment of a starch composition in preparation for fermentation can be expensive and labor intensive as it commonly involves the addition of purified starch-degrading enzymes to the starch material, and requires additional steps prior to carrying out fermentation. Further, complete hydrolysis to glucose adds significant cost, so most commercially available glucose products tend to contain a small amount of various oligomeric polysaccharides.

A significant portion of the cost to produce starch based ethanol is the enzymes that break down the starch into fermentable sugars. Various molecular techniques have been attempted in in *Saccharomyces cerevisiae* to reduce or eliminate the need to add amylolytic enzymes to the fermentation medium, but these approaches have yielded varying degrees of success. A potential limiting factor affecting the commercial viability of engineered strains is the ability of *Saccharomyces cerevisiae* to secrete large amounts of foreign protein, and for the protein to function in a desired manner in the fermentation medium after it is secreted.

SUMMARY OF THE INVENTION

The invention relates to engineered yeast and fermentation methods, wherein the engineered yeast are able to secrete a modified glucoamylase into a fermentation medium and provide glucoamylase activity on a fermentation substrate. The current invention also relates to glucoamylase enzymes (E.C. 3.2.1.3) that are modified to partially or fully replace their natural secretion sequence with a heterologous secretion sequence. The invention also relates to genes encoding these secretion sequence-modified glucoamylase enzymes, as well as microorganisms expressing these genes. The invention also relates to methods of for producing bio-derived products (fermentation products) manufactured by the organism, such as ethanol. The invention also relates to fermentation co-products which can be used for other types of compositions and method, such as animal feed compositions and related methods.

In experimental studies associated with the current application, it has been found that N-terminal amino acid sequences derived from *Aspergillus nidulans* alpha amylase (An AA), *Saccharomyces cerevisiae* alpha mating factor (Sc FAKS, Sc AKS, Sc AK, and Sc MFα1), *Saccharomyces cerevisiae* invertase (Sc IV), *Gallus gallus* lyzozyme (Gg LZ), and *Homo sapiens* albumin (Hs SA), can be used as heterologous secretion signals for glucoamylase fusion polypeptides, and these heterologous secretion signals are able to promote secretion of the fusion polypeptides into a fermentation medium. The fusions are enzymatically active against starch products, causing glucose formation and fermentation to a desired bioproduct, such as ethanol.

It has also been found that these N-terminal amino acid sequences share a common structural feature which is thought to promote secretion of the glucoamylase fusions, and do not interfere with the ability of the fusion protein to have glucoamylase activity. In particular, these secretion sequences include a stretch of 5-8 continuous hydrophobic amino acid residues. A common hydrophobic amino acid found at least one time in this stretch is leucine. Further, in some secretion signals, it was found that the stretch was typically immediately adjacent to one or two polar amino acid residue(s) such as serine.

Therefore, aspects of the invention provide an engineered polypeptide that includes (a) a secretion signal amino acid sequence comprising 5-8 continuous hydrophobic amino acid residues; and (b) a glucoamylase amino acid sequence from a yeast, fungal, or bacterial glucoamylase polypeptide, wherein the secretion signal amino acid sequence is heterologous to the glucoamylase amino acid sequence, and the engineered polypeptide has glucoamylase activity. For example, the stretch of 5-8 continuous hydrophobic amino acid residues can be present within a heterologous leader sequence having about 15 to about 30 amino acids.

Accordingly, in aspects of the invention, the engineered polypeptide includes (a) a secretion signal amino acid sequence having 80% or greater sequence identity to: (i) an amino acid sequence of at least AA 1-19 of SEQ ID NO: 73, (ii) an amino acid sequence of at least AA 1-19 of SEQ ID NO: 74, (iii) SEQ ID NO: 77 (An aa), (iv) SEQ ID NO: 75 (Sc IV), (v) SEQ ID NO: 76 (Gg LZ), or (vi) SEQ ID NO: 78(Hs SA); and (b) a glucoamylase amino acid sequence from a yeast, fungal, or bacterial glucoamylase polypeptide, wherein the polypeptide has glucoamylase activity.

Aspects of the invention also provide a nucleic acid sequence that encodes an engineered polypeptide including a secretion signal amino acid sequence comprising 5-8 continuous hydrophobic amino acid residues; and (b) a glucoamylase amino acid sequence from a yeast, fungal, or bacterial glucoamylase polypeptide, wherein the secretion signal amino acid sequence is heterologous to the glucoamylase amino acid sequence, and the engineered polypeptide has glucoamylase activity. These aspects include constructs wherein the nucleic acid is present on a vector construct, which may include one or more of the following sequences: a promoter sequence, a terminator sequence, a selectable marker sequence, a genomic integration sequence, and/or a replication origin sequence. The nucleic acid can be integrated into one or more locations of the hosts genomic DNA, or can be present within the cell but not integrated, such as on a plasmid or episomal construct. The invention also provides nucleic acids, such as DNA oligomers (e.g., single stranded DNA PCR primers, or longer linear DNA segments) that can be useful for the detection of the glucoamylase gene with the secretion sequence as described in a cell.

Aspects of the invention also provide host cells including the nucleic acid sequence encoding the secretion signal-modified glucoamylase enzymes. Is some aspects, the host cell expresses the signal-modified glucoamylase enzymes and is capable of secreting the enzyme into medium in which the cell is present. Exemplary host cells include yeast, such as species of *Saccharomyces* (e.g., *Saccharomyces cerevisiae*). The engineered yeast can be tolerant to a bio-derived product of the cell, such as ethanol or another product, derived from precursors resulting from the amylolytic activity of the enzyme. For example, the host cell can be a commercially available strain or one having one or more specific genetic modifications that provide an increase in tolerance to a bioderived product, such as increased ethanol tolerance, such as ethanol tolerant *Saccharomyces cerevisiae.*

Another aspect of the invention provides an engineered yeast that expresses a polypeptide comprising (a) a secretion signal amino acid sequence having 80% or greater sequence identity to: (i) an amino acid sequence of at least AA 1-19 of SEQ ID NO: 73, (ii) an amino acid sequence of at least AA 1-19 of SEQ ID NO: 74, (iii) SEQ ID NO: 77 (An aa), (iv) SEQ ID NO: 75 (Sc IV),_(v) SEQ ID NO: 76 (Gg LZ), or (vi) SEQ ID NO: 78 (Hs SA); (vii) SEQ ID NO: 80 (MFα2); or (viii) SEQ ID NO: 81 (Pho5) and (b) a glucoamylase amino acid sequence having at least 50% sequence identity to a glucoamylase sequence selected from the group consisting of (1) amino acids 26-604 of SEQ ID NO: 42 (*Rhizopus oryzae* GA); (ii) amino acids 19-639 of SEQ ID NO: 43 (*Aspergillus shirousami* GA); (iii) amino acids 21-636 of SEQ ID NO: 44 (*Aspergillus terreus* GA).

Aspects of the invention also provide a method for producing ethanol by fermentation, wherein the ethanol is present in the fermentation medium at a concentration of 90 g/L or greater. In the method, a liquid medium comprising a starch material and an engineered yeast as described herein is fermented. Fermentation can provide an ethanol concentration of about 90 g/L or greater in the liquid medium, such as in the range of about 90 g/L to about 170 g/L. In some aspects, during at least one time point during fermenting, the fermentation medium has a temperature of greater than 32° C., and fermenting provides an amount of ethanol in the fermentation medium of 110 g/L or greater.

In another aspect, the invention provides methods and compositions that can be used to prepare feed compositions. The feed compositions include fermentation medium co-products obtained from a fermentation medium derived from the non-natural yeast of the disclosure. For example, after a fermentation process has been completed, some or all of a bioproduct can be removed from the fermentation medium to provide a refined composition comprising non-bioproduct solids. The non-bioproduct solids can include the non-natural yeast, feedstock material in the medium that is not utilized by the yeast, as well as fermentation by-products. The refined composition can be used to form a feed composition, such as a livestock feed composition. The refined composition comprising non-bioproduct solids can provide carbohydrate and protein supplements to improve the nutritional content of a feed composition.

DETAILED DESCRIPTION

Figure 1:
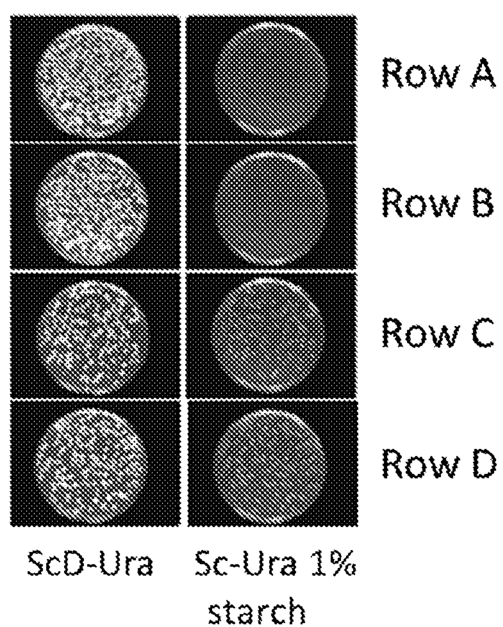
FIG. 1 is a photograph of yeast culture plates showing growth of strain expressing different versions of the *Rhizopus oryzae* glucoamylase.

The aspects of the present invention described below are not intended to be exhaustive or to limit the invention to the precise forms disclosed in the following detailed description. Rather a purpose of the aspects chosen and described is so that the appreciation and understanding by others skilled in the art of the principles and practices of the present invention can be facilitated.

Aspects of the invention relate to glucoamylase genes that are modified to replace their natural secretion sequence with a heterologous secretion sequence. By replacing the natural leader sequence of a glucoamylase with a heterologous leader sequence based on SEQ ID NOs: 73-78, heterologous leader sequence-GA fusions are able to be secreted into a fermentation medium and are enzymatically active against starch products, causing glucose formation and fermentation to a desired bioproduct, such as ethanol. Nucleic acids capable of serving as templates for the expression of these enzymes are also aspects of the invention.

Aspects of the invention also relate to as microorganisms expressing these enzymes, in particular, fungal organisms such as yeast (e.g., *Saccharomyces cerevisiae*). Such organisms can express a glucoamylase enzyme with a secretion signal based on a sequence derived from one or more of SEQ ID NOs: 73-78.

The glucoamylase enzyme can be secreted from the cell to a fermentation medium where the enzyme can have amylolytic activity on glucose polymers present in the fermentation medium. In turn, the enzyme can cause degradation of the glucose polymers to glucose, which can enter the cell and be used as a carbon source for the production of a target compound, such as ethanol.

The term "exogenous" as used herein, means that a molecule, such as a nucleic acid, or an activity, such as an enzyme activity, is introduced into the host organism. An exogenous nucleic acid can be introduced in to the host organism by well-known techniques and can be maintained external to the hosts chromosomal material (e.g., maintained on a non-integrating vector), or can be integrated into the host's chromosome, such as by a recombination event. An exogenous nucleic acid can encode an enzyme, or portion thereof, that is either homologous or heterologous to the host organism.

The term "heterologous" refers to a molecule or activity that is from a source that is different than the referenced molecule or organism. For example, in the context of the disclosure, a "heterologous signal sequence" refers to a signal sequence that is different from the sequence of the referenced polypeptide or enzyme. For example, a native signal sequence can be removed from a glucoamylase enzyme and replaced with a signal sequence from a different polypeptide, the modified glucoamylase has a "heterologous signal sequence." Accordingly, a gene or protein that is heterologous to a referenced organism is a gene or protein not found in that organism. For example, a specific glucoamylase gene found in a first fungal species and exogenously introduced into a second fugal species that is the host organism is "heterologous" to the second fungal organism.

Glucoamylases (E.C. 3.2.1.3) are amylolytic enzymes that hydrolyze 1,4-linked a-D-glucosyl residues successively from the nonreducing end of oligo- and polysaccharide chains with the release of D-glucose.

Glucoamylases and can also cleave α-1,6 bonds on amylopectin branching points. As used herein, the term "amylolytic activity" pertains to these enzymatic mechanisms. A glucoamylase polypeptide can be a variant of a naturally occurring glucoamylase, or a portion of a naturally occurring glucoamylase (such as a glucoamylase that is truncated at its N-terminus, its C-terminus, or both), while the glucoamylase polypeptide retains amylolytic activity.

Alternative names for glucoamylases include amyloglucosidase; γ-amylase; lysosomal α-glucosidase; acid maltase; exo-1,4-α-glucosidase; glucose amylase; γ-1,4-glucan glucohydrolase; acid maltase; 1,4-α-D-glucan glucohydrolase.

Most glucoamylases are multidomain enzymes. Many glucoamylases include a starch-binding domain connected to a catalytic domain via an O-glycosylated linker region. The starch-binding domain may fold as an antiparallel beta-barrel and may have two binding sites for starch or beta-cyclodextrin. However, some glucoamylases do not include a starch binding domain (e.g., see Hostinova et al., Archives of Biochemistry and Biophysics, 411:189-195, 2003), or include a non-canonical starch binding domain. For example, the *Rhizopus oryzae* glucoamylase possesses a N-terminal raw starch binding domain, and the *Saccharomycopsis fibuligera* IFO 0111 glucoamylase lacks a clear starch binding domain (Hostinova et al., supra). Therefore, some aspects of the invention are directed to glucoamylases that do not include a starch binding domain and that have an N-terminus modified with the heterologous secretion signal, and other aspects are directed to glucoamylases that include a starch binding domain and that have an N-terminus modified with the heterologous secretion signal.

Glucoamylases may also have a catalytic domain having a configuration of a configured twisted (alpha/alpha)(6)-barrel with a central funnel-shaped active site. Glucoamylases may have a structurally conserved catalytic domain of approximately 450 residues. In some glucoamylases the catalytic domain generally followed by a linker region consisting of between 30 and 80 residues that are connected to a starch binding domain of approximately 100 residues.

Glucoamylase properties may be correlated with their structural features. A structure-based multisequence alignment was constructed using information from catalytic and starch-binding domain models (see, e.g., Coutinho, P. M., and Reilly, P. J., 1994. Protein Eng. 7:393-400 and 749-760). It has been shown that the catalytic and starch binding domains are functionally independent based on structure-function relationship studies, and there are structural similarities in microbial glucoamylases. From other studies, specific glucoamylase residues have been shown to be involved in directing protein conformational changes, substrate binding, thermal stability, and catalytic activity (see, for example, Sierks, M. R., et al. 1993. Protein Eng. 6:75-79;

and Sierks, M. R., and Svensson, B. 1993. Biochemistry 32:1113-1117). Therefore, the correlation between glucoamylase sequence and protein function is understood in the art, and one of skill could design and express variants of amylolytically active glucoamylases having one or more amino acid deletion(s), substitution(s), and/or additions. For example, in some aspects, the glucoamylase portion of the heterologous secretion signal-glucoamylase can contain a truncated version of a naturally occurring glucoamylase, the truncated version having, in the least, a catalytic and optionally a starch-binding domain having amylolytic activity as described herein.

Shibuya, I., et al. (Agric. Biol. Chem., 58:1905-1914, 1990) describes the nucleotide sequence of the glucoamylase enzyme (GAase) gene from *Aspergillus shirousami* (see glaA, accession number P22832 in Table 1). The deduced amino acid sequence of GAase contains 639 amino acid residues with a relative molecular mass of approximately 68,000 daltons (non-glycosylated form). Amino acids 19-639 of *Aspergillus shirousami* GA is set forth in SEQ ID NO: 43.

Ghose, A., et al. (FEMS Microbiol Lett. 54:345-349, 1990) describes a glucoamylase enzyme from a strain of *Aspergillus terreus* having extracellular amylolytic activity with optimally activity at pH 5.0 and stable between pH 3.0-8.0. Ventura, L., et al. (Appl. Environ. Microbiol. 61: 399-402 1995) describes cloning of the *Aspergillus terreus* gla1 gene by homology to the *A. niger* glaA gene. The gla1 coding sequence contains an open reading frame of 2,132 bp interrupted by four introns (GenBank accession L15383), providing a polypeptide of 636 amino acids in length with deduced Mr of 67,789 (UniProt Q0CPK9). The Gla1 amino acid sequence was compared with other fungal glucoamylases which identified a putative leader peptide of 28 amino acids, an N-terminal catalytic domain containing enzyme activity regions, a linker region with high Thr and Ser content, and a C-terminal starch-binding domain. Amino acids 21-636 of *Aspergillus terreus* GA is set forth in SEQ ID NO: 44.

Ashikari, T, et al. (Agric. Biol. Chem. 49:2521-2523, 1985) describes cloning of the *Rhizopus* sp. glucoamylase gene by determination of the N- and C-terminal sequences of the purified protein and generation of probe oligos which were used to identify a cDNA encoding a 604 amino acid long protein. As reviewed by Lin, S.-C., et al. (BMC Biochemistry 8:9, 2007), *Rhizopus oryzae* glucoamylase (Ro GA) is synthesized as a precursor containing 25 amino acid secretion signal, with the mature form of Ro GA consisting of an SBD domain (residues 26-131), a Thr/Ser-rich linker region (residues 132-167), and a catalytic domain (residues 168-604). The SBD domain belongs to the carbohydrate-binding module (CBM) family 21 and the C-terminal catalytic domain of Ro GA hydrolyzes starch and has high sequence similarity catalytic domains of other fungal GAs. Amino acids 26-604 of *Rhizopus oryzae* GA is set forth in SEQ ID NO: 42.

Hostinova et al. (Archives of Biochemistry and Biophysics, 411:189-195, 2003) describes the nucleotide sequence of the glucoamylase gene Glm in the yeast strain *Saccharomycopsis fibuligera* IFO 0111 (referred to herein as "Sf GA-1"). According to Hostinova et al., the *Saccharomycopsis fibuligera* Glm gene is transcribed into a 1.7 kb RNA transcript that codes for a 515 amino acid protein, and is represented by SEQ ID NO:1. In the 515 amino acid-long polypeptide chain 26 N-terminal amino acid residues constitute the signal peptide and subsequent 489 amino acid residues constitute the mature protein. Mature Glm, which lacks the signal sequence and is 489 amino acids long, has a predicted molecular weight of 54,590 Da in deglycosylated form. In an alignment with other glucoamylases, Glm was shown to have homology in the catalytic domain.

Itoh et al. (J. Bacteriol. 169:4171-4176) describes the nucleotide sequence of another glucoamylase gene, GLU1, in the yeast *Saccharomycopsis fibuligera* (referred to herein as "Sf GA-2"). The *Saccharomycopsis fibuligera* GLU1 gene is transcribed into a 2.1 kb RNA transcript that codes for a 519 amino acid protein and has a molecular weight of 57,000 Da. GLU1 has four potential glycosylation sites (for asparagine-linked glycosides having a molecular weight of 2000 Da). GLU1 has four potential glycosylation sites (for asparagine-linked glycosides having a molecular weight of 2000 Da). GLU1 has a natural signal sequence for secretion that is cleaved off, likely during export of the protein. The cleaved site is preceded by the basic amino acids Lys-Arg, thought to be a proteolytic processing signal to yield mature protein.

Itoh et al. (supra) also describes alignment of amino acid sequences of glucoamylases from yeast and fungi. *Saccharomycopsis fibuligera, A. niger, Rhizopus oryzae*, and *Saccharomyces diastaticus*, and *Saccharomyces cerevisiae* were aligned showing five highly homologous segments (S1-S5). These parts of the respective conserved segments were shown to be conformationally similar to each other. The S5 segment, generally located at the carboxy termini, appears to be nonessential to amylolytic activities, since glucoamylases from *Saccharomyces* species lack this region.

In this regard, the invention also contemplates variants and portions of polypeptides having glucoamylase activity. Tables 1 and 2 present a list of various fungal and bacterial glucoamylase genes, including the amino acid location of the native signal sequence, and in some sequences, the propeptide, of the glucoamylase.

TABLE 1

Fungal Glucoamylases

| Name | Accession | Organism | Signal peptide | Pro-peptide | Chain |
|---|---|---|---|---|---|
| GAMP (AMYG_AMORE) | Q03045 | *Amorphotheca resinae* (Creosote fungus) (*Hormoconis resinae*) | 1-29 | | 30-616 |
| GLAA (AMYG_ASPNG) | P69328 | *Aspergillus niger* | 1-18 | 19-24 | 25-640 |
| STA1 (AMYH_YEASX) | P04065 | *Saccharomyces cerevisiae* | 1-21 | | 22-767 |
| STA2 (AMYI_YEASX) | P29760 | *Saccharomyces cerevisiae* | 1-21 | | 22-768 |
| GLAA | P69327 | *Aspergillus awamori* | 1-18 | 19-24 | 25-640 |

TABLE 1-continued

| Fungal Glucoamylases | | | | | |
|---|---|---|---|---|---|
| Name | Accession | Organism | Signal peptide | Pro-peptide | Chain |
| (AMYG_ASPAW) | | (Black koji mold) | | | |
| glaA (AMYG_ASPOR) | P36914 | *Aspergillus oryzae* (strain ATCC 42149/ RIB 40) (Yellow koji mold) | 1-19 | 20-25 | 26-612 |
| GAA (AMYG_BLAAD) | P42042 | *Blastobotrys adeninivorans* (Yeast) (*Arxula adeninivorans*) | 1-18 | | 19-624 |
| GAM1 (AMYG_SCHOC) | P22861 | *Schwanniomyces occidentalis* (Yeast) (*Debaryomyces occidentalis*) | 1-22 | | 23-958 |
| gaI (AMYG_ASPKA) | P23176 | *Aspergillus kawachii* (White koji mold) (*Aspergillus awamori* var. *kawachi*) | 1-18 | 19-24 | 25-639 |
| glaA (AMYG_ASPSH) | P22832 | *Aspergillus shirousami* | 1-18 | 19-24 | 25-639 |
| GAM1 (AMYG_CANAL) | O74254 | *Candida albicans* (strain SC5314/ATCC MYA-2876) | 1-20 | | 21-946 |
| | ABB77799 | *Rhizopus oryzae* (Mucormycosis agent) (*Rhizopus arrhizus* var. *delemar*) | 1-25 | | 26-604 |
| meu17 (mAMYG_SCHPO) | O60087 | *Schizosaccharomyces pombe* (strain 972/ ATCC 24843) (Fission yeast) | 1-16 | 17-28 | 29-450 |
| | I2K2N7 | *Brettanomyces bruxellensis* AWRI1499 | 1-21 | | 22-575 |
| SGA1 | A0A0H5C3I6 | *Cyberlindnera* jadinii (Torula yeast) (*Pichia jadinii*) | 1-16 | | 17-577 |
| GLA1 (AMYH_SACFI) ("Sf GA-3") | P26989 | *Saccharomycopsis fibuligera* (Hostinova et al. 2001) | 1-27 | | 28-519 |
| GLU1 AMYG_SACFI ("Sf GA-2") | P08017.1 | *Saccharomycopsis fibuligera* (Itoh et al. 1987) | 1-27 | | 28-519 |
| Glm ("Sf GA-1") | CAC83969 | *Saccharomycopsis fibuligera* IFO 0111 (Hostinova et al. 2003) | 1-26 | | 27-515 |
| | Q0CPK9 | *Aspergillus terreus* (strain NIH 2624/ FGSC A1156) | 1-20 | | 21-636 |
| | Q0CK04 | *Aspergillus terreus* (strain NIH 2624/ FGSC A1156) | 1-17 | | 18-510 |
| | | *Trichoderma reesei* QM6a (ATCC, Accession No. 13631) US 2007/0015266 | 1-20 | 21-33 | 34-632 |

TABLE 2

| Bacterial Glucoamylases | | | | | |
|---|---|---|---|---|---|
| Amylase gene | Accession | Organism | Signal peptide | Pro-peptide | Chain |
| SusB (SUSB_BACTN) | G8JZS4 | *Bacteroides thetaiotaomicron* (strain ATCC 29148/DSM 2079/ NCTC 10582/E50/ VPI-5482) | 1-21 | | 22-738 |
| cga (AMYG_CLOS0) | P29761 | *Clostridium* sp. (strain G0005) | 1-21 | | 22-702 |

As noted herein and in Tables 1 and 2, glucoamylases enzymes from various fungal and bacterial species also generally include a native "signal sequence." Various other terms may be used to indicate a "signal sequence" as known in the art, such as where the word "signal" is replaced with "secretion" or "targeting" or "localization" or "transit" or leader," and the word "sequence" is replaced with "peptide" or "signal." Generally, a signal sequence is a short amino acid stretch (typically in the range of 5-30 amino acids in length) that is located at the amino terminus of a newly synthesized protein. Most signal peptides include a basic N-terminal region (n-region), a central hydrophobic region (h-region) and a polar C-terminal region (c-region) (e.g., see von Heijne, G. (1986) Nucleic Acids Res. 14, 4683-4690). A signal sequence can target the protein to a certain part of the cell, or can target the protein for secretion from the cell. For example, it has been shown that the native N-terminal signal sequence of the *S. diastaticus* Glucoamylase STAI gene can target it to the endoplasmic reticulum of the secretory apparatus (for example, see Yamashita, I. et al., (1985) J. Bacteriol. 161, 567-573).

In one aspect, the current invention provides the partial or full replacement of the native signal sequence of a glucoamylase enzyme with a secretion signal based on a sequence at the N-terminal portion of An aa, Sc FAKS, Sc AKS, Sc MFα1, Sc IV, Gg LZ, and Hs SA, which represent heterologous secretion signals in the context of a glucoamylase. These secretion signals can be used as a replacement to the native secretion signal of the glucoamylase, or can be used in addition to the native secretion signal. In view of the addition of the heterologous secretion signal, the proteins may be referred to as "fusion proteins," and annotated as follows: [An aa-SS]-[GA], [Sc IV-SS]-[GA], etc.

In some aspects, fusion proteins of the disclosure can include a signal sequence having 80% or greater, 85% or greater, 90% or greater, 95% or greater, 96% or greater, 97% or greater, 98% or greater, or 99% or greater sequence identity to an amino acid sequence of at least AA 1-19 of SEQ ID NO: 73 (Sc-FAKS). SEQ ID NO:73 is a sequence of 90 amino acids derived from the N-terminal portion of the *Saccharomyces cerevisiae* peptide mating phermone α-factor (e.g., see Brake, A., et al., *Proc. Natl. Acad. Sci.,* 81:4642-4646, 1984; Kurjan, J. & Herskowitz, I., *Cell* 30:933-943, 1982), and the signal sequence can be selected from 1-x, wherein x is an integer in the range of 19 to 89.

For heterologous signal sequences that are shorter than SEQ ID NO:73, the signal sequence can be selected from 1-x, wherein x is an integer in the range of 19 to 88 (19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88).

An example of a portion of SEQ ID NO:73 that can be used as a heterologous signal sequence is *Saccharomyces cerevisiae* alpha mating factor (Sc-MFα1) which is amino acids 1-19 of SEQ ID NO:73.

Exemplary amino acid substitutions in amino acids 1-19 of SEQ ID NO:73, can include conservative amino acid substitutions at positions 7 (F→L, V, I, A, G; nonpolar) and 10 (V→L, F, I, A, G; nonpolar).

Fusion proteins of the disclosure can include a signal sequence having 80% or greater, 85% or greater, 90% or greater, 95% or greater, 96% or greater, 97% or greater, 98% or greater, or 99% or greater sequence identity to an amino acid sequence of that includes AA 1-19 and one or more portions of AA 20-89 of SEQ ID NO:73 (Sc-FAKS). In embodiments, the signal sequence can have identity to SEQ ID NO:73 with deletions of one or more portions of AA 20-89 of SEQ ID NO:73. For example, the signal sequence can have identity to SEQ ID NO:73 without amino acids 29-33, 57-70, or both. An exemplary signal sequence is the amino acid SEQ ID NO:74 (Sc-AKS; i.e., SEQ ID NO:73 without amino acids 29-33 and 57-70). Another exemplary signal sequence is a portion of SEQ ID NO:74, (referred to as Sc-AK; i.e., SEQ ID NO:73 without amino acids 29-33, 57-70, and 86-89).

Fusion proteins of the disclosure can include a signal sequence having 80% or greater, 85% or greater, 90% or greater, or 95% or greater sequence identity to SEQ ID NO:75, which is derived from the N-terminus the *Saccharomyces cerevisiae* invertase (Sc IV). Sc IV is a sucrose hydrolase enzyme of 532 amino acids having a 19 amino acid N-terminal signal peptide (e.g., see, Carlson M., et al. (1983) *Mol. Cell. Biol.* 3:439-447).

Exemplary amino acid substitutions in SEQ ID NO: 75, can include conservative amino acid substitutions at positions 6 (F→L, V, I, A, G; nonpolar) and 9 (L→V, F, I, A, G; nonpolar).

Fusion proteins of the disclosure can include a signal sequence having 80% or greater, 85% or greater, 90% or greater, or 95% or greater sequence identity to SEQ ID NO:76, which is derived from the N-terminus the *Gallus gallus* lyzozyme (Gg LZ). Gg LZ (also known as egg white lysozyme) is a glycoside hydrolase enzyme of 129 amino acids having an 18 amino acid N-terminal signal peptide (e.g., see, Jigami et al. (1986) *Gene* 43:273-279).

Exemplary amino acid substitutions in SEQ ID NO:76, can include conservative amino acid substitutions at positions 10 (L→F, V, I, A, G; nonpolar) and 13 (V→L, F, I, A, G; nonpolar).

Fusion proteins of the disclosure can include a signal sequence having 80% or greater, 85% or greater, 90% or greater, or 95% or greater sequence identity to SEQ ID NO:78, which is derived from the N-terminus the *Homo sapiens* albumin (Hs SA). Hs SA is a serum protein of 609 amino acids having an 18 amino acid N-terminal signal peptide (e.g, see, Kober et al. (2013) *Biotechnology and Bioengineering;* 110:1164-1173.).

Exemplary amino acid substitutions in SEQ ID NO:78, can include conservative amino acid substitutions at positions 6 (F→L, V, I, A, G; nonpolar) and 9 (L→V, F, I, A, G; nonpolar).

In some aspects, fusion proteins of the disclosure can include a signal sequence having 80% or greater, 85% or greater, 90% or greater, or 95% or greater sequence identity to SEQ ID NO:80, which is derived from the N-terminus the *Saccharomyces cerevisiae* mating factor alpha 2 gene (Sc MFα2). Sc MFα2-secretion signal modified glucoamylase polypeptides and engineered yeast strains that express the same are described in International Application serial no. PCT/US2016/016822, and filed Feb. 5, 2016 (Miller, et al.).

The *Saccharomyces cerevisiae* mating factor alpha 2 (Sc MFα2) secretion signal is described in U.S. Pat. No. 4,546,082 (Kurjan et al.). The Sc MFα2 SS sequence is as follows: MKFISTFLTFILAAVSVTA (SEQ ID NO:80). The Sc MFα2 sequence is from the gene YGL089C (YGL089C), whereas MFα1 is coded by the gene YPL187W MFα1 and MFα2 are pheromones secreted by MATa cells.

Based on an alignment of SEQ ID NOs: 73-78 and 80, a common structural feature in the secretion signals that promoted GA secretion and activity was identified. This common structural feature is a stretch of 5-8 continuous hydrophobic amino acid residues within the secretion signal.

This common structural feature is a stretch of 5-8 continuous hydrophobic amino acid residues within the secretion signal. For example, the stretch can be of five, six, seven, or eight hydrophobic amino acids. Hydrophobic amino acids are alanine, isoleucine, leucine, valine, and phenylalanine, methionine, tryptophan, and tyrosine). Preferably the stretch includes one or more of alanine, isoleucine, leucine, phenylalanine, and valine residues. Even more preferably, the stretch includes one or more leucine residues.

This stretch can be present within a heterologous secretion signal amino acid sequence that has at least 15, 16, 17, 18, or 19, or more amino acid residues, such as about 15 to about 30 amino acids. The heterologous secretion signal amino acid sequence has a different amino acid sequence than the native secretion sequence of the glucoamylase sequence the heterologous sequence is fused to.

The stretch is typically bordered by two amino acid residues that are not hydrophobic. In some embodiments, the stretch of hydrophobic amino acid residues are immediately adjacent to one or two polar amino acid residue(s). In preferred aspects, the polar amino acid residue is a serine residue.

In some aspects the 5-8 continuous hydrophobic amino acid residues comprise a sequence selected from the group consisting of AVLFAA (SEQ ID NO:82), AFLFLL (SEQ ID NO:83), LVLVLL (SEQ ID NO:84), LLFLF (SEQ ID NO:85), and FILAAV (SEQ ID NO:86).

In other aspects, fusion proteins of the disclosure can include a signal sequence having 80% or greater, 85% or greater, 90% or greater, or 95% or greater sequence identity to SEQ ID NO:81, which is derived from the N-terminus of the *Saccharomyces cerevisiae* repressible acid phosphatase (Sc PHO5). The Sc PHO5 secretion signal is described in U.S. Pat. No. 5,521,086 (Scott et al.) and Meyhack et al. (EMBO J. 6:675-680, 1982). The Sc PHO5 SS sequence is as follows: MFKSVVYSILAASLANA (SEQ ID NO:81). The Sc PHO5 sequence is from PHO5 which is a structural gene that encodes a *S. cerevisiae* acid phosphatase, which is regulated by the concentration or inorganic phosphate ($P_i$) in the medium. Sc PHO5-secretion signal modified glucoamylase polypeptides and engineered yeast strains that express the same are described in International Application serial no. PCT/US2016/016822, and filed Feb. 5, 2016 (Miller, et al.).

Molecular techniques can be performed to create a nucleic acid sequence that is a template for the expression of the glucoamylase gene with the heterologous signal sequence (if the glucoamylase protein/nucleotide sequences are known in the art). As a general matter, a nucleic acid is prepared to encode a protein comprising the heterologous signal sequence and a glucoamylase sequence.

Any sequence encoding a functional glucoamylase polypeptide can be used. In some aspects, the glucoamylase sequence can be a native ("wild type") sequence of a glucoamylase gene, where the sequence of the glucoamylase portion of the heterologous signal sequence-glucoamylase gene does not differ from the native sequence at any amino acid position. In other aspects, the sequence of the glucoamylase portion of the heterologous signal sequence-glucoamylase gene differs from the native sequence at one or more amino acid position(s). The difference can be, for example, (a) the removal of one or more amino acids from the wild type sequence, (b) the addition of one or more amino acids to the wild type sequence, (c) the substitution of the wild type sequence, a combination of (a) and (c), or a combination of (b) and (c).

For example, in one aspect the native sequence of the glucoamylase can be altered at its N-terminus prior to adding the heterologous signal sequence. In some aspects, all or a portion of the native glucoamylase signal sequence is removed prior to attaching the heterologous signal sequence. For example, a portion of a native leader sequence of the glucoamylase can be altered by deletion of one or more, but not all, amino acids of the native secretion signal (e.g., deletion of up to 50%, 60%, 70%, 80, 90%, or 95% of the native leader sequence). Such deletion of a portion of the native leader sequence may cause the native glucoamylase leader to lose its native functionality, which is replaced with the functionality provided by the heterologous signal sequence (a secretion signal based on a sequence derived from SEQ ID NOs: 73-78 and 80. In other aspects, all of the native secretion signal can be removed from the glucoamylase and replaced with the heterologous signal sequence.

For example, and with reference to Table 1, in preparing a fusion protein construct some or all of the first 25 amino acids of the *Rhizopus oryzae* glucoamylase (Ro GA; P07683), which corresponds to the predicted leader sequence using the CBS prediction server (i.e., amino acids 1-25 of the native protein), is removed. Therefore, all or a portion of the *Rhizopus oryzae* glucoamylase native secretion signal is replaced with a heterologous secretion signal sequence having (a) a secretion signal amino acid sequence having 80% or greater sequence identity to: (i) an amino acid sequence of at least AA 1-19 of SEQ ID NO:73, (ii) an amino acid sequence of at least AA 1-19 of SEQ ID NO:74, (iii) SEQ ID NO:77 (An aa), (iv) SEQ ID NO:75 (Sc IV), (v) SEQ ID NO:76 (Gg LZ), or (vi) SEQ ID NO: 78(Hs SA).

The heterologous secretion signal sequence can be attached directly or indirectly to the remaining portion of the Ro GA polypeptide (e.g., amino acids 26-604; SEQ ID NO:42). When heterologous secretion signal sequences of the disclosure are fused directly to the remaining portion of the Ro GA polypeptide, fusion proteins having lengths in the range of about 597 to about 668 amino acids are provided.

In some aspects the disclosure provides a polypeptide having 50% or greater, 60% or greater, 70% or greater, 80% or greater, 90% or greater, 95% or greater, 96% or greater, 97% or greater, 98% or greater, or 99% or greater sequence identity a polypeptide selected from the group consisting of: (i) SEQ ID NO: 52 (Sc-FAKS)-*Rhizopus oryzae* GA; (ii) SEQ ID NO: 53 (Sc-AKS)-*Rhizopus oryzae* GA; (iii) SEQ ID NO: 54 (An aa)-*Rhizopus oryzae* GA; (iv) SEQ ID NO: 55 (Sc IV)-*Rhizopus oryzae* GA; (v) SEQ ID NO: 56 (Gg LZ)-*Rhizopus oryzae* GA; (vi) SEQ ID NO: 57 (Hs SA)-*Rhizopus oryzae* GA; and (vii) SEQ ID NO:58 (Sc MFα1)-*Rhizopus oryzae* GA.

In some aspects the disclosure provides a polypeptide having 50% or greater, 60% or greater, 70% or greater, 80% or greater, 90% or greater, 95% or greater, 96% or greater, 97% or greater, 98% or greater, or 99% or greater sequence identity to a polypeptide selected from the group consisting of: (i) SEQ ID NO:45 (Sc-FAKS)-*Saccharomycopsis fibuligera* GA; (ii) SEQ ID NO: 46 (Sc-AKS)-*Saccharomycopsis fibuligera* GA; (iii) SEQ ID NO:47 (An aa)-*Saccharomycopsis fibuligera* GA; (iv) SEQ ID NO:48 (Sc IV)-*Saccharomycopsis fibuligera* GA; (v) SEQ ID NO:49 (Gg LZ)-*Saccharomycopsis fibuligera* GA; (vi) SEQ ID NO:50 (Hs SA)-*Saccharomycopsis fibuligera* GA; and (vii) SEQ ID NO: 51 (Sc MFα1)-*Saccharomycopsis fibuligera* GA.

In some aspects the disclosure provides a polypeptide having 50% or greater, 60% or greater, 70% or greater, 80% or greater, 90% or greater, 95% or greater, 96% or greater, 97% or greater, 98% or greater, or 99% or greater sequence identity to a polypeptide selected from the group consisting of: (i) SEQ ID NO: 59 (Sc-FAKS)-*Aspergillus shirousami*

GA; (i) SEQ ID NO: 60 (Sc-AKS)-*Aspergillus shirousami* GA; (ii) SEQ ID NO: 61(An aa)-*Aspergillus shirousami* GA; (iii) SEQ ID NO: 62 (Sc IV)-*Aspergillus shirousami* GA; (iv) SEQ ID NO: 63(Gg LZ)-*Aspergillus shirousami* GA; (vi) SEQ ID NO: 64 (Hs SA)-*Aspergillus shirousami* GA; and (vii) SEQ ID NO: 65 (Sc MFα1)-*Aspergillus shirousami* GA.

In some aspects the disclosure provides a polypeptide having 50% or greater, 60% or greater, 70% or greater, 80% or greater, 90% or greater, 95% or greater, 96% or greater, 97% or greater, 98% or greater, or 99% or greater sequence identity to a polypeptide selected from the group consisting of: (i) SEQ ID NO: 66 (Sc-FAKS)-*Aspergillus terreus* GA; (ii) SEQ ID NO: 67 (Sc-AKS)-*Aspergillus terreus* GA (iii) SEQ ID NO: 68 (An aa)-*Aspergillus terreus* GA; (iv) SEQ ID NO: 69 (Sc IV)-*Aspergillus terreus* GA; (v) SEQ ID NO: 70 (Gg LZ)-*Aspergillus terreus* GA; (vi) SEQ ID NO: 71 (Hs SA)-*Aspergillus terreus* GA; and (vii) SEQ ID NO: 72 (Sc MFα1)-*Aspergillus terreus* GA.

As another example, one or more amino acids of a native leader sequence of the glucoamylase can be altered by substitution, which is the replacement of the native amino acid at a particular location in the native glucoamylase leader with an amino acid that is different than the native amino acid. For example, a portion of a native leader sequence of the glucoamylase can be altered by substitution of one or more amino acids of the native secretion signal (e.g., up to 50%, 60%, 70%, 80%, 90%, or 95% of the native leader sequence amino acids can be substituted). Substitution of one or more amino acids may cause the native glucoamylase leader to lose its native functionality, which is replaced with the functionality provided by the heterologous secretion signal sequence.

In other aspects, the fusion polypeptide comprising the heterologous secretion signal sequence and glucoamylase sequence optionally comprises additional sequence that is not present in the native glucoamylase polypeptide, or the heterologous secretion signal sequence. The additional sequence, in some aspects, can provide functionality to the secretion signal-modified glucoamylase that is not present in the native polypeptide. Additional functionalities include, for example, protease sites or binding sites for other proteins or materials, or linker regions between the heterologous secretion signal and glucoamylase portion.

An example of an additional sequence that may not be present in the native glucoamylase polypeptide, or the heterologous secretion signal sequence, but that can be added, is a linker or spacer sequence. A linker sequence can be located between the heterologous secretion sequence and the glucoamylase sequence. Such fusion polypeptides [secretion signal modified polypeptide] can be annotated as follows: [SS]-[L]-[GA], wherein "L" denotes one or more amino acids that link the signal sequence to the glucoamylase. Exemplary linkers include one or more amino acids such as up to 5, 10, 15, 20, 25, 30, 35, 50, 100, or 200 amino acids. A linker can include amino acids that cause the linker to be rigid and prevent interactions between the secretion signal and other portions of the glucoamylase. Rigid linkers may include residues such as Pro, Arg, Phe, Thr, Glu, and Gln, and frequently form alpha-helical structures.

Alternatively, the fusion polypeptide can include a flexible linker. Flexible linkers can include glycine residues and connect the signal sequence to the glucoamylase portion of the fusion protein without interfering with their respective functions. In some linker sequences the majority (>50%) of the amino acids residues are glycine. Exemplary linker sequences include one or more linker block(s), with each block having one or more glycine residues and one amino acid selected from serine, glutamic acid, aspartic acid, and lysine. For example linker region can include the formula $[G_aX]_n$, wherein a is an integer in the range of 1-6, X is S, E, D, or K, and n is an integer in the range of 1-10.

In some aspects the polypeptide includes a linker having a protease cleavage sequence. Exemplary protease cleavage sequences include those for thrombin, factor Xa, rhinovirus 3C, TEV protease, Ssp DnaB, intein, Sce VMA1 intein, enterokinase, and KEX2 (see, for example, Waugh, D. S., Protein Expr Purif. 80(2): 283-293, 2011; Zhou et al., Microbial Cell Factories 13:44, 2014; and Bourbonnais et al., J. Bio. Chem. 263(30):15342, 1988).

Another example of an additional sequence that may not be present in the native glucoamylase polypeptide, or heterologous secretion signal sequence, but that can be added, is a tag sequence. A tag sequence can be located at the C-terminus of the glucoamylase sequence, and such proteins can be annotated as follows: [SS]-[GA]-[T] and [SS]-[L]-[GA]-[T], wherein "T" denotes one or more amino acids that provide the tag sequence. Exemplary peptide tags include up to 5, 10, 15, or 20 amino acids. The peptide tag can be useful for any one or more of a variety of purposes. For example, the tag can allow purification of the enzyme from the medium by the ability of a tag-binding member to specifically interact with the tag. The tag can also allow detection or identification of the protein using a tag-binding member with a detectable label. Exemplary short peptide tags are poly-Arg, FLAG, poly-His, c-myc, S, and Strep II.

Secretion signal modified polypeptides of the disclosure can also have deletions to one or more regions of the native glucoamylase polypeptide other than the native secretion sequence, wherein the deletions do not affect the polypeptides' amylolytic activity. The deletions can be based on known information regarding the structure and function of native glucoamylases, including mutational studies and sequence alignments (e.g., see Coutinho, supra, and Sierks, supra.). In some aspects the secretion signal modified polypeptides have up to 1%, up to 2%, up to 4%, up to 6%, up to 8%, up to 10%, up to 12%, up to 14%, up to 16%, up to 18%, up to 20%, or up to 25% of the glucoamylase polypeptide's sequence is deleted. In some aspects, the secretion signal modified polypeptides of the disclosure have a deletion of a portion of the C-terminus corresponding to the native glucoamylase polypeptide.

Truncated forms of glucoamylase have been generated and have been shown to have enzymatic activity. For example Evans et al. (Gene, 91:131; 1990) generated a series of truncated forms of glucoamylase to investigate how much of the O-glycosylated region was necessary for the activity or stability of GAIL a fully active form of the enzyme lacking the raw starch-binding domain. It was found that a significant portion of the C-terminus could be deleted from GAII with insignificant effect on activity, thermal stability, or secretion of the enzyme.

Various amino acids substitutions associated with causing a change in glucoamylase activity are also known in the art. Substitution(s) of amino acid(s) at various locations in the glucoamylase sequence have been shown to affect properties such as thermo stability, starch hydrolysis activity, substrate usage, and protease resistance. As such, the current disclosure contemplates use of the heterologous secretion signal with a glucoamylase sequence that includes one or more amino acids substitution(s) in the glucoamylase portion of the polypeptide, wherein the substitutions differ from the wild type sequence of the glucoamylase.

For example, U.S. Pat. No. 8,809,023 describes a method for reducing the ratio between isomaltose synthesis and starch hydrolysis activity (IS/SH ratio) during the hydrolysis of starch. In particular a *Trichoderma reesei* glucoamylase (Tr GA) is described (total length of 632 amino acids having an N-terminal having a signal peptide) that is modified at with amino acid positions as follows: D44R and A539R; or D44R, N61I, and A539R. This glucoamylase variant is reported to exhibit a reduced IS/SH ratio compared to said parent glucoamylase during the hydrolysis of starch. As an example, the current disclosure contemplates the replacement of the native leader sequence of a desired glucoamylase (e.g., a different glucoamylase with a heterologous secretion signal of the disclosure, wherein the desired glucoamylase further has amino acid substitutions corresponding to the D44R and A539R; or D44R, N61I and A539R substitutions of the modified Tr GA. In a broader sense, the heterologous secretion signal could be used with a glucoamylase variant having amino acid substitutions: D44R and A539R; or D44R, N61I and A539R, the positions corresponding to the respective position in the TrGA sequence, wherein said glucoamylase variant has at least 90% amino acid sequence identity to the entire length of the TrGA sequence. The corresponding "respective position" of a template glucoamylase sequence to the TrGA sequence can be understood by a sequence alignment of, for example, known glucoamylase polypeptide sequences (the template for construction of a heterologous secretion signal glucoamylase fusion), to the TrGA sequence.

As another example, U.S. Pat. No. 8,592,194 describes glucoamylase variants with increased thermo stability compared to wild type glucoamylase variants. Also described in this disclosure is the *Trichoderma reesei* glucoamylase but instead one or more amino acid substitutions to the native Tr GA sequence at positions 10, 14, 15, 23, 42, 45, 46, 59, 60, 61, 67, 68, 72, 73, 97, 98, 99, 102, 108, 110, 113, 114, 122, 124, 125, 133, 140, 144, 145, 147, 152, 153, 164, 175, 182, 204, 205, 214, 216, 219, 228, 229, 230, 231, 236, 239, 240, 241, 242, 244, 263, 264, 265, 268, 269, 276, 284, 291, 300, 301, 303, 310, 311, 313, 316, 338, 342, 344, 346, 349, 359, 361, 364, 379, 382, 390, 391, 393, 394, 408, 410, 415, 417, and 418. As an example, the current disclosure contemplates the replacement of the native leader sequence of a desired glucoamylase with the heterologous secretion signal, wherein the desired glucoamylase further has any one or more of the amino acid substitutions that are demonstrated in providing increased thermostability. In a broader sense, the heterologous secretion signal could be used with a glucoamylase variant having amino acid substitutions providing increased thermostability, the positions corresponding to the respective position in the TrGA sequence.

The determination of "corresponding" amino acids from two or more glucoamylases can be determined by alignments of all or portions of their amino acid sequences. Sequence alignment and generation of sequence identity include global alignments and local alignments, which typically use computational approaches. In order to provide global alignment, global optimization forcing sequence alignment spanning the entire length of all query sequences is used. By comparison, in local alignment, shorter regions of similarity within long sequences are identified.

As used herein, an "equivalent position" means a position that is common to the two sequences (e.g., a template GA sequence and a GA sequence having the desired substitution (s)) that is based on an alignment of the amino acid sequences of one glucoamylase or as alignment of the three-dimensional structures. Thus either sequence alignment or structural alignment, or both, may be used to determine equivalence.

In some modes of practice, the BLAST algorithm is used to compare and determine sequence similarity or identity. In addition, the presence or significance of gaps in the sequence which can be assigned a weight or score can be determined. These algorithms can also be used for determining nucleotide sequence similarity or identity. Parameters to determine relatedness are computed based on art known methods for calculating statistical similarity and the significance of the match determined. Gene products that are related are expected to have a high similarity, such as greater than 50% sequence identity. Exemplary parameters for determining relatedness of two or more sequences using the BLAST algorithm can be as follows.

In some modes of practice, an alignment is performed using BLAST (National Center for Biological Information (NCBI) Basic Local Alignment Search Tool) version 2.2.29 software with default parameters. A sequence having an identity score of XX % (for example, 80%) with regard to a reference sequence using the BLAST version 2.2.29 algorithm with default parameters is considered to be at least XX % identical or, equivalently, have XX % sequence identity to the reference sequence. A global alignment can align sequences with significant identity to, for example, the *Rhizopus oryzae* glucoamylase in order to determine which corresponding amino acid position(s) in the target sequence (e.g., a glucoamylase ortholog) can be substituted with the one or more of the amino acid if a glucoamylase variant is used.

Nucleic acids sequences encoding the heterologous secretion signal-glucoamylase polypeptide, as well as any regulatory sequence (e.g., terminator, promoter, etc.) and vector sequence (e.g., including a selection marker, integration marker, replication sequence, etc.) can, in some modes of practice, be prepared using known molecular techniques. General guidance for methods for preparing DNA constructs (e.g., for the DNA constructs including the heterologous secretion signal-glucoamylase gene) can be found in Sambrook et al Molecular Cloning, A Laboratory Manual, Cold Spring Harbor Laboratory Press, Cold Spring Harbor, N.Y., 1989; and Ausubel et al. Current Protocols in Molecular Biology, Greene Publishing and Wiley-Interscience, New York, N.Y., 1993.

When small amounts of glucoamylase template DNA are used as starting material in PCR, primers that include the heterologous secretion signal sequences and a portion of the glucoamylase sequence that is 3' to its native signal sequence can be used to generate relatively large quantities of a specific DNA fragment that includes the heterologous secretion signal sequence and the glucoamylase gene.

PCR techniques can be used for modifying a native glucoamylase nucleic acid sequence to add the heterologous secretion signal sequence, or to introduce one or more mutations in the glucoamylase nucleic acid sequence to provide a variant. PCR techniques are described in, for example, Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733. The techniques may optionally include site-directed (or oligonucleotide-mediated) mutagenesis, PCR mutagenesis, and cassette mutagenesis of an earlier prepared DNA encoding a glucoamylase polypeptide.

Alternatively, nucleic acid molecules can be generated by custom gene synthesis providers such as DNA2.0 (Menlo Park, Calif.) or GeneArt (Life Technologies, Thermo Fisher Scientific).

An expression vector can be constructed to include the heterologous secretion signal-glucoamylase nucleic acid sequence operably linked to expression control sequences functional in the host organism. Expression vectors applicable for use in the host organisms include, for example, plasmids, episomes and artificial chromosomes. The vectors can include selection sequences or markers operable for stable integration into a host chromosome. Additionally, the vectors can include one or more selectable marker genes and appropriate expression control sequences. Selectable marker genes also can be included that, for example, provide resistance to antibiotics or toxins, complement auxotrophic deficiencies, or supply critical nutrients not in the culture medium. Expression control sequences can include constitutive and inducible promoters, transcription enhancers, transcription terminators, and the like which are well known in the art.

In some aspects, the nucleic acid can be codon optimized. The nucleic acid template that is used for the glucoamylase portion of the heterologous secretion signal sequence-glucoamylase can be the native DNA sequence that codes for the glucoamylase, or the template can be a codon-optimized version that is optimized for expression in a desired host cell. Databases that provide information on desired codon uses in particular host organisms are known in the art.

According to one aspect of the disclosure, a DNA construct comprising a heterologous secretion signal sequence-glucoamylase is operably linked to a promoter sequence, wherein the promoter sequence is functional in a host cell of choice. In some aspects, the promoter shows transcriptional activity in a fungal host cell and may be derived from genes encoding proteins either homologous or heterologous to the host cell. In some aspects the promoter is useful for expression in *S. cerevisiae*. Examples of well-known constitutive promoters include, but are not limited to the cytochrome c promoter (pCYC), translational elongation factor promoter (pTEF), the glyceraldehyde-3-phosphate dehydrogenase promoter (pGPD), the phosphoglycerate kinase promoter (PGK), and the alcohol dehydrogenase promoter (pADH). Optionally, an additional factor that controls expression such as an enhancer or the like may also be included on the vector.

The expression vector including the heterologous secretion signal sequence-glucoamylase gene can also include any termination sequence functional in the host cell. For example, the termination sequence and the promoter sequence can be from the same cell, or the termination sequence is homologous to the host cell. The termination sequence can correspond to any promoter that is used.

The DNA construct may be introduced into a host cell using a vector. The vector may be any vector which when introduced into a host cell is stably introduced. In some aspects, the vector is integrated into the host cell genome and is replicated. Vectors include cloning vectors, expression vectors, shuttle vectors, plasmids, phage particles, cassettes and the like. In some aspects, the vector is an expression vector that comprises regulatory sequences operably linked to the glucoamylase coding sequence. SEQ ID NOs as described herein can be assembled in the cell by the transformation of multiple smaller DNA fragments (e.g., “SEQ ID NO sub-fragments”) with overlapping homology that in total constitute a particular SEQ ID NO. For example, the integration of a desired SEQ ID NO, or portion thereof, at a gene locus in the cell can be accomplished by the co-transformation of two to five DNA sub-fragments, which are subjected to recombination with each other and integration into a genetic locus in the cell having homology to portions of the sub-fragments.

The DNA construct comprising a heterologous secretion signal sequence-glucoamylase gene can further include a selectable marker, thereby facilitating the selection in a host cell. For example, the selectable marker can be for transformed yeast. Examples of yeast selectable marker include markers commonly used for selecting for transformed yeast cells. Auxotrophic markers can be used using a gene that controls an auxotrophy, meaning that the gene enables yeast to produce a nutrient required for the growth of the yeast. Examples genes that control auxotrophies include leucine auxotrophy (LEU2), histidine auxotrophy (HIS3), uracil auxotrophy (URA3, URA5), and tryptophan auxotrophy (TRP1).

The DNA construct may be one which is integrated into the genome and replicated together with the chromosome(s) into which it has been integrated. For example, a fungal cell may be transformed with the DNA construct encoding the glucoamylase, and integrating the DNA construct, in one or more copies, in the host chromosome(s). This integration is generally considered to be an advantage, as the DNA sequence is more likely to be stably maintained. Integration of the DNA constructs into the host chromosome may be performed according to conventional methods, such as by homologous or heterologous recombination.

Engineered yeast of the disclosure can include having multiple copies (two or more) of the glucoamylase gene with heterologous secretion signal sequence. For example, the engineered yeast can be an engineered *Saccharomyces* that has at least first, second, third, and fourth exogenous nucleic acids each including a sequence encoding at least one glucoamylase polypeptide with heterologous secretion signal sequence of the disclosure. If the engineered yeast includes multiple copies of a gene encoding the glucoamylase gene with heterologous secretion signal sequence, the nucleic acid sequences of the copies can be the same or different from one another. Exemplary methods and yeast strains that have been engineered to include multiple copies of glucoamylase genes are described in International Application serial no. PCT/US16/24249, and filed Mar. 25, 2016 (Miller, et al.).

The engineered yeast can also include one or other genetic modifications that are different than the modification of the glucoamylase with heterologous signal sequence. The (heterologous) modifications can include introduction of exogenous nucleic acid sequences, changes to regulatory elements that either upregulate or down regulate expression of genes; increase in gene copy numbers, and deletions or mutations that eliminate expression, reduce expression, or increase expression or activity of a gene or gene product. The heterologous modification can include one or more of the following: the use of a promoter that is different than the native promoter of the desired gene; the use of a terminator that is different than the native terminator of the desired gene; the introduction of the gene at a location in the genome that is different than its native location; the introduction of multiple copies of the desired gene.

An additional genetic modification that can be included in the engineered yeast is the alteration or introduction of an enzyme activity that converts a low molecular weight non-glucose sugar to glucose. For example, one optional additional genetic modification affects or introduces isomaltase activity in the engineered yeast. Isomaltase can converting isomaltose to glucose by hydrolyzing the 1,6 ether linkage in isomaltose. An isomaltase may also exhibit cross activity for hydrolyzing the 1,4 ether linkages in maltose. The genetic modification can cause isomaltase activity to be introduced into the cell, cause an increased amount of isomaltase in the cell, and/or cause an increase in isomaltase activity.

In some embodiments further to the glucoamylase gene with heterologous secretion signal sequence, the engineered cell includes a heterologous isomaltase gene, or an isomaltase gene under the control of a heterologous promoter that provides increased expression in the cell, or present in multiple copies in the cell. For example, an isomaltase (IMA) gene under the control of a heterologous promoter, such as a PDC promoter can be engineered into the yeast.

Examples of isomaltase genes that can be introduced into an engineered yeast include, but are not limited to *Saccharomyces cerevisiae* IMA1 (P53051), *Saccharomyces cerevisiae* IMA2 (Q08295), *Saccharomyces cerevisiae* IMA3 (P0CW40), *Saccharomyces cerevisiae* IMA4 (P0CW41), *Saccharomyces cerevisiae* IMA5 (P40884), *Bacillus subtilis* malL (006994), *Bacillus cereus* malL (P21332), *Bacillus coagulans* malL (Q45101), *Bacillus* sp. malL (P29093), etc. Preferably the isomaltase gene encodes for a polypeptide having greater than 80%, 85%, 90%, 95%, 98% or 99% sequence identity with the amino acid sequence of accession number NP 011803.3 (*Saccharomyces cerevisiae* IMA1).

In some embodiments, the engineered yeast can further include a genetic modification that provides a starch-degrading polypeptide that is different than the glucoamylase with heterologous signal sequence. For example, the genetic modification can be one that introduces a nucleic acid encoding a different polysaccharide-degrading enzyme, such as an exogenous or modified alpha-amylase, a beta-amylase, a pullulanase, or an isoamylase. The genetic modification may also be one that increases the amount of an endogenous or an exogenous starch-degrading polypeptide in the cell, such as by placing the gene under control of a strong promoter, or providing the gene in multiple copies in the cell, such as multiple copies of the gene integrated into the genome, or multiple copies present on a non-chromosomal construct (e.g., a plasmid).

In some embodiments, the engineered yeast can further include a genetic modification that provides a an exogenous or modified sugar transporter gene (such as an isomaltose transporter); See, for example, commonly assigned U.S. application Ser. No. 62/268,932 filed Dec. 17, 2015, entitled “Sugar Transporter-Modified Yeast Strains and Methods for Bioproduct Production.”

Various host cells can be transformed with a nucleic acid including the heterologous signal sequence-glucoamylase gene. In some aspects the nucleic acid including the heterologous signal sequence-glucoamylase gene is present in a bacterial cell. The bacterial cell can be used, for example, for propagation of the nucleic acid sequence or for production of quantities of the polypeptide.

In other aspects, the host cell is a eukaryotic cell, such as a fungal cell.

In some aspects the host cell is has tolerance to a higher amount of a bioderived product, such as ethanol, in the fermentation medium. In some aspects, the host cell is an “industrial yeast” which refers to any yeasts used conventionally in ethanol fermentation. Examples include sake yeasts, shochu yeasts, wine yeasts, beer yeasts, baker’s yeasts, and the like. Sake yeasts demonstrate high ethanol fermentability and high ethanol resistance and genetic stability. Typically, an industrial yeast has high ethanol resistance and preferably is viable at ethanol concentrations of 10% or greater.

In exemplary aspects, the yeast including the heterologous signal sequence-glucoamylase gene is *S. cerevisiae*. Some *S. cerevisiae* strains have high tolerance to ethanol. Various strains of ethanol tolerent yeast are commercially available, such as RED STAR® and ETHANOL REDO yeast (Fermentis/Lesaffre, USA), FALI (Fleischmann’s Yeast, USA), SUPERSTART and THERMOSACC® yeast (Ethanol Technology, Wis., USA), BIOFERM AFT and XR (NABC—North American Bioproducts Corporation, GA, USA), GERT STRAND (Gert Strand AB, Sweden), and FERMIOL (DSM Specialties).

Industrial yeasts are typically prototrophic and therefore do not have an auxotrophic marker suitable for selecting for a transformant. If the yeast does not have the genetic background that would otherwise facilitate retention of the heterologous signal sequence-glucoamylase gene within the cell upon transformation, the host cell can be engineered to introduce one or more genetic mutation(s) to establish use of a marker gene in association with and to maintain the heterologous signal sequence-glucoamylase gene in the cell. For example, a commercially available ethanol tolerant yeast cell can be genetically modified prior to introducing the heterologous signal sequence-glucoamylase gene in the cell.

A marker for a different auxotrophy can be provided by disrupting the gene that controls the auxotrophy. In one mode of practice, an ethanol tolerant strain of yeast is engineered to disrupt copies of one or more genes that control auxotrophies, such as LEU2, HIS3, URA3, URA5, and TRP1. In the case of providing uracil auxotrophy, for example, a normal ura3 gene of an ethanol tolerant yeast can be replaced with an ura3$^-$ fragment obtained from a uracil auxotrophic mutant (for example, a *Saccharomyces cervisiae* MT-8 strain) to disrupt the normal ura3 gene. In the case of a ura3 gene-disrupted strain, the presence/absence of a marker can be easily identified or selected by taking advantage of the fact that a ura3 gene-disrupted strain is able to grow in a medium containing 5-fluoroorotic acid (5-FOA) while a normal ura3 strain (wild-type yeast or usual industrial yeast) is not able to grow. In the case of a lys2 gene-disrupted strain, the presence/absence of a marker can be easily identified or selected by taking advantage of the fact that a lys2 gene-disrupted strain is able to grow in a medium containing α-aminoadipic acid while a normal lys2 strain (wild-type yeast or usual industrial yeast) is not able to grow. Methods for disrupting an auxotrophy-controlling gene and for selectively separating auxotrophy-controlling gene mutants may be used depending on the auxotrophy employed. Alternatively, one can employ dominant selection markers, such as the amdS from *Aspergillus nidulans* (U.S. Pat. No. 5,876,988), which allows for growth on acetamide as the sole nitrogen source; or ARO4-OFP, which allows for growth in the presence of fluoro-phenylalanine (Fukuda et. al.). These markers can be used repeatedly using the recyclable cre-loxP system, or alternatively can be used to create auxotrophic strains that allow additional markers to be utilized.

After the host cell has been engineered to provide a desired genetic background for introduction of the heterologous signal sequence-glucoamylase gene, the gene construct is introduced into a cell to allow for expression. Methods for introducing a gene construct into a host cell include transformation, transduction, transfection, co-transfection, electroporation. In particular, yeast transformation can be carried out suing the lithium acetate method, the protoplast method, and the like. The gene construct to be introduced may be incorporated into a chromosome in the form of a plasmid, or by insertion into the gene of a host, or through homologous recombination with the gene of a host. The transformed yeast into which the gene construct has been introduced can be selected with a selectable marker (for example, an auxotrophic marker as mentioned above). Further confirmation can be made by measuring the activity of the expressed protein.

The transformation of exogenous nucleic acid sequences including the heterologous signal sequence-glucoamylase gene can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The engineered yeast of the disclosure can be provided in any suitable form. In some aspects, the non-natural yeast is dehydrated to form a dry yeast composition. The dry yeast composition can have increased shelf life over wet compositions.

Fermentation using a host cell expressing the heterologous signal sequence-glucoamylase gene can be performed in the presence of a starch and/or sugar containing plant material, referring to a starch and/or sugar containing plant material derivable from any plant and plant part, such as tubers, roots, stems, leaves and seeds. Starch and/or sugar comprising plant material can be obtained from cereal, such as barley, wheat, maize, rye, sorghum, millet, barley, potatoes, cassava, or rice, and any combination thereof. The starch- and/or sugar comprising plant material can be processed, such as by methods such as milling, malting, or partially malting. In some aspects, the starch material is from corn flour, milled corn endosperm, sorghum flour, soybean flour, wheat flour, biomass derived starch, barley flour, and combinations thereof.

In some aspects, the fermentation medium includes a treated starch. For example, the fermentation medium can include a partially hydrolyzed starch. The partially hydrolyzed starch can include high molecular weight dextrins and high molecular weight maltodextrins. In some modes of practice, a partially hydrolyzed starch product having a dextrose equivalent ("DE") in the range of about 5 to about 95 or more preferably about 45 to about 65, is used in the fermentation medium. Partially hydrolyzed starches and preparation thereof are well known in the art. Partially hydrolyzed starches can be prepared by heating the starch with an acid such as hydrochloric or sulfuric acid at a high temperature and then neutralizing the hydrolysis mixture with a suitable base such as sodium carbonate. Alternatively, partially hydrolyzed starches can be prepared by an enzymatic process, such as by adding alpha-amylase to a starch preparation. An alpha amylase can cause the endohydrolysis of (1→4)-alpha-D-glucosidic linkages in polysaccharides containing three or more (1→4)-alpha-linked D-glucose units. A partially hydrolyzed starch product can be used that have amounts of starch and starch degradation products within desired ranges.

"Liquifact" as used herein, is corn starch that has undergone liquefaction, with a dextrose equivalents in the range of about 10 to about 15. A corn wet milling process can be used to provide steep-water, which can be used for fermentation. Corn kernels can be steeped and then milled, and separated into their major constituent fractions. Light steep water is a byproduct of the steeping process, and contains a mixture of soluble proteins, amino acids, organic acids, carbohydrates, vitamins, and minerals.

In aspects of the disclosure, given production and secretion of the glucoamylase from the engineered yeast into the fermentation medium, the fermentation method may omit addition of purified or enriched commercial glucoamylase into the medium, or at least allow significantly less commercial glucoamylase to be used in a fermentation method. For example, the engineered yeast of the disclosure can allow addition of commercial glucoamylase to be eliminated or at least reduced by about 50%, 60%, 70%, 80%, 90%, or 95%. Typically, amounts of glucoamylase in the range of about 7 units to about 50 units per liter would be used in fermentation methods that do not use a glucoamylase-secreting engineered yeast.

The fermentation medium includes water and preferably includes nutrients, such as a nitrogen source (such as proteins), vitamins and salts. A buffering agent can also be present in the fermentation medium. Other components may also be present in the fermentation broth after a period of fermentation, such as fermentation products which can accumulate as the fermentation progresses, and other metabolites. Optionally, the fermentation broth can be buffered with a base such as calcium hydroxide or calcium carbonate, ammonia or ammonium hydroxide, sodium hydroxide, or potassium hydroxide in order to maintain a pH at which the organism functions well.

The engineered yeast of the current disclosure can also be described in terms of the engineered yeast's specific growth rate. The growth rate of yeast can be defined by L=log (numbers) where numbers is the number of yeast cells formed per unit volume (mL), versus T (time).

The fermentation is carried out under conditions so that fermentation can occur. Although conditions can vary depending on the particular organism and desired fermentation product, typical conditions include a temperature of about 20° C. or greater, and more typically in the range of about 30° C. to about 50° C. During fermentation the reaction mixture can be mixed or agitated. In some modes of practice, the mixing or agitation can occur by the mechanical action of sparging gas to the fermentation broth. Alternatively direct mechanical agitation such as by an impellor or by other means can be used during fermentation.

The disclosure also provides non-natural yeast that have the ability to grow, and/or can produce a fermentation product at temperatures that are greater than those in which yeast, such *Saccharomyces cerevisiae*, typically are used in fermentation processes. For example, *S. cerevisiae* typically have optimal growth at a temperature of about 30° C. In experiments associated with the current disclosure, yeast have been identified that have a greater tolerance to elevated temperatures, such as 32° C. or greater, such as in the range of greater than 32° C. to about 40° C. Exemplary ranges for elevated temperature are $T_1$ to $T_2$, wherein $T_1$ is selected from 32.2° C., 32.4° C., 32.6° C., 32.8° C., 33° C., 33.2° C., 33.3° C., 33.4° C., 33.6° C., 33.8° C., 34° C., 34.2° C., 34.4° C., 34.6° C., 34.8° C., 35° C., and 36° C.; and $T_2$ is selected from 36° C., 37° C., 38° C., 39° C., and 40° C. For the purposes of this disclosure, a yeast is considered "thermotolerant" if the yeast can continue to grow, reproduce, and/or produce a fermentation product during or after being exposed to a fermentation medium having an elevated temperature.

During a fermentation process the fermentation medium can reach an elevated temperature of 32° C. or greater during one or more time(s) during the fermentation process. The temperature can be elevated during part of the fermentation period, or during the entire fermentation period. The temperature can be elevated for 5 minutes of greater, 10 minutes of greater, 30 minutes or greater, 1 hour or greater, 2 hours or greater, 5 hours or greater, or 10 hours or greater. The time of elevated temperature can also be expressed as a total of the overall fermentation period, such as about 0.1% to 100%, about 0.1% to about 75%, about 0.1% to about 50%, about 0.1% to about 25%, about 0.1% to about 10%, about 0.1% to about 5%, about 0.1% to about 2.5%, about 0.1% to about 1%, or about 0.1% to about 0.5% of the fermentation period.

The engineered yeast can also provide a commercially relevant titer of ethanol during or after the period of elevated temperature. For example, during or after the period of elevated temperature, for example, any of the ranges corresponding to $T_1$ to $T_2$, the ethanol titer can be in the range of about 110 g/L to about 170 g/L, in the range of about 125 g/L to about 170 g/L, or in the range of about 140 g/L to about 170 g/L. Accordingly, the engineered yeast described herein can produce ethanol at a commercially useful titer during or after a period of high temperature that would typically cause issues in other currently available yeast strains used in ethanol-producing fermentation processes. Such issues include but are not limited to: death to a significant percentage of yeast cells; deleterious effects on the ability of the yeast to reproduce; and/or reduction or elimination of the ability of the yeast to produce a fermentation product.

An engineered *S. cerevisiae* having the heterologous signal sequence-glucoamylase gene can be put under temperature selection pressure to select for strains that demonstrate increased tolerance to growth at higher temperatures. The engineered yeast can be subjected to random mutagenesis (e.g., UV, chemical) prior to application of the higher temperature selection to generate mutation(s) that can confer improved tolerance to growth at these higher temperatures. For example, an engineered yeast of the disclosure can have a specific growth rate at a temperature in the range of 32° C. or greater that that is 10%, 20%, 30%, 40%, or 50% greater than the growth rate of a reference yeast.

In some cases fermentation is carried out in industrial capacity fermenters in order to achieve commercial scale economic benefits and control. In an aspect, the fermentation is carried out in a fermenter that has a capacity of about 10,000 liters or more.

The pH of the fermentation medium can be adjusted to provide optimal conditions for glucoamylase activity, cell growth, and fermentation activity to provide a desired product, such as ethanol. For example, pH of the solution can be adjusted to in the range of 3 to 5.5. In one mode of practice, the pH of the fermentation medium is in the range of 4 to 4.5.

As noted above, the present fermentation process using genetically modified microorganisms expressing the heterologous signal sequence-glucoamylase gene and capable of secreting the enzyme produced into the fermentation medium. These enzymes are therefore directly exposed to the broth conditions and affect the carbohydrate composition in the fermentation medium. In the fermentation medium the glucoamylase can cause hydrolysis and release of D-glucose from the non-reducing ends of the starch or related oligo- and polysaccharide molecules by cleaving alpha-(1,4) and alpha-(1,6) glucosidic bonds.

Starch may also be acted on by one or more other amylases (e.g., alpha-amylase) present in the fermentation medium. For example, if alpha-amylase is present in the fermentation medium it can cause partial hydrolysis of precursor starch and cause a partial breakdown of the starch molecules by hydrolyzing internal alpha-(1,4)-linkages.

In some modes of practice, the fermentation is carried out as a single batch until completion. In other modes of practice, the fermentation is carried out as a fed batch fermentation process. In this mode of practice, a first portion of a total amount of starch material to be fermented is added to the fermentation medium wherein the glucoamylase enzyme acts on the starch to cause formation of glucose to be used as a substrate for fermentation. Additional starch material can be added in one or more portions to provide more substrate for the glucoamylase enzyme in the medium. The addition of starch can be regulated and the formation of glucose can be monitored to provide efficient fermentation.

Preferably, the fermentation is carried out in a continuous mode of operation. In this mode, multiple fermenters operate in series in which a starch hydrolysate is supplied in the first fermenter, which is fed to second fermenter and so on until the starch hydrolysate is converted to ethanol. Continuous operation can be operated using between 2-7 fermenters.

In some modes of practice, a portion of the total amount of starch material is added to the fermentation broth using a variable rate addition system. Examples of such systems include a variable speed pump or a metering valve (such as a throttle valve) operably connected to a pump, which pump or valve can be utilized to vary the amount of starch material introduced into the fermentation broth over time. In some modes of practice, during the addition of a portion of the starch material, glucose concentration is monitored by a real-time monitoring system.

Real-time monitoring systems include systems that directly monitor glucose concentration and systems that indirectly monitor glucose concentration. Examples of real-time monitoring systems that typically directly monitor glucose concentration include systems based on infrared (IR) spectroscopy, near-infrared (NIR) spectroscopy systems, Fourier transform infrared (FTIR) systems, systems based on refractive index, automated enzyme based measurement systems such as a YSI 2950 Biochemistry Analyzer sold by YSI Life Sciences systems, high performance liquid chromatography (HPLC) based systems, gas chromatography (GC) based systems, and other real-time monitoring systems known to one of skill in the art. Additionally real-time monitoring systems that indirectly monitor/measure the glucose concentration of a fermentation process can be developed by determining the typical carbon distribution in a particular fermentation process and correlating the glucose concentration present in the fermentation broth to another parameter exhibited by the fermentation, such as, for example, a correlation of the glucose level present in the fermentation broth with a measurement of the carbon dioxide evolution rate and the amount of carbon dioxide present in an off-gas stream from the fermentation vessel. The carbon dioxide can be readily measured through use of a mass spectrometer or other suitable instrumental technique for measuring the components of the off-gas stream. In a preferred aspect, the glucose concentration is monitored by a real-time monitoring system using infrared spectroscopy. In another one aspect, the glucose concentration is monitored by a real-time monitoring system using near-infrared spectroscopy. The real time monitoring systems interface with equipment that controls the introduction of starch material into the fermentation broth to modulate the formation of glucose to a desired concentration in the fermentation broth.

During the fermentation process a sample of the fermentation medium can be taken to determine the amount of glucoamylase activity in the medium. The amount of glucoamylase activity in the medium can be referred to as extracellular glucoamylase activity as it corresponds to glucoamylase secreted from the engineered yeast. In some modes of measuring, the amount of glucoamylase activity in the medium can be determined by the amount of glucoamylase activity per amount of biomass per volume of medium.

As used herein "biomass" refers to the weight of the engineered yeast, which can be measured in grams of dried cell weight per liter of medium (DCW/L).

A unit (U) of GA activity can be defined as the amount of enzyme that catalyzes the release of 1 mg glucose/min from starch. Glucoamylase activity can be measured in concentrated broth by coupling starch hydrolysis to a HXK/G6PDH reaction mix (Sigma G3293) in a two-step end point assay. Broth can be concentrated from a predetermined amount of cells grown using a non-glucose carbon source (i.e. raffinose) to avoid interference with the assay.

The specific activity is equal to the activity in a given volume of broth divided by the wet weight of cells in the same volume of broth. Specific activity has the following units, U of GA activity per gram of biomass (U/g biomass). The amount of biomass used in the assay can be measured by determining the wet cell weight after removing the broth, either by filtration or centrifugation.

A starch solution is prepared by dissolving 1.1 g of corn starch (S4126, Sigma) in 50 mL of near boiling water, then adding 1 mL of 3M sodium acetate pH 5.2. A volume of concentrated broth ($V_b$), typically in the range of 1-20 ul (prepared by using a 10 Kb Kd cutoff column, Millipore #UFC901008) is added to the starch slurry ($V_s$), in a total volume of 200 ul, and allowed to incubate at 37° C. for a specific period of time (T), typically between 5-60 minutes. Parameters are selected such that the glucose formation is linear within a desired time. 20 μL of each sample is added to 2 μL 0.6N NaOH and mixed well. 200 μL of the HXK/G6PDH mix is then added and incubated at 30° C. for 30 minutes. The absorbance at 340 nm is measured using a spectrophotometer (SpectraMax™ M2). Regression analysis using known glucose standards is used to calculate the amount of glucose released in each sample. The specific enzyme activity per gram of biomass (U/g biomass) can be calculated by obtaining the weight in grams of the sample used prior to concentration. Unit of activity=(mg glucose/T)*(($V_b$+$V_s$)/($V_b$))*(222/20). Specific activity=Unit of activity/g biomass.

In some aspects, in the fermentation method the medium has an amount of glucoamylase activity of 2.25 U or greater per gram of biomass. In some aspects the medium has an amount of glucoamylase activity of about 2.3 U or greater, about 2.35 U or greater, about 2.4 U or greater, about 2.45 U or greater, about 2.5 U or greater, about 2.6 U or greater, about 2.7 U or greater, about 2.8 U or greater, about 2.9 U or greater, about 3 U or greater, about 3.5 U or greater, about 4 U or greater, about 4.5 U or greater, about 5 U or greater, about 5.5 U or greater, about 6 U or greater, about 6.5 U or greater, about 7 U or greater, about 7.5 U or greater, or about 8 U or greater per gram of biomass. In some aspects the medium has an amount of glucoamylase activity in the range of about 2.3 U to about 15 U, about 2.4 U to about 15 U, about 2.5 U to about 15 U, about 3 U to about 15 U, about 3.5 U to about 15 U, about 4 U to about 15 U, about 4.5 U to about 15 U, about 5 U to about 15 U, about 5.5 U to about 15 U, about 6 U to about 15 U, about 6.5 U to about 15 U, about 7 U to about 15 U, about 7.5 U to about 15 U, or about 8 U to about 15 U per gram of biomass.

In other aspects, an amount of glucoamylase activity in a fermentation medium provided by a non-natural yeast of the disclosure can be described relative to a reference yeast. For example, the amount of glucoamylase activity that a non-natural yeast expressing an exogenous glucoamylase having a heterologous signal sequence (e.g., having 90% or greater identity to SEQ ID NO:52) can be compared to an otherwise identical yeast expressing the exogenous glucoamylase with its native signal sequence.

In some aspects, the non-natural yeast expressing an exogenous glucoamylase having a heterologous signal sequence provides an amount of glucoamylase activity in the fermentation medium that is at least 1.125 times greater (12.5% greater) than a reference yeast. In some aspects the amount of glucoamylase activity is at least 1.15 times greater, at least 1.175 times greater, at least 1.225 times greater, at least 1.25 times greater, at least 1.3 times greater, at least 1.35 times greater, at least 1.4 times greater, at least 1.45 times greater, at least 1.5 times greater, at least 1.75 times greater, at least 2 times greater, at least 2.25 times greater, at least 2.5 times greater, at least 2.75 times greater, at least 3 times greater, at least 3.25 times greater, at least 3.5 times greater, at least 3.75 times greater, or at least 4 times greater in the non-natural yeast over the reference yeast. In some aspects the glucoamylase activity provided by non-natural yeast over the reference yeast in an amount in the range of about 1.15 to about 7.5 times greater, about 1.175 to about 7.5 times greater, about 1.225 to about 7.5 times greater, about 1.25 to about 7.5 times greater, about 1.3 to about 7.5 times greater, about 1.35 to about 7.5 times greater, about 1.4 to about 7.5 times greater, about 1.45 to about 7.5 times greater, about 1.5 to about 7.5 times greater, about 1.75 to about 7.5 times greater, about 2 to about 7.5 times greater, about 2.25 to about 7.5 times greater, about 2.5 to about 7.5 times greater, about 2.75 to about 7.5 times greater, about 3 to about 7.5 times greater, about 3.25 to about 7.5 times greater, about 3.5 to about 7.5 times greater, about 3.75 to about 7.5 times greater, or about 4 to about 7.5 times greater in the non-natural yeast over the reference yeast.

Measurement of glucoamylase activity in the fermentation medium can be performed at a desired time point during fermentation. For example, a sample from the fermentation media can be taken about $1/10^{th}$, about $2/10^{th}$, about $3/10^{th}$, about $4/10^{th}$, about $5/10^{th}$, about $6/10^{th}$, about $7/10^{th}$, about $8/10^{th}$, about $9/10^{th}$ of the way through the fermentation process, or at the end of the fermentation process, and the sample can be tested for glucoamylase activity.

In some modes of practice, the fermentation period is about 30 hours or greater, about 40 hours or greater, about 50 hours or greater, or about 60 hours or greater, such as a period of time in the range of about 40 to about 120 hours, or 50 to about 110 hours.

The fermentation product (also referred to herein as a "bio-derived product" or "bioproduct") can be any product that can be prepared by enzymatic degradation of a starch material by the glucoamylase, formation of glucose, and fermentation of glucose. In aspects, In an embodiment, the fermentation product is selected from the group consisting of: amino acids, organic acids, alcohols, diols, polyols, fatty acids, fatty acid alkyl esters (such as fatty acid methyl or ethyl esters (for example C6 to C12 fatty acid methyl esters (preferably C8 to C10 fatty acid methyl esters))), monacyl glycerides, diacyl glycerides, triacyl glycerides, and mixtures thereof. Preferred fermentation products are organic acids, amino acids, fatty acid alkyl esters (such as fatty acid methyl esters (for example C8 to C12 fatty acid methyl esters (preferably C8 to C10 fatty acid methyl esters))), and their salts thereof, and especially where the organic acid is selected from the group consisting of hydroxyl carboxylic acids (including mono-hydroxy and di-hydroxy mono-, di-, and tri-carboxylic acids), monocarboxylic acids, dicarboxylic acids, and tricarboxylic acids and mixtures thereof. Examples of fermentation products that are prepared by the present process are organic acids or amino acids such as lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, acetic acid, methyl hexanoate, methyl octanoate, methyl nonanoate, methyl decanoate, methyl dodecanoate, ethyl hexanoate, ethyl octanoate, ethyl nonanoate, ethyl decanoate, ethyl dodecanoate, and mixtures thereof and derivatives thereof and salts thereof. In a preferred aspect, a fermentation method of the disclosure produces ethanol as the bioproduct.

The fermentation product is recovered from the fermentation broth. The manner of accomplishing this will depend on the particular product. However, in some modes of practice, the organism is separated from the liquid phase, typically via a filtration step or centrifugation step, and the product recovered via, for example, distillation, extraction, crystallization, membrane separation, osmosis, reverse osmosis, or other suitable technique.

The present process provides the ability to make fermentation products on a production scale level with excellent yields and purity. In an aspect, the process is carried out in fermentation broth quantities of at least 25,000 gallons. In an aspect, the batch process is carried out in to produce batches of at least 25,000 gallons of final fermentation broth. In some aspects the process is a continuous process, performed in vessels of at least 200,000 gallons.

A composition comprising a heterologous secretion signal-glucoamylase can optionally be used in combination with any one or in any combination with the following enzymes that are different than the glucoamylase. Exemplary other enzymes include alpha amylases, beta-amylases, peptidases (proteases, proteinases, endopeptidases, exopeptidases), pullulanases, isoamylases, cellulases, hemicellulases, endo-glucanases and related beta-glucan hydrolytic accessory enzymes, xylanases and xylanase accessory enzymes, acetolactate decarboxylases, cyclodextrin glycotransferases, lipases, phytases, laccases, oxidases, esterases, cutinases, granular starch hydrolyzing enzymes and other glucoamylases.

In some aspects, a heterologous secretion signal-glucoamylase can be used for starch conversion processes, such as for the production of dextrose for fructose syrups, specialty sugars and in alcohol and other end-product (e.g., organic acid, ascorbic acid, and amino acids). Production of alcohol from the fermentation of starch substrates using glucoamylases of the disclosure can include the production of fuel alcohol or potable alcohol.

The production of alcohol can be greater when a heterologous secretion signal-glucoamylase of used under the same conditions as compared to the parent or wild-type glucoamylase. For example, the increase in alcohol production using the glucoamylases of the disclosure can be 1.1× or greater, 1.2× or greater, 1.3× or greater, 1.4× or greater, 1.5× or greater, 1.6× or greater, 1.7× or greater, 1.7× or greater, 1.8× or greater, 1.9× or greater, 2.0× or greater, 2.1× or greater, 2.2× or greater, 2.3× or greater, 2.4× or greater, or 2.5× or greater that alcohol production in a wild type strain.

In some aspects, the disclosure provides a method for producing ethanol by fermentation, wherein the ethanol is present in the fermentation medium at a concentration of 90 g/L or greater. In the method, a liquid medium comprising a starch material and a non-natural yeast comprising a exogenous nucleic acid encoding polypeptide comprising a glucoamylase portion and a signal sequence heterologous to the glucoamylase is fermented. Fermentation can provide an ethanol concentration of about 90 g/L or greater in the liquid medium, such as in the range of about 90 g/L to about 170 g/L, in the range of about 110 g/L to about 170 g/L, in the range of about 125 g/L to about 170 g/L, or in. in the range of about 140 g/L to about 170 g/L.

The method includes fermenting a liquid medium comprising a starch material and a non-natural yeast comprising a exogenous nucleic acid encoding polypeptide comprising a glucoamylase portion and a signal sequence heterologous to the glucoamylase, wherein said fermenting provides an ethanol concentration of 90 g/L or greater in the liquid medium.

Ethanol mass yield can be calculated by dividing the ethanol concentration by the total glucose consumed. Since glucose can be present as free glucose or tied up in oligomers, one needs to account for both. To determine the total glucose present at the beginning and end of fermentation, a total glucose equivalents measurement is determined. Total glucose equivalence measurement is as follows. Glucose is measured with HPLC using RI detection. Separation is completed with a Bio Rad 87H column using a 10 mM H2504 mobile phase. Glucose is measured in triplicate for each sample. An acid hydrolysis is performed in triplicate in 6% (v/v) trifluoroacetic acid at 121° C. for 15 minutes. The resulting glucose after hydrolysis is measured by the same HPLC method. The total glucose equivalents present in each sample is the amount of glucose measured after acid hydrolysis. The total glucose consumed is calculated by subtracting the total glucose equivalents present at the end of fermentation from the total glucose equivalents present at the beginning of the fermentation.

Use of the non-natural yeast of the current disclosure may also provide benefits with regards to increased titers, reduced volatile organic acids (VOCs), and reduced fusel oil compounds (volatile organic acids, higher alcohols, aldehydes, ketones, fatty acids and esters).

The fermentation product may be first treated with one or more agents a treatment system. The treated fermentation product can then be sent to a distillation system. In the distillation system, the fermentation product can be distilled and dehydrated into ethanol. In some aspects, the components removed from the fermentation medium include water, soluble components, oil and unfermented solids. Some of these components can be used for other purposes, such as for an animal feed product. Other co-products, for example, syrup can be recovered from the stillage.

The present disclosure also provides a method for the production of a food, feed, or beverage product, such as an alcoholic or non-alcoholic beverage, such as a cereal- or malt-based beverage like beer or whiskey, such as wine, cider, vinegar, rice wine, soya sauce, or juice, said method comprising the step of treating a starch and/or sugar containing plant material with a composition as described herein. In another aspect, the invention also relates to a kit comprising a glucoamylase of the current disclosure, or a composition as contemplated herein; and instructions for use of said glucoamylase or composition. The invention also relates to a fermented beverage produced by a method using the glucoamylase.

After the fermentation process is complete, materials present in the fermentation medium can be of use. In some aspects, after a fermentation process has been completed, or while a fermentation process is ongoing, some or all of a bioproduct can be removed from the fermentation medium to provide a refined composition comprising non-bioproduct solids. The non-bioproduct solids the non-natural yeast, feedstock material in the medium that is not utilized by the yeast, as well as fermentation co-products. These materials can provide sources of carbohydrates and proteins that are useful as supplements to improve the nutritional content of a feed composition. The feed material can be a co-product from a fermentation process such as stillage (whole stillage, thin stillage, etc.) or composition prepared therefrom including dried distillers grains (DDG), distillers dry grains with solubles (DDGS), distillers wet grains (DWG), and distillers solubles (DS).

A fermentation medium, optionally with some or all of the target bioproduct removed, can be further treated, such as to remove water, or to cause precipitation or isolation of the non-bioproduct solids from the medium. In some cases the medium is treated by freeze drying or oven drying. After treatment the refined composition may be in the form of, for example, a liquid concentrate, a semi-wet cake, or a dry solid. The refined composition can be used as a feed composition itself, or an ingredient in the preparation of a feed composition. In preferred preparations, the feed composition is a livestock feed composition such as for sheep, cattle, pigs, etc.

The solids in the fermentation medium can provide a source of one or more amino acids. Introduced into an animal feed, the fermentation co-product can provide an enhanced amino acid content with regard to one or more essential amino acids. Essential amino acids can include histidine, isoleucine, lysine, methionine, phenylalanine, threonine, and tryptophan. These amino acids can be present in the feed composition as free amino acids or can be derived from proteins or peptides rich in the amino acids. The solids in the fermentation medium can provide a source of one prebiotics, which are nondigestible food substances, such as nondigestible oligosaccharides, that selectively stimulate the growth of favorable species of bacteria in the gut, thereby benefitting the host. The solids in the fermentation medium can provide a source of phytases, β-glucanases, proteases, and xylanases.

The feed composition can be used in aquaculture, is the farming of aquatic organisms such as fish, shellfish, or plants. Aquaculture includes the cultivation of both marine and freshwater species and can range from land-based to open-ocean production.

A feed composition, in addition to material obtained from the fermentation media, can include one or more feed additives. Feed additives can be used, for example, to help provide a balanced diet (e.g., vitamins and/or trace minerals), to protect the animals from disease and/or stress (e.g., antibiotics, probiotics) and/or to stimulate or control growth and behavior (e.g., hormones). Additive product ingredients may include, for example: growth promoters, medicinal substances, buffers, antioxidants, enzymes, preservatives, pellet-binding agents, direct-fed microbials, etc. Additive product ingredients may also include, for example, ionophores (e.g. monesin, lasalocid, laidlomycin, etc.), β-agonist (zilpaterol, ractompamine, etc.), antibiotics (e.g., chlortetracycline (CTC), oxytetracycline, bacitrain, tylosin, aureomycin), probiotics and yeast cultures, coccidiostats (e.g., amprollium, decoquinate, lasalocid, monensin), and hormones (e.g., growth hormones or hormones that inhibit estrus and/or ovulation such as melengestrol acetate), pheromones, nutraceuticals, pharmaceuticals, flavanoids, nutritive and non-nutritive supplements, detoxicants, etc. Some commercially available additives are sold under the trade names Rumensin®, Bovatec®, Deccox®, Tylan®, Optaflexx®, and MGA®.

Example 1

Generation of a *Saccharomyces cerevisiae* Base Strain

Strain 1 is transformed with SEQ ID NO 1. SEQ ID NO 1 contains the following elements: 5' homology to integration locus A (1-436 bp), a loxP recombination site (445-478 bp), an expression cassette for a mutant version of a 3-deoxy-D-arabino-heptulosonate-7-phosphate (DAHP) synthase gene from *Saccharomyces cerevisiae* (ARO4-OFP) (479-20647 bp), a loxP recombination site (2648-2681 bp), and 3' homology to integration locus A (2691-3182 bp). Transformants are selected on synthetic complete media containing 3.5 g/L of p-fluorophenylalanine, and 1 g/L L-tyrosine (ScD-PFP). Resulting transformants are streaked for single colony isolation on ScD-PFP. A single colony is selected. Correct integration of SEQ ID NO 1 into one allele of locus A is verified by PCR in the single colony. A PCR verified isolate is designated Strain 1-1.

Stain 1-1 is transformed with SEQ ID NO 2. SEQ ID NO 2 contains the following elements: 5' homology to integration locus A (1-435 bp), a loxP recombination site (444-477 bp), an expression cassette for an acetamidase (amdS) gene from *Aspergillus nidulans* (478-2740 bp), a loxP recombination site (2741-2774 bp), 3' homology to integration locus A (2783-3275 bp). Transformants are selected on Yeast Nitrogen Base (without ammonium sulfate or amino acids) containing 80 mg/L uracil and 1 g/L acetamide as the sole nitrogen source (YNB+acetamide+uracil). Resulting transformants are streaked for single colony isolation on YNB+acetamide+uracil plates. A single colony is selected. Correct integration of SEQ ID NO 2 into the second allele of locus A is verified by PCR in the single colony. A PCR verified isolate is designated Strain 1-2.

Strain 1-2 is co-transformed with SEQ ID NO 3 and SEQ ID NO 4. SEQ ID NO 3 contains the following elements: an open reading frame for a cre recombinase from P1 bacteriophage (52-1083 bp), and flanking DNA homologous to SEQ ID NO 4. SEQ ID NO 4 contains the following elements: CYC1 terminator from *Saccharomyces cerevisiae* (10-199 bp), a 2μ origin of replication (2195-3350 bp), a URA3 selectable marker from *Saccharomyces cerevisiae* (3785-4901 bp), and a PGK promoter from *Saccharomyces cerevisiae* (5791-6376 bp). Transformants are selected on synthetic dropout media lacking uracil (ScD-Ura). Resulting transformants are streaked for single colony isolation on ScD-Ura. A single colony is selected. The isolated colony is screened for growth on ScD-PFP and YNB+acetamide+uracil. Loss of the ARO4-OFP and amdS genes is verified by PCR. The PCR verified isolate is streaked to YNB containing 1 g/L 5-fluoroorotic acid to select for loss of the 2μ plasmid. The PCR verified isolate is designated Strain 1-3.

Example 2

Construction of Strains Expressing Modified Fungal Glucoamylases

Strain 1-3 is co-transformed with SEQ ID NO 5 and SEQ ID NO 6. SEQ ID NO 5 contains the following elements:

linearized plasmid containing the ScCYC1 terminator (4-227), a ScURA3 expression cassette (952-2049 bp), the CEN6 centromere for stable replication (2308-2826 bp), a beta-lactamase (2958-3815 bp), and the ScTDH3 promoter (5052-5734 bp). SEQ ID NO 6 contains the following elements: homology to SEQ ID NO 5 (1-44 bp), and open reading frame expressing a codon optimized glucoamylase from *Aspergillus shirousami* (50-1969 bp), and homology to SEQ ID NO 5 (1975-2017 bp). Transformants are selected on ScD-Ura. A single colony isolate from each of the individual ScD-Ura transformations is obtained by streaking a colony from the ScD-Ura transformation plate onto similar media and incubating the plate for 1-2 days at 30° C. until single colonies arise. One isolate is saved as Strain 1-4.

Strain 1-3 is co-transformed with SEQ ID NO 5 and SEQ ID NO 7. SEQ ID NO 7 contains the following elements: homology to SEQ ID NO 5 (1-44 bp), and open reading frame expressing a codon optimized glucoamylase from *Aspergillus shirousami* with modified secretion signal (50-1966 bp), and homology to SEQ ID NO 5 (1972-2014 bp). Transformants are selected on ScD-Ura. A single colony isolate from each of the individual ScD-Ura transformations is obtained by streaking a colony from the ScD-Ura transformation plate onto similar media and incubating the plate for 1-2 days at 30° C. until single colonies arise. One isolate is saved as Strain 1-5.

Strain 1-3 is co-transformed with SEQ ID NO 5 and SEQ ID NO 8. SEQ ID NO 8 contains the following elements: homology to SEQ ID NO 5 (1-44 bp), and open reading frame expressing a codon optimized glucoamylase from *Aspergillus shirousami* with modified secretion signal (50-1972 bp), and homology to SEQ ID NO 5 (1978-2020 bp). Transformants are selected on ScD-Ura. A single colony isolate from each of the individual ScD-Ura transformations is obtained by streaking a colony from the ScD-Ura transformation plate onto similar media and incubating the plate for 1-2 days at 30° C. until single colonies arise. One isolate is saved as Strain 1-6.

Strain 1-3 is co-transformed with SEQ ID NO 5 and SEQ ID NO 9. SEQ ID NO 9 contains the following elements: homology to SEQ ID NO 5 (1-44 bp), and open reading frame expressing a codon optimized glucoamylase from *Aspergillus terreus* (50-1960 bp), and homology to SEQ ID NO 5 (1966-2008 bp). Transformants are selected on ScD-Ura. A single colony isolate from each of the individual ScD-Ura transformations is obtained by streaking a colony from the ScD-Ura transformation plate onto similar media and incubating the plate for 1-2 days at 30° C. until single colonies arise. One isolate is saved as Strain 1-7.

Strain 1-3 is co-transformed with SEQ ID NO 5 and SEQ ID NO 10. SEQ ID NO 10 contains the following elements: homology to SEQ ID NO 5 (1-44 bp), and open reading frame expressing a codon optimized glucoamylase from *Aspergillus terreus* with a modified secretion signal (50-1951 bp), and homology to SEQ ID NO 5 (1957-1999 bp). Transformants are selected on ScD-Ura. A single colony isolate from each of the individual ScD-Ura transformations is obtained by streaking a colony from the ScD-Ura transformation plate onto similar media and incubating the plate for 1-2 days at 30° C. until single colonies arise. One isolate is saved as Strain 1-8.

Strain 1-3 is co-transformed with SEQ ID NO 5 and SEQ ID NO 11. SEQ ID NO 11 contains the following elements: homology to SEQ ID NO 5 (1-44 bp), and open reading frame expressing a codon optimized glucoamylase from *Aspergillus terreus* with a modified secretion signal (50-1957 bp), and homology to SEQ ID NO 5 (1963-2005 bp). Transformants are selected on ScD-Ura. A single colony isolate from each of the individual ScD-Ura transformations is obtained by streaking a colony from the ScD-Ura transformation plate onto similar media and incubating the plate for 1-2 days at 30° C. until single colonies arise. One isolate is saved as Strain 1-9.

Strain 1-3 is co-transformed with SEQ ID NO 12. SEQ ID NO 12 contains the same elements as in SEQ ID NO 5 with the exception that the DNA is in circular form. Transformants are selected on ScD-Ura. A single colony isolate from each of the individual ScD-Ura transformations is obtained by streaking a colony from the ScD-Ura transformation plate onto similar media and incubating the plate for 1-2 days at 30° C. until single colonies arise. One isolate is saved as Strain 1-10.

Example 3

Small Scale Fermentation of Yeast Strains Expressing Modified Fungal Glucoamylases Strain 1-4 through 1-10 are struck to a ScD-Ura plate and incubated at 30° C. until single colonies are visible (1-2 days). A single colony is inoculated into 2 mls of media (consisting of 850 g liquifact, 150 g filter sterilized light steep water, 25 g glucose, 1 g urea) contained in a 15 ml falcon culture tube. Each tube is placed in a rotary shaker with an agitation of 100 rpm and a temperature of 30° C. After 48 hours, samples were taken and analyzed by HPLC to quantify ethanol production (Table 3). Table 3 demonstrates that both fungal glucoamylases tested are able to ferment more ethanol than the empty vector control, and the *Aspergillus shirousami* and *Aspergillus terreus* glucoamylases both benefit from the leader modification.

TABLE 3

Table showing ethanol titers from small scale tube fermentations. This data demonstrates the beneficial effects of the leader modifications on ethanol titer.

| Strain | Gene description | Signal sequence | Ethanol Titer (g/l) |
|---|---|---|---|
| 1-4 | *Aspergillus shirousami* glucoamylase | Native | 58.953 |
| 1-5 | *Aspergillus shirousami* glucoamylase | *Saccharomyces cerevisiae* Pho5 | 89.401 |
| 1-6 | *Aspergillus shirousami* glucoamylase | *Saccharomyces cerevisiae* Mfα2 | 73.811 |
| 1-7 | *Aspergillus terreus* glucoamylase | Native | 40.357 |
| 1-8 | *Aspergillus terreus* glucoamylase | *Saccharomyces cerevisiae* Pho5 | 46.082 |
| 1-9 | *Aspergillus terreus* glucoamylase | *Saccharomyces cerevisiae* Mfα2 | 73.530 |
| 1-10 | No glucoamylase | NA | 20.990 |

Example 4

Transformation of Strain 1-3 with Plasmids Expressing Wild Type and Signal Sequence Modified *Rhizopus oryzae* Glucoamylase Strain 1-3 is co-transformed with SEQ ID NO 5 and SEQ ID NO 13. SEQ ID NO 5 contains the following elements: the ScCYC1 terminator (4-227), linearized plasmid containing a ScURA3 expression cassette (952-2049 bp), the CEN6 centromere for stable replication (2308-2826 bp), a beta-lactamase (2958-3815 bp), and the ScTDH3 promoter (5052-5734 bp). SEQ ID NO 13 contains the following elements: homology to SEQ ID NO 5, and open reading frame expressing a codon optimized glucoamylase from *Rhizopus oryzae*, and homology to SEQ ID NO 5. Transformants are selected on ScD-Ura and replica plated to both ScD-Ura and Sc-Ura 1% starch (w/v). The resulting plates are shown in FIG. 1, Row A.

Strain 1-3 is co-transformed with SEQ ID NO 5 and SEQ ID NO 14. SEQ ID NO 14 contains the following elements: homology to SEQ ID NO 5, and open reading frame expressing a codon optimized glucoamylase from *Rhizopus oryzae* with a modified secretion signal, and homology to SEQ ID NO 5. Transformants are selected on ScD-Ura and replica plated to both ScD-Ura and Sc-Ura 1% starch (w/v). The resulting plates are shown in FIG. 1, Row B.

Strain 1-3 is co-transformed with SEQ ID NO 5 and SEQ ID NO 15. SEQ ID NO 15 contains the following elements: homology to SEQ ID NO 5, and open reading frame expressing a codon optimized glucoamylase from *Rhizopus oryzae* with a modified secretion signal, and homology to SEQ ID NO 5. Transformants are selected on ScD-Ura and replica plated to both ScD-Ura and Sc-Ura 1% starch (w/v). The resulting plates are shown in FIG. 1, Row C.

Strain 1-3 is co-transformed with SEQ ID NO 5 and SEQ ID NO 16. SEQ ID NO 16 contains the following elements: homology to SEQ ID NO 5, and open reading frame expressing a codon optimized glucoamylase from *Rhizopus oryzae* with a modified secretion signal, and homology to SEQ ID NO 5. Transformants are selected on ScD-Ura and replica plated to both ScD-Ura and Sc-Ura 1% starch (w/v). The resulting plates are shown in FIG. 1, Row D.

The results are shown in FIG. 1. This result demonstrates the improvement in growth resulting from the leader modification.

Example 5

Strains Expressing Either Wild Type or Modified *Rhizopus oryzae* Glucoamylase Strain 1-3 is transformed with SEQ ID NO 17. SEQ ID NO 17 contains: a ScTDH3 promoter (6-688 bp), a codon optimized glucoamylase from *Rhizopus oryzae* with a modified secretion signal (695-2491 bp), a ScCYC1 terminator (2500-2723 bp), a ScURA3 expression cassette (3448-4545 bp), a centromere for stable replication, CEN6 (4804-5322 bp), and a beta-lactamase (5454-6311 bp). Transformants are selected on synthetic dropout media lacking uracil (ScD-Ura). Resulting transformants are streaked for single colony isolation on ScD-Ura. A single colony is selected. A PCR verified isolate is saved as Strain 1-4.

Strain 1-3 is transformed with SEQ ID NO 18. SEQ ID NO 18 contains: a ScTDH3 promoter (1-683 bp), a codon optimized glucoamylase from *Rhizopus oryzae* with a native secretion signal (685-2509 bp), a ScCYC1 terminator (2513-2736 bp), a ScURA3 expression cassette (3461-4558 bp), a centromere for stable replication, CEN6 (4817-5335 bp), and a beta-lactamase (5467-6324 bp). Transformants are selected on synthetic dropout media lacking uracil (ScD-Ura). Resulting transformants are streaked for single colony isolation on ScD-Ura. A single colony is selected. A PCR verified isolate is saved as Strain 1-5.

Strain 1-3 is transformed with SEQ ID NO 12. Transformants are selected on synthetic dropout media lacking uracil (ScD-Ura). Resulting transformants are streaked for single colony isolation on ScD-Ura. A single colony is selected. A PCR verified isolate is saved as Strain 1-6.

Example 6

Figure 2:
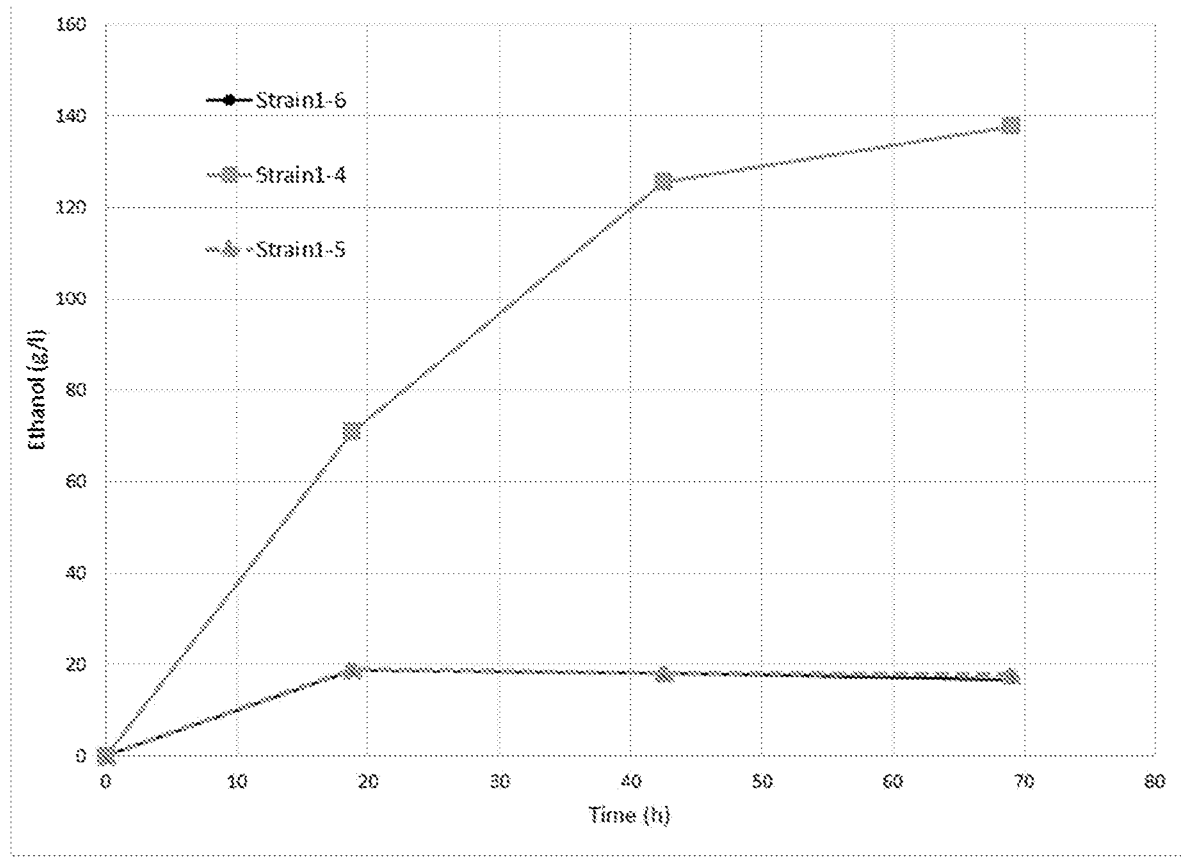
FIG. 2 is a graph of ethanol production over time from fermentations with strains containing a modified glucoamylase from *Rhizopus oryzae*, a wild type *Rhizopus oryzae* glucoamylase, and a strain lacking a glucoamylase.

SSF Fermentations Comparing Strain 1-4 and Strain 1-5, Expressing Either the Wild Type or Modified *Rhizopus oryzae* Glucoamylase Strain 1-4, Strain 1-5, and Strain 1-6 are struck to a ScD-Ura plate and incubated at 30° C. until single colonies are visible (1-2 days). Cells from the ScD-Ura plate are scraped into sterile shake flask medium and the optical density ($OD_{600}$) is measured. Optical density is measured at wavelength of 600 nm with a 1 cm path length using a model Genesys20 spectrophotometer (Thermo Scientific). A shake flask is inoculated with the cell slurry to reach an initial $OD_{600}$ of 0.1-0.3. Immediately prior to inoculating, 50 mL of shake flask medium is added to a 250 mL non-baffled shake flask (Corning 4995-250) fitted with a screw cap containing a gas-permeable seal (corning 1395-45LTMC) The shake flask medium consists of 725 g partially hydrolyzed corn starch in the form of liquifact, 150 g filtered light steep water, 50 g water, 25 g glucose, and 1 g urea. Duplicate flasks for each strain are incubated at 30° C. with shaking in an orbital shake at 100 rpm for 69 hours. Samples are taken and analyzed for relevant metabolite concentrations in the broth during fermentation by HPLC. The ethanol production profile is shown in FIG. 2. This demonstrates that the wild type *Rhizopus oryzae* glucoamylase is not functional as it produces equivalent ethanol as a control strain lacking a glucoamylase. This also demonstrates that the secretion signal modification significantly improves ethanol production.

Example 7

Evaluating Additional Leader Modifications to the *Rhizopus oryzae* Glucoamylase Strain 1-3 is transformed with SEQ ID NO 19. SEQ ID NO 19 contains the following elements: an expression cassette for a modified glucoamylase gene from *Rhizopus oryzae* containing an N-terminal secretion leader from alpha mating factor (FAKS) corresponding to nucleotides 695-2701, including a TDH3 promoter corresponding to nucleotides 6-668 and a CYC1 terminator corresponding to nucleotides 2710-2933, a centromere to allow for stable replication (CEN6) corresponding to nucleotides 5014-5532, and an expression cassette for an orotidine-5'-phosphate decarboxylase (URA3) corresponding to nucleotides 4755-3739. SEQ ID NO 19 also includes an ampicillin resistance gene corresponding to nucleotides 5664-6521. Transformants are selected on ScD-Ura. Resulting transformants are streaked for single colony isolation on ScD-Ura. A single colony is selected. Presence of the plasmid is verified by PCR. The PCR verified isolate is designated Strain 1-7.

Strain 1-3 is transformed with SEQ ID NO 20. SEQ ID NO 20 contains the following elements: an expression cassette for a modified glucoamylase gene from *Rhizopus oryzae* containing an N-terminal secretion leader from alpha mating factor (AKS) corresponding to nucleotides 695-2617, including a TDH3 promoter corresponding to nucleotides 6-668 and a CYC1 terminator corresponding to nucleotides 2626-2849, a centromere to allow for stable replication (CEN6) corresponding to nucleotides 4930-5448, and an expression cassette for an orotidine-5'-phosphate decarboxylase (URA3) corresponding to nucleotides 4671-3655. SEQ ID NO 20 also includes an ampicillin resistance gene corresponding to nucleotides 5580-6437. Transformants are selected on ScD-Ura. Resulting transformants are streaked for single colony isolation on ScD-Ura. A single colony is selected. Presence of the plasmid is verified by PCR. The PCR verified isolate is designated Strain 1-8.

Strain 1-3 is transformed with SEQ ID NO 21. SEQ ID NO 21 contains the following elements: an expression cassette for a modified glucoamylase gene from *Rhizopus oryzae* containing an N-terminal secretion leader from alpha mating factor (AK) corresponding to nucleotides 695-2605, including a TDH3 promoter corresponding to nucleotides 6-668 and a CYC1 terminator corresponding to nucleotides 2614-2837, a centromere to allow for stable replication (CEN6) corresponding to nucleotides 4918-5436, and an expression cassette for an orotidine-5'-phosphate decarboxylase (URA3) corresponding to nucleotides 4659-3643. SEQ ID NO 21 also includes an ampicillin resistance gene corresponding to nucleotides 5568-6425. Transformants are selected on ScD-Ura. Resulting transformants are streaked for single colony isolation on ScD-Ura. A single colony is selected. Presence of the plasmid is verified by PCR. The PCR verified isolate is designated Strain 1-9.

Strain 1-3 is transformed with SEQ ID NO 22. SEQ ID NO 22 contains the following elements: an expression cassette for a modified glucoamylase gene from *Rhizopus oryzae* containing an N-terminal secretion leader from alpha factor T (AT) corresponding to nucleotides 695-2491, including a TDH3 promoter corresponding to nucleotides 6-668 and a CYC1 terminator corresponding to nucleotides 2500-2723, a centromere to allow for stable replication (CEN6) corresponding to nucleotides 4804-3522, and an expression cassette for an orotidine-5'-phosphate decarboxylase (URA3) corresponding to nucleotides 4545-3529. SEQ ID NO 22 also includes an ampicillin resistance gene corresponding to nucleotides 5454-6311. Transformants are selected on ScD-Ura. Resulting transformants are streaked for single colony isolation on ScD-Ura. A single colony is selected. Presence of the plasmid is verified by PCR. The PCR verified isolate is designated Strain 1-10.

Strain 1-3 is transformed with SEQ ID NO 23. SEQ ID NO 23 contains the following elements: an expression cassette for a modified glucoamylase gene from *Rhizopus oryzae* containing an N-terminal secretion leader from alpha amylase (AA) corresponding to nucleotides 695-2494, including a TDH3 promoter corresponding to nucleotides 6-668 and a CYC1 terminator corresponding to nucleotides 2503-2726, a centromere to allow for stable replication (CEN6) corresponding to nucleotides 4807-5325, and an expression cassette for an orotidine-5'-phosphate decarboxylase (URA3) corresponding to nucleotides 4548-3532. SEQ ID NO 23 also includes an ampicillin resistance gene corresponding to nucleotides 5457-6314. Transformants are selected on ScD-Ura. Resulting transformants are streaked for single colony isolation on ScD-Ura. A single colony is selected. Presence of the plasmid is verified by PCR. The PCR verified isolate is designated Strain 1-11.

Strain 1-3 is transformed with SEQ ID NO 24. SEQ ID NO 24 contains the following elements: an expression cassette for a modified glucoamylase gene from *Rhizopus oryzae* containing an N-terminal secretion leader from *Aspergillus awamori* glucoamylase (GA) corresponding to nucleotides 695-2488, including a TDH3 promoter corresponding to nucleotides 6-668 and a CYC1 terminator corresponding to nucleotides 2497-3720, a centromere to allow for stable replication (CEN6) corresponding to nucleotides 4801-5319, and an expression cassette for an orotidine-5'-phosphate decarboxylase (URA3) corresponding to nucleotides 4542-3526. SEQ ID NO 24 also includes an ampicillin resistance gene corresponding to nucleotides 5451-6308. Transformants are selected on ScD-Ura. Resulting transformants are streaked for single colony isolation on ScD-Ura. A single colony is selected. Presence of the plasmid is verified by PCR. The PCR verified isolate is designated Strain 1-12.

Strain 1-3 is transformed with SEQ ID NO 25. SEQ ID NO 25 contains the following elements: an expression cassette for a modified glucoamylase gene from *Rhizopus oryzae* containing an N-terminal secretion leader from inulinase (IN) corresponding to nucleotides 695-2482, including a TDH3 promoter corresponding to nucleotides 6-668 and a CYC1 terminator corresponding to nucleotides 2491-2714, a centromere to allow for stable replication (CEN6) corresponding to nucleotides 4795-5313, and an expression cassette for an orotidine-5'-phosphate decarboxylase (URA3) corresponding to nucleotides 4536-3520. SEQ ID NO 25 also includes an ampicillin resistance gene corresponding to nucleotides 5445-6302. Transformants are selected on ScD-Ura. Resulting transformants are streaked for single colony isolation on ScD-Ura. A single colony is selected. Presence of the plasmid is verified by PCR. The PCR verified isolate is designated Strain 1-13.

Strain 1-3 is transformed with SEQ ID NO 26. SEQ ID NO 26 contains the following elements: an expression cassette for a modified glucoamylase gene from *Rhizopus oryzae* containing an N-terminal secretion leader from invertase (IV) corresponding to nucleotides 695-2491, including a TDH3 promoter corresponding to nucleotides 6-668 and a CYC1 terminator corresponding to nucleotides 2500-2723, a centromere to allow for stable replication (CEN6) corresponding to nucleotides 4804-5322, and an expression cassette for an orotidine-5'-phosphate decarboxylase (URA3) corresponding to nucleotides 4545-3529. SEQ ID NO 26 also includes an ampicillin resistance gene corresponding to nucleotides 5454-6311. Transformants are selected on ScD-Ura. Resulting transformants are streaked for single colony isolation on ScD-Ura. A single colony is selected. Presence of the plasmid is verified by PCR. The PCR verified isolate is designated Strain 1-14.

Strain 1-3 is transformed with SEQ ID NO 27. SEQ ID NO 27 contains the following elements: an expression cassette for a modified glucoamylase gene from *Rhizopus oryzae* containing an N-terminal secretion leader from lyzozyme (LZ) corresponding to nucleotides 695-2512, including a TDH3 promoter corresponding to nucleotides 6-668 and a CYC1 terminator corresponding to nucleotides 2521-2744, a centromere to allow for stable replication (CEN6) corresponding to nucleotides 4825-5343, and an expression cassette for an orotidine-5'-phosphate decarboxylase (URA3) corresponding to nucleotides 4566-3550. SEQ ID NO 27 also includes an ampicillin resistance gene corresponding to nucleotides 5475-6332. Transformants are selected on ScD-Ura. Resulting transformants are streaked for single colony isolation on ScD-Ura. A single colony is selected. Presence of the plasmid is verified by PCR. The PCR verified isolate is designated Strain 1-15.

Strain 1-3 is transformed with SEQ ID NO 28. SEQ ID NO 28 contains the following elements: an expression cassette for a modified glucoamylase gene from *Rhizopus oryzae* containing an N-terminal secretion leader from albumin (SA) corresponding to nucleotides 695-2488, including a TDH3 promoter corresponding to nucleotides 6-668 and a CYC1 terminator corresponding to nucleotides 2497-2720, a centromere to allow for stable replication (CEN6) corresponding to nucleotides 4801-5319, and an expression cassette for an orotidine-5'-phosphate decarboxylase (URA3) corresponding to nucleotides 4542-3526. SEQ ID NO 28 also includes an ampicillin resistance gene corresponding to nucleotides 5451-6308. Transformants are selected on ScD-Ura. Resulting transformants are streaked for single colony isolation on ScD-Ura. A single colony is selected. Presence of the plasmid is verified by PCR. The PCR verified isolate is designated Strain 1-16.

Example 8

SSF Fermentation Testing Additional Leader Modifications to the *Rhizopus oryzae* Glucoamylase Strains 1-6 through 1-16 are struck onto a ScD-Ura plate and incubated at 30° C. until single colonies are visible (1-2 days). Cells from the ScD-Ura plate are scraped into sterile shake flask medium and the optical density ($OD_{600}$) is measured. Optical density is measured at wavelength of 600 nm with a 1 cm path length using a model Genesys20 spectrophotometer (Thermo Scientific).

A shake flask is inoculated with the cell slurry to reach an initial $OD_{600}$ of 0.1-0.3. Immediately prior to inoculating, 50 g of shake flask medium is added to a 250 mL non-baffled shake flask (Corning 4995-250) fitted with a screw cap containing a gas-permeable seal (corning 1395-45LTMC) The shake flask medium consists of 725 g partially hydrolyzed corn starch in the form of liquifact, 150 g filtered light steep water, 25 g glucose, and 1 g urea (Sigma U6504). Shake flasks are weighed before and after filling with media and inoculation. Pre-fill/inoculation weight is subtracted from post-fill/inoculation weight to establish a starting shake flask weight.

Figure 3:
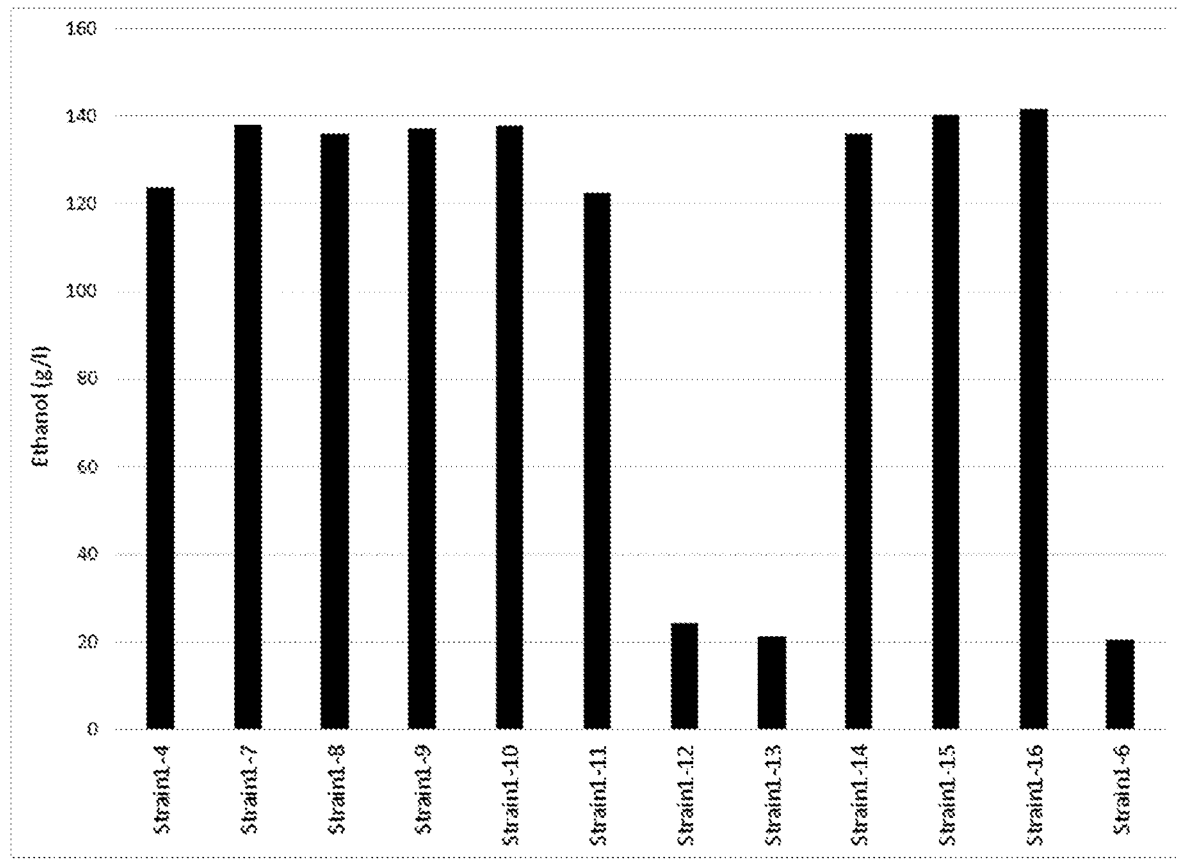
FIG. 3 is a graph of ethanol titers at final time point for strains expressing a modified *Rhizopus oryzae* glucoamylase.

The inoculated flask is incubated at 33.3° C., shaking in an orbital shaker at 100 rpm for 74 hours. Final time points are taken and analyzed for ethanol concentrations in the broth by high performance liquid chromatography with refractive index detector. The results of the shake flask experiments are shown in FIG. 3. These results demonstrate the effectiveness of additional leader modifications to the *Rhizopus oryzae* glucoamylase, with the exception of the GA and IN leaders, all modifications result in strains capable of producing more than 120 g/L ethanol in the given time frame.

Example 9

Construction of a Strain Containing Overexpression of an Endogenous Isomaltase and Heterologous Maltose Transporter Strain 1-3 is transformed with SEQ ID NO 29. SEQ ID NO 29 contains the following elements: homology to integration locus B (1-303 bp), a ScPGK1 promoter (309-895 bp), a codon optimized *Saccharomyces cerevisiae* isomaltose (902-2671 bp), a ScGAL10 terminator (2680-2935 bp), a loxP recombination site (2978-3011 bp), a ScURA3 expression cassette (3012-4641 bp), a loxP recombination site (4642-4675 bp), a ScADH1 promoter (4690-5435 bp), a *Saccharomyces mikatae* maltose transporter (5436-7289 bp), a ScCYC1 terminator (7299-7521 bp), and homology to integration locus B. Transformants are selected on synthetic complete media lacking uracil. (ScD-Ura). Resulting transformants are streaked for single colony isolation on ScD-Ura. A single colony is selected. Correct integration of SEQ ID NO 29 into one allele of integration locus B is verified by PCR in the single colony. A PCR verified isolate is designated Strain 1-17.

Strain 1-17 is transformed with SEQ ID NO 30. SEQ ID NO 30 contains the following elements: homology to integration locus B (2-303 bp), a ScPGK1 promoter (309-895 bp), a codon optimized *Saccharomyces cerevisiae* isomaltase (902-2671 bp), a ScGAL10 terminator (2680-2935 bp), a loxP recombination site (2985-3018 bp), a ScTEF1 terminator (3019-3178 bp), a *Aspergillus nidulans* acetamidase (3179-4825 bp), a ScTEF1 promoter (4826-5281 bp), a loxP recombination site (5282-5315 bp), a ScCYC1 terminator (5324-5547 bp), a *Saccharomyces mikatae* maltose transporter (5556-7409 bp), a ScADH1 promoter (7410-8148 bp), and homology to integration locus B (8155-8685 bp). Transformants are selected on Yeast Nitrogen Base (without ammonium sulfate or amino acids) containing 20 g/L glucose and 1 g/L acetamide as the sole nitrogen source (YNB+acetamide). Resulting transformants are streaked for single colony isolation on YNB+acetamide. A single colony is selected. Correct integration of SEQ ID NO 30 into the second allele of integration locus B is verified by PCR in the single colony. A PCR verified isolate is designated Strain 1-18.

Strain 1-18 is transformed with SEQ ID NO 31. SEQ ID NO 31 contains the following elements: 1) an expression cassette for a mutant version of a 3-deoxy-D-arabino-heptulosonate-7-phosphate (DAHP) synthase gene from *Saccharomyces cerevisiae* (ARO4-OFP), 2) an expression cassette for a cre recombinase from P1 bacteriophage; 3) an expression cassette containing the native URA3, and 4) the *Saccharomyces cerevisiae* CEN6 centromere. Transformants are selected on synthetic complete media containing 3.5 g/L of p-fluorophenylalanine, and 1 g/L L-tyrosine (ScD-PFP). Resulting transformants are streaked for single colony isolation on ScD-PFP. A single colony is selected. The PCR verified isolate is designated Strain 1-19.

Example 10

Construction of Strains Containing Multiple Copies of the *Aspergillus shirousami* Glucoamylase with a Modified Secretion Signal in Strain 1-19

Strain 1-19 is transformed with SEQ ID NO 32 and SEQ ID NO 33. SEQ ID NO 32 contains the following elements: homology to integration locus C (2-1003 bp), a ScTDH3 promoter (1010-1691 bp), a *Aspergillus shirousami* glucoamylase containing a modified signal sequence (1698-3614 bp), a ScCYC1 terminator (3623-3846 bp), a loxP recombination site (3855-3888 bp), a ScURA3 promoter (3889-4395 bp), and the upstream portion of the ScURA3 gene (4396-4999 bp). SEQ ID NO 33 contains the following elements: the downstream portion of the ScURA3 gene (7-606 bp), a URA3 terminator (607-927 bp), a loxP recombination site (928-961 bp), an ADH1 promoter (968-1714 bp), a *Aspergillus shirousami* glucoamylase containing a modified signal sequence (1721-3637 bp), a GAL10 terminator (3646-4116 bp), and homology to integration locus C (4125-5124 bp). Transformants are selected on synthetic complete media lacking uracil. (ScD-Ura). Resulting transformants are streaked for single colony isolation on ScD-Ura. A single colony is selected. Correct integration of SEQ ID NO 32 and SEQ ID NO 33 into one allele of integration locus C is verified by PCR in the single colony. A PCR verified isolate is designated Strain 1-20.

Strain 1-20 is transformed with SEQ ID NO 34 and SEQ ID NO 35. SEQ ID NO 34 contains the following elements: homology to integration locus C (2-1003 bp), a ScTDH3 promoter (1010-1691 bp), an *Aspergillus shirousami* glucoamylase containing a modified signal sequence (1698-3614 bp), a ScCYC1 terminator (3623-3846 bp), a loxP recombination site (3855-3888 bp), a ScTEF1 promoter (3889-4344 bp), and the upstream portion of the *Aspergillus nidulans* acetamidase (4345-5384 bp). SEQ ID NO 35 contains the following elements: the downstream portion of the *Aspergillus nidulans* amdS (7-1032 bp), a ScADH1 terminator (1033-1335 bp), a loxP recombination site (1336-1369 bp), a ScADH1 promoter (1376-2123 bp), an *Aspergillus shirousami* glucoamylase with a modified signal sequence (2129-4045 bp), a ScGAL10 terminator (4054-4524 bp), and homology to integration locus C (4533-5532 bp). Transformants are selected on Yeast Nitrogen Base (without ammonium sulfate or amino acids) containing 20 g/L glucose and 1 g/L acetamide as the sole nitrogen source. Resulting transformants are streaked for single colony isolation on Yeast Nitrogen Base (without ammonium sulfate or amino acids) containing 20 g/l glucose and 1 g/L acetamide as the sole nitrogen source. A single colony is selected. Correct integration of SEQ ID NO 35 and SEQ ID NO 57 into the second allele of integration locus C is verified by PCR in the single colony. A PCR verified isolate is designated as Strain 1-21.

Example 11

Construction of Strains Containing Multiple Copies of the *Rhizopus oryzae* Glucoamylase with a Modified Secretion Signal in Strain 1-19 and in Strain 1-3

Strain 1-3 is transformed with SEQ ID NO 36 and SEQ ID NO 37. SEQ ID NO 36 contains the following elements: homology to integration locus C (2-1003 bp), a ScTDH3 promoter (1010-1691 bp), a *Rhizopus oryzae* glucoamylase with modified signal sequence (1698-3494 bp), a ScCYC1 terminator (3503-3726 bp), a loxP recombination site (3735-3768 bp), a ScURA3 promoter (3769-4275 bp), the upstream portion of the ScURA3 (4276-4879 bp). SEQ ID NO 37 contains the following elements: downstream portion of the ScURA3 (7-606 bp), a ScURA3 terminator (607-927 bp), a loxP recombination site (928-961 bp), a ScADH1 promoter (968-1714 bp), a *Rhizopus oryzae* glucoamylase with modified signal sequence (1720-3516 bp), a ScGAL10 terminator (3525-3995 bp), and homology to integration locus C. Transformants are selected on synthetic complete media lacking uracil. (ScD-Ura). Resulting transformants are streaked for single colony isolation on ScD-Ura. A single colony is selected. Correct integration of SEQ ID NO 36 and SEQ ID NO 37 into one allele of integration locus C is verified by PCR in the single colony. A PCR verified isolate is designated Strain 1-22.

Strain 1-22 is transformed with SEQ ID NO 38 and SEQ ID NO 39. SEQ ID NO 38 contains the following elements: homology to integration locus C (2-1003 bp), a ScTDH3 promoter (1010-1691 bp), a *Rhizopus oryzae* glucoamylase with modified signal sequence (1698-3494 bp), a ScCYC1 terminator (3503-3726 bp), a loxP recombination site (3735-3768 bp), a ScTEF1 promoter (3769-4224 bp), and the upstream portion of the *Aspergillus nidulans* acetamidase (4225-5264 bp). SEQ ID NO 39 contains the following elements: the downstream portion of the *Aspergillus nidulans* acetamidase (7-1032 bp), a ScADH1 terminator (1033-1335 bp), a loxP recombination site (1336-1369 bp), a ScADH1 promoter (1376-2123 bp), a *Rhizopus oryzae* glucoamylase with modified signal sequence (2129-3925 bp), a ScGAL10 terminator (3934-4404 bp), and homology to integration locus C. Transformants are selected on Yeast Nitrogen Base (without ammonium sulfate or amino acids) containing 20 g/L glucose and 1 g/L acetamide as the sole nitrogen source. Resulting transformants are streaked for single colony isolation on Yeast Nitrogen Base (without ammonium sulfate or amino acids) containing 20 g/l glucose and 1 g/L acetamide as the sole nitrogen source. A single colony is selected. Correct integration of SEQ ID NO 38 and SEQ ID NO 39 into the second allele of is verified by PCR in the single colony. A PCR verified isolate is designated Strain 1-23.

Strain 1-19 is transformed with SEQ ID NO 36 and SEQ ID NO 37. Transformants are selected on synthetic complete media lacking uracil. (ScD-Ura). Resulting transformants are streaked for single colony isolation on ScD-Ura. A single colony is selected. Correct integration of SEQ ID NO 36 and SEQ ID NO 37 into one allele of integration locus C is verified by PCR in the single colony. A PCR verified isolate is designated Strain 1-24. Strain 1-24 is transformed with SEQ ID NO 38 and SEQ ID NO 39. Transformants are selected on YNB+acetamide plates. Resulting transformants are streaked for single colony isolation on YNB+acetamide. A single colony is selected. Correct integration of SEQ ID NO 38 and SEQ ID NO 39 into the second allele of integration locus C is verified by PCR in the single colony. A PCR verified isolate is designated Strain 1-25.

Example 12

Figure 4:
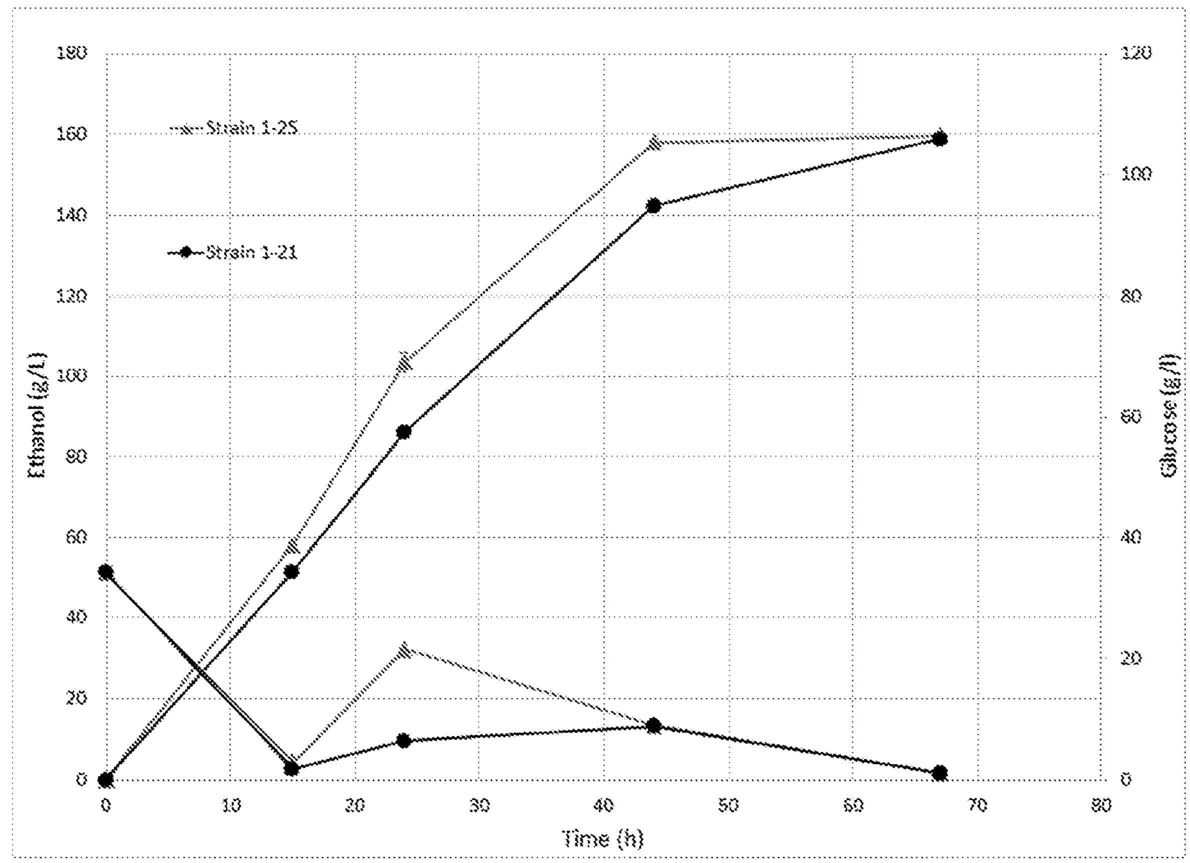
FIG. 4 is a graph of ethanol and glucose profiles for strains expressing multiple copies of secretion signal modified glucoamylases.

SSF Fermentation for Strains Containing Multiple Copies of the Pho5-As GA and Mfα2-Ro GA Versus Sf GA Strain 1-25 and Strain 1-21 are struck to a YPD plate and incubated at 30° C. until single colonies are visible (1-2 days). Cells from the YPD plate are scraped into sterile shake flask medium and the optical density ($OD_{600}$) is measured. Optical density is measured at wavelength of 600 nm with a 1 cm path length using a model Genesys20 spectrophotometer (Thermo Scientific). A shake flask is inoculated with the cell slurry to reach an initial $OD_{600}$ of 0.1-0.3. Immediately prior to inoculating, 50 mL of shake flask medium is added to a 250 mL non-baffled shake flask (Corning 4995-250) fitted with a screw cap containing a gas-permeable seal (corning 1395-45LTMC) The shake flask medium consists of 800 g partially hydrolyzed corn starch in the form of liquifact, 150 g filtered light steep water, 50 g water, 25 g glucose, and 1 g urea. Duplicate flasks for each strain are incubated at 30° C. with shaking in an orbital shake at 100 rpm for 67 hours. Samples are taken and analyzed for relevant metabolite concentrations in the broth during fermentation by HPLC. FIG. 4 shows the ethanol production profiles. This result demonstrates the ability of the engineered GA-expressing strains to produce high ethanol titers without the need to supplement GA. A similar fermentation with a commercial wild type strain supplemented with a commercial glucoamylase will reach similar titers in a similar time frame.

Example 13

Corn Mash Fermentations Using Gas Permeable Membrane Caps at 30° C. and 33.3° C.

Figure 5:
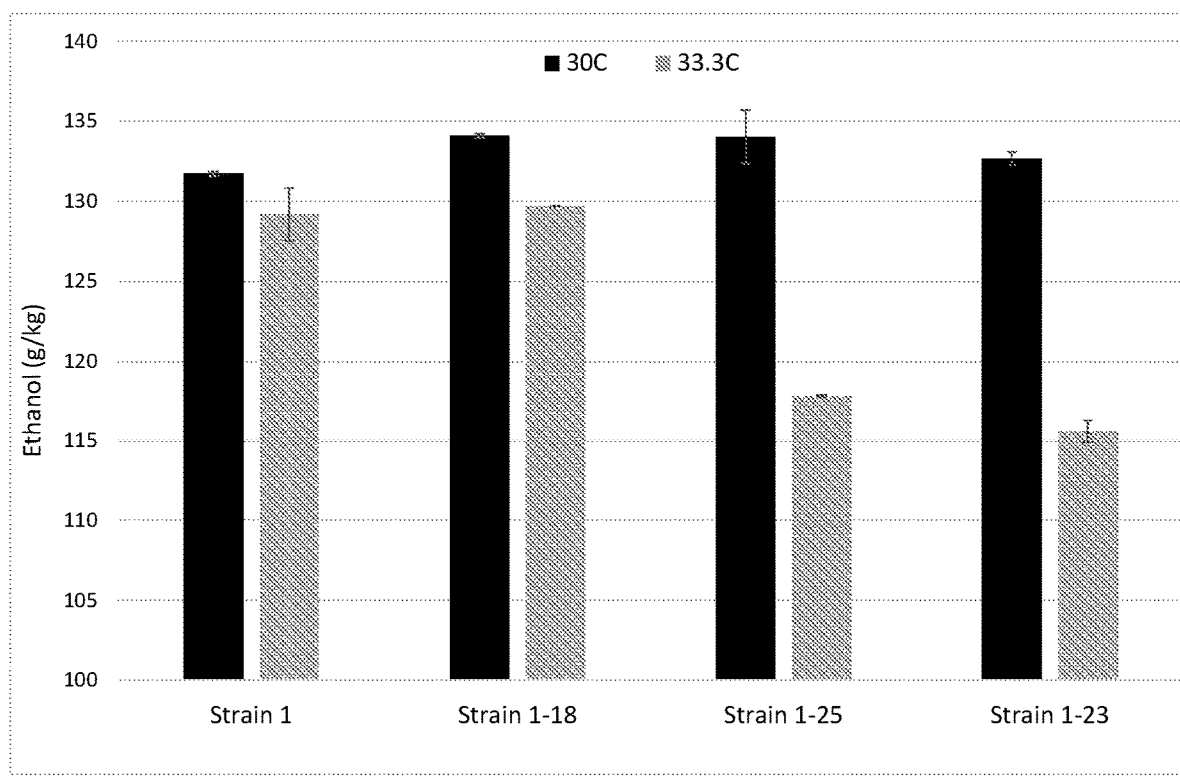
FIG. 5 is a graph of ethanol levels from corn mash fermentations comparing secretion signal modified glucoamylase expressing strains.

Strain 1, Strain 1-18, Strain 1-25, and Strain 1-23 are struck to a YPD plate and incubated at 30° C. until single colonies are visible (1-2 days). A single colony from each strain is inoculated into a 250 ml seed flask containing 50 mls of YPD (10 g/L yeast extract, 20 g/L peptone, 100 g/L glucose) and grown overnight at 30° C. and 250 RPM. 50 grams of liquified corn mash is weighed into a pre-weighed 250 ml baffled screw-cap shake flask (Corning 4995-250), fitted with a screw cap containing a gas permeable seal (Corning 1395-45LTMC). 0.190 mls of a 50% (w/v) urea solution is added to each flask. 25 ul of a 10 mg/ml ampicillin solution is added to each flask. 70 μl of a 1:10 dilution of Spirizyme™ is added to flasks containing Strain 1 and Strain 1-18. Finally, an appropriate amount of seed inoculum from an overnight culture is added to target an initial $OD_{600}$ of 0.1. The weight of the flask is recorded. Flask are incubated at both 30° C. and 33.3 C with 100 RPM agitation. Each strain is run in duplicate. Flasks are weighed periodically to calculate weight loss, which can be converted to ethanol using methods known in the art. Time final samples, at 67.75 hours are submitted for HPLC. FIG. 5 demonstrates the benefit of the ScIMA1 and SmMAL11 at 30° C., Strain 1-18 produces 2.4 g/L more ethanol than Strain 1. FIG. 5 demonstrates strains expressing secretion signal modified *Rhizopus oryzae* glucoamylase achieve at least as much ethanol as Strain 1 supplemented with a commercial glucoamylase. FIG. 5 also shows the reduction of ethanol titers when the temperature is increased to 33.3° C. in all backgrounds. The effect is more pronounced in the glucoamylase expressing strains. At this temperature, strains expressing the secretion signal modified *Rhizopus oryzae* GA produce 8.8% (Strain 1-25) or 10.5% (Strain 1-21) less ethanol than Strain 1.

Corn mash (or liquefied corn mash) can be prepared as follows: A predetermined amount of yellow dent #2 corn is milled and passed through a US #20 sieve. Overs (twice-ground corn that was retained on a US #20 sieve) are added back at a X:Y ratio of overs to sieved corn (0.020 overs/total corn mass ratio). The moisture content is measured by the halogen moisture balance method to determine the dry weight of the milled corn. Water is added to create a 32% slurry (w/w, dry weight basis). Concentrated sulfuric acid is added to reach a pH between 5.7-5.9. Calcium chloride dihydrate powder is added to achieve a Calcium concentration of 35 ppm. Amylase (Liquozyme™ Novozymes Liquozyme Supra 2.2X) is added based on the corn dry starch weight at a dosage ratio of 2.84 kg/ton dry basis starch dosage and the slurry is transferred to a Buchi Rotovapor R-220 flask equipped with an oil bath preset at 120° C. The reaction is allowed to proceed for 2 hours, stopping once the dextrose equivalents (DE) reaches 30+/−2 by reducing the temperature to between 34-36° C. The pH is adjusted to 5.0 with additional concentrated sulfuric acid. The DE can be determined by using an osmometer (Advanced™ Model 3D3 and Precion system Model Osmette XL™). Sugar and oligocarbohydrates contents are determined using HPLC with Aminex HPX-87H column (300 mm×7.8 mm) at 60 C, 0.01N sulfuric acid mobile phase, 0.6 mL/min flow rate.

Example 14

Corn Mash Fermentations Using Flasks Fitted with Air-Lock Stoppers at 30° C. and 33.3° C.

Figure 6:
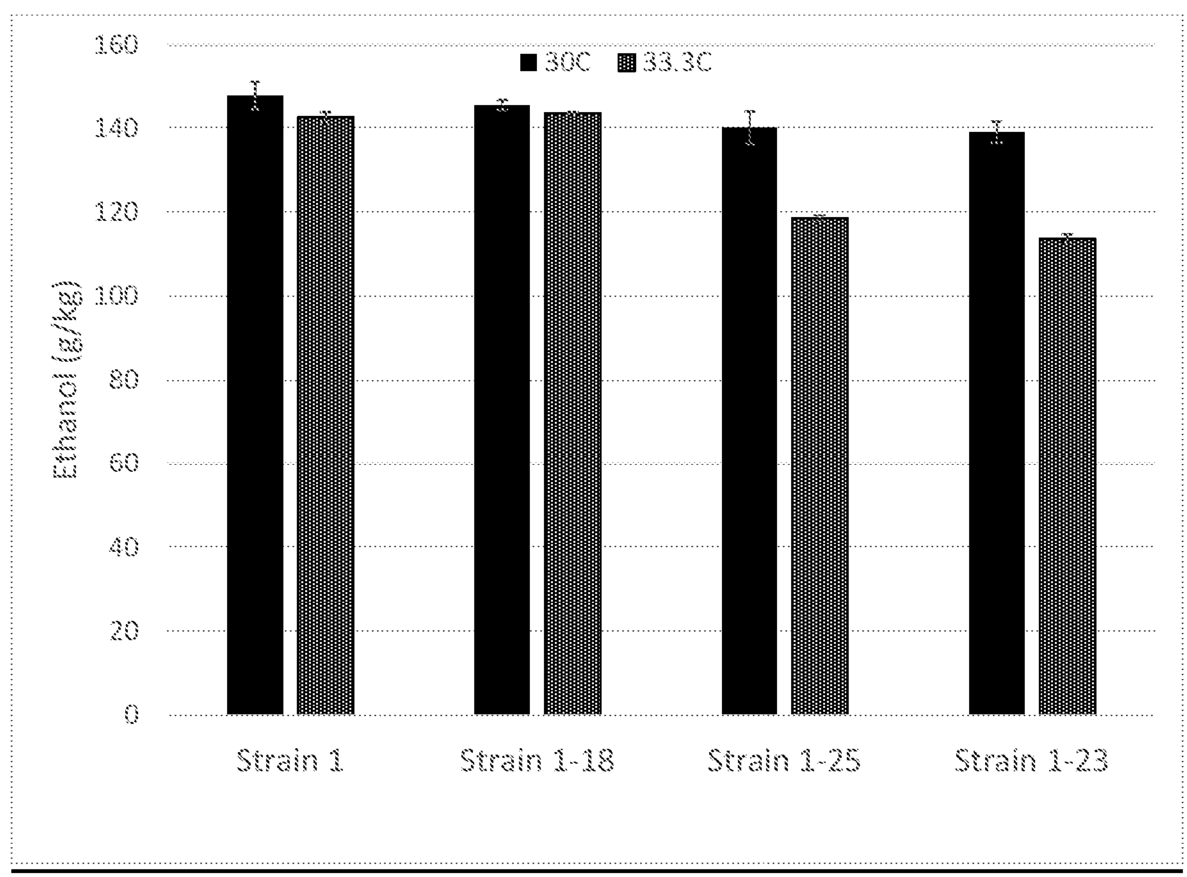
FIG. 6 is a graph of ethanol levels from corn mash fermentations comparing secretion signal modified glucoamylase expressing strains compared to a non-glucoamylase expressing strain.

Strain 1, Strain 1-18, Strain 1-25, and Strain 1-23 are struck to a YPD plate and incubated at 30° C. until single colonies are visible (1-2 days). A single colony from each strain is inoculated into a 250 ml seed flask containing 50 mls of YPD (10 g/L yeast extract, 20 g/L peptone, 100 g/L glucose) and grown overnight at 30° C. and 250 RPM. 50 grams of liquified corn mash is weighed into a pre-weighed 250 ml baffled shake flasks, fitted with a air-lock and stopper containing 5 mls of canola oil. 0.190 mls of a 50% (w/v) urea solution is added to each flask. 25 ul of a 10 mg/ml ampicillin solution is added to each flask. 70 μl of a 1:10 dilution of Spirizyme™ is added to flasks containing Strain 1 and Strain 1-18. Finally, an appropriate amount of seed inoculum from an overnight culture is added to target an initial $OD_{600}$ of 0.1. The weight of the flask is recorded. Flask are incubated at both 30° C. and 33.3 C with 100 RPM agitation. Each strain is run in duplicate. Flasks are weighed periodically to calculate weight loss, which can be converted to ethanol using methods known in the art. Time final samples are submitted for HPLC. FIG. 6 demonstrates strains expressing secretion signal modified *Rhizopus oryzae* glucoamylase achieves similar ethanol as Strain 1 supplemented with a commercial glucoamylase at 30° C. FIG. 6 also shows the reduction of ethanol titers when the temperature is increased to 33.3° C. in all backgrounds. At this temperature, strains expressing the secretion signal modified *Rhizopus oryzae* GA produce 16.9% (Strain 1-25) or 20.3% (Strain 1-21) less ethanol than Strain 1.

Example 15

Corn Mash Fermentations Using Flasks Fitted with Air-Lock Stoppers at 30° C. and 33.3° C.

Figure 7:
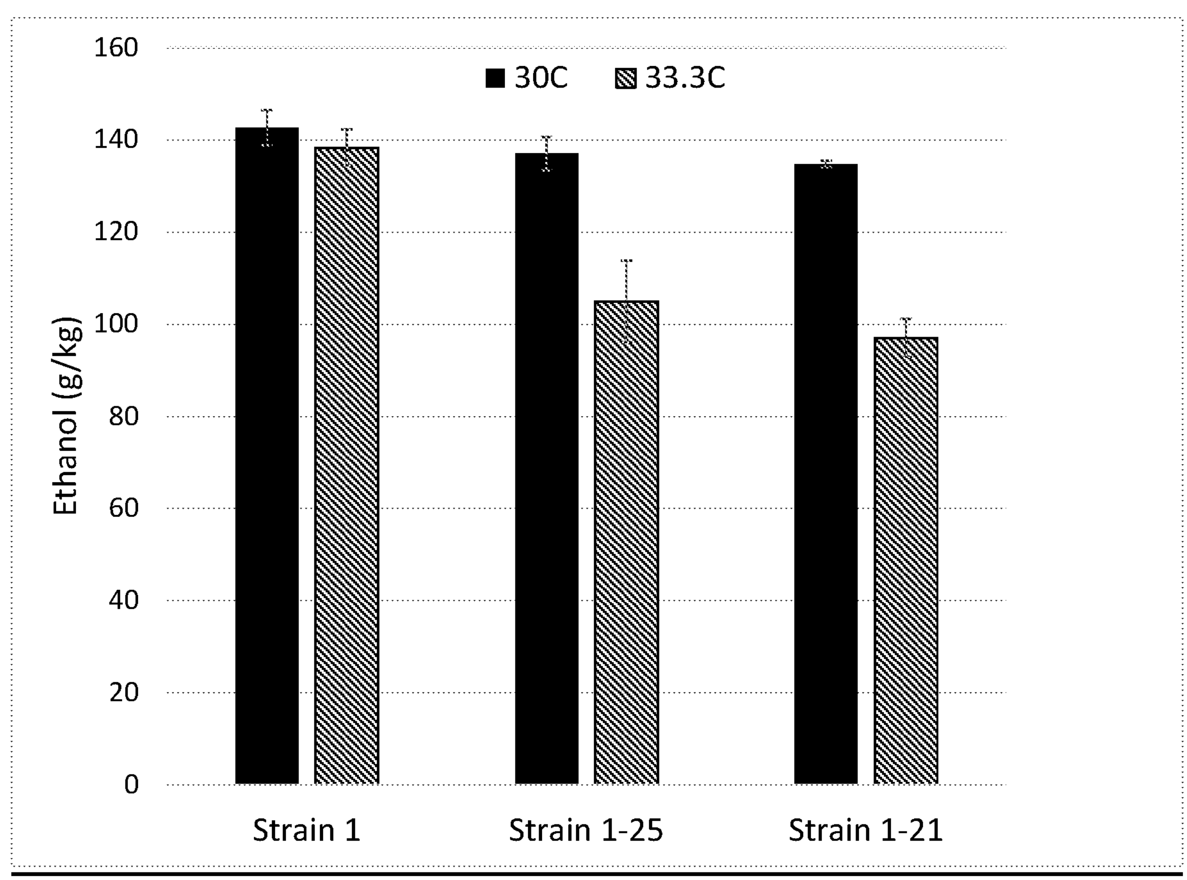
FIG. 7 is a graph of ethanol titers from corn mash fermentations comparing strains expressing either a modified *Rhizopus oryzae* or a modified *Aspergillus shirousami* glucoamylase compared to a non-glucoamylase expressing strain at 30 and 33.3° C.
Figure 8:
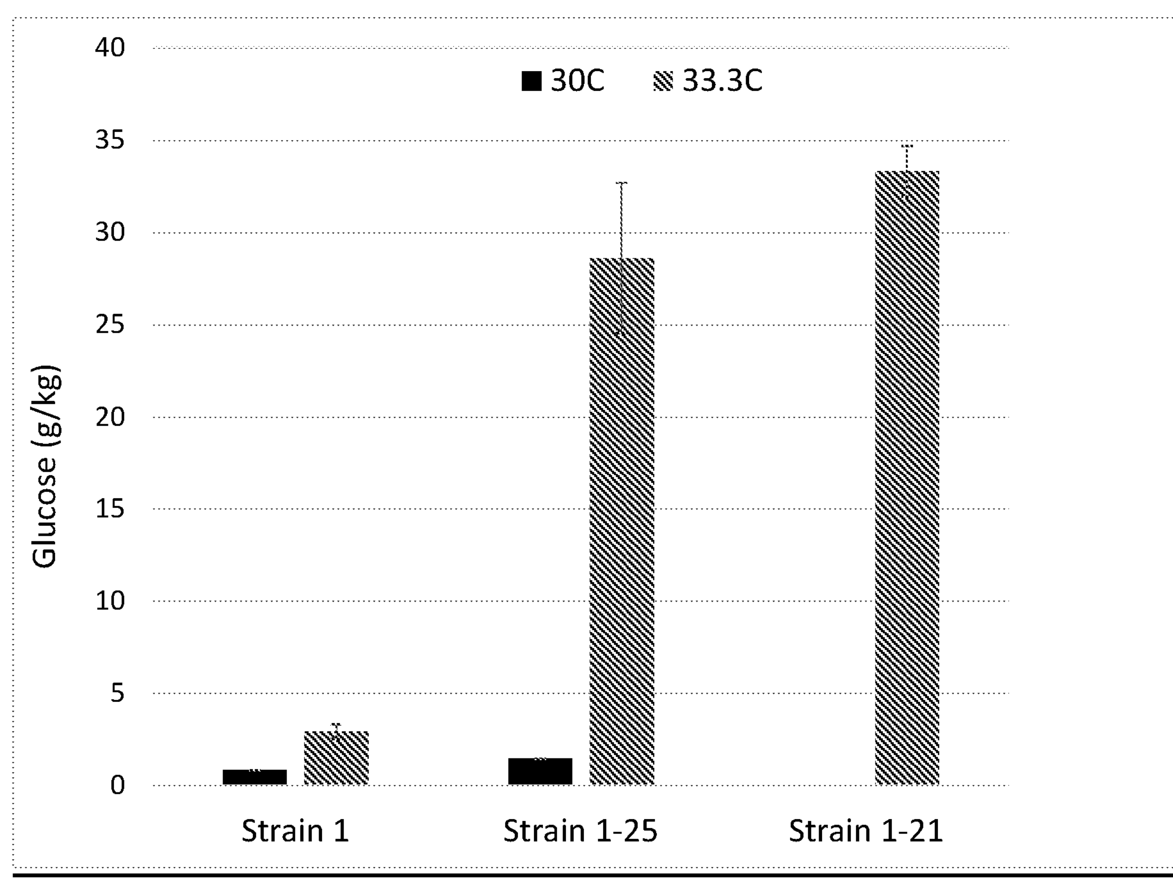
FIG. 8 is a graph of residual glucose levels in corn mash fermentations comparing strains expressing either a modified *Rhizopus oryzae* or a modified *Aspergillus shirousami* glucoamylase compared to a non-glucoamylase expressing strain at 30 and 33.3° C.

Strains 1, Strain 1-25, Strain 1-21 and Strain 1-23 are struck to a YPD plate and incubated at 30° C. until single colonies are visible (1-2 days). A single colony from each strain is inoculated into a 250 ml seed flask containing 50 mls of YM broth (3 g/L yeast extract, 3 g/L malt extract, 5 g/l yeast peptone, 10 g/L glucose) and grown overnight at 30° C. and 250 RPM. 50 grams of liquified corn mash is weighed into a pre-weighed 250 ml baffled shake flask, fitted with an air-lock and stopper containing 5 mls of canola oil. 0.190 mis of a 50% (w/v) urea solution is added to each flask. 25 ul of a 10 mg/ml ampicillin solution is added to each flask. 70 μl of a 1:10 dilution of Spirizyme™ is added to flasks containing Strain 1. Finally, an appropriate amount of seed inoculum from an overnight culture is added to target an initial $OD_{600}$ of 0.1. The weight of the flask is recorded. Flask are incubated at both 30° C. and 33.3° C. with 100 RPM agitation. Each strain is run in duplicate. Flasks are weighed periodically to calculate weight loss, which can be converted to ethanol using methods known in the art. Time final samples are submitted for HPLC after 72 hours of fermentation. FIG. 7 demonstrate strains expressing secretion signal modified *Rhizopus oryzae* or modified *Aspergillus shirousami* glucoamylase achieves similar ethanol as Strain 1 supplemented with a commercial glucoamylase at 30° C. FIG. 7 also shows the reduction of ethanol titers when the temperature is increased to 33.3° C. in all backgrounds. FIG. 8 shows the residual glucose left at the end of fermentation.

Example 16

Restoration of URA3 in Strain 1-25

Strain 1-25 is transformed with SEQ ID NO 31. Transformants are selected on synthetic complete media containing 3.5 g/L of p-fluorophenylalanine, and 1 g/L L-tyrosine (ScD-PFP). Resulting transformants are streaked for single colony isolation on ScD-PFP. A single colony is selected.

The PCR verified isolate is designated Strain 1-26. Strain 1-26 is transformed with SEQ ID NO 40. SEQ ID NO 40 contains a ScURA3 expression cassette with homology to the disrupted locus in Strain 1-3. Transformants are selected on synthetic complete media lacking uracil (ScD-Ura). Resulting transformants are streaked for single colony isolation on ScD-Ura. A single colony is selected. Correct integration of SEQ ID NO 40 into one allele of integration locus A is verified by PCR in the single colony. A PCR verified isolate is designated Strain 1-27.

Example 17

Mutagenesis of Strain 1-27

Strain 1-27 is struck to a YPD plate and incubated overnight at 30° C. Cells are inoculated into 9 mls of butterfields buffer to an $OD_{600}$ of 4.0. 100 μl is aliquoted and spread onto a YNB 1% starch plate (6.7 g/L yeast nitrogen base without amino acids or ammonium sulfate, 20 g/l agar, 10 g/l starch). The plate is placed agar size down without a lid into a UV crosslinker (Stratalinker, Stratagene) and mutagenized using a energy setting of 300 J/cm2. The plate is incubated at 30° C. for seven days. Mutants are struck to a similar plate and incubated for an additional 3 days at 30° C. A single colony is struck to YPD, and saved as Strain 1-28.

Strain 1-28 is struck to a YPD plate and incubated overnight at 30° C. Cells are inoculated into 9 mls of butterfields buffer to an $OD_{600}$ of 4.0. 100 μl is aliquoted and spread onto a YNB 1% starch plate (6.7 g/L yeast nitrogen base without amino acids or ammonium sulfate, 20 g/l agar, 10 g/l starch). The plate is placed agar size down without a lid into a UV crosslinker (Stratalinker, Stratagene) and mutagenized using a energy setting of 200 J/cm2. The plate is incubated at 37° C. for seven days. Mutants are struck to a similar plate and incubated for an additional 3 days at 37° C. A single colony is struck to YPD, and saved as Strain 1-29.

Example 18

Corn Mash Fermentations Comparing Strain 1-25 and Strain 1-28

Figure 9:
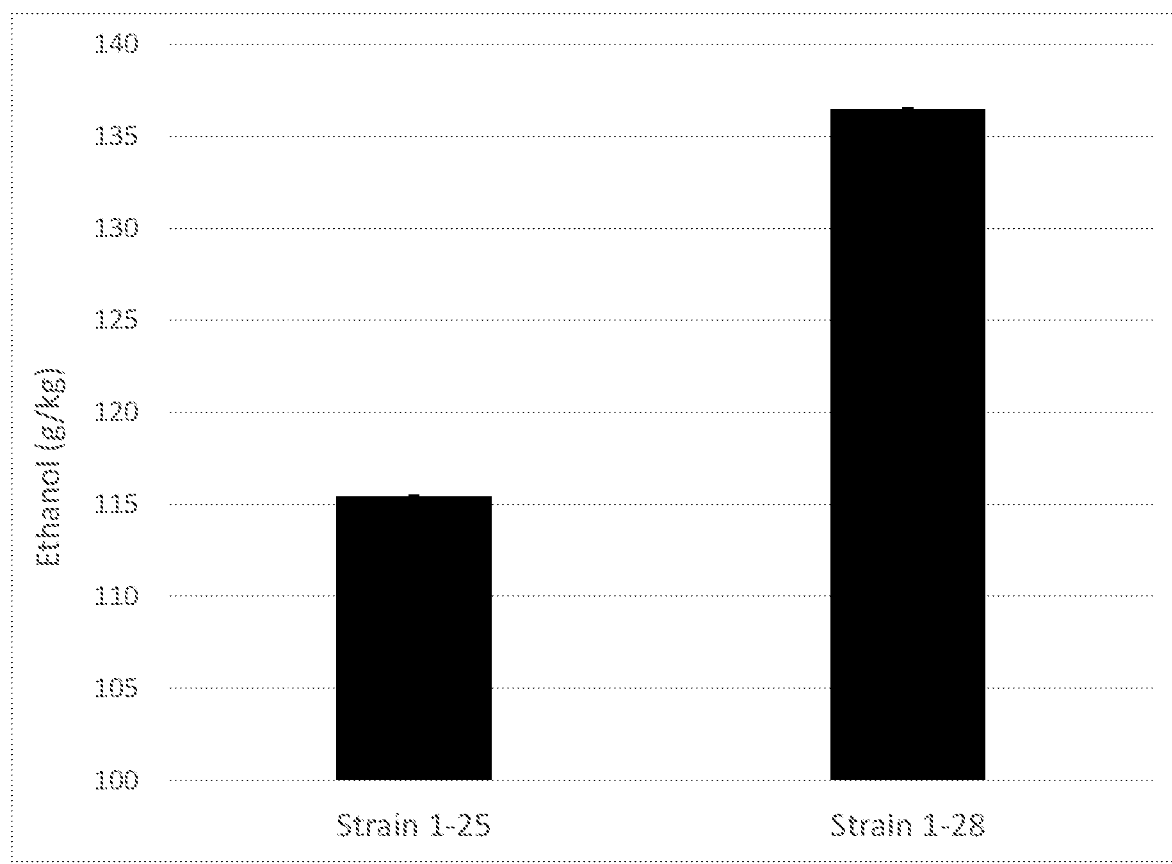
FIG. 9 is a graph of ethanol levels from corn mash fermentations comparing the mutant strain 1-28 to the parent Strain 1-25 at 33.3° C.

Strain 1-25 and Strain 1-28 are struck to a YPD plate and incubated at 30° C. until single colonies are visible (1-2 days). A single colony from each strain is inoculated into a 250 ml seed flask containing 50 mls of YPD (10 g/L yeast extract, 20 g/L peptone, 100 g/L glucose) and grown overnight at 30° C. and 250 RPM. 50 grams of liquified corn mash is weighed into a pre-weighed 250 ml baffled shake flask, fitted with an air-lock and stopper containing 5 mls of canola oil. 0.190 mls of a 50% (w/v) urea solution is added to each flask. 25 ul of a 10 mg/ml ampicillin solution is added to each flask. Finally, an appropriate amount of seed inoculum from an overnight culture is added to target an initial $OD_{600}$ of 0.1. The weight of the flask is recorded. Flask are incubated at 33.3° C. with 100 RPM agitation. Each strain is run in duplicate. Flasks are weighed periodically to calculate weight loss, which can be converted to ethanol using methods known in the art. Time final samples at 69 hours are submitted for HPLC. FIG. 9 demonstrates the improvement in ethanol production in Strain 1-28 compared to Strain 1-25. Ethanol production in Strain 1-28 is 18.2% higher compared to the parent Strain 1-25 at 33.3° C.

Example 19

Corn Mash Fermentations Comparing Strain 1 and Strain 1-28 at 37° C.

Viable cell count is measured using a Nexcelcom Bioscience Cellometer. Cells are diluted 1:40 in Nexcelcom Yeast buffer (Product number CSO-0110); this is further diluted 1:1 in ViaStain yeast live/dead AO/PI stain (Nexcelom #CS0-0102-10ML, from Kit #CSK-0102). Samples are vortexed for 5-10 sec after dilutions and prior to loading into the cytometer slides. Samples are incubated in the dark for 2-5 min prior to counting live CFU/ml.

Strains 1-28 and Strain 1 are inoculated into a corn mash seed flask from stock cultures targeting an initial CFU/ml of viable cells of 5.0e7 to 1.e8 for both strains. Seed media consists of 50 g of liquefied corn mash per 250 ml baffled flask. Seed is incubated at 30 C, 250 rpm for 15-18 hours. Production flasks are inoculated from these seed flasks targeting an initial CFU/ml of viable cells of 1.95e7 for both strains. Cell counts are taken at this time point again using the cellometer method to correctly normalize the inoculum level transferred from seed to production flask.

For production flasks, 50 g of liqufied corn mash is weighed into a pre-weighed 250 ml baffled shake flasks, fitted with an air-lock and stopper containing 5 mls of canola oil. 0.315 mls of a 50% (w/v) urea solution is added to each flask. 25 ul of a 10 mg/ml ampicillin solution is added to each flask. 100 μl of a 1:10 dilution of Distillase™ is added to flasks containing Strain 1, 75 uL of a 1:100 dilution of Distillase™ is added to Strain 1-28 flasks (0.075× dose). Seed is added as detailed above to 1.95e7 CFU/ml per flask for both strains. The weight of the flask is recorded. Flask are incubated at 37° C. and 100 RPM agitation using and Infors Multitron shaker, at 24 hours the temperature in the shaker is decreased to 32.5° C. Each strain is run in duplicate. Flasks are weighed periodically to calculate weight loss, which can be converted to ethanol using methods known in the art. Samples at 75 hr are submitted for HPLC using methods know in the art. Tables 4 and 5 demonstrate that Strain 1-28 shows at least equal performance to Strain 1 when subjected to high initial temperatures.

TABLE 4

Final ethanol titer in corn mash fermentation.

| Strain | 75 h Ethanol titer in 37 C. condition |
|---|---|
| Strains 1-28 0.075x enzyme | 125.7 g/L |
| Strain 1 + 1x enzyme | 124.7 g/L |

TABLE 5

Yield of ethanol in corn mash fermentations.

| Strain | Mass Yield % g ethanol per g total sugar |
|---|---|
| Strain 1-28 + 0.075x enzyme | 46.0% |
| Strain 1 + 1x enzyme | 45.6% |

Exemplary Embodiments

A. An engineered polypeptide comprising:

(a) a secretion signal amino acid sequence comprising 5-8 continuous hydrophobic amino acid residues; and (b) a glucoamylase amino acid sequence from a yeast, fungal, or bacterial glucoamylase polypeptide, wherein the secretion signal amino acid sequence is heterologous to the glucoamylase amino acid sequence, and the engineered polypeptide has glucoamylase activity.

B. The engineered polypeptide of embodiment A wherein the secretion signal amino acid sequence comprises 5 or 6 continuous hydrophobic amino acid residues.

C. The engineered polypeptide of embodiment A wherein amino acids of the 5-8 continuous hydrophobic amino acid residues are selected from the group consisting of alanine, isoleucine, leucine, phenylalanine, and valine.

D. The engineered polypeptide of embodiment C wherein the 5-8 continuous hydrophobic amino acid residues comprise one or more leucine residue(s).

E. The engineered polypeptide of embodiment A wherein the 5-8 continuous hydrophobic amino acid residues are immediately adjacent to one or two polar amino acid residue (s).

F. The engineered polypeptide of embodiment E wherein the polar amino acid residue is a serine residue.

G. The engineered polypeptide of embodiment A wherein the 5-8 continuous hydrophobic amino acid residues comprise a sequence selected from the group consisting of AVLFAA, AFLFLL, LVLVLL, LLFLF, and FILAAV.

H. The engineered polypeptide of embodiment A wherein the secretion signal amino acid sequence comprises at least 15, 16, 17, 18, or 19 amino acid residues.

I. The engineered polypeptide of embodiment A comprising:

(a) a secretion signal amino acid sequence having 80% or greater sequence identity to: (i) an amino acid sequence of at least AA 1-19 of SEQ ID NO: 73; (ii) an amino acid sequence of at least AA 1-19 of SEQ ID NO: 74; (iii) SEQ ID NO: 77 (An aa); (iv) SEQ ID NO: 75 (Sc IV); (v) SEQ ID NO: 76 (Gg LZ); or (vi) SEQ ID NO: 78(Hs SA); and (b) a glucoamylase amino acid sequence from a yeast, fungal, or bacterial glucoamylase polypeptide, wherein the polypeptide has glucoamylase activity.

J. The engineered polypeptide of embodiment I wherein the (a) secretion signal amino acid sequence has 90% or greater sequence identity to:

(i) an amino acid sequence of at least AA 1-19 of SEQ ID NO: 73; (ii) an amino acid sequence of at least AA 1-19 of SEQ ID NO: 74; (iii) SEQ ID NO: 77 (An aa); (iv) SEQ ID NO: 75 (Sc IV); (v) SEQ ID NO: 76 (Gg LZ); or (vi) SEQ ID NO: 78(Hs SA).

K. The engineered polypeptide of embodiment J wherein the (a) secretion signal amino acid sequence is:

i) an amino acid sequence of at least AA 1-19 of SEQ ID NO: 73; (ii) an amino acid sequence of at least AA 1-19 of SEQ ID NO: 74; (iii) SEQ ID NO: 77 (An aa); (iv) SEQ ID NO: 75 (Sc IV); (v) SEQ ID NO: 76 (Gg LZ); or (vi) SEQ ID NO: 78(Hs SA).

L. The engineered polypeptide of any of embodiments A-K wherein the glucoamylase amino acid sequence is from a yeast or fungal glucoamylase.

M. The engineered polypeptide of any of embodiments A-L wherein the glucoamylase amino acid sequence is an enzymatically active portion of a yeast or fungal glucoamylase polypeptide.

N. The engineered polypeptide of any of embodiments A-M wherein the glucoamylase amino acid sequence is from a yeast or fungal organism selected from the group consisting of *Amorphotheca resinae, Aspergillus niger, Aspergillus awamori, Aspergillus oryzae, Aspergillus kawachii, Aspergillus shirousami, Aspergillus terreus, Aureobasidium pullulans, Blastobotrys adeninivorans, Brettanomyces bruxellensis, Candida albicans, Cyberlindnera jadinii, Penicillium oxalicum, Rhizopus oryzae, Schizosaccharomyces pombe, Saccharomyces cerevisiae, Saccharomycopsis fibuligera, Talaromyces emersonii, Trametes cingulate*, and *Trichoderma reesei.*

O. The engineered polypeptide of embodiment N wherein the glucoamylase amino acid sequence has 95% or greater, 96% or greater, 97% or greater, 98% or greater, or 99% or greater sequence identity SEQ ID NO:42 (to amino acids 26-604 of *Rhizopus oryzae* GA).

P. The engineered polypeptide of embodiment N wherein the glucoamylase amino acid sequence has 95% or greater, 96% or greater, 97% or greater, 98% or greater, or 99% or greater sequence identity to SEQ ID NO:43 (amino acids 19-639 of *Aspergillus shirousami* GA).

Q. The engineered polypeptide of embodiment N wherein the glucoamylase amino acid sequence has 95% or greater, 96% or greater, 97% or greater, 98% or greater, or 99% or greater sequence identity to SEQ ID NO:44 (amino acids 21-636 of *Aspergillus terreus* GA).

R. The engineered polypeptide of embodiment A wherein the glucoamylase amino acid sequence has 95% or greater, 96% or greater, 97% or greater, 98% or greater, or 99% or greater sequence identity to amino acids to a polypeptide selected from the group consisting of:

(i) SEQ ID NO:45 (Sc-FAKS)-*Saccharomycopsis fibuligera* GA;

(ii) SEQ ID NO: 46 (Sc-AKS)-*Saccharomycopsis fibuligera* GA;

(iii) SEQ ID NO:47 (An aa)-*Saccharomycopsis fibuligera* GA;

(iv) SEQ ID NO:48 (Sc IV)-*Saccharomycopsis fibuligera* GA;

(v) SEQ ID NO:49 (Gg LZ)-*Saccharomycopsis fibuligera* GA;

(vi) SEQ ID NO:50 (Hs SA)-*Saccharomycopsis fibuligera* GA; and (vii) SEQ ID NO: 51 (Sc MF$\alpha$1)-*Saccharomycopsis fibuligera* GA S. The engineered polypeptide of embodiment A wherein the glucoamylase amino acid sequence has 95% or greater, 96% or greater, 97% or greater, 98% or greater, or 99% or greater sequence identity to amino acids to a polypeptide selected from the group consisting of:

(i) SEQ ID NO: 52 (Sc-FAKS)-*Rhizopus oryzae* GA;

(ii) SEQ ID NO: 53 (Sc-AKS)-*Rhizopus oryzae* GA;

(iii) SEQ ID NO: 54 (An aa)-*Rhizopus oryzae* GA;

(iv) SEQ ID NO: 55 (Sc IV)-*Rhizopus oryzae* GA;

(v) SEQ ID NO: 56 (Gg LZ)-*Rhizopus oryzae* GA;

(vi) SEQ ID NO: 57 (Hs SA)-*Rhizopus oryzae* GA; and (vii) SEQ ID NO:58 (Sc MF$\alpha$1)-*Rhizopus oryzae* GA.

T. The engineered polypeptide of embodiment A wherein the glucoamylase amino acid sequence has 95% or greater, 96% or greater, 97% or greater, 98% or greater, or 99% or greater sequence identity to amino acids to a polypeptide selected from the group consisting of:

(i) SEQ ID NO: 59 (Sc-FAKS)-*Aspergillus shirousami* GA;

(i) SEQ ID NO: 60 (Sc-AKS)-*Aspergillus shirousami* GA;

(ii) SEQ ID NO: 61(An aa)-*Aspergillus shirousami* GA;

(iii) SEQ ID NO: 62 (Sc IV)-*Aspergillus shirousami* GA;

(iv) SEQ ID NO: 63(Gg LZ)-*Aspergillus shirousami* GA;

(vi) SEQ ID NO: 64(Hs SA)-*Aspergillus shirousami* GA; and (vii) SEQ ID NO: 65 (Sc MFα1)-*Aspergillus shirousami* GA.

U. The engineered polypeptide of embodiment A wherein the glucoamylase amino acid sequence has 95% or greater, 96% or greater, 97% or greater, 98% or greater, or 99% or greater sequence identity to amino acids to a polypeptide selected from the group consisting of:

(i) SEQ ID NO: 66 (Sc-FAKS)-*Aspergillus terreus* GA;

(ii) SEQ ID NO: 67 (Sc-AKS)-*Aspergillus terreus* GA (iii) SEQ ID NO: 68 (An aa)-*Aspergillus terreus* GA;

(iv) SEQ ID NO: 69 (Sc IV)-*Aspergillus terreus* GA;

(v) SEQ ID NO: 70 (Gg LZ)-*Aspergillus terreus* GA;

(vi) SEQ ID NO: 71 (Hs SA)-*Aspergillus terreus* GA; and (vii) SEQ ID NO: 72 (Sc MFα1)-*Aspergillus terreus* GA.

V. The engineered polypeptide of any of embodiments A-U further comprising a third sequence that is different than the (a) secretion signal amino acid sequence and the (b) glucoamylase amino acid, wherein the third sequence is positioned between (a) and (b), or is at the C-terminus of (b).

W. A nucleic acid comprising a nucleic acid sequence that encodes the polypeptide of any one of embodiments A-V.

X. The nucleic acid of embodiment W further comprising a transcriptional regulatory sequence.

Y. The nucleic acid of embodiment X wherein the transcriptional regulatory sequence comprises an ADH promoter or a TDH3 promoter.

Z. A vector comprising the nucleic acid of any one of embodiments W-Y.

AA. The vector of embodiment Z comprising an auxotrophic gene marker for selection in yeast.

AB. An engineered cell that expresses the polypeptide of any one of embodiments A-V.

AC. An engineered cell that comprises the nucleic acid or vector of any one of embodiments W-AB (i.e., any of W-Z, AA, or AB).

AD. The engineered host cell of embodiment AC which is an engineered yeast.

AE. The engineered yeast of embodiment AD, which is a species of *Saccharomyces*.

AF. The engineered yeast of embodiment AE which is *Saccharomyces cerevisiae*.

AG. The engineered yeast of any of embodiments AE-AF further comprising (i) a heterologous isomaltase, or an endogenous isomaltase expressed at levels higher than in an unmodified yeast; (ii) a heterologous sugar transporter polypeptide, (iii) a heterologous starch-degrading enzyme that is different than a glucoamylase, or a combination of any of (i)-(iii).

AH. The engineered yeast of embodiment AG wherein the endogenous isomaltase is selected from the group consisting of IMA1, IMA2, IMA3, IMA4, and IMA5; or the heterologous sugar transporter polypeptide has 90% or greater identity to SEQ ID NO:79 (SmMAL11).

AI. The engineered yeast of any one of embodiments AE-AH which is (a) capable of producing ethanol at a titer of greater than 90 g/L, 100 g/L, 110 g/L, 120 g/L, 130 g/L, or 140 g/L; (b) thermotolerant at temperatures in the range of 33° C. to 40° C., 33° C. to 39° C., 33° C. to 38° C., 33° C. to 37° C., 34° C. to 37° C., 35° C. to 37° C., or 36° C. to 38° C.; or both (a) and (b).

AJ. A fermentation medium comprising the polypeptide of any one of embodiments A-V or the engineered yeast of any one of embodiments AE-AH.

AK. Use of the polypeptide of any one of embodiments A-V, the engineered yeast of any one of embodiments AE-AI, or the fermentation medium of embodiment AJ for the preparation of a bioproduct or a feed composition.

AL. The fermentation medium of embodiment AJ comprising ethanol at a concentration of about 90 g/L or greater.

AM. The fermentation medium of embodiment AL comprising ethanol at a concentration in the range of 90 g/L to 170 g/L.

AN. A feed composition prepared from the fermentation medium of any one of embodiments AJ, AL, or AM.

AO. The feed composition of embodiment AN prepared by a process comprising steps of (a) removing some or all of a bioproduct from the fermentation medium to provide a refined composition comprising non-bioproduct solids, and (b) using the refined composition for form a feed composition.

AP. A fermentation method for producing a fermentation product, comprising a step of:

fermenting a liquid medium comprising a starch material and the polypeptide of any one of embodiments A-V, or the engineered yeast of any one of embodiments AE-AI to provide a fermentation product.

AQ. The fermentation method of embodiment AP wherein the fermentation product is ethanol.

AR. The fermentation method of embodiment AQ wherein ethanol is produced to a concentration of 90 g/L or greater in the medium.

AS. The fermentation method of embodiment AR wherein said fermenting provides ethanol in the range of 90 g/L to 170 g/L.

AT. The fermentation method of embodiment AS wherein said fermenting provides ethanol in the range of 110 g/L to 170 g/L.

AU. The fermentation method of embodiment AT wherein said fermenting provides ethanol in the range of 125 g/L to 170 g/L.

AV. The method of any of embodiments AP-AU, wherein the fermentation medium is at least 33° C., at least 34° C., at least 35° C., at least 36° C., or at least 37° C. during at least one time point during the fermentation.

AW. The method of any of embodiments AP-AV, wherein the fermenting provides an amount of ethanol in the fermentation medium of 120 g/L or greater, 130 g/L or greater, or 140 g/L or greater.

What is claimed is:

1. An engineered cell that expresses an engineered polypeptide, wherein the engineered polypeptide comprises:

(a) a secretion signal amino acid sequence comprising 5-8 continuous hydrophobic amino acid residues; and (b) a glucoamylase amino acid sequence at least 80% identical to SEQ ID NO:42, wherein the secretion signal amino acid sequence is heterologous to the glucoamylase amino acid sequence, and wherein the engineered polypeptide has glucoamylase activity, and wherein the engineered cell is capable of producing ethanol at a titer of greater than 90 g/L.

2. The engineered cell of claim 1 wherein amino acids of the 5-8 continuous hydrophobic amino acid residues are selected from the group consisting of alanine, isoleucine, leucine, phenylalanine, and valine.

3. The engineered cell of claim 1 wherein the secretion signal amino acid sequence comprise a sequence selected from the group consisting of AVLFAA (SEQ ID NO:82), AFLFLL (SEQ ID NO:83), LVLVLL (SEQ ID NO:84), LLFLF (SEQ ID NO:85), and FILAAV (SEQ ID NO:86).

4. The engineered cell of claim 1 comprising:

a secretion signal amino acid sequence having 80% or greater sequence identity to: (i) amino acids 1-x of SEQ ID NO:73, wherein x is an integer between 19 and 89; (ii) SEQ ID NO: 74; (iii) SEQ ID NO: 77; (iv) SEQ ID NO: 75; (v) SEQ ID NO: 76; (vi) SEQ ID NO: 78; or (vii) amino acids 1-57 of SEQ ID NO:74.

5. The engineered cell of claim 1 wherein the (a) secretion signal amino acid sequence has 90% or greater sequence identity to (i) amino acids 1-x of SEQ ID NO: 73, wherein x is an integer between 19 and 89; (ii) SEQ ID NO: 74; (iii) SEQ ID NO: 77; (iv) SEQ ID NO: 75; (v) SEQ ID NO: 76; (vi) SEQ ID NO: 78; or (vii) amino acids 1-57 of SEQ ID NO:74.

6. The engineered cell of claim 1 wherein the glucoamylase amino acid sequence has 90% or greater sequence identity to SEQ ID NO: 42.

7. The engineered cell of claim 1 wherein the engineered cell is an engineered *Saccharomyces cerevisiae.*

8. The engineered cell of claim 1 which is capable of producing ethanol at a titer of greater than 90 g/L and is thermotolerant at temperatures in the range of 33° C. to 40° C.

9. A fermentation method for producing a fermentation product, comprising a step of:

fermenting a liquid medium comprising a starch material with the engineered cell of claim 1 to provide a fermentation product.

10. The fermentation method of claim 9 wherein said fermenting produces ethanol at a titer in the range of 90 g/L to 170 g/L.

11. The engineered cell of claim 1, wherein the sequence of the engineered polypeptide is at least 80% identical to at least one of SEQ ID NOs: 52-58.

12. The engineered cell of claim 1, wherein the sequence of the engineered polypeptide is at least 90% identical to at least one of SEQ ID NOs:52-58.

* * * * *